US009701723B2

(12) United States Patent
Garcia-Sastre et al.

(10) Patent No.: US 9,701,723 B2
(45) Date of Patent: Jul. 11, 2017

(54) VACCINES FOR USE IN THE PROPHYLAXIS AND TREATMENT OF INFLUENZA VIRUS DISEASE

(75) Inventors: Adolfo Garcia-Sastre, New York, NY (US); Peter Palese, New York, NY (US); Taia T. Wang, Stanford, CA (US); Gene S. Tan, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 108 days.

(21) Appl. No.: 13/579,845

(22) PCT Filed: Feb. 18, 2011

(86) PCT No.: PCT/US2011/025467

§ 371 (c)(1),
(2), (4) Date: Dec. 19, 2012

(87) PCT Pub. No.: WO2011/103453

PCT Pub. Date: Aug. 25, 2011

(65) Prior Publication Data

US 2013/0209499 A1 Aug. 15, 2013
US 2017/0114103 A9 Apr. 27, 2017

Related U.S. Application Data

(63) Continuation-in-part of application No. 12/788,103, filed on May 26, 2010, now Pat. No. 8,673,314.

(60) Provisional application No. 61/305,898, filed on Feb. 18, 2010, provisional application No. 61/354,160, filed on Jun. 11, 2010, provisional application No. 61/385,083, filed on Sep. 21, 2010.

(51) Int. Cl.
*C07K 14/11* (2006.01)
*A61K 39/12* (2006.01)
*C07K 14/005* (2006.01)
*A61K 39/00* (2006.01)

(52) U.S. Cl.
CPC ............. *C07K 14/11* (2013.01); *A61K 39/12* (2013.01); *C07K 14/005* (2013.01); *A61K 2039/53* (2013.01); *A61K 2039/55566* (2013.01); *A61K 2039/6012* (2013.01); *A61K 2039/6081* (2013.01); *C12N 2760/16111* (2013.01); *C12N 2760/16122* (2013.01); *C12N 2760/16134* (2013.01)

(58) Field of Classification Search
CPC .. A61K 2300/00; A61K 39/145; A61K 39/12; A61K 2039/525; C12N 7/00; C12N 2760/16122; C12N 2760/16034; C12N 2760/16111; C12N 2760/16222; C12N 2760/16234; C12N 2760/16322; C12N 2760/18134; C07K 14/005; C07K 16/1018

See application file for complete search history.

(56) References Cited

U.S. PATENT DOCUMENTS

| | | | |
|---|---|---|---|
| 5,182,192 A | 1/1993 | Steplewski et al. | |
| 5,545,806 A | 8/1996 | Lonberg et al. | |
| 5,569,825 A | 10/1996 | Lonberg et al. | |
| 5,571,709 A | 11/1996 | Devauchelle et al. | |
| 5,573,916 A * | 11/1996 | Cheronis .............. | C07K 14/005 424/204.1 |
| 5,589,174 A | 12/1996 | Okuno et al. | |
| 5,625,126 A | 4/1997 | Lonberg et al. | |
| 5,631,350 A | 5/1997 | Okuno et al. | |
| 5,633,425 A | 5/1997 | Lonberg et al. | |
| 5,661,016 A | 8/1997 | Lonberg et al. | |
| 5,820,871 A | 10/1998 | Palese et al. | |
| 5,854,037 A | 12/1998 | Palese et al. | |
| 5,885,793 A | 3/1999 | Griffiths et al. | |
| 5,916,771 A | 6/1999 | Hori et al. | |
| 6,001,634 A | 12/1999 | Palese et al. | |
| 6,165,476 A | 12/2000 | Strom et al. | |
| 6,337,070 B1 | 1/2002 | Okuno et al. | |
| 6,720,409 B2 | 4/2004 | Okuno et al. | |
| 6,867,293 B2 | 3/2005 | Andrews et al. | |
| 6,887,699 B1 | 5/2005 | Palese et al. | |
| 8,367,077 B2 * | 2/2013 | Zurbriggen et al. ........ | 424/278.1 |
| 8,603,467 B2 * | 12/2013 | Chen et al. ................ | 424/130.1 |
| 8,673,314 B2 * | 3/2014 | Garcia-Sastre .... | C07K 16/1018 424/133.1 |

(Continued)

FOREIGN PATENT DOCUMENTS

| | | |
|---|---|---|
| CA | 2121559 | 10/1994 |
| CA | 2718923 | 9/2009 |

(Continued)

OTHER PUBLICATIONS

Wang TT, Tan GS, Hai R, Pica N, Ngai L, Ekiert DC, Wilson IA, Garcia-Sastre A, Moran TM, Palese P. Vaccination with a synthetic peptide from the influenza virus hemagglutinin provides protection against distinct viral subtypes. Proc Natl Acad Sci U S A. Nov 2, 2010;107(44):18979-84. doi: 10.1073/pnas.1013387107. Epub Oct. 18, 2010.*

Zamarin D, Ortigoza MB, Palese P. Influenza A virus PB1-F2 protein contributes to viral pathogenesis in mice. J Virol. Aug. 2006;80(16):7976-83.*

Bianchi E, Liang X, Ingallinella P, Finotto M, Chastain MA, Fan J, Fu TM, Song HC, Horton MS, Freed DC, Manger W, Wen E, Shi L, Ionescu R, Price C, Wenger M, Emini EA, Cortese R, Ciliberto G, Shiver JW, Pessi A. Universal influenza B vaccine based on the maturational cleavage site of the hemagglutinin precursor. J Virol. Jun. 2005;79(12):7380-8.*

(Continued)

*Primary Examiner* — Rachel B Gill
(74) *Attorney, Agent, or Firm* — Jones Day

(57) ABSTRACT

Provided herein are polypeptides comprising portions of the influenza virus hemagglutinin, compositions comprising such polypeptides that can be used as immunogens in vaccines and methods of their use to generate an immune response against multiple influenza subtypes in a subject.

23 Claims, 27 Drawing Sheets

(56) References Cited

U.S. PATENT DOCUMENTS

Figure 2A:
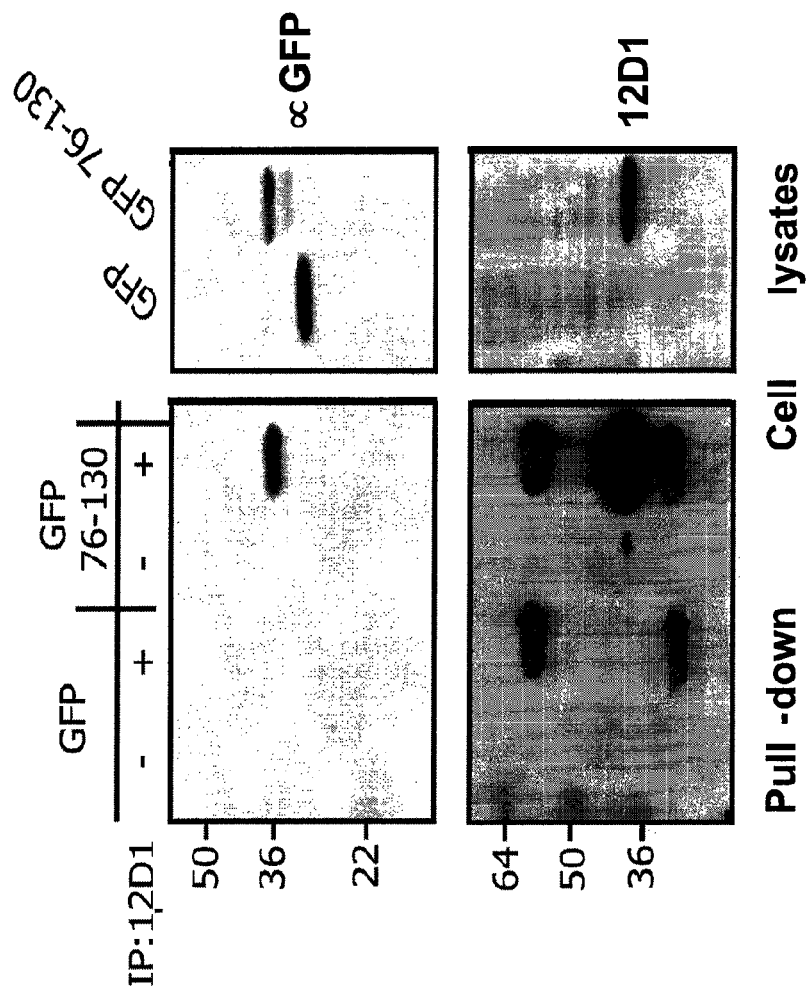

| | | | |
|---|---|---|---|
| 8,828,406 B2 | 9/2014 | Garcia-Sastre et al. | |
| 9,051,359 B2 | 6/2015 | Garcia-Sastre et al. | |
| 9,175,069 B2* | 11/2015 | Garcia-Sastre | C07K 16/1018 |
| 9,371,366 B2 | 6/2016 | Garcia-Sastre et al. | |
| 9,452,211 B2 | 9/2016 | Meijberg et al. | |
| 2002/0164770 A1* | 11/2002 | Hoffmann | 435/235.1 |
| 2003/0134338 A1 | 7/2003 | Makarocskiy | |
| 2004/0002061 A1 | 1/2004 | Kawaoka | |
| 2005/0009008 A1 | 1/2005 | Robinson et al. | |
| 2005/0048074 A1 | 3/2005 | Cardineau et al. | |
| 2005/0064391 A1 | 3/2005 | Segal et al. | |
| 2005/0106178 A1* | 5/2005 | O'Hagan | 424/209.1 |
| 2005/0201946 A1* | 9/2005 | Friede | A61K 9/0043 424/45 |
| 2006/0008473 A1* | 1/2006 | Yang et al. | 424/204.1 |
| 2006/0280754 A1* | 12/2006 | Garry | 424/204.1 |
| 2007/0020238 A1 | 1/2007 | Baltimore et al. | |
| 2007/0036809 A1 | 2/2007 | Michl et al. | |
| 2008/0019998 A1 | 1/2008 | Wang et al. | |
| 2008/0032921 A1 | 2/2008 | Alexander et al. | |
| 2008/0152657 A1 | 6/2008 | Horowitz et al. | |
| 2008/0176247 A1 | 7/2008 | Chou et al. | |
| 2009/0081255 A1 | 3/2009 | Bublot et al. | |
| 2009/0291472 A1* | 11/2009 | Lu | A61K 39/145 435/69.1 |
| 2009/0304730 A1* | 12/2009 | Arnon | A61K 39/145 424/186.1 |
| 2009/0304739 A1* | 12/2009 | Rappuoli | A61K 39/145 424/206.1 |
| 2009/0311669 A1 | 12/2009 | Kawaoka | |
| 2010/0297165 A1* | 11/2010 | Berzofsky | A61K 39/39 424/193.1 |
| 2010/0297174 A1* | 11/2010 | Garcia-Sastre | C07K 14/005 424/210.1 |
| 2011/0027270 A1 | 2/2011 | Garcia-Sastre et al. | |
| 2011/0111494 A1* | 5/2011 | Hill | C07K 14/70578 435/325 |
| 2011/0182938 A1* | 7/2011 | Weiner | A61K 31/7088 424/209.1 |
| 2012/0039898 A1 | 2/2012 | Throsby et al. | |
| 2012/0122185 A1 | 5/2012 | Palese et al. | |
| 2012/0189658 A1 | 7/2012 | Couture et al. | |
| 2012/0244183 A1* | 9/2012 | Garcia-Sastre | C07K 14/005 424/209.1 |
| 2013/0129747 A1 | 5/2013 | Schrader | |
| 2013/0129761 A1* | 5/2013 | Garcia-Sastre | A61K 39/145 424/186.1 |
| 2013/0209499 A1 | 8/2013 | Garcia-Sastre et al. | |
| 2014/0170163 A1* | 6/2014 | Garcia-Sastre | C07K 16/1018 424/159.1 |
| 2014/0328875 A1 | 11/2014 | Garcia-Sastre et al. | |
| 2015/0132330 A1 | 5/2015 | Garcia-Sastre et al. | |
| 2015/0239960 A1* | 8/2015 | Garcia-Sastre | C07K 16/1018 424/139.1 |
| 2015/0297712 A1 | 10/2015 | Garcia-Sastre et al. | |
| 2015/0335729 A1 | 11/2015 | Garcia-Sastre et al. | |
| 2016/0362455 A1 | 12/2016 | Meijberg et al. | |
| 2016/0376347 A1 | 12/2016 | Saelens et al. | |

FOREIGN PATENT DOCUMENTS

| | | |
|---|---|---|
| EP | 0621339 A2 | 10/1994 |
| JP | 2004258814 | 9/2004 |
| JP | 2006-347922 | 12/2006 |
| JP | 2011-057653 | 3/2011 |
| WO | WO84/00687 A1 * | 3/1984 |
| WO | WO 92/01047 | 1/1992 |
| WO | WO 94/09136 | 4/1994 |
| WO | WO 94/16109 | 7/1994 |
| WO | WO 94/17826 | 8/1994 |
| WO | WO 95/34324 | 12/1995 |
| WO | WO 96/33735 | 10/1996 |
| WO | WO 96/34096 | 10/1996 |
| WO | WO 98/24893 | 6/1998 |
| WO | WO 2007/045674 | 4/2007 |
| WO | WO 2007/064802 | 6/2007 |
| WO | WO 2007/103322 | 9/2007 |
| WO | WO 2007/134327 A2 | 11/2007 |
| WO | WO 2008/005777 | 1/2008 |
| WO | WO 2008/028946 A2 | 3/2008 |
| WO | WO 2008/032219 | 3/2008 |
| WO | WO 2009/009876 | 1/2009 |
| WO | WO 2009/025770 A2 | 2/2009 |
| WO | WO 2009/036157 A1 | 3/2009 |
| WO | WO 2009/068992 A1 | 6/2009 |
| WO | WO 2009/076778 | 6/2009 |
| WO | WO 2009/079259 A2 | 6/2009 |
| WO | WO 2009/121004 A2 | 10/2009 |
| WO | WO 2009/150532 A1 | 12/2009 |
| WO | WO 2009/156405 | 12/2009 |
| WO | WO 2010/003235 | 1/2010 |
| WO | WO 2010/117786 | 10/2010 |
| WO | WO 2010/130636 | 11/2010 |
| WO | WO 2010/138564 A1 | 12/2010 |
| WO | WO 2010/148511 | 12/2010 |
| WO | WO 2011/014645 | 2/2011 |
| WO | WO 2011/087092 | 7/2011 |
| WO | WO 2011/103453 | 8/2011 |
| WO | WO 2011/111966 | 9/2011 |
| WO | WO 2011/123495 | 10/2011 |
| WO | WO 2012/009790 | 1/2012 |
| WO | WO 2013/043729 | 3/2013 |
| WO | WO 2013/079473 | 6/2013 |
| WO | WO 2014/099931 | 6/2014 |

OTHER PUBLICATIONS

Bowie JU, Reidhaar-Olson JF, Lim WA, Sauer RT. Deciphering the message in protein sequences: tolerance to amino acid substitutions. Science. Mar. 16, 1990;247(4948)1306-10.*

Fleury D, Wharton SA, Skehel JJ, Knossow M, Bizebard T. Hemagglutinin. GenBank Acc. No. P03437, Updated Apr. 3, 2007.*

Lebendiker M. "Purification Protocols." The Wolfson Centre for Applied Structural Biology. http://wolfson.huji.ac.il/purification/Purification_Protocols.html. Apr. 5, 2006.*

Ekiert et al., 2009, "Antibody recognition of a highly conserved influenza virus epitope", Science; 324(5924):246-251.

Kistner et al., 2007, "Cell culture (Vero) derived whole virus (H5N1) vaccine based on wild-type virus strain induces cross-protective immune responses", Vaccine; 25(32):6028-6036.

Leroux-Roels, et al., 2008, Broad clade 2 cross-reactive immunity induced by an adjuvanted clade 1 rH5N1 pandemic influenza vaccine; PLOS One 3(2):1-5.

Lowen et al. 2009, "Blocking interhost transmission of influenza virus by vaccination in the guinea pig model", Journal of Virology; 83(7):2803-2818.

Marasco et al., 2007, "The growth and potential of human antiviral monoclonal antibody therapeutics", Nat Biotechnol; 25(12):1421-1434.

Mo et al., 2003, "Coexpression of complementary fragments of CIC-5 and restoration of chloride channel function in a Dent's disease mutation", Am J Physiol Cell Physiol; 286:C79-C89.

Simmons et al., 2007, "Prophylactic and therapeutic efficacy of human monoclonal antibodies against H5N1 influenza", PLOS Medicine; 4(5):928-936.

Sui et al., 2009, "Structural and functional bases for broad-spectrum neutralization of avian and human influenza A viruses", Nat Struct Mol Biol; 16(3):265-273.

Thoennes et al., 2008, "Analysis of residues near the fusion peptide in the influenza hemagglutinin structure for roles in triggering membrane fusion", Virology; 370(2):403-414.

Throsby et al., 2008, "Heterosubtypic neutralizing monoclonal antibodies cross-protective against H5N1 and H1N1 recovered from human IgM+ memory B cells", PLoS ONE; 3(12):e3942.

Vanlandschoot et al., 1998, "An antibody which binds to the membrane-proximal end of influenza virus haemagglutinin (H3

(56) References Cited

OTHER PUBLICATIONS subtype) inhibits the low-pH-induced conformational change and cell-cell fusion but does not neutralize virus", Journal of General Virology; 79:1781-1791.
Wang et al., 2009, "Universal epitopes of influenza virus hemagglutinins?", Nature Structural and Molecular Biology; 16(3):233-234.
Wang et al., 2010, "Broadly protective monoclonal antibodies against H3 influenza viruses following sequential immunization with different hemagglutinins", PLOS Pathogens; 6(2):1-9.
Wang et al., 2009, "Characterization of cross-reactive antibodies against the influenza virus hemagglutinin", American Society for Virology 28th Annual Meeting, University of British Columbia, Vancouver, BC, Canada dated Jul. 11-15, 2009; Abstract W30-6.
Stephenson et al., 2005, "Cross-Reactivity to Highly Pathogenic Avian Influenza H5N1 Viruses after Vaccination with Nonadjuvanted and MF59-Adjuvanted Influenza A/Duck/Singapore/97 (H5N3) Vaccine: A Potential Priming Strategy," The Journal of Infectious Diseases; 191:1210-1215.
Berry, 2007, "Cross-reactive MAb to the binding domain of botulinum neurotoxin A, B, and E developed using a sequential immunization strategy: anti-botulinum neurotoxin", Hybridoma, 26(6).
Chen et al., 2011, "Vaccine design of hemagglutinin glycoprotein against influenza", Trends in Biotechnology, 29(9):426-434.
Copeland et al., 2005, "Functional chimeras of human immunodeficiency virus type 1 Gp120 and influenza A virus (H3) hemagglutinin", Journal of Virology; 79:6459-6471.
Corti et al., 2011, "A neutralizing antibody selected from plasma cells that binds to group 1 and group 2 influenza A hemagglutinins", Science. 333(6044):850-856.
D'Aoust et al., 2008, "Influenza virus-like particles produced by transient expression in Nicotiana benthaminana induce a protective immune response against a lethal viral challenge in mice", J. Plant Biotechnology, 6(9):930-940.
Eda et al., 2006, "Sequential immunization with V3 peptides from primary human immunodeficiency virus type 1 produces cross-neutralizing antibodies against primary isolates with a matching narrow-neutralization sequence motif" J Virol, 80(11):5552-5562.
Ekiert et al., 2011, "A highly conserved neutralizing epitope on group 2 influenza A viruses", Science 333:843-850.
Ekiert et al., 2012, "Cross-neutralization of influenza A viruses mediated by a single antibody loop", Nature, 489:526-532.
Flandorfer et al., 2003, "Chimeric Influenza A Viruses with a Functional Influenza B Virus Neuraminidase or Hemagglutinin", J. Virol., 77(17):9116-9123.
Fodor et al., 1999, "Rescue of influenza A virus from recombinant DNA", J Virol 73:9679-9682.
Fujii et al., 2003, "Selective incorporation of influenza virus RNA segments into virions", Proc. Natl. Acad. Sci. USA 100:2002-2007.
Gao & Palese, 2009, "Rewiring the RNAs of influenza virus to prevent reassortment", PNAS 106:15891-15896.
Gao et al., 2013, "Human infection with a novel avian-origin influenza A(H7N9) virus", N. Engl. J. Med. 368:1888-1897.
García-Sastre et al., 1994, "Introduction of foreign sequences into the genome of influenza A virus", Dev. Biol. Stand, 82:237-246.
García-Sastre et al., 1994, "Use of a mammalian internal ribosomal entry site element for expression of a foreign protein by a transfectant influenza virus", J. Virol. 68:6254-6261.
Goff et al., 2013, "Adjuvants and immunization strategies to induce influenza virus hemagglutinin stalk antibodies", PLoS One 8:e79194.
Hai et al., 2008, "Influenza B virus NS1-truncated mutants: live-attenuated vaccine approach", J Virol 82:10580-10590.
Hai et al., 2011, "A reassortment-incompetent live attenuated influenza virus vaccine for protection against pandemic virus strains", Journal of virology 85:6832-6843.
Hai et al., 2012, "Influenza viruses expressing chimeric hemagglutinins: globular head and stalk domains derived from different subtypes", J. Virol. 86:5774-5781.

Krammer et al., 2010, "Trichoplusia ni cells (High Five) are highly efficient for the production of influenza A virus-like particles: a comparison of two insect cell lines as production platforms for influenza vaccines", Mol Biotechnol; 45:226-34.
Krammer et al., 2012, "A carboxy-terminal trimerization domain stabilizes conformational epitopes on the stalk domain of soluble recombinant hemagglutinin substrates", PLoS One. 7:e43603. doi:10.1371/journal.pone.0043603.
Krammer et al., 2013, "Chimeric hemagglutinin influenza virus vaccine constructs elicit broadly protective stalk-specific antibodies", J. Virol. 87:6542-6550.
Krammer et al., 2013, "Influenza virus hemagglutinin stalk-based antibodies and vaccines", Current Opinion in Virology 3:521-530.
Krause et al., 2012, "Human monoclonal antibodies to pandemic 1957 H2N2 and pandemic 1968 H3N2 influenza viruses", J. Virol. 86:6334-6340.
Lee et al., 2012, "Heterosubtypic antibody recognition of the influenza virus hemagglutinin receptor binding site enhanced by avidity", Proc. Natl. Acad. Sci. U.S.A. 109:17040-17045.
Li et al., 1992, "Influenza A virus transfectants with chimaeric haemagglutinins containing epitopes from different subtypes", Journal of Virology, 67:399-404.
Manabu Igarashi et al.: 2008, "Genetically destined potentials for N-linked glycosylation of influenza virus hemagglutinin" Virology, 376:323-329.
Margine et al., 2013, "H3N2 influenza virus infection induces broadly reactive hemagglutinin stalk antibodies in humans and mice", J. Virol. 87:4728-4737.
Miller et al., 2013, "1976 and 2009 H1N1 influenza virus vaccines boost anti-hemagglutinin stalk antibodies in humans", J. Infect. Dis. 207:98-105.
Neumann et al., 1999, "Generation of influenza A viruses entirely from cloned cDNAs", PNAS 96:9345-9350.
Ott et al., 2000. The Adjuvant MF59: A 10-Year Perspective, p. 211-228. In O'Hagan DT (ed.), Vaccine Adjuvants, vol. 42. Springer.
Papanikolopoulou et al., 2004, "Formation of highly stable chimeric trimers by fusion of an adenovirus fiber shaft fragment with the foldon domain of bacteriophage t4 fibritin", J. Biol. Chem. 279(10):8991-8998.
Pleschka et al., 1996, "A plasmid-based reverse genetics system for influenza A virus", J Virol 70:4188-92.
Ponomarenko et al., "B-Cell Epitope Prediction" Chap. 35 in Structural Bioinformatics, 2nd Edition, Gu and Bourne. Editors; 2009 John Wiley & Sons. Inc. pp. 849-879.
Rudikoff et al., Single amino acid substitution altering antigen-binding specificity. Proc Nat Acad Sci U S A. 1982; 79(6): I 979-83.
Salem, 2000, "In vivo acute depletion of CD8(+) T cells before murine cytomegalovirus infection upregulated innate antiviral activity of natural killer cells", Int. J. Immunopharmacol. 22:707-718.
Schulze, 1997, "Effects of Glycosylation on the Properites and Functions of Influenza Virus Hemagglutinin", The Journal of Infectious Diseases, 176(S1):S24-S28.
Shoji et al., 2008, "Plant-expressed HA as a seasonal influenza vaccine candidate", Vaccine, 26(23):2930-2934.
Stech et al., 2005, "A new approach to an influenza live vaccine: modification of the cleavage site of hemagglutinin", Nature Med. 11(6):683-689.
Stevens et al., 2006, "Structure and Receptor Specificity of the Hemagglutinin from an H5N1 Influenza Virus" Science, 312:404-409.
Strobel et al., 2000, "Efficient Expression of the Tumor-Associated Antigen MAGE-3 in Human Dendritic Cells, Using an Avian Influenza Virus Vector", Human Gene Therapy 11:2207-2218.
Sui et al.. 2009, "Structural and functional bases for broad-spectrum neutralization of avian and human influenza A viruses", Nat Struct Mol Biol; 16(3):265-273; Supplementary Information.
Tamura et al., 1998, "Definition of amino acid residues on the epitope responsible for recognition by influenza A virus H1-specific, H2-specific, and H1- and H2-cross-reactive murine cytotoxic T-lymphocyte clones", J. Virol. 72:9404-9406.

(56) References Cited

OTHER PUBLICATIONS

Tan et al., 2012, "A pan-H1 anti-hemagglutinin monoclonal antibody with potent broad-spectrum efficacy in vivo", J. Virol. 86:6179-6188.
Tao et al., 2009, "Enhanced protective immunity against H5N1 influenza virus challenge by vaccination with DNA expressing a chimeric hemagglutinin in combination with an MHC class I-restricted epitope of nucleoprotein in mice", Antiviral research. 2009; 81(3); 253-260.
Thomson et al., 2012, "Pandemic H1N1 Influenza Infection and Vaccination in Humans Induces Cross-Protective Antibodies that Target the Hemagglutinin Stem", Front. Immunol 3:87.
Vigerust et al., 2007, "N-Linked Glycosylation Attenuates H3N2 Influenza Viruses", Journal of Virology, 81(16): 8593-8600.
Wang et al., 2008, "Simplified recombinational approach for influenza A virus reverse genetics", J. Virol. Methods 151:74-78.
Weldon et al., 2010, "Enhanced immunogenicity of stabilized trimeric soluble influenza hemagglutinin", PLoSONE 5(9): e12466.
Wrammert et al., 2011, "Broadly cross-reactive antibodies dominate the human B cell response against 2009 pandemic H1N1 influenza virus infection", J. Exp. Med. 208:181-193.
Yang et al., 2006, "Targeting lentiviral vectors to specific cell types in vivo", PNAS 103: 11479-11484.
Yasugi et al., 2013, "Human monoclonal antibodies broadly neutralizing against influenza B virus", PLoS Pathog. 9(2): e1003150.
Yoshida et al., A. Cross-protective potential of a novel monoclonal antibody directed against antigenic site B of the hemagglutinin of influenza A viruses. PLoS Pathog. 2009; 5(3);e1000350.
Zheng, et al., 1996, "Nonconserved nucleotides at the 3' and 5' ends of an influenza A virus RNA play an important role in viral RNA replication", Virology 217:242-251.
Wohlbold et al., 2015, "Vaccination with adjuvanted recombinant neuraminidase induces broad heterologous, but not heterosubtypic, cross-protection against influenza virus infection in mice." MBio, 6(2):e02556.
Wohlbold et al., 2015, "Vaccination with soluble headless hemagglutinin protects mice from challenge with divergent influenza viruses." Vaccine, 33(29):3314-3321.
Boni et al., 2010, "Guidelines for identifying homologous recombination events in influenza A virus", PLoS One, 5(5):e10434.
Boni et al., 2012, "No evidence for intra-segment recombination of 2009 H1N1 influenza virus in swine", Gene, 494(2):242-245.
Chen et al., 2016, "Influenza A viruses expressing intra- or intergroup chimeric hemagglutinins", doi:10.1128/JVI.03060-15.
D'Aoust et al., 2010, "The production of hemagglutinin-based virus-like particles in plants: a rapid, efficient and safe response to pandemic influenza", Plant Biotechnology, 8(5):607-619.
Dillon et al., 1992, "Induction of protective class I MHC-restricted CTL in mice by a recombinant influenza vaccine in aluminum hydroxide adjuvant", Vaccine, 10(5):309-318.
Gibbs et al., 2001, Recombination in the hemagglutinin gene of the 1918 "Spanish Flu". Science, 293(5536):1842-1845.
Haynes, 2009, "Influenza virus-like particle vaccines", Expert Rev. Vaccines, 8(4): 435-445.
Kaverin et al., 2004, "Structural Differences Among Hemagglutinins of Influenza A Virus Subtypes Are Reflected in Their Antigenic Architecture: Analysis of H9 Escape Mutants", Journal of Virology, 78(1):240-249.
Krause et al., 2011, "A broadly neutralizing human monoclonal antibody that recognizes a conserved, novel epitope on the globular head of the influenza H1N1 virus hemagglutinin", J. Virol., 85(20):10905-10908.
Landry et al., 2010, "Preclinical and Clinical Development of Plant-Made Virus-Like Particle Vaccine against Avian H5N1 Influenza", PLoS One, 5(12): e15559.
Mbawuike et al., 1994, "Influenza A subtype cross-protection after immunization of outbred mice with purified chimeric NS1/HA2 influenza virus protein", Vaccine, 1994: 12(14):1340-1348.

Mett et al., 2008, "A plant-produced influenza subunit vaccine protects ferrets against virus challenge", Influenza and Other Respiratory Viruses, 2(1):33-40.
Nachbagauer et al., 2015, "Hemagglutinin stalk immunity reduces influenza virus replication and transmission in ferrets", J. Virol., doi:10.1128/JVI.02481-15.
Reid et al., Hemagglutinin [Influenza A virus (A/South Carolina/1/1918(H1N1))]. GenBank Acc. No. AAD17229.1. Dep. Oct. 11, 2000.
Ryder et al., 2016, "Vaccination with VSV-vectored chimeric hemagglutinins protects mice against divergent influenza virus challenge strains", J. Virol., 90(5):2544-2550.
Webby et al., 2010, Hemagglutinin [Influenza A virus (A/Brisbane/59/2007(H1N1))]. GenBank Acc. No. ADE28750.1. Dep. Mar. 29, 2010.
Wiley, 1987, "The Structure and Function of the Hemagglutinin Membrane Glycoprotein of Influenza Virus", Ann. Rev. Biochem. 56:365-394.
Worobey et al., 2002, "Questioning the Evidence for Genetic Recombination in the 1918 "Spanish Flu" Virus", Science, 296(5566): 211a.
Doms RW & Moore J.P., 2000, "HIV-1 Membrane Fusion: Targets of Opportunity" JCB, 151(2): F9-F13.
Palese, P. & Shaw M. (2007). Orthomyxoviridae: The Viruses and Their Replication. In D.M. Knipe, & P.M. Howley (Eds.), Fields Virology (pp. 1647-1689). Philadelphia, PA: Wolters Kluwer Lippincott Williams & Wilkins.
Vanlandschoot et al., 1995. "A fairly conserved epitope on the Hemagglutinin of influenza A (H3N2) virus with variable accessibility to neutralizing antibody." Virology, 212(2)526-34.
Bommakanti et al., 2012, "Design of *Eschericia coli*-Expressed Stalk Domain Immunogens of H1N1 Hemagglutinin That Protect Mice from Lethal Challenge." J. Virol., 86(24):13434-13444.
Impagliazzo et al., 2015, "A stable trimeric influenza hemagglutinin stem as a broadly protective immunogen." Science, 349(6254):1301-1306.
Kanekiyo et al., 2013, "Self-assembling influenza nanoparticle vaccines elicit broadly neutralizing H1N1 antibodies." Nature, 499(7456):102-6.
Lu et al., 2013, "Production and stabilization of the trimeric influenza hemagglutinin stem domain for potentially broadly protective influenza vaccines." PNAS, 111(1):125-130.
Mallajosyula et al., 2014, "Influenza hemagglutinin stem-fragment immunogen elicits broadly neutralizing antibodies and confers heterologous protection." PNAS, 111(25):E2514-23.
Yassine et al., 2015, "Hemagglutinin-stem nanoparticles generate heterosubtypic influenza protection." Nat. Med. 21(9):1065-70.
Babu et al., 2014, "Live attenuated H7N7 influenza vaccine primes for a vigorous antibody response to inactivated H7N7 influenza vaccine," Vaccine, 32:6798-6804.
Dunand et al., 2016, "Both Neutralizing and Non-Neutralizing Human H7N9 Influenza Vaccine-Induced Monoclonal Antibodies Confer Protection," Cell Host & Microbe, 19:1-14.
Graham et al., 2013, "DNA Vaccine Delivered by a Needle-Free Injection Device Improves Potency of Priming for Antibody and CD8+ TCell Responses after rAd5 Boost in a Randomized Clinical Trial," PLoS ONE, 8(4): 1-11, e59340.
Hallily et al., 2015, "High-Affinity H7 Head and Stalk Domain-Specific Antibody Response to an Inactivated Influenza H7N7 Vaccine After Priming With Live Attenuated Influenza Vaccine," Journal of Infectious Diseases, 212: 1270-1278.
Khurana et al., 2013, "DNA Priming Prior to Inactivated Influenza A(H5N1) Vaccination Expands the Antibody Epitope Repertoire and Increases Affinity Maturation in a Boost-Interval-Dependent Manner in Adults," Journal of Infectious Disease, 208:413-417.
Ledgerwood, et al., 2013, "Prime-Boost Interval Matters: A Randomized Phase 1 Study to Identify the Minimum Interval Necessary to Observe the H5 DNA Influenza Vaccine Priming Effect," Journal of Infectious Diseases, 208:418-422.
Luke et al., 2014, "Improving pandemic H5N1 influenza vaccines by combining different vaccine platforms," Expert Review of Vaccines 13(7):873-883.

(56) References Cited

OTHER PUBLICATIONS

Rudenko et al., 2015, "Assessment of immune responses to H5N1 inactivated influenza vaccine among individuals previously primed with H5N2 live attenuated influenza vaccine," Human Vaccines & Immunotherapeutics, 11(12):2839-2848.
Talaat et al., 2014, "A Live Attenuated Influenza A(H5N1) Vaccine Induces Long-Term Immunity in the Absence of a Primary Antibody Response," Journal of Infectious Disease; 208:1860-1869.
Wei et al., 2010, "Induction of Broadly Neutralizing H1N1 Influenza Antibodies by Vaccination," Science; 329: 1060-1064.
Bullough et al., 1994, "Structure of influenza haemagglutinin at the pH of membrane fusion." Nature, 371:37-43.
Casali et al., 2008, "Site-directed mutagenesis of the hinge peptide from the hemagglutinin protein: enhancement of the pH-responsive conformational change." Protein Engineering Design & Selection, 21(6):395-404.
Chen et al., 1999, "N- and C-terminal residues combine in the fusion-pH influenza hemagglutinin HA2 subunit to form an N cap that terminates the triple-stranded coiled coil." Proc. Natl. Acad Sci., 91:8967-8972.
Chen et al., 2007, "Influenza Virus Hemagglutinin and Neuraminidase, but Not the Matrix Protein, Are Required for Assembly and Budding of Plasmid-Derived Virus-Like Particles", J. Virol. 81(13):7111-7123.
Das et al., 2010, "Glycosylation Focuses Sequence Variation in the Influenza A Virus H1 Hemagglutinin Globular Domain" PLoS Pathogens, 6(11):e1001211.
Doyle et al., 1986, "Analysis of Progressive Deletions of the Transmembrane and Cytoplasmic Domains of Influenza Hemagglutinin", JCB, 103:1193-1204.
Fluzone®, 2009-2010 Fluzone Seasonal influenza vaccine package insert, 2009.
Genbank, NCBI Reference Sequence: YP_163736.1, HA2 [Influenza A virus (A/Puerto Rico/8/1934(H1N1))].
Giddings et al., 2000, "Transgenic plants as factories for biopharmaceuticals", Nature Biotechnology, 18:1151-1155.
Gomord et al., 2005, "Biopharmaceutical production in plants: problems, solutions and opportunities." TRENDS in Biotechnology, 23(11):559-565.
Horimoto et al., 2004, "Influenza A viruses possessing type B hemagglutinin and neuraminidase: potential as vaccine components." Microbes and Infection, 6(6): 579-583.
Lorieau, et al., 2010, "The complete influenza hemagglutinin fusion domain adopts a tight helical hairpin arrangement at the lipid:water interface." PNAS, 107(25):11341-11346
Sun et al., 2011, "Glycosylation Site Alteration in the Evolution of Influenza A (H1N1) Viruses." PLoS Pathogens, 6(7):e22844.
Tate et al., 2001, "Specific Sites of N-Linked Glycosylation on the Hemagglutinin of H1N1 Subtype Influenza A Virus Determine Sensitivity to Inhibitors of the Innate Immune Systema nd Virulence in Mice." Journal of Immunology, 187(4):1884-1894.
Vajdos et al., 2002, "Comprehensive Functional Maps of the Antigen binding Site of an Anti-ErbB2 Antibody Obtained with Shotgun Scanning Mutagenesis,"Journal of Molecular Biology, 320:415-428.
Wang et al., 2007, "Incorporation of High Levels of Chimeric Human Immunodeficiency Virus Envelope Glycoproteins into Virus-Like Particles", J. Virol., 81(20):10869-10878.
Wang et al., 2009, "Glycans on influenza hemagglutinin affect receptor binding and immune response." PNAS, 106(43): 18137-18142.
Weis and Brunger, 1990, "Refinement of the Influenza Virus Hemagglutinin by Simulated Annealing." J. Mol. Biol. 212:737-761.
Weis et al., 1988, "Structure of the influenza virus haemagglutinin complexed with its receptor, sialic acid." Nature, 333:426-431.
Wiley and Skehel, 1983, "The three-dimensional structure and antigenic variation of the influenza virus haemagglutinin." Division of Virology, 107-111.
Wilson et al., 1981, "Structure of the haemagglutinin membrane glycoprotein of influenza virus at 3 A resolution." Nature, 289:366-373.
Yang et al., 2007, "Immunization by Avian H5 Influenza Hemagglutinin Mutants with Altered Receptor Binding Specificity", Science, 317(5839):825-828.
Babai et al: "A novel loposomal influenza vaccine (influsome-vac) containing hemagglutinin-neuraminidase and IL-2 or GM-CSF induces protective anti-neuraminidase antibodies cross-reacting with a wide specrum of incluenza A viral strains", Vaccine, Elsevier Ltd, GB, vol. 20, No. 3-4, Nov. 12, 2011 (Nov. 12, 2011), pp. 505-515, XP004310159, ISSN: 0264-410X, DOI: 10.1016/S0264-410X(01)00326-7.
Bianchi et al., 2005, "Universal influenza B vaccine based on the maturational cleavage site of the hemagglutinin precursor", Journal of Virology; 79(12):7380-7388.
Database Geneseq "Influenza A virus hemagglutinin protein, H1PR8", Accession No. AJG95109, dated Nov. 15, 2007.
Gerhard et al., 2006, "Prospects for universal influenza virus vaccine", Emerging Infectious Diseases; 12(4):569-574.
Graves et al., 1983, "Preparation of influenza virus subviral particles lacking the HA1 subunit of hemagglutinin: unmasking of cross-reactive HA2 determinants," Virology, 126(1):106-116.
Horimoto et al. "Generation of influenza A viruses with chimeric (type A/B) hemagglutinins," J Virol, Jul. 2003, vol. 77, No. 14, pp. 8031-8038.
Horvath et al., 1998, "Hemagglutinin-based multipeptide construct elicits enhanced protective immune response in mice against influenza A virus infection", Immunology Letters; 60(Feb. 2003):127-136.
International Preliminary Report on Patentability of International application No. PCT/US11/30441, dated Oct. 2, 2012.
International Search Report of International application No. PCT/US11/30441, dated Jul. 13, 2011.
International Search Report of International application No. PCT/US2010/029202, dated Aug. 24, 2010.
International Search Report of International application No. PCT/US2010/036170, dated Aug. 17, 2010.
International Search Report of International application No. PCT/US2012/056122, dated Feb. 19, 2013.
International Search Report of International application No. PCT/US2011/025467, dated Oct. 19, 2011.
International Search Report of International application No. PCT/US2013/75697, dated Apr. 15, 2014.
Kashyap et al., 2008, "Combinatorial antibody libraries from survivors of the Turkish H5N1 avian influenza outbreak reveal virus neutralization strategies", Proc Natl Acad Sci USA; 105:5986-5991.
Landry, 2008, "Three-dimensional structure determines the pattern of CD4+ T-cell epitope dominance in influenza virus hemagglutinin", Journal of Virology; 82(3):1238-1248.
Mok et al., 2008, "Enhancement of the CD8<+> T cell response to a subdominant epitope respiratory syncytial virus by deletion of an immunodominant epitope", Vaccine; 26(37):4775-4782.
Okuno et al., 1993, "A common neutralizing epitope conserved between the hemagglutinins of influenza A virus H1 and H2 strains," J. Virol., 67(5):2552-2558.
Okuno et al., 1994, "Protection against the mouse-adapted A/FM/1/47 strain of influenza A virus in mice by a monoclonal antibody with cross-neutralizing activity among H1 and H2 strains," J. Virol., 68(1):517-520.
Pica et al., 2012, "Hemagglutinin stalk antibodies elicited by the 2009 pandemic influenza virus as a mechanism for the extinction of seasonal H1N1 viruses," PNAS, 109(7): 2573-2578.
Sagawa et al., 1996, "The immunological activity of a deletion mutant of influenza virus haemagglutinin lacking the globular region", J Gen Virol; 77:1483-1487.
Santak. Old and new ways to combat human influenza virus. Periodicum Biologororum. 2012, vol. 114, No. 2; pp. 221-234.
Steel et al., 2010, "Influenza Virus Vaccine Based on the Conserved Hemagglutinin Stalk Domain," mBIO, 1(1):1-9, pii: e00018-10.
Written Opinion of International application No. PCT/US2011/30441, dated Jul. 13, 2011.

(56) References Cited

OTHER PUBLICATIONS

Written Opinion of International application No. PCT/US2010/029202, dated Aug. 24, 2010.
Written Opinion of International application No. PCT/US2010/036170, dated Aug. 17, 2010.
Written Opinion of International application No. PCT/US2012/056122, dated Feb. 19, 2013.
Written Opinion of International application No. PCT/US2011/25467, dated Oct. 19, 2011.
Written Opinion of International application No. PCT/US2013/75697, dated Apr. 28, 2014.
Schneeman et al., 2012, "A Virus-Like Particle That Elicits Cross-Reactive Antibodies to the Conserved Stem of Influenza Virus Hemagglutinin," J. Virol., 86(21): 11686-22697.
Song et al., 2007, "Influenza A Virus Hemagglutinin Protein, H1PR8," GENESEQ, XP002595511.
Extended European Search Report for European Application No. 11763347.9, dated Feb. 2, 2015.
Vareckova et al., 2008, "HA2-specific monoclonal antibodies as tools for differential recognition of influenza A virus antigenic subtypes," Virus Research, 132:181-186.
Roberts et al., 1993, "Role of conserved glycosylation sites in maturation and transport of influenza A virus hemagglutinin," J Virol, 67(6):3048-3060.
Gould et al., 1987, "Mouse H-2k-Restricted Cytotoxic T Cells Recognize Antigenic Determinants in Both the HA1 and HA2 Subunits of the Influenza A/PR/8/34 Hemagglutinin," J. Exp. Med., 166:693-701.
Gocnik et al., 2008, "Antibodies Induced by the HA2 Glycopolypeptide of Influenza Virus Haemagglutinin Improve Recovery from Influenza A Virus Infection," J Gen Virol., 89:958-967.
Bommakanti et al., 2010, "Design of an HA2-based *Escherichia coli* expressed influenza immunogen that protects mice from pathogenic challenge", Proc Natl Acad Sci USA, 107:13701-13706.
Chen et al., 2010, "Generation of Live Attenuated Novel Influenza Virus A/California/7/09 (H1N1) Vaccines with High Yield in Embryonated Chicken Eggs." J. Virol. 84(1):44-51.
Cotter et al., 2014, "A Single Amino Acid in the Stalk Region of the H1N1pdm Influenza Virus HA Protein Affects Viral Fusion, Stability and Infectivity." PLoS Pathogens, 10(1):e1003831.
Krammer et al., 2012, "Hemagglutinin stalk-reactive antibodies are boosted following sequential infection with seasonal and pandemic H1N1 influenza virus in mice", J Virol, 86:10302-10307.
Krammer et al., 2014, "Assessment of influenza virus hemagglutinin stalk-based immunity in ferrets", J Virol, 88:3432-3442.
Krammer et al., 2014, "H3 stalk-based chimeric hemagglutinin influenza virus constructs protect mice from H7N9 challenge", J Virol, 88:2340-2343.
Krammer, 2015, "The quest for a universal flu vaccine: headless HA 2.0", Cell Host Microbe, 18:395-397.
Krammer, 2016, "Novel universal influenza virus vaccine approaches", Current Opinion in Virology, 17:95-103.
Margine et al., 2013, "Hemagglutinin stalk-based universal vaccine constructs protect against group 2 influenza A viruses", J Virol, 10435-10446.
Tran et al., 2016, "Cryo-electron microscopy structures of chimeric hemagglutinin displayed on a universal influenza vaccine candidate", MBio, 7(2): e00257-16.
Wang et al., 2012, "Generation of recombinant pandemic H1N1 influenza virus with the HA cleavable by bromelain and identification of the residues influencing HA bromelain cleavage." Vaccine, 30(4):872-8.
Yang et al., 2014, "Structural stability of influenza A(H1N1)pdm09 virus hemagglutinins." J. Virol., 88(9):4828-38.

\* cited by examiner

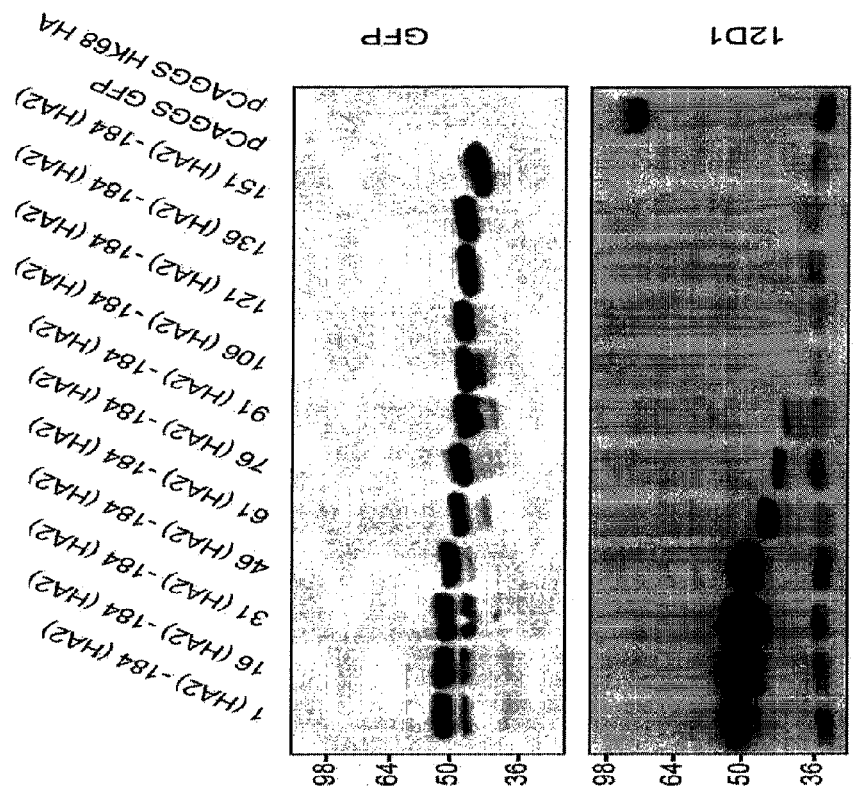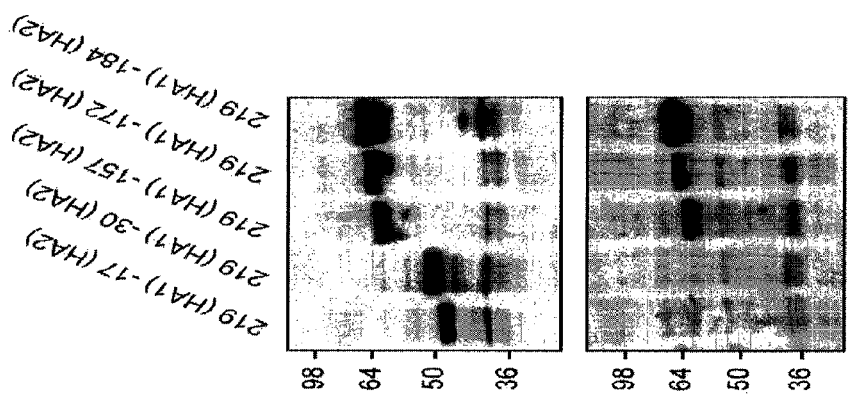
Fig. 1

D

| | H2 | H1 | H3 | H7 |
|---|---|---|---|---|
| H5 | 94.5/98.2 | 83.6/98.2 | 52.5/72.1 | 50.8/68.9 |
| H2 | | 80.0/96.4 | 49.2/70.5 | 47.5/67.2 |
| H1 | | | 53.3/71.7 | 47.5/67.2 |
| H3 | | | | 60.0/75.0 |

Identity/Similarity

Fig. 3D

```
                                           460                                480
                                            |                                  |
A/Viet Nam/1203/2004 (H5)  RIENLNKKME  DGFLDVWTYN  AELLVLMENE  RTLDFHDSNV  KNLYDKVRLQ  LRDNA  55
A/Singapore/1/1957 (H2)    .L........  ..........  ..........  ..........  ........M.  ....V  55
A/California/07/2009 (H1)  ........VD  .....I....  ......L...  ....Y.....  ....E...S.  .KN..  55
A/Canada/rv504/2004 (H7)   Q.G.VINWTR  .SMTE..S..  .....A...Q  H.I.LA..EM  NK..ER..K.  ..E..  55
A/Hong Kong/1/68 (H3)      ..QD.E.YV.  .TKI.L.S..  .....AL..Q  H.I.LT..EM  NK.FE.T.R.  ..E..  55
Consensus                  RIENLNKKXE  DGFLDVWTYN  AELLVLMENE  RTLDXHDSNV  KNLYEKVRXQ  LRXNA
```

Fig. 5A

```
         | H5  RIENLNKKMEDGFLDVWTYNAELLVLMENERTLDFHDSNVKNLYDKVRLQLRDNA
Group 1  | H2  RLENLNKKMEDGFLDVWTYNAELLVLMENERTLDFHDSNVKNLYDKVRMQLRDNV
         | H1  RIENLNKKVDDGFLDIWTYNAELLVLLENERTLDYHDSNVKNLYEKVRSQLKNNA
         | H3  RIQDLEKYVEDTKIDLWSYNAELLVALENQHTIDLTDSEMNKLFEKTRRQLRENA
Group 2  | H7  QIGNVINWTRDSMTEVWSYNAELLVAMENQHTIDLADSEMNKLYERVKRQLRENA
                         *      * *******  **  * *  **    *      **  *
```

** = amino acids identical between subtypes

H3N2

| | | 440 | | 460 | |
|---|---|---|---|---|---|
| A/Denmark/191/2005 | R I QDLEKYVEDTKIDLWSYNAELLVALENQHTIDLTDSEMNKLFERTKKQLRENA | 55 |
| A/Arkansas/05/2008 | ..........................................K.......... | 55 |
| A/Brisbane/10/2007 | ..........................................K.......... | 55 |
| A/Auckland/610/2002 | ...................................................... | 55 |
| A/Hong Kong/1/68 | ........................................K.RR........ | 55 |
| A/Albany/1/1976 | ........................................K.RR........ | 55 |
| A/Memphis/1/81 | ........................................K.RR........ | 55 |
| Consensus | R I QDLEKYVEDTKIDLWSYNAELLVALENQHTIDLTDSEMNKLFEKTKKQLRENA | |

Fig. 6C

H5N1

| | | 440 | | 460 | |
|---|---|---|---|---|---|
| A/Viet Nam/1203/2004 | R I ENLNKKME DGFLDVWTYN AELLVLMENE RTLDFHDSNV KNLYDKVRLQ LRDNA | 55 |
| goose/Hong Kong/ww26/2000 | .................................................... | 55 |
| A/goose/Shantou/753/2002 | .................................................... | 55 |
| A/Indonesia/5/2005 | .................................................... | 55 |
| A/Egypt/N03450/2009 | .................................................... | 55 |
| Consensus | R I ENLNKKME DGFLDVWTYN AELLVLMENE RTLDFHDSNV KNLYDKVRLQ LRDNA | |

Fig. 6D

H7

```
                                                       440                   460
A/green winged teal/California/AKS1370/2008  QIGNVINWTR DSMTEVWSYN AELLVAMENQ HTIDLADSEM NKLYERVRKQ LRENA 55
A/Canada/rv504/2004                          .......... .......... .......... .......... .......... ..... 55
A/duck/New Jersey/Sg-00286/1996              .......... .A........ .......... .......... .......... ..... 55
A/avian/New York/Sg-00338/1999               .......... .A...I.... .......... .......... S......... ..... 55
A/chicken/New Jersey/Sg-00431/2004           .......... .A...I.... .......... .......... S......K.. ..... 55
Consensus                                    QIGNVINWTR DAMTEVWSYN AELLVAMENQ HTIDLADSEM NKLYERVRKQ LRENA
```

Fig. 6E

H4

```
                                                               20                  40
A/mallard/Ohia/324/1988                     RIQDLEKYVEDTKIDLWSYNAELLVALENQHTIDVTDSEMNKLFERVRRQLRENA 55
A/mallard duck/ALB/630/1984                 ....................................................... 55
A/mallard/Minnesota/271/1999                ................................................H...... 55
A/American wigeon/Minnesota/Sg-00231/2007   ....................................................... 55
A/gray teal/AUS/3/1979                      ....................................................... 55
Consensus                                   RIQDLEKYVEDTKIDLWSYNAELLVALENQHTIDVTDSEMNKLFERVRRQLRENA
```

Fig. 6F

H6

```
                                              420                                       440                                       460
                                               |                                         |                                         |
A/blue winged teal/ALB/69/1985        R I G N L N K R M E D G F L D V W T Y N A E L L V L L E N E R T L D M H D A N V K N L H E K V K S Q L R D N A   55
A/Canada goose/Ohio/127/1989          . . D . . . . . . . . . . . . . . . . . . . . . . . . . . . . . . . . . . . . . . K . . . . .   55
A/blu-winged teal/ALB/368/1978        . . D . . . . . . . . . . . . . . . . . . . . . . . . . . . . . . . . . . . . L . . . . . .   55
A/northern pintail/California/HKWF151/2007  . . D . . . . . . . . . . . . . . G . . . . . . . . . . . . . . . . . . . . . . . . Y . . . . . .   55
A/chicken/CA/S0403106/2004            . . D . M . . . . . . . . . . . . . . . . . . . . . . . . . L . . . . . . . S . . . . . . .
Consensus                             R I D N L N K R M E D G F L D V W T Y N A E L L V L L E N E R T L D M H D A N V K N L H E K V K S Q L R D N A
```

Fig. 6G

H8

```
                                              20                                        40
                                               |                                         |
A/pintail duck/Alberta/114/1979       R I N M I N D K I D   D Q I E D L W A Y N   A E L L V L L E N Q   K T L D E H D S N V   K N L F D E V K R R   L S A N A   55
A/turkey/Ontario/6118/1968            . . . . . . . . . .   . . . . . . . . . .   . . . . . . . . . .   . . . . . . . . . .   . . . . . . . . . .   . . . . . . .   55
A/duck/LA/B174/1986                   . . . . . . . . . .   . . . . . . . . . .   . . . . . . . . . .   . . . . . . . . . .   . . . . . . . . . .   . . . . . . .   55
A/northern shoveler/Cal/AKS273/2007   . . . . . . . . . .   . . . . . N . . . .   . . . . . . . . . .   . . . . . . . . . .   . . . . . . . . . .   . . . . . . .   55
A/pintail/Barrow/38/2005              . . . . . . . . . .   . . . . . . . . . .   . . . . . . . . . .   . . . . . . . . . .   . . . . . . . . . .   . . . . . . .   55
Consensus                             R I N M I N D K I D   D Q I E D L W A Y N   A E L L V L L E N Q   K T L D E H D S N V   K N L F D E V K R R   L S A N A
```

```
                                            420                 440                 460
                                             |                   |                   |
A/GF/NY/26410-17/1995              RINQLSKHVDDSVIDIWSYNAQLLVLLENEKTLDLHDSNVRNLHEKVRRMLKDNA  55
A/mallard duck/Tennessee/11457/1985 ......................................................  55
A/green winged teal/California/AKS1305/2008 ..............................................  55
A/duck/Memphis/546/1974             ......................................................  55
A/duck/England/1/1956               ...............V......................................  55
                           Consensus RINQLSKHVDDSVIDIWSYNAQLLVLLENEKTLDLHDSNVRNLHEKVRRMLKDNA
```

Fig. 6L

H12

```
                                             20                  40
                                              |                   |
A/duck/Alberta/60/1976              RINMINSKIDDQITDIWAYNAELLVLLENQKTLDEHDANVRNLHDRVRRVLRENA  55
A/mallard/Ohio/407/1987             ......................................................  55
A/northern shoveler/Interior Alaska/1/2007 ...........................................K....  55
A/duck/Hokkaido/66/01               ...................................................K..  55
A/red-necked stint/Australia/5745/1981 ........................................I..K........  55
                           Consensus RINMINSKIDDQITDIWAYNAELLVLLENQKTLDEHDANVRNLHDRVRRVLRENA
```

H13

```
                                    420            440                460
                                    |              |                  |
A/black-headed gull/Askrakhan/227/1984   RINMLADRIDDAVTDVWSYNAKLLVLLENDKTLDMHDANVRNLHDQVRRALKTNA  55
A/great black-headed gull/Astrakhan/1420/79  ......................................................  55
A/American white pelican/Minnesota/Sg-0611/2008  ...............................................S......  55
A/duck/Siberia/272PF/1998            .................................................E....E...D..  55
A/gull/Astrakhan/998/1990            .................................................E....E...D..  55
                           Consensus  RINMLADRIDDAVTDVWSYNAKLLVLLENDKTLDMHDANVRNLHDQVRRXLKTNA
```

Fig. 6M

H14

```
                                          20                   40
                                          |                    |
A/herring gull/Astrakhan/267/1982   RIQDLEKYVEDTKIDLWSYNAELLVALENQHTIDVTDSEMNKLFERVRRQLRENA  55
A/mallard duck/Astrakhan/263/1982   ......................................................  55
A/mallard/Gurjev/263/1982           ......................................................  55
                         Consensus  RIQDLEKYVEDTKIDLWSYNAELLVALENQHTIDVTDSEMNKLFERVRRQLRENA
```

| | 440 | 460 | |
|---|---|---|---|
| A/Australian shelduck/Western Australia/1756/1983 | QIGNVINWTRDSLTEIWSYNAELLVAMENQHTIDLADSEMNKLYERVRRQLRENA | 55 |
| A/sooty tern/Western Australia/2190/1983 | ................................................. | 55 |
| A/wedge-tailed shearwater/Western Australia/2327/1983 | ................................................. | 55 |
| A/shearwater/Australia/2576/1979 | ................................................. | 55 |
| A/duck/Australia/341/83 | ................................................. | |
| Consensus | QIGNVINWTRDSLTEIWSYNAELLVAMENQHTIDLADSEMNKLYERVRRQLRENA | |

Fig. 6P

H16

| | 420 | 440 | 460 | |
|---|---|---|---|---|
| A/black-headed gull/Turkmenistan/13/76 | RINMLADRVDDAVTDIWSYNAKLLVLIENDRTLDLHDANVRNLHDQVKRALKSNA | 55 |
| A/Fulica atra/Volga/635/1986 | ................................................. | 55 |
| A/slnder-billed gull/Astrakhan/28/76 | .....................L........................... | 55 |
| A/herring gull/DE/712/1988 | ...........................................K...E...N.. | 55 |
| A/shorebird/NJ/840/1986 | ...........................................K...E...N.. | 55 |
| Consensus | RINMLADRVDDAVTDIWSYNAKLLVLIENDRTLDLHDANVRNLHDQVKRALKSNA | |

VACCINES FOR USE IN THE PROPHYLAXIS AND TREATMENT OF INFLUENZA VIRUS DISEASE

This application is a national stage entry of International patent application No. PCT/US2011/025467, filed Feb. 18, 2011, which is a continuation-in-part of prior U.S. nonprovisional patent application Ser. No. 12/788,103, filed May 26, 2010, now U.S. Pat. No. 8,673,314, and which claims priority benefit of U.S. provisional application No. 61/305,898, filed Feb. 18, 2010, U.S. provisional patent application No. 61/354,160, filed Jun. 11, 2010 and U.S. provisional patent application No. 61/385,083, filed Sep. 21, 2010, each of which is incorporated herein by reference in its entirety.

This invention was made with United States Government support under award numbers U01 AI070469-02 and 1RC1 AI086061-01 awarded by the National Institutes of Health (NIH). The United States Government has certain rights in this invention.

1. INTRODUCTION

Provided herein are polypeptides comprising portions of the influenza virus hemagglutinin, compositions comprising such polypeptides that can be used as immunogens in vaccines and methods of their use to generate an immune response against multiple influenza subtypes in a subject.

2. BACKGROUND

Influenza viruses are enveloped RNA viruses that belong to the family of Orthomyxoviridae (Palese and Shaw (2007) Orthomyxoviridae: The Viruses and Their Replication, 5th ed. Fields' Virology, edited by B. N. Fields, D. M. Knipe and P. M. Howley. Wolters Kluwer Health/Lippincott Williams & Wilkins, Philadelphia, USA, p 1647-1689). The natural host of influenza viruses are avians, but influenza viruses (including those of avian origin) also can infect and cause illness in humans and other animal hosts (canines, pigs, horses, sea mammals, and mustelids). For example, the H5N1 avian influenza virus circulating in Asia has been found in pigs in China and Indonesia and has also expanded its host range to include cats, leopards, and tigers, which generally have not been considered susceptible to influenza A (CIDRAP—Avian Influenza: Agricultural and Wildlife Considerations). The occurrence of influenza virus infections in animals could potentially give rise to human pandemic influenza strains.

Influenza A and B viruses are major human pathogens, causing a respiratory disease that ranges in severity from sub-clinical infection to primary viral pneumonia which can result in death. The clinical effects of infection vary with the virulence of the influenza strain and the exposure, history, age, and immune status of the host. The cumulative morbidity and mortality caused by seasonal influenza is substantial due to the relatively high rate of infection. In a normal season, influenza can cause between 3-5 million cases of severe illness and is associated with 200,000 to 500,000 deaths worldwide (World Health Organization (April, 2009) Influenza (Seasonal) Fact Sheet 211). In the United States, influenza viruses infect an estimated 10-15% of the population (Glezen and Couch R B (1978) Interpandemic influenza in the Houston area, 1974-76. N Engl J Med 298: 587-592; Fox et al. (1982) influenza virus infections in Seattle families, 1975-1979. II. Pattern of infection in invaded households and relation of age and prior antibody to occurrence of infection and related illness. Am J Epidemiol 116: 228-242) and are associated with approximately 30,000 deaths each year (Thompson W W et al. (2003) Mortality Associated with Influenza and Respiratory Syncytial Virus in the United States. JAMA 289: 179-186; Belshe (2007) Translational research on vaccines: influenza as an example. Clin Pharmacol Ther 82: 745-749).

In addition to annual epidemics, influenza viruses are the cause of infrequent pandemics. For example, influenza A viruses can cause pandemics such as those that occurred in 1918, 1957 and 1968. Due to the lack of pre-formed immunity against the major viral antigen, hemagglutinin (HA), pandemic influenza viruses can affect greater than 50% of the population in a single year and often cause more severe disease than seasonal influenza viruses. A stark example is the pandemic of 1918, in which an estimated 50-100 million people were killed (Johnson and Mueller (2002) Updating the Accounts: Global Mortality of the 1918-1920 "Spanish" Influenza Pandemic Bulletin of the History of Medicine 76: 105-115). Since the emergence of the highly pathogenic avian H5N1 influenza virus in the late 1990s (Claas et al. (1998) Human Influenza A H5N1 virus related to a highly pathogenic avian influenza virus. Lancet 351: 472-7), there have been concerns that the virus may become transmissible between humans and cause a major pandemic.

An effective way to protect against influenza virus infection is through vaccination; however, current vaccination approaches rely on achieving a good match between circulating strains and the isolates included in the vaccine formulation. Such a match is often difficult to attain due to a combination of factors. First, influenza viruses are constantly undergoing change: every 3-5 years the predominant strain of influenza A virus is replaced by a variant that has undergone sufficient antigenic drift to evade existing antibody responses. Isolates to be included in vaccine preparations must therefore be selected each year based on the intensive surveillance efforts of the World Health Organization (WHO) collaborating centers. Second, to allow sufficient time for vaccine manufacture and distribution, strains must be selected approximately six months prior to the initiation of the influenza season. Occasionally, the predictions of the vaccine strain selection committee are inaccurate, resulting in a substantial drop in the efficacy of vaccination.

The possibility of a novel subtype of influenza A virus entering the human population also presents a significant challenge to current vaccination strategies. Since it is impossible to predict what subtype and strain of Influenza virus will cause the next pandemic, current, strain-specific approaches cannot be used to prepare a pandemic influenza vaccine.

3. SUMMARY

Polypeptide compositions ("flu polypeptides") are described that can be used in a subject (animal subjects, including human subjects) to generate an immune response that is cross-reactive with a plurality of influenza virus strains of a particular subtype or strains from different subtypes. In particular, the flu polypeptides comprise "core polypeptides" that correspond in amino acid sequence and/or structure to a region of the long alpha helix of the HA2 subunit of influenza hemagglutinin described herein, or modified core polypeptides.

The invention is based, in part, on the design of flu polypeptides that mimic the structure and function/activity of the long alpha helix region of the HA2 subunit of influenza hemagglutinin. Surprisingly, immunization with a flu polypeptide corresponding to the HA2 long alpha helix of a particular influenza subtype induces serum antibodies that cross-react with hemagglutinin from multiple influenza subtypes. The data described herein also demonstrate that animals immunized with a flu polypeptide corresponding to the HA2 long alpha helix of one particular subtype are protected against lethal influenza viral challenges with different influenza virus subtypes. Accordingly, the flu polypeptides provided herein may be used in immunogenic compositions (e.g., vaccines) capable of generating immune responses against a plurality of different influenza strains and subtypes—in other words, a "universal" flu vaccine.

While not intending to be bound by any particular theory of operation, it may be that despite the variability of HA in the different influenza subtypes, the long alpha helix region of the HA2 subunit of influenza hemagglutinin contains a conserved epitope(s)/region recognized by rare, cross reactive antibodies (e.g., such as monoclonal antibody 12D1 which has broad neutralizing activity against H3 influenza viruses). Flu polypeptides presented to the immune system in a construct designed to expose this epitope/region in the proper conformation and confer enhanced immunogenicity to the cross-reactive or "universal" epitope/region and which can be used to generate a serum antibody response in a subject, and preferably a neutralizing response, against multiple influenza subtypes.

In other aspects, described herein are nucleic acids encoding a flu polypeptide(s), viruses and immunogenic compositions comprising a flu polypeptide(s) and methods of immunization.

3.1 Terminology

The terms "about" or "approximate," when used in reference to an amino acid position refer to the particular amino acid position in a sequence or any amino acid that is within five, four, three, two or one residues of that amino acid position, either in an N-terminal direction or a C-terminal direction.

As used herein, the term "about" or "approximately" when used in conjunction with a number refers to any number within 1, 5 or 10% of the referenced number.

The term "amino acid" or any reference to a specific amino acid is meant to include naturally occurring proteogenic amino acids as well as non-naturally occurring amino acids such as amino acid analogs. Those skilled in the art would know that this definition includes, unless otherwise specifically noted, naturally occurring proteogenic (L)-amino acids, their optical (D)-isomers, chemically modified amino acids, including amino acid analogs such as penicillamine (3-mercapto-D-valine), naturally occurring non-proteogenic amino acids such as norleucine and chemically synthesized amino acids that have properties known in the art to be characteristic of an amino acid. Additionally, the term "amino acid equivalent" refers to compounds that depart from the structure of the naturally occurring amino acids, but which have substantially the structure of an amino acid, such that they can be substituted within a peptide, which retains its biological activity despite the substitution. Thus, for example, amino acid equivalents can include amino acids having side chain modifications or substitutions, and also include related organic acids, amides or the like. The term "amino acid" is intended to include amino acid equivalents.

The term "amino acid sequence identity" refers to the degree of identity or similarity between a pair of aligned amino acid sequences, usually expressed as a percentage. As used herein, the terms "percent identity," "percent identical," "% identity," and "% identical" with respect to amino acid sequence refer to the percentage of amino acid residues in a candidate sequence that are identical (i.e., the amino acid residues at a given position in the alignment are the same residue) to the corresponding amino acid residue in the peptide after aligning the sequences and introducing gaps, if necessary, to achieve the maximum percent sequence homology. As used herein, the terms "percent similarity," "percent similar," "% similarity," and "% similar" with respect to amino acid sequence refer to the percentage of amino acid residues in a candidate sequence that are similar (i.e., the amino acid substitution at a given position in the alignment is a conservative substitution, as discussed below), to the corresponding amino acid residue in the peptide after aligning the sequences and introducing gaps, if necessary, to achieve the maximum percent sequence homology. Sequence homology, including percentages of sequence identity and similarity, are determined using sequence alignment techniques well-known in the art, preferably computer algorithms designed for this purpose, using the default parameters of said computer algorithms or the software packages containing them. Non-limiting examples of computer algorithms and software packages incorporating such algorithms include the following. The BLAST family of programs exemplify a particular, non-limiting example of a mathematical algorithm utilized for the comparison of two sequences (e.g., Karlin & Altschul, 1990, *Proc. Natl. Acad. Sci. USA* 87:2264-2268 (modified as in Karlin & Altschul, 1993, *Proc. Natl. Acad. Sci. USA* 90:5873-5877), Altschul et al., 1990, *J. Mol. Biol.* 215:403-410, (describing NBLAST and XBLAST), Altschul et al., 1997, *Nucleic Acids Res.* 25:3389-3402 (describing Gapped BLAST, and PSI-Blast). Another particular example is the algorithm of Myers and Miller (1988 CABIOS 4:11-17) which is incorporated into the ALIGN program (version 2.0) and is available as part of the GCG sequence alignment software package. Also, another particular example is the FASTA program (Pearson W. R. and Lipman D. J., *Proc. Nat. Acad. Sci. USA*, 85:2444-2448, 1988), available as part of the Wisconsin Sequence Analysis Package. Additional examples include BESTFIT, which uses the "local homology" algorithm of Smith and Waterman (Advances in Applied Mathematics, 2:482-489, 1981) to find the best single region of similarity between two sequences, and which is preferable where the two sequences being compared are dissimilar in length; and GAP, which aligns two sequences by finding a "maximum similarity" according to the algorithm of Neddleman and Wunsch (*J. Mol. Biol.* 48:443-354, 1970), and is preferable where the two sequences are approximately the same length and an alignment is expected over the entire length.

"Conservative substitution" refers to replacement of an amino acid of one class is with another amino acid of the same class. In particular embodiments, a conservative substitution does not alter the structure or function, or both, of a polypeptide. Classes of amino acids for the purposes of conservative substitution include hydrophobic (Met, Ala, Val, Leu, Ile), neutral hydrophilic (Cys, Ser, Thr), acidic (Asp, Glu), basic (Asn, Gln, His, Lys, Arg), conformation disrupters (Gly, Pro) and aromatic (Trp, Tyr, Phe).

As used herein, the term "core polypeptide" refers to a polypeptide segment that corresponds to a region of an influenza hemagglutinin HA2 polypeptide, i.e., core polypeptides as referred to herein do not comprise an entire influenza hemagglutinin HA2 polypeptide. In a specific embodiment, the term refers to a polypeptide segment that corresponds to a region of the long alpha helix region of an influenza hemagglutinin HA2 polypeptide. See Section 5.1.1 for examples of core polypeptides.

As used here, the term "fragment" refers to a portion of a particular polypeptide. In certain embodiments, a fragment of a polypeptide (e.g., a core polypeptide) is at least 8, 9, 10, 11, 12, 13, 14, 15, 16, 17, 18, 19, 20, 25, 40, 35, 40, 45 or 50 amino acids in length. In some embodiments, a fragment of a polypeptide (e.g., a core polypeptide) is between 8 to 15, 8 to 20, 8 to 25, 8 to 30, 8 to 40, 10 to 15, 10 to 20, 10 to 25, 10 to 30, 10 to 40, 10 to 45, 10 to 50, 15 to 20, 15 to 25, 15 to 30, 15 to 35, 15 to 40, 15 to 45, 15 to 50, 25 to 30, 25 to 40, 25 to 45 or 25 to 50 amino acids in length.

As used herein, the term "modified core polypeptide" refers to a core polypeptide that has been modified in some manner to extend or increase the half-life of the core polypeptide in vivo. Techniques of modifying a polypeptide to extend or increase the half-life of the core polypeptide are known to those of skill in the art. In some embodiments, the core polypeptide may be modified by substitution of terminal L-amino acids with D-amino acids, by pegylation of the polypeptide, by amidation of the C-terminus of the polypeptide, or by acetylation of the N-terminus of the polypeptide. See Section 5.1.2 for examples of modified core polypeptides.

As used herein, the term "flu polypeptide" refers to a polypeptide comprising a core polypeptide or a modified core polypeptide. In some embodiments, the flu polypeptide consists of a core polypeptide. In certain embodiments, the flu polypeptide consists of a modified core polypeptide. In certain embodiments, the flu polypeptide comprises a pegylated core polypeptide. In certain embodiments, the flu polypeptide is pegylated at its N- and/or C-terminus. In certain embodiments, the flu polypeptide comprises a core polypeptide acetylated at its N- and/or C-terminus. In certain embodiments, the flu polypeptide is acetylated at its N- and/or C-terminus. In certain embodiments, the flu polypeptide comprises a core polypeptide or modified core polypeptide and a linker. In certain embodiments, the flu polypeptide comprises a core polypeptide or modified core polypeptide linked to a carrier.

In certain embodiments, the flu polypeptide comprises one, two, three or more core polypeptides and/or modified core polypeptides and one, two, three or more or all of the following: 1) one, two, or more T cell epitopes (e.g., CD8 T cell epitope); 2) one, two, or more immunogenic polypeptides; 3) a polypeptide that facilitates multimerization of the flu polypeptide; 4) one, two, or more protein tags that facilitate purification and/or solubility of the flu polypeptide; 5) one, two or more carriers; and 6) one, two or more linkers.

As used herein, the term "effective amount" in the context of administering a therapy to a subject refers to the amount of a therapy which has a prophylactic and/or therapeutic effect(s). In certain embodiments, an "effective amount" in the context of administration of a therapy to a subject refers to the amount of a therapy which is sufficient to achieve one, two, three, four, or more of the following effects: (i) reduce or ameliorate the severity of an influenza virus infection, disease or symptom associated therewith; ii) reduce the duration of an influenza virus infection, disease or symptom associated therewith; (iii) prevent the progression of an influenza virus infection, disease or symptom associated therewith; (iv) cause regression of an influenza virus infection, disease or symptom associated therewith; (v) prevent the development or onset of an influenza virus infection, disease or symptom associated therewith; (vi) prevent the recurrence of an influenza virus infection, disease or symptom associated therewith; (vii) reduce or prevent the spread of an influenza virus from one cell to another cell, one tissue to another tissue, or one organ to another organ; (ix) prevent or reduce the spread of an influenza virus from one subject to another subject; (x) reduce organ failure associated with an influenza virus infection; (xi) reduce hospitalization of a subject; (xii) reduce hospitalization length; (xiii) increase the survival of a subject with an influenza virus infection or disease associated therewith; (xiv) eliminate an influenza virus infection or disease associated therewith; (xv) inhibit or reduce influenza virus replication; (xvi) inhibit or reduce the entry of an influenza virus into a host cell(s); (xviii) inhibit or reduce replication of the influenza virus genome; (xix) inhibit or reduce synthesis of influenza virus proteins; (xx) inhibit or reduce assembly of influenza virus particles; (xxi) inhibit or reduce release of influenza virus particles from a host cell(s); (xxii) reduce influenza virus titer; and/or (xxiii) enhance or improve the prophylactic or therapeutic effect(s) of another therapy.

In certain embodiments, the effective amount does not result in complete protection from an influenza virus disease, but results in a lower titer or reduced number of influenza viruses compared to an untreated subject. In certain embodiments, the effective amount results in a 0.5 fold, 1 fold, 2 fold, 4 fold, 6 fold, 8 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of influenza virus relative to an untreated subject. In some embodiments, the effective amount results in a reduction in titer of influenza virus relative to an untreated subject of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs. Benefits of a reduction in the titer, number or total burden of influenza virus include, but are not limited to, less severe symptoms of the infection, fewer symptoms of the infection and a reduction in the length of the disease associated with the infection.

As used herein, "Hemagglutinin" and "HA" refer to any hemagglutinin known to those of skill in the art. In certain embodiments, the hemagglutinin is influenza hemagglutinin, such as an influenza A hemagglutinin, an influenza B hemagglutinin or an influenza C hemagglutinin. There are currently 16 hemagglutinin subtypes of influenza viruses that fall into two different groups: Group 1 and Group 2. A typical hemagglutinin comprises domains known to those of skill in the art including a signal peptide (optional herein), a stem domain, a globular head domain, a luminal domain (optional herein), a transmembrane domain (optional herein) and a cytoplasmic domain (optional herein). In certain embodiments, a hemagglutinin consists of a single polypeptide chain, such as HA0. In certain embodiments, a hemagglutinin consists of more than one polypeptide chain in quaternary association, e.g., HA1 and HA2. Those of skill in the art will recognize that an immature HA0 might be cleaved to release a signal peptide (approximately 20 amino acids) yielding a mature hemagglutinin HA0. A hemagglutinin HA0 might be cleaved at another site to yield HA1 polypeptide (approximately 320 amino acids, including the globular head domain and a portion of the stem domain) and HA2 polypeptide (approximately 220 amino acids, including the remainder of the stem domain, a luminal domain, a transmembrane domain and a cytoplasmic domain). In certain embodiments, a hemagglutinin comprises a signal peptide, a transmembrane domain and a cytoplasmic domain. In certain embodiments, a hemagglutinin lacks a signal peptide, i.e. the hemagglutinin is a mature hemagglutinin. In certain embodiments, a hemagglutinin lacks a transmembrane domain or cytoplasmic domain, or both. As used herein, the terms "hemagglutinin" and "HA" encompass hemagglutinin polypeptides that are modified by post-translational processing such as signal peptide cleavage, disulfide bond formation, glycosylation (e.g., N-linked glycosylation), protease cleavage and lipid modification (e.g., S-palmitoylation).

As used herein, "HA2" refers to a polypeptide domain that corresponds to the HA2 domain of an influenza hemagglutinin polypeptide known to those of skill in the art. In certain embodiments, an HA2 consists of a stem domain, a luminal domain, a transmembrane domain and a cytoplasmic domain (see, e.g., Scheiffle et al., 2007, *EMBO J.* 16(18):5501-5508, the contents of which are incorporated by reference in their entirety). In certain embodiments, an HA2 consists of a stem domain, a luminal domain and a transmembrane domain. In certain embodiments, an HA2 consists of a stem domain and a luminal domain; in such embodiments, the HA2 might be soluble. In certain embodiments, an HA2 consists of a stem domain; in such embodiments, the HA2 might be soluble.

As used herein, the term "heterologous" in the context of a polypeptide, nucleic acid or virus refers to a polypeptide, nucleic acid or virus, respectively, that is not normally found in nature or not normally associated in nature with a polypeptide, nucleic acid or virus of interest. For example, a "heterologous polypeptide" may refer to a polypeptide derived from a different virus, e.g., a different influenza strain or subtype, or an unrelated virus or different species.

As used herein, the term "in combination," in the context of the administration of two or more therapies to a subject, refers to the use of more than one therapy (e.g., more than one prophylactic agent and/or therapeutic agent). The use of the term "in combination" does not restrict the order in which therapies are administered to a subject. For example, a first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is not replicating. In certain embodiments, an infection refers to the pathological state resulting from the presence of the virus in a cell or a subject, or by the invasion of a cell or subject by the virus.

As used herein, the term "influenza virus disease" refers to the pathological state resulting from the presence of an influenza (e.g., influenza A or B virus) virus in a cell or subject or the invasion of a cell or subject by an influenza virus. In specific embodiments, the term refers to a respiratory illness caused by an influenza virus.

As used herein, the phrases "IFN deficient system" or "IFN-deficient substrate" refer to systems, e.g., cells, cell lines and animals, such as pigs, mice, chickens, turkeys, rabbits, rats, etc., which do not produce one or more types of interferon (IFN)(e.g., IFN-γ) or produce low levels of IFN (i.e., a reduction in IFN expression of 5-10%, 10-20%, 20-30%, 30-40%, 40-50%, 50-60%, 60-70%, 70-80%, 80-90% or more when compared to IFN-competent systems under the same conditions), do not respond or respond less efficiently to one or more types of IFN, and/or are deficient in the activity of one or more antiviral genes induced by one or more types of IFN.

As used herein, the numeric term "log" refers to $\log_{10}$.

As used herein, the phrase "multiplicity of infection" or "MOI" is the average number of infectious virus particles per infected cell. The MOI is determined by dividing the number of infectious virus particles added (ml added×PFU/ml) by the number of cells added (ml added×cells/ml).

As used herein, the term "nucleic acid" is intended to include DNA molecules (e.g., cDNA or genomic DNA) and RNA molecules (e.g., mRNA) and analogs of the DNA or RNA generated using nucleotide analogs. The nucleic acid can be single-stranded or double-stranded. As used herein, a nucleic acid may include natural (e.g., A, G, C, or T) or modified nucleotide bases (6-dimethylamino purine, 5-fluoro cystine, 2-pyridone, 7-deazaguanosine, inosine, etc.).

"Polypeptide" refers to a polymer of amino acids linked by amide bonds as is known to those of skill in the art. The polypeptide can be a polymer of 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550 or more amino acids linked by covalent amide bonds. In some embodiments, the polypeptide is a polymer of 10 to 25, 10 to 30, 10 to 40, 10 to 50, or 25 to 50 amino acids linked by covalent amide bonds. In certain embodiments, the polypeptide is a polymer of 100 to 150, 100 to 200, 100 to 250, 100 to 300, 100 to 350, 100 to 400, 100 to 450, 100 to 500, 100 to 550, 100 to 600, 100 to 650, 100 to 700, or 100 to 750 amino acids linked by covalent amide bonds. In certain embodiments, the polypeptide is a polymer of 50 to 55, 50 to 60, 50 to 65, 50 to 75, 50 to 80, 50 to 85, 50 to 90, 50 to 95, 50 to 100, 75 to 80, 75 to 85, 75 to 90, 75 to 95, or 75 to 100 amino acids linked by covalent amide bonds. In some embodiments, the polypeptide is 55 to 60, 55 to 65, 55 to 70, 55 to 75, 55 to 80, 55 to 85, 55 to 90, 55 to 95, 55 to 100, or 60 to 75 amino acids linked by covalent amide bonds. As used herein, the term can refer to a single polypeptide chain linked by covalent amide bonds. The term can also refer to multiple polypeptide chains associated by non-covalent interactions such as ionic contacts, hydrogen bonds, Van der Waals contacts and hydrophobic contacts. Those of skill in the art will recognize that the term includes polypeptides that have been modified, for example by post-translational processing such as signal peptide cleavage, disulfide bond formation, glycosylation (e.g., N-linked glycosylation), protease cleavage and lipid modification (e.g., S-palmitoylation).

As used herein, the terms "purified" and "isolated" when used in the context of a polypeptide (including antibody) that is obtained from a natural source, e.g., cells, refers to a polypeptide which is substantially free of contaminating materials from the natural source, e.g., soil particles, minerals, chemicals from the environment, and/or cellular materials from the natural source, such as but not limited to cell debris, cell wall materials, membranes, organelles, the bulk of the nucleic acids, carbohydrates, proteins, and/or lipids present in cells. Thus, a polypeptide that is isolated includes preparations of a polypeptide having less than about 30%, 20%, 10%, 5%, 2%, or 1% (by dry weight) of cellular materials and/or contaminating materials. As used herein, the terms "purified" and "isolated" when used in the context of a polypeptide (including antibody) that is chemically synthesized refers to a polypeptide which is substantially free of chemical precursors or other chemicals which are involved in the syntheses of the polypeptide. Accordingly, such preparations of the polypeptide have less than about 30%, 20%, 10%, or 5% (by dry weight) of chemical precursors or compounds other than the peptide of interest. In a specific embodiment, a flu polypeptide is chemically synthesized. In another specific embodiment, a flu polypeptide is recombinantly expressed. In another specific embodiment, a flu polypeptide is isolated.

As used herein, the terms "replication," "viral replication" and "virus replication" in the context of a virus refer to one or more, or all, of the stages of a viral life cycle which result in the propagation of virus. The steps of a viral life cycle include, but are not limited to, virus attachment to the host cell surface, penetration or entry of the host cell (e.g., through receptor mediated endocytosis or membrane fusion), uncoating (the process whereby the viral capsid is removed and degraded by viral enzymes or host enzymes thus releasing the viral genomic nucleic acid), genome replication, synthesis of viral messenger RNA (mRNA), viral protein synthesis, and assembly of viral ribonucleoprotein complexes for genome replication, assembly of virus particles, post-translational modification of the viral proteins, and release from the host cell by lysis or budding and acquisition of a phospholipid envelope which contains embedded viral glycoproteins. In some embodiments, the terms "replication," "viral replication" and "virus replication" refer to the replication of the viral genome. In other embodiments, the terms "replication," "viral replication" and "virus replication" refer to the synthesis of viral proteins. In other embodiments, the terms "replication," "viral replication" and "virus replication" refer to the synthesis of new viral particles.

As used herein, the terms "subject" or "patient" are used interchangeably to refer to an animal (e.g., birds, reptiles, and mammals). In a specific embodiment, a subject is a bird. In another embodiment, a subject is a mammal including a non-primate (e.g., a camel, donkey, zebra, cow, pig, horse, goat, sheep, cat, dog, rat, and mouse) and a primate (e.g., a monkey, chimpanzee, and a human). In certain embodiments, a subject is a non-human animal. In some embodiments, a subject is a farm animal or pet (e.g., a dog, cat, horse, goat, sheep, pig, donkey, or chicken). In another embodiment, a subject is a human. In another embodiment, a subject is a human infant. In another embodiment, a subject is a human child. In another embodiment, a subject is a human adult. In another embodiment, a subject is an elderly human. In another embodiment, a subject is a premature human infant.

As used herein, the term "premature human infant" refers to a human infant born at less than 37 weeks of gestational age.

As used herein, the term "human infant" refers to a newborn to 1 year old human.

As used herein, the term "human toddler" refers to a human that is 1 years to 3 years old.

As used herein, the term "human child" refers to a human that is 1 year to 18 years old.

As used herein, the term "human adult" refers to a human that is 18 years or older.

As used herein, the term "elderly human" refers to a human 65 years or older.

The terms "tertiary structure" and "quaternary structure" have the meanings understood by those of skill in the art. Tertiary structure refers to the three-dimensional structure of a single polypeptide chain. Quaternary structure refers to the three dimensional structure of a polypeptide having multiple polypeptide chains.

As used herein, the terms "therapies" and "therapy" can refer to any protocol(s), method(s), compound(s), composition(s), formulation(s), and/or agent(s) that can be used in the prevention or treatment of a viral infection or a disease or symptom associated therewith. In certain embodiments, the terms "therapies" and "therapy" refer to biological therapy, supportive therapy, and/or other therapies useful in the treatment or prevention of a viral infection or a disease or symptom associated therewith known to one of skill in the art. In some embodiments, the term "therapy" refers to a nucleic acid encoding a flu polypeptide, or a vector, or composition comprising said nucleic acid encoding a flu polypeptide. In some embodiments, the term "therapy" refers to an antibody that specifically binds to a flu polypeptide.

As used herein, the terms "prevent," "preventing" and "prevention" in the context of the administration of a therapy(ies) to a subject to prevent an influenza virus disease refer to one or more of the following effects resulting from the administration of a therapy or a combination of therapies: (i) the inhibition of the development or onset of an influenza virus disease or a symptom thereof; (ii) the inhibition of the recurrence of an influenza virus disease or a symptom associated therewith; and (iii) the reduction or inhibition in influenza virus infection and/or replication.

As used herein, the terms "prevent", "preventing" and "prevention" in the context of administering a therapy to a subject to prevent an influenza virus infection refers to the inhibition or reduction of onset or development of one or more symptoms associated with influenza virus infection.

As used herein, the terms "treat," "treatment," and "treating" refer in the context of administration of a therapy(ies) to a subject to treating an influenza virus disease to obtain a beneficial or therapeutic effect of a therapy or a combination of therapies. In specific embodiments, such terms refer to one, two, three, four, five or more of the following effects resulting from the administration of a therapy or a combination of therapies: (i) the reduction or amelioration of the severity of an influenza virus infection or a disease or a symptom associated therewith; (ii) the reduction in the duration of an influenza virus infection or a disease or a symptom associated therewith; (iii) the regression of an influenza virus infection or a disease or a symptom associated therewith; (iv) the reduction of the titer of an influenza virus; (v) the reduction in organ failure associated with an influenza virus infection or a disease associated therewith; (vi) the reduction in hospitalization of a subject; (vii) the reduction in hospitalization length; (viii) the increase in the survival of a subject; (ix) the elimination of an influenza virus infection or a disease or symptom associated therewith; (x) the inhibition of the progression of an influenza virus infection or a disease or a symptom associated therewith; (xi) the prevention of the spread of an influenza virus from a cell, tissue, organ or subject to another cell, tissue, organ or subject; (xii) the inhibition or reduction in the entry of an influenza virus into a host cell(s); (xiii) the inhibition or reduction in the replication of an influenza virus genome; (xiv) the inhibition or reduction in the synthesis of influenza virus proteins; (xv) the inhibition or reduction in the release of influenza virus particles from a host cell(s); and/or (xvi) the enhancement or improvement the therapeutic effect of another therapy.

As used herein, the terms "treat", "treatment" and "treating" in the context of administering a therapy to a subject to treat an influenza virus infection refers to: (i) the reduction in influenza virus replication; (ii) the reduction in influenza virus titers; (iii) the reduction in the spread of influenza virus from one cell, organ or tissue to another cell, organ or tissue; (iv) the reduction in the severity and/or number of symptoms associated with an influenza virus infection; (v) the reduction in the duration of a symptom(s) associated with an influenza virus infection; and/or (vi) the inhibition or reduction in the progression of an influenza virus infection.

As used herein, in some embodiments, the phrase "wild-type" in the context of a virus refers to the types of a virus that are prevalent, circulating naturally and producing typical outbreaks of disease. In other embodiments, the term "wild-type" in the context of a virus refers to a parental virus.

4. BRIEF DESCRIPTION OF THE DRAWINGS

FIG. 1: MAb 12D1 reacts by Western blot with truncated hemagglutinin constructs. 12D1 makes dominant contacts with the HA2 subunit in the region of amino acids 30 to 106 (H3 numbering (see, e.g., Wilson et al., Nature 1981; 289 (5796): 366-73)). Diminished 12D1 binding without diminished GFP expression in the HA2 76-184 and HA2 91-184 truncations along with loss of binding with the HA2 106-184 truncation suggests that the binding epitope lies in the region from amino acids HA2 76-106. These 30 amino acids fall within the membrane distal half of the long alpha-helix of HA2.

FIG. 2: Monoclonal antibody (mAb) 12D1 reacts with the long alpha-helix of HA2. Lysates from 293T cells transfected with GFP or GFP HA76-130 were incubated with mAb 12D1 and pulled-down with protein G beads. Pulled-down fractions were blotted with mAb 12D1 or rabbit anti-GFP. Anti-mouse HRP used to detect 12D1 binding reacts with the mouse Ig heavy and light chains within the pulled-down fraction (A). Structural integrity of the 12D1 epitope within the HApep-KLH conjugate was confirmed by direct binding ELISA. MAb 36A7 binds outside of the 76-130 region of HA2 (B).

FIG. 3: Flu polypeptide (76-130)-KLH ("HApep-KLH") acts as a robust immunogen and serum antibody elicited by HApep-KLH reacts with multiple hemagglutinin subtypes. Sera from individual mice were taken 10-days post primary and secondary immunization and were tested for binding to H3 or H1 HA by ELISA (A). Pooled sera taken post-secondary immunization with HApep-KLH was tested for reactivity by Western blot with purified H3 or H1 subtype influenza viruses or with Newcastle disease virus (NDV) (B). Pooled sera were tested for binding activity against H2, H5 or H7 HA by ELISA (C). Percent identity/similarity of core polypeptide (76-130) between influenza subtypes (D).

FIG. 4: Immunization with flu polypeptide (76-130)-KLH ("HApep-KLH") protects mice against lethal challenge. Average weight change of mice infected with lethal dose of H3N2 virus (A). Vaccination with HApep-KLH protects H3N2-infected mice against death (B). HApep-KLH vaccine protects 80% of mice against lethal dose of H1N1 virus (C). Anti-H1 titer correlates with weight loss after PR8 challenge (D).

FIG. 5: Sequence alignment between various influenza A virus subtypes using selected strains from subtypes H1, H2, H3, H5 and H7 (SEQ ID NOS: 22, 13, 11, 31, 2, and 4, from the top to bottom, respectively) (A). Sequence alignment shows conserved amino acids between the different subtypes (SEQ ID NOS: 22, 13, 11, 31, 2, and 4, from the top to bottom, respectively) (B).

FIG. 6: Sequence alignment between strains of various influenza A virus subtypes including H1N1 (A) (SEQ ID NOS: 8, 9, 8, 8, 10, 11, and 12, from top to bottom, respectively), H2N2 (B) (SEQ ID NOS: 13, 13, 13, 14, 14, and 15, from top to bottom, respectively), H3N2 (C) (SEQ ID NOS: 16, 17, 17, 16, 18, 18, 18, and 19, from top to bottom, respectively), H5N1 (D) (SEQ ID NO: 22), H7 (E) (SEQ ID NOS: 31, 31, 32, 33, 34, and 35, from top to bottom, respectively), H4 (F) (SEQ ID NOS: 20, 20, 21, 20, 20 and 23, from top to bottom, respectively), H6 (G) (SEQ ID NOS: 24, 25, 26, 27, 28, and 29, from top to bottom, respectively), H8 (H) SEQ ID NOS: 37, 37, 37, 37, 38, and 39, from top to bottom, respectively), H9 (I) (SEQ ID NOS: 40, 40, 41, 41, 41, and 42, from top to bottom, respectively), H10 (J) (SEQ ID NOS: 43, 43, 43, 43, 44, and 45, from top to bottom, respectively), H11 (K) (SEQ ID NOS: 46, 46, 46, 46, 47, and 48, from top to bottom, respectively), H12 (L) (SEQ ID NOS: 49, 49, 49, 50, 50, and 51, from top to bottom, respectively), H13 (M) (SEQ ID NOS: 52, 52, 53, 54, 54, and 55, from top to bottom, respectively), H14 (N) (SEQ ID NO: 56), H15 (0) (SEQ ID NO: 57), and H16 (P) (SEQ ID NO: 58, 58, 59, 60, 60, and 58, from top to bottom, respectively).

FIG. 7: Monoclonal antibody 12D1 reacts with the long alpha-helix of HA2. (A) Hemagglutinin monomer. Amino acids 76-130 of HA2 are depicted. (B) Lysates from 293T cells were transfected with pCAGGs-GFP or pCAGGs-GFP HA2 76-130, incubated with mAb 12D1 and pulled-down with protein G beads. Pulled-down fractions were blotted with mAb 12D1 or rabbit anti-GFP. Arrows indicate location of 76-130 GFP fusion protein. Anti-mouse HRP was used to detect 12D1 binding with the mouse Ig heavy and light chains within the pulled-down fraction. (C) Structural integrity of the 12D1 epitope within the LAH-KLH conjugate was confirmed by direct binding ELISA. Hemagglutinin specific mAb 36A7 does not bind within the 76-130 region of HA2.

FIG. 8: LAH-KLH vaccine acts as a robust immunogen and serum antibody elicited reacts with multiple hemagglutinin subtypes. (A, B) Sera from individual mice were taken 10-days post primary and secondary immunization and were tested for binding to H3 or H1 hemagglutinin by ELISA. (C) Pooled sera from 20 mice taken post-secondary immunization with LAH-KLH was tested for reactivity by Western blot with purified A/Hong Kong/1/1968 (H3) or A/USSR/90/1977 (H1) subtype influenza viruses, purified A/California/04/09 hemagglutinin (transmembrane domain absent), or with Newcastle disease virus. (D) Pooled sera were tested for binding activity against H2, H5 or H7 HA by ELISA. LAH-KLH anti-serum has considerable binding activity against all 3 HA subtypes. Positive sera used were from mice infected with either a Group 1 influenza virus (for H2 and H5 ELISAs) or a Group 2 virus (for H7 ELISA) (see Steel (2010) mBio 1(1):1-9). (E) LAH amino acids 76-130 from the HA2 of different hemagglutinin subtypes (SEQ ID NOS: 11, 13, 4, 22, and 62, from top to bottom, respectively).

Black highlight/white letters: residue conserved in all 5 HAs. Conserved residues fall into one of four groups: 1) D/N/E/Q 2) I/L/V/M 3) K/R 4) S/T. Gray highlight/white letters: residue conserved in 4/5 HAs OR less stringent conservation (R vs H near middle conserves charge but change in size). Bold text, white background: partial conservation (3/5) OR less stringent (L vs A at middle, or F vs M towards left) (F) Isotype profile of hemagglutinin specific antibody in serum pools from normal mice, mice infected with A/Hong Kong/1/1968 (H3), or mice immunized with LAH-KLH. Recombinant hemagglutinin from A/Hong Kong/1/1968 was used to coat plates for ELISA.

FIG. 9: Immunization with LAH-KLH protects mice in vivo. (A, B) Two weeks following secondary immunization, mice were challenged with $4 \times 10^5$ pfu of X31, a mouse adapted H3 influenza virus, (C, D) 500 pfu of the mouse adapted H1 virus PR8, or (E, F) with 500 pfu of an H5 highly-pathogenic avian influenza virus modified to remove the poly-basic cleavage site in the viral hemagglutinin (HAlo virus) (see Steel J, et al. (2009) J Virol 83(4):1742-1753). Each experimental group comprises 5 BALB/c mice. Because of differences in pathogenicity, survival was defined as 20% weight loss for X31 (H3) and PR8 (H1) viruses, 30% weight loss for VN/2004 virus (H5).

FIG. 10: Antibody mediates protection afforded by immunization with LAH-KLH. (A) Analysis of pre-challenge serum from mice infected with PR8 reveals a positive correlation between hemagglutinin-specific antibody titer and increase in body weight on days 1-3 following infection. (B, C) Pooled sera from mice immunized with LAH-KLH, mice infected with H1 or H3 virus, or from mice immunized with KLH alone were transferred to mice two hours prior to infection with A/Georgia/81, a seasonal human H3 virus, or with the H1 virus PR8. Lung titers were evaluated on day 2 post infection. (D, E) Human sera taken pre or post-immunization with the TIV were evaluated for binding activity with the LAH polypeptide. Data shown are from serum samples diluted 1:3000. (D) Subjects responded variably to seasonal vaccination and (E) serum demonstrates minimal binding activity against the LAH peptide.

Figures 11A, 11B, 11C, 11D, 11E, 11F:
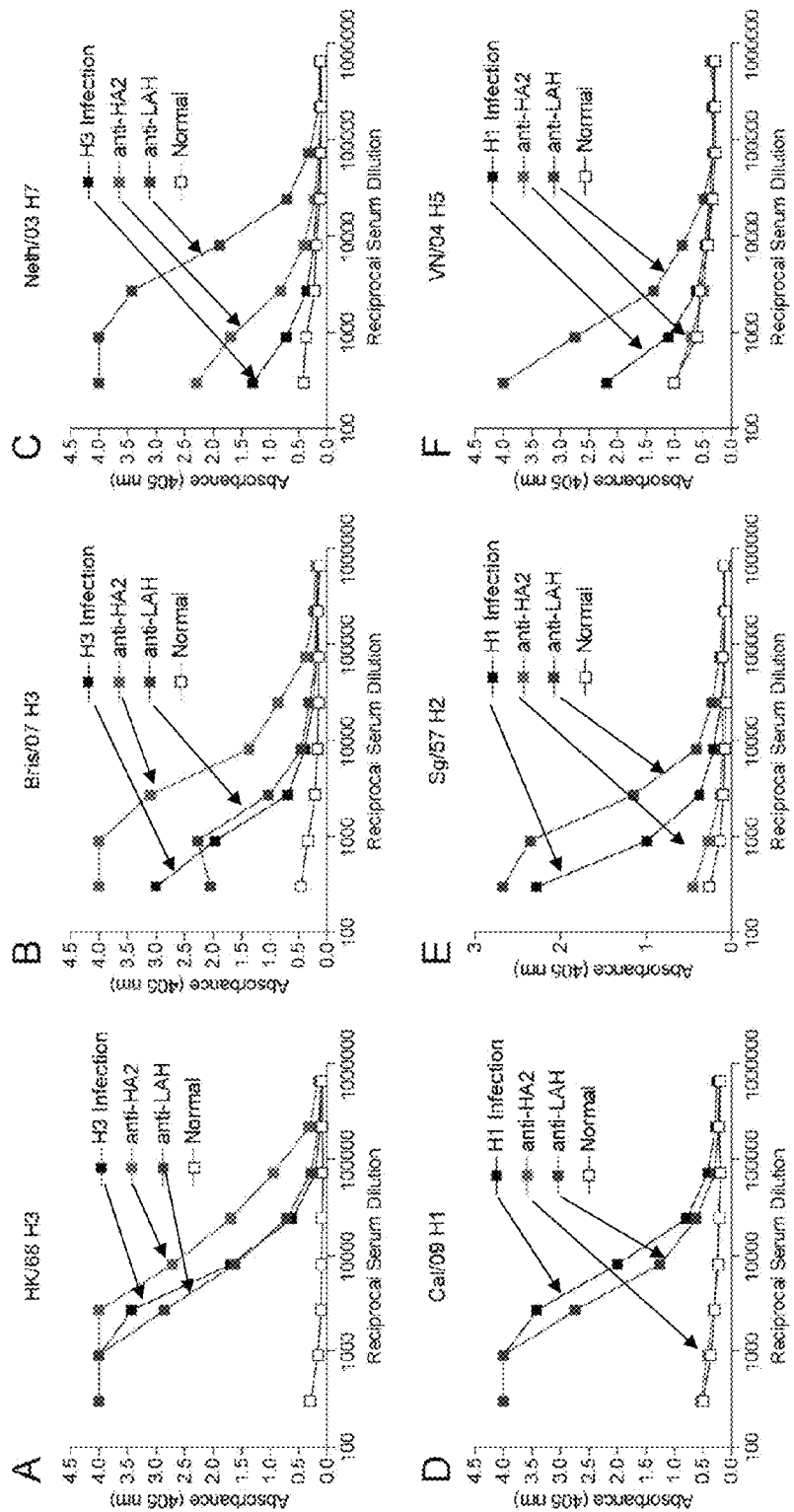
Figures 11G, 11H:
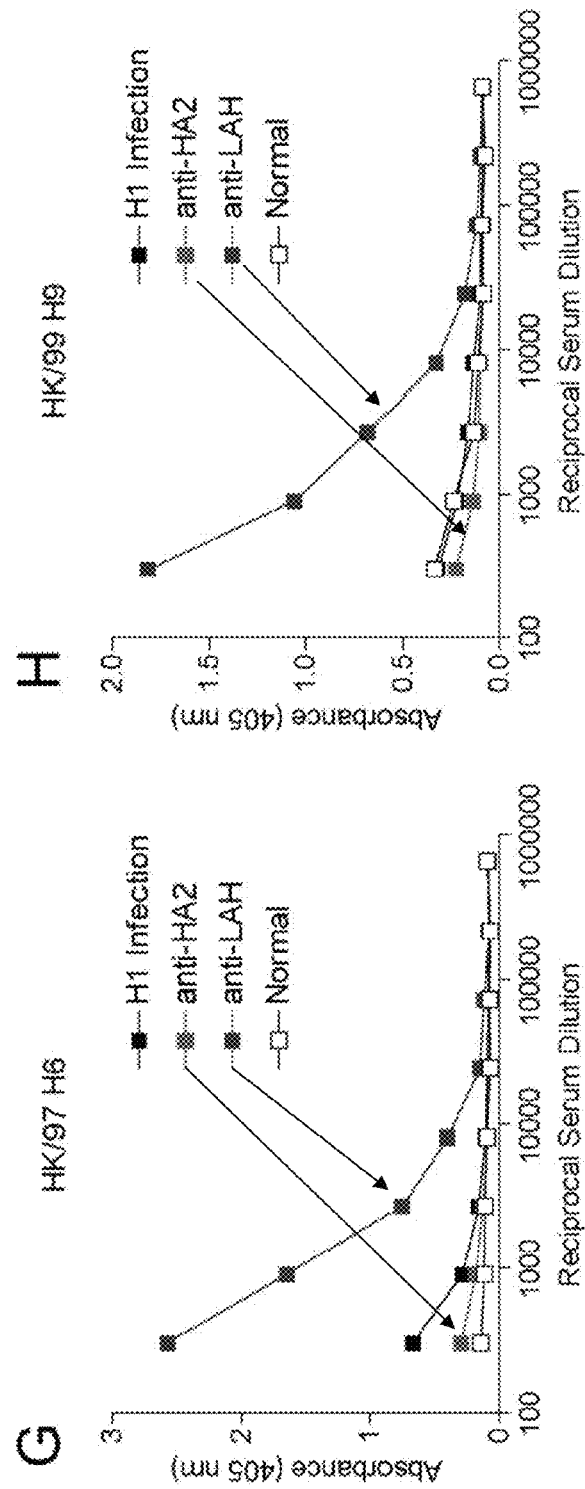

FIG. 11: LAH-KLH antiserum reacts with both Group 1 and Group 2 hemagglutinin proteins while HA2 antiserum reacts with Group 2 hemagglutinin proteins only. (A, B, and C) Activity of antisera against Group 2 hemagglutinin proteins. HA2 and LAH-KLH serum pools demonstrate comparable binding activity against the HK/68 H3 hemagglutinin but have different binding activities against other Group 2 hemagglutinins (D, E, F, G, and H) Activity of antisera against Group 1 hemagglutinin proteins. The LAH-KLH serum pool reacts with all Group 1 hemagglutinin proteins tested while the HA2 antiserum does not. Positive control serum was from mice infected with either the Group 2 H3 subtype X31 virus or the Group 1 H1 subtype PR8 virus.

5. DETAILED DESCRIPTION

5.1 Flu Polypeptides

Provided herein are flu polypeptides. While not intending to be bound by any particular theory of operation, it is believed that the flu polypeptides are useful for presenting one or more relatively conserved antigenic regions of the HA2 hemagglutinin subunit (e.g., the HA2 hemagglutinin subunit long alpha-helix) to a subject's immune system in order to generate an immune response that is capable of cross reacting with, and preferably protecting against, a plurality of influenza virus strains from a single subtype or 2, 3, 4 or more different subtypes.

In certain embodiments, a flu polypeptide comprises a core polypeptide or modified core polypeptide.

In certain embodiments, a flu polypeptide is acetylated at its N- and/or C-terminus. In certain embodiments, a flu polypeptide is pegylated.

In certain embodiments, a flu polypeptide comprises one, two, three or more core polypeptides and/or modified polypeptides.

In certain embodiments, a flu polypeptide comprises one, two, three or more core polypeptides or modified polypeptides and one, two, three or more T cell epitopes.

In some embodiments, a flu polypeptide comprises one, two, three or more core polypeptides or modified polypeptides and one, two, three or more immunogenic polypeptides.

In certain embodiments, a flu polypeptide comprises one, two, three or more core polypeptides or modified core polypeptides and a polypeptide that facilitates multimerization (e.g., trimerization of the flu polypeptide).

In certain embodiments, a flu polypeptide comprises one, two, three or more core polypeptides or modified core polypeptides and one, two, three or more, or all of the following: 1) one, two, three or more carriers; 2) one, two, three or more T cell epitopes (e.g., CD8 T cell epitopes); 3) one, two, three or more immunogenic polypeptides (e.g., *Salmonella* flagellin, see, Section 5.1.6); 4) one, two, three or more protein tags (e.g., His- or FLAG-tag, see, Section 5.1.3); 5) one or more polypeptides that facilitate multimerization of the flu polypeptide (e.g., T4 foldon domain, see, Section 5.1.8)

In certain embodiments, a flu polypeptide comprises a core polypeptide or a modified core polypeptide linked to a linker polypeptide. In certain embodiments, a flu polypeptide comprises a core polypeptide or modified core polypeptide linked to a carrier protein.

5.1.1 Core Polypeptides

In certain embodiments, the flu polypeptide comprises a core polypeptide. In certain embodiments, the core polypeptide comprises one or more relatively conserved antigenic regions of the HA2 hemagglutinin subunit long alpha-helix. In a specific embodiment, the core polypeptide is capable of generating an immune response in a subject that is capable of cross reacting with, and preferably protecting against, a plurality of influenza virus strains from a single subtype, or strains from 2, 3, 4 or more subtypes. The ability of a core polypeptide to generate an immune response in a subject that is capable of cross reacting with, and preferably protecting against, a plurality of influenza virus strains from a single subtype, or strains from 2, 3, 4 or more subtypes can be assessed using methods known to those of skill in the art and described herein (see Sections 5.13 and 6, infra) In another specific embodiment, the core polypeptide is capable of generating an immune response in a subject that is capable of neutralizing a plurality of influenza virus strains from a single subtype, or strains from 2, 3, 4 or more subtypes. The ability of a core polypeptide to generate an immune response that is capable of neutralizing a plurality of influenza virus strains from a single subtype, or strains from 2, 3, 4 or more subtypes can be assessed using methods known to those of skill in the art and described herein (see Sections 5.13 and 6, infra). In another specific embodiment, the core polypeptide is capable of generating an immune response in a subject that is capable of inhibiting or reducing the replication of a plurality of influenza virus strains from a single subtype, or strains from 2, 3, 4 or more subtypes. The ability of a core polypeptide to generate an immune response that is capable of inhibiting or reducing the replication of a plurality of influenza virus strains from a single subtype, or strains from 2, 3, 4 or more subtypes can be assessed using methods known to those of skill in the art and described herein (see Sections 5.13 and 6, infra).

In a specific embodiment, a core polypeptide comprises the long alpha-helix of the HA2 hemagglutinin subunit of an influenza virus. In a specific embodiment, a core polypeptide comprises a portion of the long alpha-helix of the HA2 hemagglutinin subunit of an influenza virus. In a specific embodiment, a core polypeptide comprises a portion of the long alpha-helix of the HA2, wherein the native conformation of the portion is maintained. In a specific embodiment, a core polypeptide comprises a portion of the long alpha-helix of the HA2, wherein the portion maintains a native alpha-helix conformation. One of skill in the art can determine whether or not the alpha-helix conformation is maintained using any method known in the art such as, e.g., NMR, X-ray crystallographic methods, or secondary structure prediction methods, e.g., circular dichroism.

In specific embodiments, a core polypeptide does not include the amino acid sequence of a full length influenza virus hemagglutinin. In certain embodiments, a core polypeptide comprises or consists of between 25 to 50, 50 to 55, 50 to 60, 50 to 65, 50 to 70, 50 to 75, 50 to 80, 50 to 85, 50 to 90, 50 to 95, 50 to 100, 100 to 150, 100 to 200, or 100 to 250 amino acids. In other embodiments, a core polypeptide comprises or consists of between 50 to 55, 50 to 60, 50 to 65, 50 to 75, 50 to 80, 50 to 85, 50 to 90, 50 to 95, 50 to 100, 75 to 80, 75 to 85, 75 to 90, 75 to 95, or 75 to 100 amino acids In a specific embodiment, a core polypeptide comprises or consists of amino acids 1(±5) to 184(±5), 16(±5) to 184(±5), 30(±5) to 184(±5), 31(±5) to 184(±5), 46(±5) to 184(±5), 61(±5) to 184(±5), 70(±5) to 110(±5), 76(±5) to 106(±5), 76(±5) to 130(±5) or 76(±5) to 184(±5) of a hemagglutinin polypeptide numbered according to the classic H3 subtype numbering system. In some embodiments, a core polypeptide comprises or consists of amino acids 1(±5) to 184(±5), 16(±5) to 184(±5), 30(±5) to 184(±5), 31(±5) to 184(±5), 46(±5) to 184(±5), 61(±5) to 184(±5), 70(±5) to 184(±5), (70(±5) to 110(±5), 76(±5) to 106(±5), 76(±5) to 130(±5) or 76(±5) to 184(±5) of a hemagglutinin polypeptide numbered according to the classic H3 subtype numbering system, wherein the core polypeptide is less than 300, 275, 250, 200, 190, 185, or 180 amino acids in length. In a specific embodiment, a core polypeptide comprises or consists of amino acids 76 to 106 of a hemagglutinin polypeptide numbered according to the classic H3 subtype numbering system.

In another specific embodiment, a core polypeptide comprises amino acids 76 to 130 of a hemagglutinin polypeptide numbered according to the classic H3 subtype numbering system. In certain embodiments, a core polypeptide comprises or consists of amino acids 76 to 130 of a hemagglutinin polypeptide numbered according to the classic H3 subtype numbering system, wherein the core polypeptide is less than 300, 275, 250, 200, 190, 185, 180, 175, 150, 145, 130, 130, 125, 100, or 75 amino acids in length. In another specific embodiment, a core polypeptide consists of amino acids 76 to 130 of a hemagglutinin polypeptide numbered according to the classic H3 subtype numbering system.

In a specific embodiment, a core polypeptide comprises or consists of amino acids 70(±5) to 125(±5), 80(±5) to 115 (±5), 90(±5) to 105(±5), or 76(±5) to 95(±5) of a hemagglutinin polypeptide numbered according to the classic H3 subtype numbering system. In certain embodiments, a core polypeptide comprises or consists of amino acids 70(±5) to 125(±5), 80(±5) to 115(±5), 90(±5) to 105(±5), or 76(±5) to 95(±5) of a hemagglutinin polypeptide numbered according to the classic H3 subtype numbering system, wherein the core polypeptide is less than 300, 275, 250, 200, 190, 185, 180, 175, 150, 145, 130, 130, 125, 100, or 75 amino acids in length.

In a specific embodiment, a core polypeptide comprises or consists of amino acids 70(±5) to 130(±5), 70(±5) to 120 (±5), 70(±5) to 110(±5), 70(±5) to 100(±5), or 70(±5) to 95(±5) of a hemagglutinin polypeptide numbered according to the classic H3 subtype numbering system. In certain embodiments, a core polypeptide comprises or consists of amino acids 70(±5) to 130(±5), 70(±5) to 120(±5), 70(±5) to 110(±5), 70(±5) to 100(±5), or 70(±5) to 95(±5) of a hemagglutinin polypeptide numbered according to the classic H3 subtype numbering system, wherein the core polypeptide is less than 300, 275, 250, 200, 190, 185, 180, 175, 150, 145, 130, 130, 125, 100, or 75 amino acids in length.

In a specific embodiment, a core polypeptide comprises or consists of amino acids 70(±5) to 130(±5), 80(±5) to 130 (±5), 90(±5) to 130(±5), 100(±5) to 130(±5), or 110(±5) to 130(±5) of a hemagglutinin polypeptide numbered according to the classic H3 subtype numbering system. In certain embodiments, a core polypeptide comprises or consists of amino acids 70(±5) to 130(±5), 80(±5) to 130(±5), 90(±5) to 130(±5), 100(±5) to 130(±5), or 110(±5) to 130(±5) of a hemagglutinin polypeptide numbered according to the classic H3 subtype numbering system, wherein the core polypeptide is less than 300, 275, 250, 200, 190, 185, 180, 175, 150, 145, 130, 130, 125, 100, or 75 amino acids in length.

In a specific embodiment, a core polypeptide comprises or consists of amino acids 1-184, 10(±5) to 184, 20(±5) to 184, 30(±5) to 184, 40(±5) to 184, 50(±5) to 184, 60(±5) to 184, 70(±5) to 184 or 80(±5) to 184 of a hemagglutinin polypeptide numbered according to the classic H3 subtype numbering system. In certain embodiments, a core polypeptide comprises or consists of amino acids 1-184, 10(±5) to 184, 20(±5) to 184, 30(±5) to 184, 40(±5) to 184, 50(±5) to 184, 60(±5) to 184, 70(±5) to 184 or 80(±5) to 184 of a hemagglutinin polypeptide numbered according to the classic H3 subtype numbering system, wherein the core polypeptide is less than 300, 275, 250, 200, 190, 185, 180, 175, 150, 145, 130, 130, 125, 100, or 75 amino acids in length.

In a specific embodiment, a core polypeptide comprises or consists of the long alpha-helix of the HA2 hemagglutinin subunit of the influenza virus strain A/Hong Kong/1/1968 (H3) or a fragment thereof (i.e., amino acids 76-130, numbered according to the classic H3 subtype numbering system or a fragment thereof), i.e., the core polypeptide comprises or consists of the following amino acid sequence:

```
                                           (SEQ ID NO: 2)
RIQDLEKYVEDTKIDLWSYNAELLVALENQHTIDLTDSEMNKLFEKT

RRQLRENA or a fragment thereof).
```

In some embodiments, the core polypeptide comprising the amino acid sequence SEQ ID NO: 2 comprises at least 56 amino acids or more. The core polypeptide corresponding to SEQ ID NO:2 can be modified at the N-terminus, at the C-terminus, or both. In some embodiments, the core polypeptide is modified at the N-terminus. In some embodiments, the core polypeptide is modified at the C-terminus. In a specific embodiment, the core polypeptide is acetylated at the N-terminus. In another specific embodiment, the core polypeptide is linked to a linker, such as a FLAG-tag, at the C-terminus. In another specific embodiment, the C-terminus of the core polypeptide is linked to a linker, e.g., a FLAG-tag, and a cysteine residue which can be used, e.g., to couple/link the core polypeptide to a carrier (e.g., KLH).

In a specific embodiment, a core polypeptide comprises or consists of a region of hemagglutinin subunit of the influenza virus strain A/Hong Kong/1/1968 (H3) or a fragment thereof that corresponds to amino acids 79-134, numbered according to the classic H3 subtype numbering system or a fragment thereof (i.e., the core polypeptide comprises or consists of the following amino acid sequence:

```
LEKYVEDTKIDLWSYNAELLVALENQHTIDLTDSEMNKLFEKT

RRQLRENAEDMG or a fragment thereof).
```

In a specific embodiment, a core polypeptide is linked to a FLAG-tag and a C-terminal cysteine residue, and such a polypeptide with the FLAG-tag and cysteine residue comprises or consists of the following amino acid sequence:

```
                                              (SEQ ID NO: 1)
RIQDLEKYVEDTKIDLWSYNAELLVALENQHTIDLTDSEMNKLFEKT

RRQLRENADYKDDDDKC.
```

In some embodiments, such a polypeptide is acetylated at the N-terminus.

In certain embodiments, the core polypeptide shares at least 50% amino acid sequence identity with the amino acid sequence of SEQ ID NO: 1 or SEQ ID NO: 2 and maintains the native conformation of amino acids 76-130 of the influenza virus strain A/Hong Kong/1/1968 (H3), numbered according to the classic H3 subtype numbering system. In certain embodiments, the core polypeptide shares at least 60% amino acid sequence identity with the amino acid sequence of SEQ ID NO:1 or SEQ ID NO:2 and maintains the native conformation of amino acids 76-130 of the influenza virus strain A/Hong Kong/1/1968 (H3), numbered according to the classic H3 subtype numbering system. In certain embodiments, the core polypeptide shares at least 65% amino acid sequence identity with the amino acid sequence of SEQ ID NO:1 or SEQ ID NO:2 and maintains the native conformation of amino acids 76-130 of the influenza virus strain A/Hong Kong/1/1968 (H3), numbered according to the classic H3 subtype numbering system. In certain embodiments, the core polypeptide shares at least 70% amino acid sequence identity with the amino acid sequence of SEQ ID NO:1 or SEQ ID NO:2 and maintains the native conformation of amino acids 76-130 of the influenza virus strain A/Hong Kong/1/1968 (H3), numbered according to the classic H3 subtype numbering system. In certain embodiments, the core polypeptide shares at least 75% amino acid sequence identity with the amino acid sequence of SEQ ID NO:1 or SEQ ID NO:2 and maintains the native conformation of amino acids 76-130 of the influenza virus strain A/Hong Kong/1/1968 (H3), numbered according to the classic H3 subtype numbering system. In certain embodiments, the core polypeptide shares at least 80% amino acid sequence identity with the amino acid sequence of SEQ ID NO:1 or SEQ ID NO:2 and maintains the native conformation of amino acids 76-130 of the influenza virus strain A/Hong Kong/1/1968 (H3), numbered according to the classic H3 subtype numbering system. In certain embodiments, the core polypeptide shares at least 85% amino acid sequence identity with the amino acid sequence of SEQ ID NO:1 or SEQ ID NO:2 and maintains the native conformation of amino acids 76-130 of the influenza virus strain A/Hong Kong/1/1968 (H3), numbered according to the classic H3 subtype numbering system. In certain embodiments, the core polypeptide shares at least 90% amino acid sequence identity with the amino acid sequence of SEQ ID NO:1 or SEQ ID NO:2 and maintains the native conformation of amino acids 76-130 of the influenza virus strain A/Hong Kong/1/1968 (H3), numbered according to the classic H3 subtype numbering system. In certain embodiments, the core polypeptide shares at least 95% amino acid sequence identity with the amino acid sequence of SEQ ID NO:1 or SEQ ID NO:2 and maintains the native conformation of amino acids 76-130 of the influenza virus strain A/Hong Kong/1/1968 (H3), numbered according to the classic H3 subtype numbering system. In certain embodiments, the core polypeptide shares at least 98% amino acid sequence identity with the amino acid sequence of SEQ ID NO:1 or SEQ ID NO:2 and maintains the native conformation of amino acids 76-130 of the influenza virus strain A/Hong Kong/1/1968 (H3), numbered according to the classic H3 subtype numbering system. In certain embodiments, the core polypeptide shares at least 99% amino acid sequence identity with the amino acid sequence of SEQ ID NO:1 or SEQ ID NO:2 and maintains the native conformation of amino acids 76-130 of the influenza virus strain A/Hong Kong/1/1968 (H3), numbered according to the classic H3 subtype numbering system.

In certain embodiments, the core polypeptide shares at least 50% amino acid sequence similarity with the amino acid sequence of SEQ ID NO:1 or SEQ ID NO:2 and maintains the native conformation of amino acids 76-130 of the influenza virus strain A/Hong Kong/1/1968 (H3), numbered according to the classic H3 subtype numbering system. In certain embodiments, the core polypeptide shares at least 60% amino acid sequence similarity with the amino acid sequence of SEQ ID NO:1 or SEQ ID NO:2 and maintains the native conformation of amino acids 76-130 of the influenza virus strain A/Hong Kong/1/1968 (H3), numbered according to the classic H3 subtype numbering system. In certain embodiments, the core polypeptide shares at least 65% amino acid sequence similarity with the amino acid sequence of SEQ ID NO:1 or SEQ ID NO:2 and maintains the native conformation of amino acids 76-130 of the influenza virus strain A/Hong Kong/1/1968 (H3), numbered according to the classic H3 subtype numbering system. In certain embodiments, the core polypeptide shares at least 70% amino acid sequence similarity with the amino acid sequence of SEQ ID NO:1 or SEQ ID NO:2 and maintains the native conformation of amino acids 76-130 of the influenza virus strain A/Hong Kong/1/1968 (H3), numbered according to the classic H3 subtype numbering system. In certain embodiments, the core polypeptide shares at least 75% amino acid sequence similarity with the amino acid sequence of SEQ ID NO:1 or SEQ ID NO:2 and maintains the native conformation of amino acids 76-130 of the influenza virus strain A/Hong Kong/1/1968 (H3), numbered according to the classic H3 subtype numbering system. In certain embodiments, the core polypeptide shares at least 80% amino acid sequence similarity with the amino acid sequence of SEQ ID NO:1 or SEQ ID NO:2 and maintains the native conformation of amino acids 76-130 of the influenza virus strain A/Hong Kong/1/1968 (H3), numbered according to the classic H3 subtype numbering system. In certain embodiments, the core polypeptide shares at least 85% amino acid sequence similarity with the amino acid sequence of SEQ ID NO:1 or SEQ ID NO:2 and maintains the native conformation of amino acids 76-130 of the influenza virus strain A/Hong Kong/1/1968 (H3), numbered according to the classic H3 subtype numbering system. In certain embodiments, the core polypeptide shares at least 90% amino acid sequence similarity with the amino acid sequence of SEQ ID NO:1 or SEQ ID NO:2 and maintains the native conformation of amino acids 76-130 of the influenza virus strain A/Hong Kong/1/1968 (H3), numbered according to the classic H3 subtype numbering system. In certain embodiments, the core polypeptide shares at least 95% amino acid sequence similarity with the amino acid sequence of SEQ ID NO:1 or SEQ ID NO:2 and maintains the native conformation of amino acids 76-130 of the influenza virus strain A/Hong Kong/1/1968 (H3), numbered according to the classic H3 subtype numbering system. In certain embodiments, the core polypeptide shares at least 98% amino acid sequence similarity with the amino acid sequence of SEQ ID NO:1 or SEQ ID NO:2 and maintains the native conformation of amino acids 76-130 of the influenza virus strain A/Hong Kong/1/1968 (H3), numbered according to the classic H3 subtype numbering system. In certain embodiments, the core polypeptide shares at least 99% amino acid sequence similarity with the amino acid sequence of SEQ ID NO:1 or SEQ ID NO:2 and maintains the native conformation of amino acids 76-130 of the influenza virus strain A/Hong Kong/1/1968 (H3), numbered according to the classic H3 subtype numbering system.

In a specific embodiment, a core polypeptide does not comprise the long alpha-helix of the HA2 hemagglutinin subunit of the influenza virus strain A/Hong Kong/1/1968 (H3) (i.e., amino acids 76-130, numbered according to the classic H3 subtype numbering system), i.e., the core polypeptide does not comprise the following amino acid sequence:

```
                                       (SEQ ID NO: 2)
RIQDLEKYVEDTKIDLWSYNAELLVALENQHTIDLTDSEMNKLFEKT

RRQLRENA.
```

In certain embodiments, a core polypeptide is not linked to a FLAG-tag and a C-terminal cysteine residue which can be used, e.g., to couple/link the core polypeptide to a carrier (e.g., KLH). In some specific embodiments, a core polypeptide described herein does not comprise the following amino acid sequence:

```
                                       (SEQ ID NO: 1)
RIQDLEKYVEDTKIDLWSYNAELLVALENQHTIDLTDSEMNKLFEKT

RRQLRENADYKDDDDKC,
``` wherein the FLAG-tag is represented by the amino acid sequence DYKDDDDK (SEQ ID NO: 61). In some embodiments, a core polypeptide is not acetylated at the N-terminus.

In a specific embodiment, a core polypeptide does not comprise amino acids 70(±5) to 125(±5) of a hemagglutinin polypeptide numbered according to the classic H3 subtype numbering system. In a specific embodiment, a core polypeptide does not comprise amino acids 80(±5) to 115(±5) of a hemagglutinin polypeptide numbered according to the classic H3 subtype numbering system. In a specific embodiment, a core polypeptide does not comprise amino acids 90(±5) to 105(±5) of a hemagglutinin polypeptide numbered according to the classic H3 subtype numbering system. In a specific embodiment, a core polypeptide does not comprise amino acids 76(±5) to 95(±5), of a hemagglutinin polypeptide numbered according to the classic H3 subtype numbering system.

In a specific embodiment, a core polypeptide does not comprise amino acids 70(±5) to 130(±5) of a hemagglutinin polypeptide numbered according to the classic H3 subtype numbering system. In a specific embodiment, a core polypeptide does not comprise amino acids 70(±5) to 120(±5) of a hemagglutinin polypeptide numbered according to the classic H3 subtype numbering system. In a specific embodiment, a core polypeptide does not comprise amino acids 70(±5) to 110(±5) of a hemagglutinin polypeptide numbered according to the classic H3 subtype numbering system. In a specific embodiment, a core polypeptide does not comprise amino acids 70(±5) to 100(±5) of a hemagglutinin polypeptide numbered according to the classic H3 subtype numbering system. In a specific embodiment, a core polypeptide does not comprise amino acids 70(±5) to 95(±5) of a hemagglutinin polypeptide numbered according to the classic H3 subtype numbering system.

In a specific embodiment, a core polypeptide does not comprise amino acids 70(±5) to 130(±5) of a hemagglutinin polypeptide numbered according to the classic H3 subtype numbering system. In a specific embodiment, a core polypeptide does not comprise amino acids 80(±5) to 130(±5) of a hemagglutinin polypeptide numbered according to the classic H3 subtype numbering system. In a specific embodiment, a core polypeptide does not comprise amino acids 90(±5) to 130(±5) of a hemagglutinin polypeptide numbered according to the classic H3 subtype numbering system. In a specific embodiment, a core polypeptide does not comprise amino acids 100(±5) to 130(±5) of a hemagglutinin polypeptide numbered according to the classic H3 subtype numbering system. In a specific embodiment, a core polypeptide does not comprise amino acids 110(±5) to 130(±5) of a hemagglutinin polypeptide numbered according to the classic H3 subtype numbering system.

In a specific embodiment, a core polypeptide does not comprise amino acids 1-184 of a hemagglutinin polypeptide numbered according to the classic H3 subtype numbering system. In a specific embodiment, a core polypeptide does not comprise amino acids 10(±5) to 184 of a hemagglutinin polypeptide numbered according to the classic H3 subtype numbering system. In a specific embodiment, a core polypeptide does not comprise amino acids 20(±5) to 184 of a hemagglutinin polypeptide numbered according to the classic H3 subtype numbering system. In a specific embodiment, a core polypeptide does not comprise amino acids 30(±5) to 184 of a hemagglutinin polypeptide numbered according to the classic H3 subtype numbering system. In a specific embodiment, a core polypeptide does not comprise amino acids 40(±5) to 184 of a hemagglutinin polypeptide numbered according to the classic H3 subtype numbering system. In a specific embodiment, a core polypeptide does not comprise amino acids 50(±5) to 184 of a hemagglutinin polypeptide numbered according to the classic H3 subtype numbering system. In a specific embodiment, a core polypeptide does not comprise amino acids 60(±5) to 184 of a hemagglutinin polypeptide numbered according to the classic H3 subtype numbering system. In a specific embodiment, a core polypeptide does not comprise amino acids 70(±5) to 184 of a hemagglutinin polypeptide numbered according to the classic H3 subtype numbering system. In a specific embodiment, a core polypeptide does not comprise amino acids 80(±5) to 184 of a hemagglutinin polypeptide numbered according to the classic H3 subtype numbering system.

In a specific embodiment, a core polypeptide does not comprise amino acids 1(±5) to 184(±5) of a hemagglutinin polypeptide numbered according to the classic H3 subtype number system. In a specific embodiment, a core polypeptide does not comprise amino acids 16(±5) to 184(±5) of a hemagglutinin polypeptide numbered according to the classic H3 subtype number system. In a specific embodiment, a core polypeptide does not comprise amino acids 30(±5) to 184(±5) of a hemagglutinin polypeptide numbered according to the classic H3 subtype number system. In a specific embodiment, a core polypeptide does not comprise amino acids 31(±5) to 184(±5) of a hemagglutinin polypeptide numbered according to the classic H3 subtype number system. In a specific embodiment, a core polypeptide does not comprise amino acids 46(±5) to 184(±5) of a hemagglutinin polypeptide numbered according to the classic H3 subtype number system. In a specific embodiment, a core polypeptide does not comprise amino acids 61(±5) to 184 (±5) of a hemagglutinin polypeptide numbered according to the classic H3 subtype number system. In a specific embodiment, a core polypeptide does not comprise amino acids 70(±5) to 184(±5) of a hemagglutinin polypeptide numbered according to the classic H3 subtype number system. In a specific embodiment, a core polypeptide does not comprise amino acids 76(±5) to 106(±5) of a hemagglutinin polypeptide numbered according to the classic H3 subtype number system. In a specific embodiment, a core polypeptide does not comprise amino acids 76(±5) to 184(±5) of a hemagglutinin polypeptide numbered according to the classic H3 subtype number system.

In a specific embodiment, the core polypeptide is a generic core polypeptide comprising the amino acid sequence:

(SEQ ID NO: 3)
$X_1X_2X_3X_4X_5X_6X_7X_8X_9X_{10}DX_{11}X_{12}X_{13}X_{14}X_{15}WX_{16}YX_{17}AELLVX_{18}X_{19}EN$ $X_{20}X_{21}TX_{22}DX_{23}X_{24}DSX_{25}X_{26}X_{27}X_{28}LX_{29}X_{30}X_{31}X_{32}X_{33}X_{34}QLX_{35}X_{36}NX_{37}$, wherein $X_1$ is a hydrophilic amino acid; $X_2$ is a hydrophobic amino acid; $X_3$ is a hydrophilic amino acid; $X_4$ is a hydrophilic amino acid; $X_5$ is a hydrophobic amino acid; $X_6$ is N, E or I; $X_7$ is a hydrophilic amino acid; $X_8$ is K, R, Y or W; $X_9$ is M, V or T; $X_{10}$ is a hydrophilic residue; $X_{11}$ is A, G, T or S; $X_{12}$ is F, I, K, L or M; $X_{13}$ is L, I or T; $X_{14}$ is a hydrophilic, acidic amino acid; $X_{15}$ is a hydrophobic amino acid; $X_{16}$ is a hydrophilic amino acid; amino acid $X_{17}$ is a hydrophilic amino acid; $X_{18}$ is a hydrophobic amino acid; $X_{19}$ is a hydrophobic amino acid; $X_{20}$ is a hydrophilic amino acid; $X_{21}$ is a hydrophilic, basic amino acid; $X_{22}$ is a hydrophobic amino acid; $X_{23}$ is a hydrophobic amino acid; $X_{24}$ is H, T or A; $X_{25}$ is a hydrophilic amino acid; $X_{26}$ is a hydrophobic amino acid; $X_{27}$ is a hydrophilic amino acid; $X_{28}$ is a hydrophilic amino acid; $X_{29}$ is a hydrophobic amino acid; $X_{30}$ is a hydrophilic, acidic amino acid; $X_{31}$ is a hydrophilic, basic amino acid; $X_{32}$ is T or V; $X_{33}$ is a hydrophilic, basic amino acid; $X_{34}$ is K, L, M, S or R; $X_{35}$ is a hydrophilic, basic amino acid; $X_{36}$ is a hydrophilic amino acid and $X_{37}$ is a hydrophobic amino acid.

In specific embodiments $X_1$ is R or Q; $X_2$ is L, M or I; $X_3$ is E, D, Q or G; $X_4$ is D or N; $X_5$ is L, M or V; $X_6$ is N, E or I; $X_7$ is K or N; $X_8$ is K, R, Y or W; $X_9$ is M, V or T; $X_{10}$ is E, D, K or R; $X_{11}$ is A, G, T or S; $X_{12}$ is F, I, K, L or M; $X_{13}$ is L, I or T; $X_{14}$ is D or E; $X_{15}$ is V, I or L; $X_{16}$ is S or T; $X_{17}$ is N or Q; $X_{18}$ is A or L; $X_{19}$ is L or M; $X_{20}$ is E or Q; $X_{21}$ is R or H; $X_{22}$ is L or I; $X_{23}$ is F, V, M, Y or L; $X_{24}$ is H, T or A; $X_{25}$ is N or E; $X_{26}$ is V or M; $X_{27}$ is K, N, R or S; $X_{28}$ is K or N; $X_{29}$ is Y or F; $X_{30}$ is D or E; $X_{31}$ is K or R; $X_{32}$ is T or V; $X_{33}$ is K or R; $X_{34}$ is K, L, M, S or R; $X_{35}$ is K or R; $X_{36}$ is D, N, Q or E and $X_{37}$ is A or V. In certain embodiments, the core polypeptide is acetylated at the N-terminus.

In certain embodiments, the core polypeptide is a fragment of a generic core polypeptide. In specific embodiments, the core polypeptide is a fragment of a generic core polypeptide, wherein the fragment lacks 1, 2, 3, 4, 5, 6, 7, 8, 9, 10(±5), 15(±5), 20(±5), 25(±5), 30(±5), or 35(±5) amino acids from either of a generic core polypeptide's N- or C-terminus. In some embodiments, the core polypeptide is a fragment of a generic core polypeptide, wherein the fragment lacks 24(±5) amino acids from its C-terminus. In specific embodiments, the core polypeptide is a fragment of a generic core polypeptide, wherein the fragment lacks 1, 2, 3, 4, 5, 6, 7, 8, 9, 10(±5), 15(±5), 20(±5) or 25(±5) amino acids from a generic core polypeptide's N-terminus and 1, 2, 3, 4, 5, 6, 7, 8, 9, 10(±5), 15(±5), 20(±5) or 25(±5) amino acids from a generic core polypeptide's C-terminus. In specific embodiments, the core polypeptide has an alpha-helical conformation.

In some embodiments, the core polypeptide is a generic core polypeptide that is not full length influenza virus HA. In some embodiments, the core polypeptide is a generic core polypeptide that is between 51 to 300, 51 to 275, 51 to 250, 51 to 225, 51 to 200, 51 to 175, 51 to 150, 51 to 125, 51 to 100, or 51 to 75, 15 to 50, 20 to 50, 25 to 50, 15 to 37, 15 to 35, 20 to 37, 20 to 35, 15 to 30, 20 to 30 or 20 to 25 amino acids in length. In some embodiments, the core polypeptide is a generic core polypeptide that is less than 500, 450, 400, 350, 300, 275, 250, 225, 200, 175, 150, 125, 100, 95, 90, 85, 80, 75, 70, 65, 60, 55, 50, 45, 40, 35, 30 or 25 amino acids in length. In certain embodiments, the core polypeptide is a generic core polypeptide less than 150, 125, 95, 90, 85, 80, 75, 65, 60, 55, 50, 45 or 40 amino acids in length but at least 15, 20, 25, 30 or 35 amino acids in length.

In specific embodiments, the core polypeptide is a derivative of the generic core polypeptide, wherein the derivative comprises a generic core polypeptide with 1, 2, 3, 4, 5, 6, 7, 8, 9, or 10(±5) amino acids attached to either of a generic core polypeptide's N- or C-terminus and wherein the core polypeptide maintains an alpha-helical conformation.

In specific embodiments, the core polypeptide is a derivative of the generic core polypeptide, wherein the derivative comprises a generic core polypeptide with 1, 2, 3, 4, 5, 6, 7, 8, 9, or 10(±5) amino acids attached to the generic core polypeptide's N-terminus and 1, 2, 3, 4, 5, 6, 7, 8, 9, or 10(±5) amino acids attached to the generic core polypeptide's C-terminus and wherein the core polypeptide maintains an alpha-helical conformation.

In a specific embodiment, the core polypeptide is a consensus core polypeptide comprising or consisting of the amino acid sequence:

(SEQ ID NO: 4)
RIENLNKKX$_1$EDGFLDVWTYNAELLVLMENERTLDX$_2$HDSNVKNLYE

KVRX$_3$QLRX$_4$NA, wherein $X_1$ is M, V, T; $X_2$ is a hydrophobic amino acid; $X_3$ is L, M, S, K, R; and $X_4$ is a hydrophilic amino acid. In a specific embodiment, $X_1$ is M, V, T; $X_2$ is F, Y or L; $X_3$ is L, M, S, K, R; and $X_4$ is D, N or E. In certain embodiments, the core polypeptide is acetylated at the N-terminus.

In certain embodiments, the core polypeptide is a fragment of the consensus core polypeptide. In specific embodiments, the core polypeptide is a fragment of a consensus core polypeptide, wherein the fragment lacks 1, 2, 3, 4, 5, 6, 7, 8, 9, 10(±5), 15(±5), 20(±5), 25(±5), 30(±5), or 35(±5) amino acids from either of a consensus core polypeptide's N- or C-terminus. In some embodiments, the core polypeptide is a fragment of a consensus core polypeptide, wherein the fragment lacks 24(±5) amino acids from its C-terminus. In specific embodiments, the core polypeptide is a fragment of a consensus core polypeptide, wherein the fragment lacks 1, 2, 3, 4, 5, or more amino acids from both of a consensus core polypeptide's N- and C-termini. In specific embodiments, the core polypeptide has an alpha-helical conformation.

In some embodiments, the core polypeptide is a consensus core polypeptide that is not full length influenza virus HA. In some embodiments, the core polypeptide is a consensus core polypeptide that is between 51 to 300, 51 to 275, 51 to 250, 51 to 225, 51 to 200, 51 to 175, 51 to 150, 51 to 125, 51 to 100, or 51 to 75, 15 to 50, 20 to 50, 25 to 50, 15 to 37, 15 to 35, 20 to 37, 20 to 35, 15 to 30, 20 to 30 or 20 to 25 amino acids in length. In some embodiments, the core polypeptide is a consensus core polypeptide that is less than 500, 450, 400, 350, 300, 275, 250, 225, 200, 175, 150, 125, 100, 95, 90, 85, 80, 75, 70, 65, 60, 55, 50, 45, 40, 35, 30 or 25 amino acids in length. In certain embodiments, the core polypeptide is a consensus core polypeptide less than 150, 125, 95, 90, 85, 80, 75, 65, 60, 55, 50, 45 or 40 amino acids in length but at least 15, 20, 25, 30 or 35 amino acids in length.

In specific embodiments, the core polypeptide is a derivative of the consensus core polypeptide, wherein the derivative comprises a consensus core polypeptide with 1, 2, 3, 4, 5, 6, 7, 8, 9, or 10(±5) amino acids attached to either of a consensus core polypeptide's N- or C-terminus and wherein the core polypeptide maintains an alpha-helical conformation.

In specific embodiments, the core polypeptide is a derivative of the consensus core polypeptide, wherein the derivative comprises a consensus core polypeptide with 1, 2, 3, 4, 5, 6, 7, 8, 9, or 10(±5) amino acids attached to both of the consensus core polypeptide's N- and C-termini and wherein the core polypeptide maintains an alpha-helical conformation.

In a specific embodiment, the core polypeptide is a group 1 core polypeptide comprising or consisting of the amino acid sequence:

(SEQ ID NO: 5)
RX$_1$ENLNKKX$_2$X$_3$DGFLDX$_4$WTYNAELLVLX$_5$ENERTLDX$_6$HDSNVKNL

YX$_7$KVR X$_8$QLX$_9$X$_{10}$NX$_{11}$, wherein $X_1$ is a hydrophobic amino acid; $X_2$ is a hydrophobic amino acid; $X_3$ is a hydrophilic amino acid; $X_4$ is a hydrophobic amino acid; $X_5$ is a hydrophobic amino acid; $X_6$ is a hydrophobic acidic amino acid; $X_7$ is a hydrophilic, acidic amino acid; $X_8$ is L, M, or S; $X_9$ is a hydrophilic, basic amino acid; $X_{10}$ is a hydrophilic amino acid and $X_{11}$ is a hydrophobic amino acid. In specific embodiments, $X_1$ is L or I; $X_2$ M or V; $X_3$ is E or D; $X_4$ V or I; $X_5$ is M or L; $X_6$ is F or Y; $X_7$ is D or E; $X_8$ L, M or S; $X_9$ R or K; $X_{10}$ is D or N and $X_{11}$ is A or V. In a specific embodiment, this core polypeptide can be used to induce an immune response against group 1 hemagglutinin subtypes. In certain embodiments, the immune response induced neutralizes 2 or more influenza virus group 1 hemagglutinin subtypes. In certain embodiments, the core polypeptide is acetylated at the N-terminus.

In certain embodiments, the core polypeptide is a fragment of a group 1 core polypeptide. In specific embodiments, the core polypeptide is a fragment of a group 1 core polypeptide, wherein the fragment lacks 1, 2, 3, 4, 5, 6, 7, 8, 9, 10(±5), 15(±5), 20(±5), 25(±5), 30(±5), or 35(±5) amino acids from either of a group 1 core polypeptide's N- or C-terminus. In some embodiments, the core polypeptide is a fragment of a group 1 core polypeptide, wherein the fragment lacks 24(±5) amino acids from its C-terminus. In specific embodiments, the core polypeptide is a fragment of the group 1 core polypeptide, wherein the fragment lacks 1, 2, 3, 4, 5, or more amino acids from both of a group 1 core polypeptide's N- and C-termini. In specific embodiments, the core polypeptide has an alpha-helical conformation.

In some embodiments, the core polypeptide is a group 1 core polypeptide that is not full length influenza virus HA. In some embodiments, the core polypeptide is a group 1 core polypeptide that is between 51 to 300, 51 to 275, 51 to 250, 51 to 225, 51 to 200, 51 to 175, 51 to 150, 51 to 125, 51 to 100, or 51 to 75, 15 to 50, 20 to 50, 25 to 50, 15 to 37, 15 to 35, 20 to 37, 20 to 35, 15 to 30, 20 to 30 or 20 to 25 amino acids in length. In some embodiments, the core polypeptide is a group 1 core polypeptide that is less than 500, 450, 400, 350, 300, 275, 250, 225, 200, 175, 150, 125, 100, 95, 90, 85, 80, 75, 70, 65, 60, 55, 50, 45, 40, 35, 30 or 25 amino acids in length. In certain embodiments, the core polypeptide is a group 1 core polypeptide less than 150, 125, 95, 90, 85, 80, 75, 65, 60, 55, 50, 45 or 40 amino acids in length but at least 15, 20, 25, 30 or 35 amino acids in length.

In specific embodiments, the core polypeptide is a derivative of the group 1 core polypeptide, wherein the derivative comprises a group 1 core polypeptide with either 1, 2, 3, 4, 5, 6, 7, 8, 9, or 10(±5) amino acids attached to either of a group 1 core polypeptide's N- or C-terminus and wherein the core polypeptide maintains an alpha-helical conformation.

In specific embodiments, the core polypeptide is a derivative of the group 1 core polypeptide, wherein the derivative comprises a group 1 core polypeptide with either 1, 2, 3, 4, 5, 6, 7, 8, 9, or 10(±5) amino acids attached to both of a group 1 core polypeptide's N- and C-termini and wherein the core polypeptide maintains an alpha-helical conformation.

In a specific embodiment, the core polypeptide is a group 2 core polypeptide comprising or consisting of the amino acid sequence:

(SEQ ID NO: 6)
X$_1$IX$_2$X$_3$X$_4$X$_5$X$_6$X$_7$X$_8$X$_9$DX$_{10}$X$_{11}$X$_{12}$X$_{13}$X$_{14}$WSYNAELLVAX$_{15}$E

NQHTIDLX$_{16}$DSEMNKLX$_{17}$E X$_{18}$X$_{19}$X$_{20}$RQLRENA, wherein $X_1$ is a hydrophilic amino acid; $X_2$ is a hydrophilic amino acid; $X_3$ is a hydrophilic amino acid; $X_4$ is a hydrophobic amino acid; $X_5$ is E or I; $X_6$ is a hydrophilic amino acid; $X_7$ is a hydrophobic amino acid; $X_8$ is V or T; $X_9$ is a hydrophilic amino acid; $X_{10}$ is a hydrophilic amino acid; $X_{11}$ is K or M; $X_{12}$ is I or T; $X_{13}$ is a hydrophilic, acidic amino acid; $X_{14}$ is a hydrophobic amino acid; $X_{15}$ is a hydrophobic amino acid; $X_{16}$ is T or A; $X_{17}$ is a hydrophobic amino acid; $X_{18}$ is a hydrophilic basic amino acid; $X_{19}$ is T or V, and $X_{20}$ is a hydrophilic, basic amino acid. In specific embodiments, $X_1$ is R or Q; $X_2$ is Q or G; $X_3$ is D or N; $X_4$ is L or V; $X_5$ is E or I; $X_6$ is K or N; $X_7$ Y or W; $X_8$ V or T; $X_9$ is E or R; $X_{10}$ is T or S; $X_{11}$ is K or M; $X_{12}$ is I or T; $X_{13}$ is D or E; $X_{14}$ is L or V; $X_{15}$ is L or M; $X_{16}$ is T or A; $X_{17}$ F or Y; $X_{18}$ is K or R; $X_{19}$ is T or V and $X_{20}$ is K or R. In a specific embodiment, this core polypeptide can be used to induce an immune response against group 2 hemagglutinin subtypes. In certain embodiments, the immune response induced neutralizes 2 or more influenza virus group 2 hemagglutinin subtypes. In certain embodiments, the core polypeptide is acetylated at the N-terminus.

In certain embodiments, the core polypeptide is a fragment of a group 2 core polypeptide. In specific embodiments, the core polypeptide is a fragment of a group 2 core polypeptide, wherein the fragment lacks 1, 2, 3, 4, 5, 6, 7, 8, 9, 10(±5), 15(±5), 20(±5), 25(±5), 30(±5), or 35(±5) amino acids from either of a group 2 core polypeptide's N- or C-terminus. In some embodiments, the core polypeptide is a fragment of a group 2 core polypeptide, wherein the fragment lacks 24(±5) amino acids from its C-terminus. In specific embodiments, the core polypeptide is a fragment of a group 2 core polypeptide, wherein the fragment lacks 1, 2, 3, 4, 5, or more amino acids from both of a group 2 core polypeptide's N- and C-termini. In specific embodiments, the core polypeptide has an alpha-helical conformation.

In some embodiments, the core polypeptide is a group 2 core polypeptide that is not full length influenza virus HA. In some embodiments, the core polypeptide is a group 2 core polypeptide that is between 51 to 511, 51 to 500, 51 to 450, 51 to 400, 51 to 350, 51 to 300, 51 to 275, 51 to 250, 51 to 225, 51 to 200, 51 to 175, 51 to 150, 51 to 125, 51 to 100, or 51 to 75, 15 to 50, 20 to 50, 25 to 50, 15 to 37, 15 to 35, 20 to 37, 20 to 35, 15 to 30, 20 to 30 or 20 to 25 amino acids in length. In some embodiments, the core polypeptide is a group 2 core polypeptide that is less than 500, 450, 400, 350, 300, 275, 250, 225, 200, 175, 150, 125, 100, 95, 90, 85, 80, 75, 70, 65, 60, 55, 50, 45, 40, 35, 30 or 25 amino acids in length. In certain embodiments, the core polypeptide is a group 2 core polypeptide less than 150, 125, 95, 90, 85, 80, 75, 65, 60, 55, 50, 45 or 40 amino acids in length but at least 15, 20, 25, 30 or 35 amino acids in length.

In specific embodiments, the core polypeptide is a derivative of a group 2 core polypeptide, wherein the derivative comprises a group 2 core polypeptide with either 1, 2, 3, 4, 5, 6, 7, 8, 9, or 10(±5) amino acids attached to either of a group 2 core polypeptide's N- or C-terminus and wherein the core polypeptide maintains an alpha-helical conformation.

In specific embodiments, the core polypeptide is a derivative of a group 2 core polypeptide, wherein the derivative comprises a group 2 core polypeptide with either 1, 2, 3, 4, 5, 6, 7, 8, 9, or 10(±5) amino acids attached to both of a group 2 core polypeptide's N- and C-termini and wherein the core polypeptide maintains an alpha-helical conformation.

In a specific embodiment, the core polypeptide is an H1 core polypeptide comprising or consisting of the amino acid sequence:

(SEQ ID NO: 7)
RX₁ENLNKKVDDGFX₂DIWTYNAELLVLLENERTLDX₃HDSNVX₄NLY

Figure 6A:
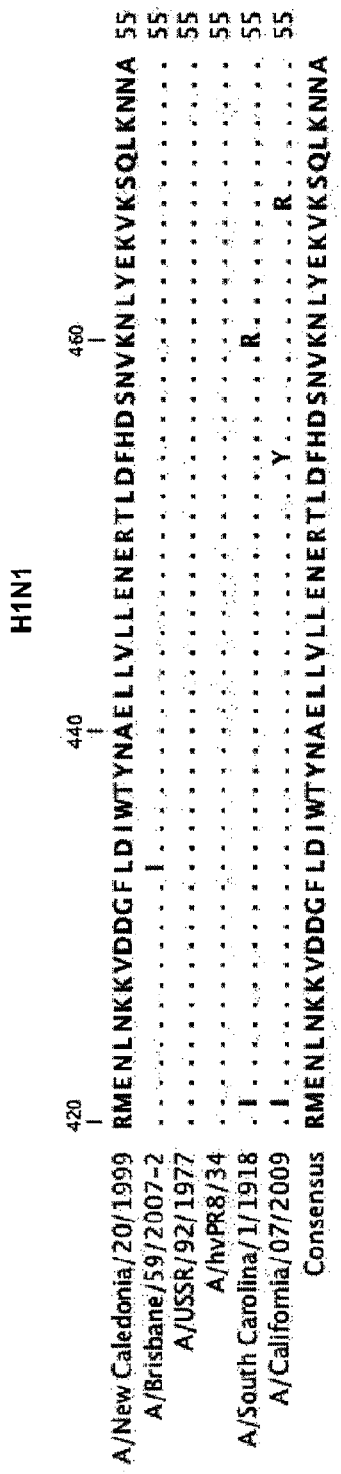

EKVX₅SQLKNNA, wherein $X_1$ is a hydrophobic amino acid; $X_2$ is a hydrophobic amino acid; $X_3$ is a hydrophobic amino acid; $X_4$ is a hydrophilic, basic amino acid, and $X_5$ is a hydrophilic, basic amino acid. In specific embodiments, $X_1$ is M or I; $X_2$ is L or I; $X_3$ is F or Y; $X_4$ is K or R; and $X_5$ is K or R. This sequence corresponds with amino acids 76-130 of an H1 subtype hemagglutinin numbered according to the classic H3 subtype numbering system. In certain embodiments, the core polypeptide is acetylated at the N-terminus. In a specific embodiment, a core polypeptide comprises any one of the amino acid sequences shown in FIG. 6A (SEQ ID NOS: 8-11) or a fragment thereof. In certain embodiments, the core polypeptide is acetylated at the N-terminus. In a specific embodiment, this core polypeptide can be used to induce an immune response against influenza virus strains of subtype H1. In certain embodiments, the immune response induced neutralizes strains of influenza virus subtype H1.

In certain embodiments, the core polypeptide is a fragment of an H1 core polypeptide. In specific embodiments, the core polypeptide is a fragment of a H1 core polypeptide, wherein the fragment lacks 1, 2, 3, 4, 5, 6, 7, 8, 9, 10(±5), 15(±5), 20(±5), 25(±5), 30(±5), or 35(±5) amino acids from either of an H1 core polypeptide's N- or C-terminus. In some embodiments, the core polypeptide is a fragment of an H1 core polypeptide, wherein the fragment lacks 24(±5) amino acids from its C-terminus. In specific embodiments, the core polypeptide is a fragment of an H1 core polypeptide, wherein the fragment lacks 1, 2, 3, 4, 5, or more amino acids from both of an H1 core polypeptide's N- and C-termini. In specific embodiments, the core polypeptide has an alpha-helical conformation.

In some embodiments, the core polypeptide is an H1 core polypeptide that is not full length influenza virus HA. In some embodiments, the core polypeptide is an H1 core polypeptide that is between 51 to 300, 51 to 275, 51 to 250, 51 to 225, 51 to 200, 51 to 175, 51 to 150, 51 to 125, 51 to 100, or 51 to 75, 15 to 50, 20 to 50, 25 to 50, 15 to 37, 15 to 35, 20 to 37, 20 to 35, 15 to 30, 20 to 30 or 20 to 25 amino acids in length. In some embodiments, the core polypeptide is an H1 core polypeptide that is less than 500, 450, 400, 350, 300, 275, 250, 225, 200, 175, 150, 125, 100, 95, 90, 85, 80, 75, 70, 65, 60, 55, 50, 45, 40, 35, 30 or 25 amino acids in length. In certain embodiments, the core polypeptide is an H1 polypeptide less than 150, 125, 95, 90, 85, 80, 75, 65, 60, 55, 50, 45 or 40 amino acids in length but at least 15, 20, 25, 30 or 35 amino acids in length.

In specific embodiments, the core polypeptide is a derivative of an H1 core polypeptide, wherein the derivative comprises an H1 core polypeptide with 1, 2, 3, 4, 5, 6, 7, 8, 9, or 10(±5) amino acids attached to either of the H1 core polypeptide's N- or C-terminus and wherein the core polypeptide maintains an alpha-helical conformation.

In specific embodiments, the core polypeptide is a derivative of an H1 core polypeptide, wherein the derivative comprises an H1 core polypeptide with 1, 2, 3, 4, 5, 6, 7, 8, 9, or 10(±5) amino acids attached to both of the H1 core polypeptide's N- or C-termini and wherein the core polypeptide maintains an alpha-helical conformation.

In a specific embodiment, the core polypeptide is an H2 core polypeptide comprising or consisting of the amino acid sequence:

(SEQ ID NO: 12)
RLENLNKKMEDGFLDVWTYNAELLVLMENERTLDFHDSNVKNLYX

Figure 6B:
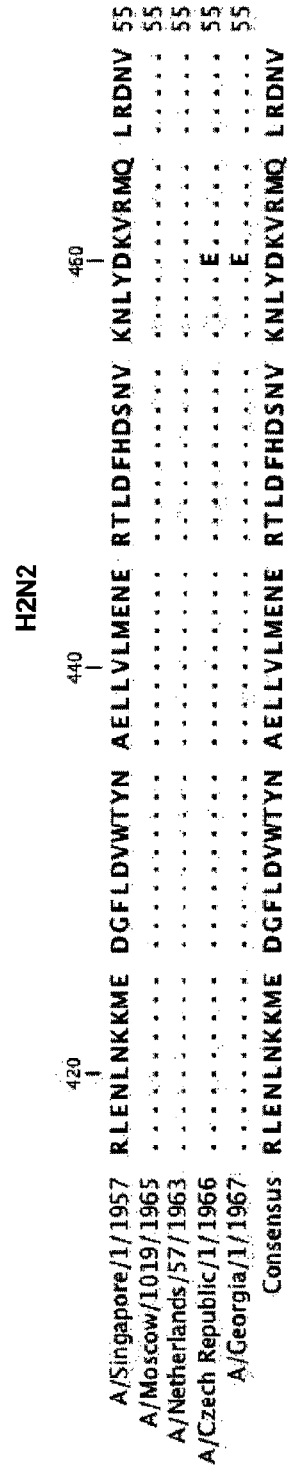

KVRMQLRDNV, wherein X is a hydrophilic, acidic amino acid. In specific embodiments, X is D or E. In certain embodiments, the core polypeptide is acetylated at the N-terminus. In a specific embodiment, a core polypeptide comprises any one of the amino acid sequences shown in FIG. 6B (SEQ ID NO: 13 or 14) or a fragment thereof. In certain embodiments, the core polypeptide is acetylated at the N-terminus. In a specific embodiment, this core polypeptide can be used to induce an immune response against influenza virus strains of subtype H2. In certain embodiments, the immune response induced neutralizes strains of influenza virus subtype H2.

In certain embodiments, the core polypeptide is a fragment of an H2 core polypeptide. In specific embodiments, the core polypeptide is a fragment of an H2 core polypeptide, wherein the fragment lacks 1, 2, 3, 4, 5, 6, 7, 8, 9, 10(±5), 15(±5), 20(±5), 25(±5), 30(±5), or 35(±5) amino acids from either of an H2 core polypeptide's N- or C-terminus. In some embodiments, the core polypeptide is a fragment of an H2 core polypeptide, wherein the fragment lacks 24(±5) amino acids from its C-terminus. In specific embodiments, the core polypeptide is a fragment of an H2 core polypeptide, wherein the fragment lacks 1, 2, 3, 4, 5, or more amino acids from both of an H2 core polypeptide's N- and C-termini. In specific embodiments, the core polypeptide has an alpha-helical conformation.

In some embodiments, the core polypeptide is an H2 core polypeptide that is not full length influenza virus HA. In some embodiments, the core polypeptide is an H2 core polypeptide that is between 51 to 300, 51 to 275, 51 to 250, 51 to 225, 51 to 200, 51 to 175, 51 to 150, 51 to 125, 51 to 100, or 51 to 75, 15 to 50, 20 to 50, 25 to 50, 15 to 37, 15 to 35, 20 to 37, 20 to 35, 15 to 30, 20 to 30 or 20 to 25 amino acids in length. In some embodiments, the core polypeptide is an H2 core polypeptide that is less than 500, 450, 400, 350, 300, 275, 250, 225, 200, 175, 150, 125, 100, 95, 90, 85, 80, 75, 70, 65, 60, 55, 50, 45, 40, 35, 30 or 25 amino acids in length. In certain embodiments, the core polypeptide is an H2 polypeptide less than 150, 125, 95, 90, 85, 80, 75, 65, 60, 55, 50, 45 or 40 amino acids in length but at least 15, 20, 25, 30 or 35 amino acids in length.

In specific embodiments, the core polypeptide is a derivative of an H2 core polypeptide, wherein the derivative comprises an H2 core polypeptide with 1, 2, 3, 4, 5, 6, 7, 8, 9, or 10(±5) amino acids attached to either of the H2 core polypeptide's N- or C-terminus and wherein the core polypeptide maintains an alpha-helical conformation.

In specific embodiments, the core polypeptide is a derivative of an H2 core polypeptide, wherein the derivative comprises an H2 core polypeptide with 1, 2, 3, 4, 5, 6, 7, 8, 9, or 10(±5) amino acids attached to both of the H2 core polypeptide's N- and C-termini and wherein the core polypeptide maintains an alpha-helical conformation.

In a specific embodiment, the core polypeptide is an H3 core polypeptide comprising or consisting of the amino acid sequence:

```
                                        (SEQ ID NO: 15)
RIQDLEKYVEDTKIDLWSYNAELLVALENQHTIDLTDSEMNKLFEX₁T

X₂X₃QLRENA,
``` wherein $X_1$ is a hydrophilic, basic amino acid; $X_2$ is a hydrophilic, basic amino acid, and $X_3$ is a hydrophilic, basic amino acid. In specific embodiments, $X_1$ is K or R; $X_2$ is K or R, and $X_3$ is K or R. In certain embodiments, the core polypeptide is acetylated at the N-terminus. In a specific embodiment, a core polypeptide comprises any one of the amino acid sequences shown in FIG. 6C (SEQ ID NOS: 16-18) or a fragment thereof. In certain embodiments, the core polypeptide is acetylated at the N-terminus. In a specific embodiment, this core polypeptide can be used to induce an immune response against influenza virus strains of subtype H3. In certain embodiments, the immune response induced neutralizes strains of influenza virus subtype H3.

In certain embodiments, the core polypeptide is a fragment of an H3 core polypeptide. In specific embodiments, the core polypeptide is a fragment of an H3 core polypeptide, wherein the fragment lacks 1, 2, 3, 4, 5, 6, 7, 8, 9, 10(±5), 15(±5), 20(±5), 25(±5), 30(±5), or 35(±5) amino acids from either of an H3 core polypeptide's N- or C-terminus. In some embodiments, the core polypeptide is a fragment of an H3 core polypeptide, wherein the fragment lacks 24(±5) amino acids from its C-terminus. In specific embodiments, the core polypeptide is a fragment of an H3 core polypeptide, wherein the fragment lacks 1, 2, 3, 4, 5, or more amino acids from both of an H3 core polypeptide's N- and C-termini. In specific embodiments, the core polypeptide has an alpha-helical conformation.

In some embodiments, the core polypeptide is an H3 core polypeptide that is not full length influenza virus HA. In some embodiments, the core polypeptide is an H3 core polypeptide that is between 51 to 300, 51 to 275, 51 to 250, 51 to 225, 51 to 200, 51 to 175, 51 to 150, 51 to 125, 51 to 100, or 51 to 75, 15 to 50, 20 to 50, 25 to 50, 15 to 37, 15 to 35, 20 to 37, 20 to 35, 15 to 30, 20 to 30 or 20 to 25 amino acids in length. In some embodiments, the core polypeptide is an H3 core polypeptide that is less than 500, 450, 400, 350, 300, 275, 250, 225, 200, 175, 150, 125, 100, 95, 90, 85, 80, 75, 70, 65, 60, 55, 50, 45, 40, 35, 30 or 25 amino acids in length. In certain embodiments, the core polypeptide is an H3 polypeptide less than 150, 125, 95, 90, 85, 80, 75, 65, 60, 55, 50, 45 or 40 amino acids in length but at least 15, 20, 25, 30 or 35 amino acids in length.

In specific embodiments, the core polypeptide is a derivative of an H3 core polypeptide, wherein the derivative comprises an H3 core polypeptide with 1, 2, 3, 4, 5, 6, 7, 8, 9, or 10(±5) amino acids attached to either of the H3 core polypeptide's N- or C-terminus and wherein the core polypeptide maintains an alpha-helical conformation.

In specific embodiments, the core polypeptide is a derivative of an H3 core polypeptide, wherein the derivative comprises an H3 core polypeptide with 1, 2, 3, 4, 5, 6, 7, 8, 9, or 10(±5) amino acids attached to both of the H3 core polypeptide's N- and C-termini and wherein the core polypeptide maintains an alpha-helical conformation.

In a specific embodiment, the core polypeptide is an H4 core polypeptide comprising or consisting of the amino acid sequence:

```
                                        (SEQ ID NO: 19)
RIQDLEKYVEDTKIDLWSYNAELLVALENQHTIDVTDSEMNKLFERV

RX₁QLRENA,
``` wherein $X_1$ is a hydrophilic, basic amino acid. In specific embodiments, $X_1$ is R or H. In certain embodiments, the core polypeptide is acetylated at the N-terminus. In a specific embodiment, a core polypeptide comprises any one of the amino acid sequences shown in FIG. 6F (SEQ ID NOS: 20 and 21) or a fragment thereof. In certain embodiments, the core polypeptide is acetylated at the N-terminus. In a specific embodiment, this core polypeptide can be used to induce an immune response against influenza virus strains of subtype H4. In certain embodiments, the immune response induced neutralizes strains of influenza virus subtype H4.

In certain embodiments, the core polypeptide is a fragment of an H4 core polypeptide. In specific embodiments, the core polypeptide is a fragment of an H4 core polypeptide, wherein the fragment lacks 1, 2, 3, 4, 5, 6, 7, 8, 9, 10(±5), 15(±5), 20(±5), 25(±5), 30(±5), or 35(±5) amino acids from either of an H4 core polypeptide's N- or C-terminus. In some embodiments, the core polypeptide is a fragment of an H4 core polypeptide, wherein the fragment lacks 24(±5) amino acids from its C-terminus. In specific embodiments, the core polypeptide is a fragment of an H4 core polypeptide, wherein the fragment lacks 1, 2, 3, 4, 5, or more amino acids from both of an H4 core polypeptide's N- and C-termini. In specific embodiments, the core polypeptide has an alpha-helical conformation.

In some embodiments, the core polypeptide is an H4 core polypeptide that is not full length influenza virus HA. In some embodiments, the core polypeptide is an H4 core polypeptide that is between 51 to 300, 51 to 275, 51 to 250, 51 to 225, 51 to 200, 51 to 175, 51 to 150, 51 to 125, 51 to 100, or 51 to 75, 15 to 50, 20 to 50, 25 to 50, 15 to 37, 15 to 35, 20 to 37, 20 to 35, 15 to 30, 20 to 30 or 20 to 25 amino acids in length. In some embodiments, the core polypeptide is an H4 core polypeptide that is less than 500, 450, 400, 350, 300, 275, 250, 225, 200, 175, 150, 125, 100, 95, 90, 85, 80, 75, 70, 65, 60, 55, 50, 45, 40, 35, 30 or 25 amino acids in length. In certain embodiments, the core polypeptide is an H4 polypeptide less than 150, 125, 95, 90, 85, 80, 75, 65, 60, 55, 50, 45 or 40 amino acids in length but at least 15, 20, 25, 30 or 35 amino acids in length.

In specific embodiments, the core polypeptide is a derivative of an H4 core polypeptide, wherein the derivative comprises an H4 core polypeptide with 1, 2, 3, 4, 5, 6, 7, 8, 9, or 10(±5) amino acids attached to either of the H4 core polypeptide's N- or C-terminus and wherein the core polypeptide maintains an alpha-helical conformation.

In specific embodiments, the core polypeptide is a derivative of an H4 core polypeptide, wherein the derivative comprises an H4 core polypeptide with 1, 2, 3, 4, 5, 6, 7, 8, 9, or 10(±5) amino acids attached to both of the H4 core polypeptide's N- and C-termini and wherein the core polypeptide maintains an alpha-helical conformation.

In a specific embodiment, the core polypeptide is an H5 core polypeptide comprising or consisting of the amino acid sequence:

(SEQ ID NO: 22)
RIENLNKKMEDGFLDVWTYNAELLVLMENERTLDFHDSNVKNLYDK

VRLQLRDNA.

In certain embodiments, the core polypeptide is acetylated at the N-terminus. In a specific embodiment, a core polypeptide comprises any one of the amino acid sequences shown in FIG. 6D (SEQ ID NO: 22) or a fragment thereof. In certain embodiments, the core polypeptide is acetylated at the N-terminus. In a specific embodiment, this core polypeptide can be used to induce an immune response against influenza virus strains of subtype H5. In certain embodiments, the immune response induced neutralizes strains of influenza virus subtype H5.

In certain embodiments, the core polypeptide is a fragment of an H5 core polypeptide. In specific embodiments, the core polypeptide is a fragment of an H5 core polypeptide, wherein the fragment lacks 1, 2, 3, 4, 5, 6, 7, 8, 9, 10(±5), 15(±5), 20(±5), 25(±5), 30(±5), or 35(±5) amino acids from either of an H5 core polypeptide's N- or C-terminus. In some embodiments, the core polypeptide is a fragment of an H5 core polypeptide, wherein the fragment lacks 24(±5) amino acids from its C-terminus. In specific embodiments, the core polypeptide is a fragment of an H5 core polypeptide, wherein the fragment lacks 1, 2, 3, 4, 5, or more amino acids from both of the H5 core polypeptide's N- and C-termini. In specific embodiments, the core polypeptide has an alpha-helical conformation.

In some embodiments, the core polypeptide is an H5 core polypeptide that is not full length influenza virus HA. In some embodiments, the core polypeptide is an H5 core polypeptide that is between 51 to 511, 51 to 500, 51 to 450, 51 to 400, 51 to 350, 51 to 300, 51 to 275, 51 to 250, 51 to 225, 51 to 200, 51 to 175, 51 to 150, 51 to 125, 51 to 100, or 51 to 75, 15 to 50, 20 to 50, 25 to 50, 15 to 37, 15 to 35, 20 to 37, 20 to 35, 15 to 30, 20 to 30 or 20 to 25 amino acids in length. In some embodiments, the core polypeptide is an H5 core polypeptide that is less than 500, 450, 400, 350, 300, 275, 250, 225, 200, 175, 150, 125, 100, 95, 90, 85, 80, 75, 70, 65, 60, 55, 50, 45, 40, 35, 30 or 25 amino acids in length. In certain embodiments, the core polypeptide is an H5 polypeptide less than 150, 125, 95, 90, 85, 80, 75, 65, 60, 55, 50, 45 or 40 amino acids in length but at least 15, 20, 25, 30 or 35 amino acids in length.

In specific embodiments, the core polypeptide is a derivative of an H5 core polypeptide, wherein the derivative comprises an H5 core polypeptide with 1, 2, 3, 4, 5, 6, 7, 8, 9, or 10(±5) amino acids attached to either of the H5 core polypeptide's N- or C-terminus and wherein the core polypeptide maintains an alpha-helical conformation.

In specific embodiments, the core polypeptide is a derivative of an H5 core polypeptide, wherein the derivative comprises an H5 core polypeptide with 1, 2, 3, 4, 5, 6, 7, 8, 9, or 10(±5) amino acids attached to both of the H5 core polypeptide's N- and C-termini and wherein the core polypeptide maintains an alpha-helical conformation.

In a specific embodiment, the core polypeptide is an H6 core polypeptide comprising or consisting of the amino acid sequence:

(SEQ ID NO: 23)
RIX$_1$NX$_2$NKRMEDGFLDVWTYNAELLVLLENX$_3$RTLDX$_4$HDANVKX$_5$L

X$_6$EKVKSX$_7$LX$_8$DNA, wherein $X_1$ is G or D; $X_2$ is a hydrophobic amino acid; $X_3$ is a hydrophilic amino acid; $X_4$ is a hydrophobic amino acid; $X_5$ is a hydrophilic amino acid; $X_6$ is H or Y; $X_7$ is Q or L and $X_8$ is a hydrophilic, basic amino acid. In specific embodiments, $X_1$ is G or D; $X_2$ is L or M; $X_3$ is E or G; $X_4$ is L or M; $X_5$ N or S; $X_6$ is H or Y; $X_7$ is Q or L and $X_8$ is R or K. In certain embodiments, the core polypeptide is acetylated at the N-terminus. In a specific embodiment, a core polypeptide comprises any one of the amino acid sequences shown in FIG. 6G (SEQ ID NOS: 24-29) or a fragment thereof. In certain embodiments, the core polypeptide is acetylated at the N-terminus. In a specific embodiment, this core polypeptide can be used to induce an immune response against influenza virus strains of subtype H6. In certain embodiments, the immune response induced neutralizes strains of influenza virus subtype H6.

In certain embodiments, the core polypeptide is a fragment of an H6 core polypeptide. In specific embodiments, the core polypeptide is a fragment of an H6 core polypeptide, wherein the fragment lacks 1, 2, 3, 4, 5, 6, 7, 8, 9, 10(±5), 15(±5), 20(±5), 25(±5), 30(±5), or 35(±5) amino acids from either of an H6 core polypeptide's N- or C-terminus. In some embodiments, the core polypeptide is a fragment of an H6 core polypeptide, wherein the fragment lacks 24(±5) amino acids from its C-terminus. In specific embodiments, the core polypeptide is a fragment of an H6 core polypeptide, wherein the fragment lacks 1, 2, 3, 4, 5, or more amino acids from both of an H6 core polypeptide's N- and C-termini. In specific embodiments, the core polypeptide has an alpha-helical conformation.

In some embodiments, the core polypeptide is an H6 core polypeptide that is not full length influenza virus HA. In some embodiments, the core polypeptide is an H6 core polypeptide that is between 51 to 300, 51 to 275, 51 to 250, 51 to 225, 51 to 200, 51 to 175, 51 to 150, 51 to 125, 51 to 100, or 51 to 75, 15 to 50, 20 to 50, 25 to 50, 15 to 37, 15 to 35, 20 to 37, 20 to 35, 15 to 30, 20 to 30 or 20 to 25 amino acids in length. In some embodiments, the core polypeptide is an H6 core polypeptide that is less than 500, 450, 400, 350, 300, 275, 250, 225, 200, 175, 150, 125, 100, 95, 90, 85, 80, 75, 70, 65, 60, 55, 50, 45, 40, 35, 30 or 25 amino acids in length. In certain embodiments, the core polypeptide is an H6 polypeptide less than 150, 125, 95, 90, 85, 80, 75, 65, 60, 55, 50, 45 or 40 amino acids in length but at least 15, 20, 25, 30 or 35 amino acids in length.

In specific embodiments, the core polypeptide is a derivative of an H6 core polypeptide, wherein the derivative comprises an H6 core polypeptide with 1, 2, 3, 4, 5, 6, 7, 8, 9, or 10($\pm$5) amino acids attached to either of the H6 core polypeptide's N- or C-terminus and wherein the core polypeptide maintains an alpha-helical conformation.

In specific embodiments, the core polypeptide is a derivative of an H6 core polypeptide, wherein the derivative comprises an H6 core polypeptide with 1, 2, 3, 4, 5, 6, 7, 8, 9, or 10($\pm$5) amino acids attached to both of the H6 core polypeptide's N- and C-termini and wherein the core polypeptide maintains an alpha-helical conformation.

In a specific embodiment, the core polypeptide is an H7 core polypeptide comprising or consisting of the amino acid sequence:

(SEQ ID NO: 30)
QIGNVINWTRDX$_1$MTEX$_2$WSYNAELLVAMENQHTIDLADSEMX$_3$KLY

ERVX$_4$KQLRENA, wherein X$_1$ is a hydrophobic amino acid or a hydrophilic amino acid; X$_2$ is a hydrophobic amino acid; X$_3$ is a hydrophilic amino acid, and X$_4$ is a hydrophilic, basic amino acid. In specific embodiments, X$_1$ is A or S; X$_2$ is V or I; X$_3$ is N or S; and X$_4$ is K or R. In certain embodiments, the core polypeptide is acetylated at the N-terminus. In a specific embodiment, a core polypeptide comprises any one of the amino acid sequences shown in FIG. 6E (SEQ ID NOS: 31-35) or a fragment thereof. In certain embodiments, the core polypeptide is acetylated at the N-terminus. In a specific embodiment, this core polypeptide can be used to induce an immune response against influenza virus strains of subtype H7. In certain embodiments, the immune response induced neutralizes strains of influenza virus subtype H7.

In certain embodiments, the core polypeptide is a fragment of an H7 core polypeptide. In specific embodiments, the core polypeptide is a fragment of an H7 core polypeptide, wherein the fragment lacks 1, 2, 3, 4, 5, 6, 7, 8, 9, 10($\pm$5), 15($\pm$5), 20($\pm$5), 25($\pm$5), 30($\pm$5), or 35($\pm$5) amino acids from either of an H7 core polypeptide's N- or C-terminus. In some embodiments, the core polypeptide is a fragment of an H7 core polypeptide, wherein the fragment lacks 24($\pm$5) amino acids from its C-terminus. In specific embodiments, the core polypeptide is a fragment of an H7 core polypeptide, wherein the fragment lacks 1, 2, 3, 4, 5, or more amino acids from both of an H7 core polypeptide's N- and C-termini. In specific embodiments, the core polypeptide has an alpha-helical conformation.

In some embodiments, the core polypeptide is an H7 core polypeptide that is not full length influenza virus HA. In some embodiments, the core polypeptide is an H7 core polypeptide that is between 51 to 300, 51 to 275, 51 to 250, 51 to 225, 51 to 200, 51 to 175, 51 to 150, 51 to 125, 51 to 100, or 51 to 75, 15 to 50, 20 to 50, 25 to 50, 15 to 37, 15 to 35, 20 to 37, 20 to 35, 15 to 30, 20 to 30 or 20 to 25 amino acids in length. In some embodiments, the core polypeptide is an H7 core polypeptide that is less than 500, 450, 400, 350, 300, 275, 250, 225, 200, 175, 150, 125, 100, 95, 90, 85, 80, 75, 70, 65, 60, 55, 50, 45, 40, 35, 30 or 25 amino acids in length. In certain embodiments, the core polypeptide is an H7 polypeptide less than 150, 125, 95, 90, 85, 80, 75, 65, 60, 55, 50, 45 or 40 amino acids in length but at least 15, 20, 25, 30 or 35 amino acids in length.

In specific embodiments, the core polypeptide is a derivative of an H7 core polypeptide, wherein the derivative comprises an H7 core polypeptide with 1, 2, 3, 4, 5, 6, 7, 8, 9, or 10($\pm$5) amino acids attached to either of the H7 core polypeptide's N- or C-terminus and wherein the core polypeptide maintains an alpha-helical conformation.

In specific embodiments, the core polypeptide is a derivative of an H7 core polypeptide, wherein the derivative comprises an H7 core polypeptide with either 1, 2, 3, 4, 5, 6, 7, 8, 9, or 10($\pm$5) amino acids attached to both of the H7 core polypeptide's N- and C-termini and wherein the core polypeptide maintains an alpha-helical conformation.

In a specific embodiment, the core polypeptide is an H8 core polypeptide comprising or consisting of the amino acid sequence:

(SEQ ID NO: 36)
RINMINDKIDDQIEX$_1$LWAYNAELLVLLENQKTLDEHDSNVKNLFDEVKR

RLSANA, wherein X$_1$ is a hydrophilic amino acid. In certain embodiments, X$_1$ is D or N. In a specific embodiment, a core polypeptide comprises any one of the amino acid sequences shown in FIG. 6H (SEQ ID NOS: 37 and 38) or a fragment thereof. In a specific embodiment, this core polypeptide can be used to induce an immune response against influenza virus strains of subtype H8. In certain embodiments, the immune response induced neutralizes strains of influenza virus subtype H8.

In certain embodiments, the core polypeptide is a fragment of an H8 core polypeptide. In specific embodiments, the core polypeptide is a fragment of an H8 core polypeptide, wherein the fragment lacks 1, 2, 3, 4, 5, 6, 7, 8, 9, 10($\pm$5), 15($\pm$5), 20($\pm$5), 25($\pm$5), 30($\pm$5), or 35($\pm$5) amino acids from either of an H8 core polypeptide's N- or C-terminus. In some embodiments, the core polypeptide is a fragment of an H8 core polypeptide, wherein the fragment lacks 24($\pm$5) amino acids from its C-terminus. In specific embodiments, the core polypeptide is a fragment of an H8 core polypeptide, wherein the fragment lacks 1, 2, 3, 4, 5, or more amino acids from both of an H8 core polypeptide's N- and C-termini. In specific embodiments, the core polypeptide has an alpha-helical conformation.

In some embodiments, the core polypeptide is an H8 core polypeptide that is not full length influenza virus HA. In some embodiments, the core polypeptide is an H8 core polypeptide that is between 51 to 300, 51 to 275, 51 to 250, 51 to 225, 51 to 200, 51 to 175, 51 to 150, 51 to 125, 51 to 100, or 51 to 75, 15 to 50, 20 to 50, 25 to 50, 15 to 37, 15 to 35, 20 to 37, 20 to 35, 15 to 30, 20 to 30 or 20 to 25 amino acids in length. In some embodiments, the core polypeptide is an H8 core polypeptide that is less than 500, 450, 400, 350, 300, 275, 250, 225, 200, 175, 150, 125, 100, 95, 90, 85, 80, 75, 70, 65, 60, 55, 50, 45, 40, 35, 30 or 25 amino acids in length. In certain embodiments, the core polypeptide is an H8 polypeptide less than 150, 125, 95, 90, 85, 80, 75, 65, 60, 55, 50, 45 or 40 amino acids in length but at least 15, 20, 25, 30 or 35 amino acids in length.

In specific embodiments, the core polypeptide is a derivative of an H8 core polypeptide, wherein the derivative comprises an H8 core polypeptide with 1, 2, 3, 4, 5, 6, 7, 8, 9, or 10(±5) amino acids attached to either of the H8 core polypeptide's N- or C-terminus and wherein the core polypeptide maintains an alpha-helical conformation.

In specific embodiments, the core polypeptide is a derivative of an H8 core polypeptide, wherein the derivative comprises an H8 core polypeptide with 1, 2, 3, 4, 5, 6, 7, 8, 9, or 10(±5) amino acids attached to both of the H8 core polypeptide's N- and C-termini and wherein the core polypeptide maintains an alpha-helical conformation.

In a specific embodiment, the core polypeptide is an H9 core polypeptide comprising or consisting of the amino acid sequence:

(SEQ ID NO: 39)
RLNMINNKIDDQIQDX$_1$WAYNAELLVLLENQKTLDEHDANVNNLYN

KVKRALGSNA, wherein X$_1$ is a hydrophobic amino acid. In specific embodiments X$_1$ is V or I. In certain embodiments, the core polypeptide is acetylated at the N-terminus. In a specific embodiment, a core polypeptide comprises any one of the amino acid sequences shown in FIG. 6I (SEQ ID NOS: 40 and 41) or a fragment thereof. In certain embodiments, the core polypeptide is acetylated at the N-terminus. In a specific embodiment, this core polypeptide can be used to induce an immune response against influenza virus strains of subtype H9. In certain embodiments, the immune response induced neutralizes strains of influenza virus subtype H9.

In certain embodiments, the core polypeptide is a fragment of an H9 core polypeptide. In specific embodiments, the core polypeptide is a fragment of an H9 core polypeptide, wherein the fragment lacks 1, 2, 3, 4, 5, 6, 7, 8, 9, 10(±5), 15(±5), 20(±5), 25(±5), 30(±5), or 35(±5) amino acids from either of an H9 core polypeptide's N- or C-terminus. In some embodiments, the core polypeptide is a fragment of an H9 core polypeptide, wherein the fragment lacks 24(±5) amino acids from its C-terminus. In specific embodiments, the core polypeptide is a fragment of an H9 core polypeptide, wherein the fragment lacks 1, 2, 3, 4, 5, or more amino acids from both of an H9 core polypeptide's N- and C-termini. In specific embodiments, the core polypeptide has an alpha-helical conformation.

In some embodiments, the core polypeptide is an H9 core polypeptide that is not full length influenza virus HA. In some embodiments, the core polypeptide is an H9 core polypeptide that is between 51 to 300, 51 to 275, 51 to 250, 51 to 225, 51 to 200, 51 to 175, 51 to 150, 51 to 125, 51 to 100, or 51 to 75, 15 to 50, 20 to 50, 25 to 50, 15 to 37, 15 to 35, 20 to 37, 20 to 35, 15 to 30, 20 to 30 or 20 to 25 amino acids in length. In some embodiments, the core polypeptide is an H9 core polypeptide that is less than 500, 450, 400, 350, 300, 275, 250, 225, 200, 175, 150, 125, 100, 95, 90, 85, 80, 75, 70, 65, 60, 55, 50, 45, 40, 35, 30 or 25 amino acids in length. In certain embodiments, the core polypeptide is an H9 polypeptide less than 150, 125, 95, 90, 85, 80, 75, 65, 60, 55, 50, 45 or 40 amino acids in length but at least 15, 20, 25, 30 or 35 amino acids in length.

In specific embodiments, the core polypeptide is a derivative of an H9 core polypeptide, wherein the derivative comprises an H9 core polypeptide with 1, 2, 3, 4, 5, 6, 7, 8, 9, or 10(±5) amino acids attached to either of the H9 core polypeptide's N- or C-terminus and wherein the core polypeptide maintains an alpha-helical conformation.

In specific embodiments, the core polypeptide is a derivative of an H9 core polypeptide, wherein the derivative comprises an H9 core polypeptide with 1, 2, 3, 4, 5, 6, 7, 8, 9, or 10(±5) amino acids attached to both of the H9 core polypeptide's N- and C-termini and wherein the core polypeptide maintains an alpha-helical conformation.

In a specific embodiment, the core polypeptide is an H10 core polypeptide comprising or consisting of the amino acid sequence:

(SEQ ID NO: 42)
QIGNVINWTKDSITDIWTYX$_1$AELLVAMENQHTIDMADSEMLNLYER

VRKQLRQNA, wherein X$_1$ is a hydrophilic amino acid. In specific embodiments, X$_1$ is Q or N. In certain embodiments, the core polypeptide is acetylated at the N-terminus. In a specific embodiment, a core polypeptide comprises any one of the amino acid sequences shown in FIG. 6J (SEQ ID NOS: 43 and 44) or a fragment thereof. In certain embodiments, the core polypeptide is acetylated at the N-terminus. In a specific embodiment, this core polypeptide can be used to induce an immune response against influenza virus strains of subtype H10. In certain embodiments, the immune response induced neutralizes strains of influenza virus subtype H10.

In certain embodiments, the core polypeptide is a fragment of an H10 core polypeptide. In specific embodiments, the core polypeptide is a fragment of an H10 core polypeptide, wherein the fragment lacks 1, 2, 3, 4, 5, 6, 7, 8, 9, 10(±5), 15(±5), 20(±5), 25(±5), 30(±5), or 35(±5) amino acids from either of an H10 core polypeptide's N- or C-terminus. In some embodiments, the core polypeptide is a fragment of an H10 core polypeptide, wherein the fragment lacks 24(±5) amino acids from its C-terminus. In specific embodiments, the core polypeptide is a fragment of an H10 core polypeptide, wherein the fragment lacks 1, 2, 3, 4, 5, or more amino acids from both of an H10 core polypeptide's N- and C-termini. In specific embodiments, the core polypeptide has an alpha-helical conformation.

In some embodiments, the core polypeptide is an H10 core polypeptide that is not full length influenza virus HA. In some embodiments, the core polypeptide is an H10 core polypeptide that is between 51 to 300, 51 to 275, 51 to 250, 51 to 225, 51 to 200, 51 to 175, 51 to 150, 51 to 125, 51 to 100, or 51 to 75, 15 to 50, 20 to 50, 25 to 50, 15 to 37, 15 to 35, 20 to 37, 20 to 35, 15 to 30, 20 to 30 or 20 to 25 amino acids in length. In some embodiments, the core polypeptide is an H10 core polypeptide that is less than 500, 450, 400, 350, 300, 275, 250, 225, 200, 175, 150, 125, 100, 95, 90, 85, 80, 75, 70, 65, 60, 55, 50, 45, 40, 35, 30 or 25 amino acids in length. In certain embodiments, the core polypeptide is an H10 polypeptide less than 150, 125, 95, 90, 85, 80, 75, 65, 60, 55, 50, 45 or 40 amino acids in length but at least 15, 20, 25, 30 or 35 amino acids in length.

In specific embodiments, the core polypeptide is a derivative of an H10 core polypeptide, wherein the derivative comprises an H10 core polypeptide with 1, 2, 3, 4, 5, 6, 7, 8, 9, or 10(±5) amino acids attached to either of the H10 core polypeptide's N- or C-terminus and wherein the core polypeptide maintains an alpha-helical conformation.

In specific embodiments, the core polypeptide is a derivative of an H10 core polypeptide, wherein the derivative comprises an H10 core polypeptide with 1, 2, 3, 4, 5, 6, 7, 8, 9, or 10(±5) amino acids attached to both of the H10 core polypeptide's N- and C-termini and wherein the core polypeptide maintains an alpha-helical conformation.

In a specific embodiment, the core polypeptide is an H11 core polypeptide comprising or consisting of the amino acid sequence:

```
                                       (SEQ ID NO: 45)
RINQLSKHVDDSVX₁DIWSYNAQLLVLLENEKTLDLHDSNVRNLHEK

VRRMLKDNA,
``` wherein X₁ is a hydrophobic amino acid. In specific embodiments, X₁ is V or I. In certain embodiments, the core polypeptide is acetylated at the N-terminus. In a specific embodiment, a core polypeptide comprises any one of the amino acid sequences shown in FIG. 6K (SEQ ID NOS: 46 and 47) or a fragment thereof. In certain embodiments, the core polypeptide is acetylated at the N-terminus. In a specific embodiment, this core polypeptide can be used to induce an immune response against influenza virus strains of subtype H11. In certain embodiments, the immune response induced neutralizes strains of influenza virus subtype H11.

In certain embodiments, the core polypeptide is a fragment of an H11 core polypeptide. In specific embodiments, the core polypeptide is a fragment of an H11 core polypeptide, wherein the fragment lacks 1, 2, 3, 4, 5, 6, 7, 8, 9, 10(±5), 15(±5), 20(±5), 25(±5), 30(±5), or 35(±5) amino acids from either of an H11 core polypeptide's N- or C-terminus. In some embodiments, the core polypeptide is a fragment of an H11 core polypeptide, wherein the fragment lacks 24(±5) amino acids from its C-terminus. In specific embodiments, the core polypeptide is a fragment of an H11 core polypeptide, wherein the fragment lacks 1, 2, 3, 4, 5, or more amino acids from both of an H11 core polypeptide's N- and C-termini. In specific embodiments, the core polypeptide has an alpha-helical conformation.

In some embodiments, the core polypeptide is an H11 core polypeptide that is not full length influenza virus HA. In some embodiments, the core polypeptide is an H11 core polypeptide that is between 51 to 300, 51 to 275, 51 to 250, 51 to 225, 51 to 200, 51 to 175, 51 to 150, 51 to 125, 51 to 100, or 51 to 75, 15 to 50, 20 to 50, 25 to 50, 15 to 37, 15 to 35, 20 to 37, 20 to 35, 15 to 30, 20 to 30 or 20 to 25 amino acids in length. In some embodiments, the core polypeptide is an H11 core polypeptide that is less than 500, 450, 400, 350, 300, 275, 250, 225, 200, 175, 150, 125, 100, 95, 90, 85, 80, 75, 70, 65, 60, 55, 50, 45, 40, 35, 30 or 25 amino acids in length. In certain embodiments, the core polypeptide is an H11 polypeptide less than 150, 125, 95, 90, 85, 80, 75, 65, 60, 55, 50, 45 or 40 amino acids in length but at least 15, 20, 25, 30 or 35 amino acids in length.

In specific embodiments, the core polypeptide is a derivative of an H11 core polypeptide, wherein the derivative comprises an H11 core polypeptide with 1, 2, 3, 4, 5, 6, 7, 8, 9, or 10(±5) amino acids attached to either of the H11 core polypeptide's N- or C-terminus and wherein the core polypeptide maintains an alpha-helical conformation.

In specific embodiments, the core polypeptide is a derivative of an H11 core polypeptide, wherein the derivative comprises an H11 core polypeptide with 1, 2, 3, 4, 5, 6, 7, 8, 9, or 10(±5) amino acids attached to both of the H11 core polypeptide's N- and C-termini and wherein the core polypeptide maintains an alpha-helical conformation.

In a specific embodiment, the core polypeptide is an H12 core polypeptide comprising or consisting of the amino acid sequence:

```
                                       (SEQ ID NO: 48)
RINMINSKIDDQITDIWAYNAELLVLLENQKTLDEHDANVRNLHDRV

RRX₁LX₂ENA,
``` wherein X₁ is a hydrophobic amino acid and X₂ is a hydrophilic, basic amino acid. In specific embodiments, X₁ is V or I and X₂ is R or K. In certain embodiments, the core polypeptide is acetylated at the N-terminus. In a specific embodiment, a core polypeptide comprises any one of the amino acid sequences shown in FIG. 6L (SEQ ID NOS: 49 and 50) or a fragment thereof. In certain embodiments, the core polypeptide is acetylated at the N-terminus. In a specific embodiment, this core polypeptide can be used to induce an immune response against influenza virus strains of subtype H12. In certain embodiments, the immune response induced neutralizes strains of influenza virus subtype H12.

In certain embodiments, the core polypeptide is a fragment of an H12 core polypeptide. In specific embodiments, the core polypeptide is a fragment of an H12 core polypeptide, wherein the fragment lacks 1, 2, 3, 4, 5, 6, 7, 8, 9, 10(±5), 15(±5), 20(±5), 25(±5), 30(±5), or 35(±5) amino acids from either of an H12 core polypeptide's N- or C-terminus. In some embodiments, the core polypeptide is a fragment of an H12 core polypeptide, wherein the fragment lacks 24(±5) amino acids from its C-terminus. In specific embodiments, the core polypeptide is a fragment of an H12 core polypeptide, wherein the fragment lacks 1, 2, 3, 4, 5, or more amino acids from both of an H12 core polypeptide's N- and C-termini. In specific embodiments, the core polypeptide has an alpha-helical conformation.

In some embodiments, the core polypeptide is an H12 core polypeptide that is not full length influenza virus HA. In some embodiments, the core polypeptide is an H12 core polypeptide that is between 51 to 300, 51 to 275, 51 to 250, 51 to 225, 51 to 200, 51 to 175, 51 to 150, 51 to 125, 51 to 100, or 51 to 75, 15 to 50, 20 to 50, 25 to 50, 15 to 37, 15 to 35, 20 to 37, 20 to 35, 15 to 30, 20 to 30 or 20 to 25 amino acids in length. In some embodiments, the core polypeptide is an H12 core polypeptide that is less than 500, 450, 400, 350, 300, 275, 250, 225, 200, 175, 150, 125, 100, 95, 90, 85, 80, 75, 70, 65, 60, 55, 50, 45, 40, 35, 30 or 25 amino acids in length. In certain embodiments, the core polypeptide is an H12 polypeptide less than 150, 125, 95, 90, 85, 80, 75, 65, 60, 55, 50, 45 or 40 amino acids in length but at least 15, 20, 25, 30 or 35 amino acids in length.

In specific embodiments, the core polypeptide is a derivative of an H12 core polypeptide, wherein the derivative comprises an H12 core polypeptide with 1, 2, 3, 4, 5, 6, 7, 8, 9, or 10(±5) amino acids attached to either of the H12 core polypeptide's N- or C-terminus and wherein the core polypeptide maintains an alpha-helical conformation.

In specific embodiments, the core polypeptide is a derivative of an H12 core polypeptide, wherein the derivative comprises an H12 core polypeptide with 1, 2, 3, 4, 5, 6, 7, 8, 9, or 10(±5) amino acids attached to both of the H12 core polypeptide's N- and C-termini and wherein the core polypeptide maintains an alpha-helical conformation.

In a specific embodiment, the core polypeptide is an H13 core polypeptide comprising or consisting of the amino acid sequence:

(SEQ ID NO: 51)
RINMLADRIDDAVTDX₁WSYNAKLLVLLENDKTLDMHDANVRNLHX₂

QVRR X₃LKX₄NA, wherein $X_1$ is a hydrophobic amino acid; $X_2$ is a hydrophilic, acidic amino acid; $X_3$ is A, S or E and $X_4$ is a hydrophilic amino acid. In specific embodiments, $X_1$ is V or I; $X_2$ is D or E; $X_3$ is A, S or E and $X_4$ is T or D. In certain embodiments, the core polypeptide is acetylated at the N-terminus. In a specific embodiment, a core polypeptide comprises any one of the amino acid sequences shown in FIG. 6M (SEQ ID NOS: 52-54) or a fragment thereof. In certain embodiments, the core polypeptide is acetylated at the N-terminus. In a specific embodiment, this core polypeptide can be used to induce an immune response against influenza virus strains of subtype H13. In certain embodiments, the immune response induced neutralizes strains of influenza virus subtype H13.

In certain embodiments, the core polypeptide is a fragment of an H13 core polypeptide. In specific embodiments, the core polypeptide is a fragment of an H13 core polypeptide, wherein the fragment lacks 1, 2, 3, 4, 5, 6, 7, 8, 9, 10(±5), 15(±5), 20(±5), 25(±5), 30(±5), or 35(±5) amino acids from either of an H13 core polypeptide's N- or C-terminus. In some embodiments, the core polypeptide is a fragment of an H13 core polypeptide, wherein the fragment lacks 24(±5) amino acids from its C-terminus. In specific embodiments, the core polypeptide is a fragment of an H13 core polypeptide, wherein the fragment lacks 1, 2, 3, 4, 5, or more amino acids from both of an H13 core polypeptide's N- and C-termini. In specific embodiments, the core polypeptide has an alpha-helical conformation.

In some embodiments, the core polypeptide is an H13 core polypeptide that is not full length influenza virus HA. In some embodiments, the core polypeptide is an H13 core polypeptide that is between 51 to 300, 51 to 275, 51 to 250, 51 to 225, 51 to 200, 51 to 175, 51 to 150, 51 to 125, 51 to 100, or 51 to 75, 15 to 50, 20 to 50, 25 to 50, 15 to 37, 15 to 35, 20 to 37, 20 to 35, 15 to 30, 20 to 30 or 20 to 25 amino acids in length. In some embodiments, the core polypeptide is an H13 core polypeptide that is less than 500, 450, 400, 350, 300, 275, 250, 225, 200, 175, 150, 125, 100, 95, 90, 85, 80, 75, 70, 65, 60, 55, 50, 45, 40, 35, 30 or 25 amino acids in length. In certain embodiments, the core polypeptide is an H13 polypeptide less than 150, 125, 95, 90, 85, 80, 75, 65, 60, 55, 50, 45 or 40 amino acids in length but at least 15, 20, 25, 30 or 35 amino acids in length.

In specific embodiments, the core polypeptide is a derivative of an H13 core polypeptide, wherein the derivative comprises an H13 core polypeptide with 1, 2, 3, 4, 5, 6, 7, 8, 9, or 10(±5) amino acids attached to either of the H13 core polypeptide's N- or C-terminus and wherein the core polypeptide maintains an alpha-helical conformation.

In specific embodiments, the core polypeptide is a derivative of an H13 core polypeptide, wherein the derivative comprises an H13 core polypeptide with 1, 2, 3, 4, 5, 6, 7, 8, 9, or 10(±5) amino acids attached to both of the H13 core polypeptide's N- and C-termini and wherein the core polypeptide maintains an alpha-helical conformation.

In a specific embodiment, the core polypeptide is an H14 core polypeptide comprising or consisting of the amino acid sequence:

(SEQ ID NO: 55)
RIQDLEKYVEDTKIDLWSYNAELLVALENQHTIDVTDSEMNKLFERV

RRQLRENA.

In certain embodiments, the core polypeptide is acetylated at the N-terminus. In a specific embodiment, a core polypeptide comprises any one of the amino acid sequences shown in FIG. 6N (SEQ ID NO: 55) or a fragment thereof. In certain embodiments, the core polypeptide is acetylated at the N-terminus. In a specific embodiment, this core polypeptide can be used to induce an immune response against influenza virus strains of subtype H14. In certain embodiments, the immune response induced neutralizes strains of influenza virus subtype H14.

In certain embodiments, the core polypeptide is a fragment of an H14 core polypeptide. In specific embodiments, the core polypeptide is a fragment of an H14 core polypeptide, wherein the fragment lacks 1, 2, 3, 4, 5, 6, 7, 8, 9, 10(±5), 15(±5), 20(±5), 25(±5), 30(±5), or 35(±5) amino acids from either of an H14 core polypeptide's N- or C-terminus. In some embodiments, the core polypeptide is a fragment of an H14 core polypeptide, wherein the fragment lacks 24(±5) amino acids from its C-terminus. In specific embodiments, the core polypeptide is a fragment of an H14 core polypeptide, wherein the fragment lacks 1, 2, 3, 4, 5, or more amino acids from both of an H14 core polypeptide's N- and C-termini. In specific embodiments, the core polypeptide has an alpha-helical conformation.

In some embodiments, the core polypeptide is an H14 core polypeptide that is not full length influenza virus HA. In some embodiments, the core polypeptide is an H14 core polypeptide that is between 51 to 300, 51 to 275, 51 to 250, 51 to 225, 51 to 200, 51 to 175, 51 to 150, 51 to 125, 51 to 100, or 51 to 75, 15 to 50, 20 to 50, 25 to 50, 15 to 37, 15 to 35, 20 to 37, 20 to 35, 15 to 30, 20 to 30 or 20 to 25 amino acids in length. In some embodiments, the core polypeptide is an H14 core polypeptide that is less than 500, 450, 400, 350, 300, 275, 250, 225, 200, 175, 150, 125, 100, 95, 90, 85, 80, 75, 70, 65, 60, 55, 50, 45, 40, 35, 30 or 25 amino acids in length. In certain embodiments, the core polypeptide is an H14 polypeptide less than 150, 125, 95, 90, 85, 80, 75, 65, 60, 55, 50, 45 or 40 amino acids in length but at least 15, 20, 25, 30 or 35 amino acids in length.

In specific embodiments, the core polypeptide is a derivative of an H14 core polypeptide, wherein the derivative comprises an H14 core polypeptide with 1, 2, 3, 4, 5, 6, 7, 8, 9, or 10(±5) amino acids attached to either of the H14 core polypeptide's N- or C-terminus and wherein the core polypeptide maintains an alpha-helical conformation.

In specific embodiments, the core polypeptide is a derivative of an H14 core polypeptide, wherein the derivative comprises an H14 core polypeptide with 1, 2, 3, 4, 5, 6, 7, 8, 9, or 10(±5) amino acids attached to both of the H14 core polypeptide's N- and C-termini and wherein the core polypeptide maintains an alpha-helical conformation.

In a specific embodiment, the core polypeptide is an H15 core polypeptide comprising or consisting of the amino acid sequence:

(SEQ ID NO: 56)
QIGNVINWTRDSLTEIWSYNAELLVAMENQHTIDLADSEMNKLYERV

RRQLRENA.

In certain embodiments, the core polypeptide is acetylated at the N-terminus. In a specific embodiment, a core polypeptide comprises any one of the amino acid sequences shown in FIG. 6O or a fragment thereof. In certain embodiments, the core polypeptide is acetylated at the N-terminus. In a specific embodiment, this core polypeptide can be used to induce an immune response against influenza virus strains of subtype H15. In certain embodiments, the immune response induced neutralizes strains of influenza virus subtype H15

In certain embodiments, the core polypeptide is a fragment of an H15 core polypeptide. In specific embodiments, the core polypeptide is a fragment of an H15 core polypeptide, wherein the fragment lacks 1, 2, 3, 4, 5, 6, 7, 8, 9, 10(±5), 15(±5), 20(±5), 25(±5), 30(±5), or 35(±5) amino acids from either of an H15 core polypeptide's N- or C-terminus. In some embodiments, the core polypeptide is a fragment of an H15 core polypeptide, wherein the fragment lacks 24(±5) amino acids from its C-terminus. In specific embodiments, the core polypeptide is a fragment of an H15 core polypeptide, wherein the fragment lacks 1, 2, 3, 4, 5, or more amino acids from both of an H15 core polypeptide's N- and C-termini. In specific embodiments, the core polypeptide has an alpha-helical conformation.

In some embodiments, the core polypeptide is an H15 core polypeptide that is not full length influenza virus HA. In some embodiments, the core polypeptide is an H15 core polypeptide that is between 51 to 300, 51 to 275, 51 to 250, 51 to 225, 51 to 200, 51 to 175, 51 to 150, 51 to 125, 51 to 100, or 51 to 75, 15 to 50, 20 to 50, 25 to 50, 15 to 37, 15 to 35, 20 to 37, 20 to 35, 15 to 30, 20 to 30 or 20 to 25 amino acids in length. In some embodiments, the core polypeptide is an H15 core polypeptide that is less than 500, 450, 400, 350, 300, 275, 250, 225, 200, 175, 150, 125, 100, 95, 90, 85, 80, 75, 70, 65, 60, 55, 50, 45, 40, 35, 30 or 25 amino acids in length. In certain embodiments, the core polypeptide is an H15 polypeptide less than 150, 125, 95, 90, 85, 80, 75, 65, 60, 55, 50, 45 or 40 amino acids in length but at least 15, 20, 25, 30 or 35 amino acids in length.

In specific embodiments, the core polypeptide is a derivative of an H15 core polypeptide, wherein the derivative comprises an H15 core polypeptide with 1, 2, 3, 4, 5, 6, 7, 8, 9, or 10(±5) amino acids attached to either of the H15 core polypeptide's N- or C-terminus and wherein the core polypeptide maintains an alpha-helical conformation.

In specific embodiments, the core polypeptide is a derivative of an H15 core polypeptide, wherein the derivative comprises an H15 core polypeptide with 1, 2, 3, 4, 5, 6, 7, 8, 9, or 10(±5) amino acids attached to both of the H15 core polypeptide's N- and C-termini and wherein the core polypeptide maintains an alpha-helical conformation.

In a specific embodiment, the core polypeptide is an H16 core polypeptide comprising or consisting of the amino acid sequence:

(SEQ ID NO: 57)
RINMLADRVDDAVTDIWSYNAKLLVLX$_1$ENDRTLDLHDANVX$_2$NLH

X$_3$QVKRALKX$_4$NA, wherein X$_1$ is a hydrophobic amino acid; X$_2$ is a hydrophilic, basic amino acid; X$_3$ is a hydrophilic, acidic amino acid and X$_4$ is a hydrophilic amino acid. In specific embodiments, X$_1$ is L or I; X$_2$ is K or R; X$_3$ is D or E and X$_4$ is S or N. In certain embodiments, the core polypeptide is acetylated at the N-terminus. In a specific embodiment, a core polypeptide comprises any one of the amino acid sequences shown in FIG. 6P (SEQ ID NOS: 58-60) or a fragment thereof. In certain embodiments, the core polypeptide is acetylated at the N-terminus. In a specific embodiment, this core polypeptide can be used to induce an immune response against influenza virus strains of subtype H16. In certain embodiments, the immune response induced neutralizes strains of influenza virus subtype H16.

In certain embodiments, the core polypeptide is a fragment of an H16 core polypeptide. In specific embodiments, the core polypeptide is a fragment of an H16 core polypeptide, wherein the fragment lacks 1, 2, 3, 4, 5, 6, 7, 8, 9, 10(±5), 15(±5), 20(±5), 25(±5), 30(±5), or 35(±5) amino acids from either of an H16 core polypeptide's N- or C-terminus. In some embodiments, the core polypeptide is a fragment of an H16 core polypeptide, wherein the fragment lacks 24(±5) amino acids from its C-terminus. In specific embodiments, the core polypeptide is a fragment of an H16 core polypeptide, wherein the fragment lacks 1, 2, 3, 4, 5, or more amino acids from both of an H16 core polypeptide's N- and C-termini. In specific embodiments, the core polypeptide has an alpha-helical conformation.

In some embodiments, the core polypeptide is an H16 core polypeptide that is not full length influenza virus HA. In some embodiments, the core polypeptide is an H16 core polypeptide that is between 51 to 300, 51 to 275, 51 to 250, 51 to 225, 51 to 200, 51 to 175, 51 to 150, 51 to 125, 51 to 100, or 51 to 75, 15 to 50, 20 to 50, 25 to 50, 15 to 37, 15 to 35, 20 to 37, 20 to 35, 15 to 30, 20 to 30 or 20 to 25 amino acids in length. In some embodiments, the core polypeptide is an H16 core polypeptide that is less than 500, 450, 400, 350, 300, 275, 250, 225, 200, 175, 150, 125, 100, 95, 90, 85, 80, 75, 70, 65, 60, 55, 50, 45, 40, 35, 30 or 25 amino acids in length. In certain embodiments, the core polypeptide is an H16 polypeptide less than 150, 125, 95, 90, 85, 80, 75, 65, 60, 55, 50, 45 or 40 amino acids in length but at least 15, 20, 25, 30 or 35 amino acids in length.

In specific embodiments, the core polypeptide is a derivative of an H16 core polypeptide, wherein the derivative comprises an H16 core polypeptide with 1, 2, 3, 4, 5, 6, 7, 8, 9, or 10(±5) amino acids attached to either of an H16 core polypeptide's N- or C-terminus and wherein the core polypeptide maintains an alpha-helical conformation.

In specific embodiments, the core polypeptide is a derivative of an H16 core polypeptide, wherein the derivative comprises an H16 core polypeptide with 1, 2, 3, 4, 5, 6, 7, 8, 9, or 10(±5) amino acids attached to both of an H16 core polypeptide's N- and C-termini and wherein the core polypeptide maintains an alpha-helical conformation.

In specific embodiments, the core polypeptide comprises or consists of the sequence:

EILELDEKVDDLRADTISSQIELAVLLSNEGIINSEDEHLLALERKLKK

MLGPSA.

In certain embodiments, the core polypeptide is acetylated at the N-terminus.

In a specific embodiment, a core polypeptide comprises or consists of any one of the amino acid sequences shown in FIG. 5A or a fragment thereof. In certain embodiments, the core polypeptide is acetylated at the N-terminus. In a specific embodiment, a core polypeptide comprises or consists of any one of the amino acid sequences shown in FIG. 5B or fragment thereof. In some embodiments, the core polypeptide is between 51 to 300, 51 to 275, 51 to 250, 51 to 225, 51 to 200, 51 to 175, 51 to 150, 51 to 125, 51 to 100, or 51 to 75, 15 to 50, 20 to 50, 25 to 50, 15 to 37, 15 to 35, 20 to 37, 20 to 35, 15 to 30, 20 to 30 or 20 to 25 amino acids in length. In some embodiments, the core polypeptide is less than 500, 450, 400, 350, 300, 275, 250, 225, 200, 175, 150, 125, 100, 95, 90, 85, 80, 75, 70, 65, 60, 55, 50, 45, 40, 35, 30 or 25 amino acids in length. In certain embodiments, the core polypeptide is less than 150, 125, 95, 90, 85, 80, 75, 65, 60, 55, 50, 45 or 40 amino acids in length but at least 15, 20, 25, 30 or 35 amino acids in length.

5.1.2 Flu Polypeptides and Core Polypeptides with Increased Half-Life

In some embodiments, the flu polypeptides and core polypeptides described herein are modified to have an extended (or increased) half-life in vivo (i.e., modified core polypeptides). In particular, provided herein are modified flu and core polypeptides which have a half-life in a subject of from about 3 days to about 180 days (or more), and in some embodiments greater than 3 days, greater than 7 days, greater than 10 days, greater than 15 days, greater than 20 days, greater than 25 days, greater than 30 days, greater than 35 days, greater than 40 days, greater than 45 days, greater than 50 days, at least about 60 days, greater than 75 days, greater than 90 days, greater than 105 days, greater than 120 days, greater than 135 days, greater than 150 days, greater than 165 days, or greater than 180 days.

In some embodiments, flu or core polypeptides having an increased half-life in vivo are generated by acetylation of the N-terminus of the flu or core polypeptides. Acetylation of polypeptides is a technique well-known to those of skill in the art and comprises the addition of an acetyl group to the N-terminus of the polypeptide. Acetylation of the core polypeptide can render the core polypeptide less vulnerable to degradation by exopeptidases.

In some embodiments, flu or core polypeptides having an increased half-life in vivo are generated by amidation of the C-terminus of the flu or core polypeptides.

In some embodiments, flu or core polypeptides having an increased half-life in vivo are generated by pegylation, i.e., attaching inert polymer molecules such as high molecular weight polyethyleneglycol (PEG) to the flu or core polypeptides with or without a multifunctional linker either through site-specific conjugation of the PEG to the N- or C-terminus of the flu or core polypeptides or via epsilon-amino groups present on lysine residues. PEG of various average molecular weights can be used such as 1000 Da, 4000 Da, 5000 Da, 8000 Da, 10000 Da, 120000 Da or even higher. In a specific embodiment, the N-terminus of the flu or core polypeptides is pegylated. Linear or branched polymer derivatization that results in minimal loss of biological activity can be used. The degree of conjugation can be closely monitored by SDS-PAGE and mass spectrometry to ensure proper conjugation of PEG molecules to the flu or core polypeptides. Unreacted PEG can be separated from flu or core polypeptide-PEG conjugates by size-exclusion or by ion-exchange chromatography. PEG-derivatized flu or core polypeptides can be tested for in vivo efficacy using methods well-known to those of skill in the art, for example, by using animal model systems described herein.

In another embodiment, flu or core polypeptides can be conjugated to albumin in order to make the core polypeptides more stable in vivo or have a longer half-life in vivo. Such techniques are well-known in the art, see, e.g., International Publication Nos. WO 93/15199, WO 93/15200, and WO 01/77137; and European Patent No. EP 413,622, all of which are incorporated herein by reference.

In some embodiments, flu or core polypeptides having an increased half-life in vivo are generated by substitution of terminal L-amino acids of the core polypeptides with D-amino acids.

5.1.3 Flu Polypeptides Comprising a Core Polypeptide and a Linker

In some embodiments, the flu polypeptides described herein comprises a core polypeptide or modified core polypeptide linked to a linker. The linkers encompassed herein can be any linker known to those of skill in the art that does not interfere with the native structure of the core polypeptide with which the linker is associated. In specific embodiments, the linkers encompassed herein are not hydrophobic.

The length of the linker may be varied to provide optimal linkage between a core polypeptide or a modified core polypeptide described herein and a substrate (e.g., carrier protein, T cell epitope, immunogenic polypeptide) to which the core polypeptide or modified core polypeptide is to be linked. Further, the length of the linker may be optimized to prevent immunogenic responses due to linker. Linker molecules are commonly known in the art and described in Denardo et al., 1998, *Clin. Cancer Res.* 4:2483-90; Peterson et al., 1999, *Bioconjug. Chem.* 10:553; and Zimmerman et al., 1999, *Nucl. Med. Biol.* 26:943-50 each of which is incorporated by reference herein in its entirety.

Linkers may be one, two, three, four, five, six, seven, eight, nine, ten, eleven, twelve, thirteen, fourteen, fifteen, twenty, or more than twenty amino acids in length. In some embodiments, the linker is less than 20 amino acids in length. In some embodiments, the linker is less than 15 amino acids in length. In some embodiments, the linker is less than 10 amino acids in length. In some embodiments, the linker is less than 9 amino acids in length. In some embodiments, the linker is less than 8 amino acids in length. In some embodiments, the linker is less than 7 amino acids in length. In some embodiments, the linker is less than 6 amino acids in length. In some embodiments, the linker is less than 5 amino acids in length. In some embodiments, the linker is less than 4 amino acids in length. In some embodiments, the linker is less than 3 amino acids in length. In some embodiments, the linker is less than 2 amino acids in length.

In some embodiments, a linker is between 1 and 50 amino acids in length. In some embodiments, a linker is between 1 to 40 amino acids, 1 to 30 amino acids, 1 to 20 amino acids, 1 to 10 amino acids, 1 to 5 amino acids, 1 to 4 amino acids, 1 to 3 amino acids, 1 to 2 amino acids or 1 amino acid in length.

In some embodiments, the linker is covalently attached to the core polypeptide or modified core polypeptide. In specific embodiments, the linker is attached to the core polypeptide or modified core polypeptide through a peptide bond. In some embodiments, the linker is attached to the N-terminus of the core polypeptide or modified core polypeptide. In some embodiments, the linker is attached to the C-terminus of the core polypeptide or modified core polypeptide.

In some embodiments, the linker comprises one or more glycine residues. In some embodiments, the linker comprises two or more glycine residues. In some embodiments, the linker comprises three or more glycine residues. In some embodiments, the linker comprises four or more glycine residues. In some embodiments, the linker comprises five or more glycine residues. In some embodiments, the linker comprises ten or more glycine residues. In some embodiments, the linker comprises 1, 2, 3, 4, 5, 6, 7, 8, 9, or 10 or more glycine residues. In some embodiments, the linker comprises 2 to 4, 2 to 6, 2 to 10, 3 to 6, 3 to 8, 3 to 10, 5 to 10, 8 to 10, 10 to 15 or 10 to 20 glycine residues. In a specific embodiment, the linker comprises three glycine residues.

In some embodiments, the linker comprises one or more cysteine amino acid residues. In some embodiments, the linker comprises 1, 2, 3, 4, 5, 6, 7, 8, 9, or 10 or more cysteine residues. In some embodiments, the linker comprises 2 to 4, 2 to 6, 2 to 10, 3 to 6, 3 to 8, 3 to 10, 5 to 10, 8 to 10, 10 to 15 or 10 to 20 cysteine residues.

In certain embodiments, the linker comprises a protein tag. Protein tags can be useful for the isolation of protein complexes, isolation of a flu polypeptide, affinity chromatography and/or localization studies. In addition, protein tags may increase the solubility of a flu polypeptide. Examples of protein tags include, but are not limited to, His tag, Strep II tag, T7-tag, FLAG-tag, S-tag, HA tag, c-Myc tag, DHFR tag, and green fluorescent protein (GFP). Protein tags may be covalently attached to the N- or C-terminus of the flu polypeptide. In some embodiments, the linker comprises a FLAG-Tag protein tag, i.e., the linker comprises the amino acid DYKDDDDK (SEQ ID NO: 61). In specific embodiments, the linker comprises a FLAG-Tag covalently linked to a cysteine residue (i.e., DYKDDDDKC, SEQ ID NO: 63). In some embodiments, a flu polypeptide comprises 1, 2, 3, 4 or more protein tags. In certain embodiments, the protein tag is not used as a linker in a flu polypeptide.

5.1.4 Flu Polypeptides Comprising Multiple Core Polypeptides

In certain embodiments, provided herein are flu polypeptides comprising two or more core polypeptides or modified core polypeptides. The two or more core polypeptides or modified core polypeptides can be directly or indirectly linked/coupled to each other. Without being bound to any particular theory of operation, it is believed that administration of flu polypeptides comprising two, three or more core polypeptides or modified core polypeptides can elicit serum antibodies with broad reactivity within a subject without co-administration of a carrier protein. In certain embodiments, the core polypeptides or modified core polypeptides are linked together via a linker such as described in Section 5.1.3 supra. In other words, in certain embodiments, a flu polypeptide can comprise, for example, a core polypeptide or modified core polypeptide, linked to a linker, which is in turned linked to a core polypeptide or modified core polypeptide.

In a specific embodiment, a flu polypeptide has a sequence $X-(L-X)_n$, wherein X is any core polypeptide or modified core polypeptide described herein, L is any linker described herein, n=1-20 and wherein X is covalently linked to L. In a specific embodiment, the flu polypeptide comprises the sequence X-L-X. In a specific embodiment, the flu polypeptide comprises the sequence X-L-X-L-X. In a specific embodiment, the flu polypeptide comprises the sequence X-L-X-L-X-L-X. In a specific embodiment, the flu polypeptide comprises the sequence X-L-X-L-X-L-X-L-X. In a specific embodiment, the flu polypeptide comprises the sequence X-L-X-L-X-L-X-L-X-L-X. In a specific embodiment, the flu polypeptide comprises the sequence X-L-X-L-X-L-X-L-X-L-X-L-X. In a specific embodiment, the flu polypeptide comprises the sequence X-L-X-L-X-L-X-L-X-L-X-L-X-L-X. In a specific embodiment, the flu polypeptide comprises the sequence X-L-X-L-X-L-X-L-X-L-X-L-X-L-X-L-X. In a specific embodiment, the flu polypeptide comprises the sequence X-L-X-L-X-L-X-L-X-L-X-L-X-L-X-L-X-L-X. In a specific embodiment, the flu polypeptide comprises the sequence X-L-X-L-X-L-X-L-X-L-X-L-X-L-X-L-X-L-X-L-X.

In some embodiments, L is absent. In other words, each of the core polypeptide or modified core polypeptide of the flu polypeptide is directly linked to one or more other core polypeptide (e.g., X-X, X-X-X, X-X-X-X, X-X-X-X-X, etc.)

In certain embodiments, a flu polypeptide comprises two or more of the same core polypeptides or modified core polypeptides. In other embodiments, the flu polypeptide comprises or two or more different core polypeptides or core polypeptides. In a specific embodiment, the flu polypeptide comprises two or more of the same core polypeptides or modified core polypeptides. In a specific embodiment, the flu polypeptide comprises three or more of the same core polypeptides or modified core polypeptides. In a specific embodiment, the flu polypeptide comprises four or more of the same core polypeptides or modified core polypeptides. In a specific embodiment, the flu polypeptide comprises five or more of the same core polypeptides or modified core polypeptides. In a specific embodiment, each of the core polypeptide or modified core polypeptide of the flu polypeptide is the same.

In a specific embodiment, the flu polypeptide comprises two or more different core polypeptides or modified core polypeptides. In a specific embodiment, the flu polypeptide comprises three or more different core polypeptides or modified core polypeptides. In a specific embodiment, the flu polypeptide comprises four or more different core polypeptides or modified core polypeptides. In a specific embodiment, the flu polypeptide comprises five or more different core polypeptides or modified core polypeptides.

In some embodiments, a flu polypeptide comprises the sequence X-L-X-L-X wherein X is a core polypeptide comprising the amino acid sequence RIQDLEKYVEDTKIDLWSYNAELLVALENQHTIDLTDSEMNKLFEKT RRQLRENA (SEQ ID NO:2) and L is a linker consisting of three glycine residues. In other embodiments, X is not RIQDLEKYVEDTKIDLWSYNAELLVALENQHTIDLTDSEMNKLFEKT RRQLRENA (SEQ ID NO: 2) and is the same or varies.

In some embodiments, a flu polypeptide, in addition to comprising two or more modified core polypeptides, comprises one, two, three or more or all of the following: a T cell epitope, a polypeptide that facilitates multimerization (e.g., a T4 foldon domain), a protein tag, or an immunogenic polypeptide as described herein. In a specific embodiment, the flu polypeptide comprises a His-tag at its N-terminus. In a specific embodiment, a flu polypeptide comprises a FLAG-tag at its C-terminus. In a specific embodiment, a flu polypeptide comprises a His-tag at its N-terminus and a FLAG-tag at its C-terminus. In a specific embodiment, a flu polypeptide comprises an influenza A nuclear protein (NP) at its C-terminus. In certain embodiments, a flu polypeptide comprises an FljB flagellin at its C-terminus.

In some embodiments, a flu polypeptide comprises the amino acid sequence H-X-L-X-L-X-F, wherein H is a His tag or another protein tag that facilitates purification and/or solubility of the flu polypeptide, X is a core polypeptide or a modified core polypeptide, L is a linker and F is a FLAG-tag or another protein tag different from H that facilitates the purification and/or solubility of the flu polypeptide. In some embodiments, L is 3 glycine residues. In some embodiments, L is the same and in other embodiments L is different.

5.1.5 Flu Polypeptides Comprising a T Cell Epitope

In certain embodiments, a flu polypeptide comprises a core polypeptide or modified core polypeptide described herein and a T cell epitope (e.g., CD4 or CD8 T cell epitope). In a specific embodiment, a flu polypeptide comprises a core polypeptide or modified core polypeptide and a CD4 T cell epitope. In a specific embodiment, a flu polypeptide comprises a core polypeptide or modified core polypeptide and a CD8 T cell epitope. In another specific embodiment, the T-cell epitope is an influenza virus CD8 T cell epitope (e.g., an influenza virus protein that contains a highly conserved T cell epitope). The T cell epitope can be directly or indirectly linked/coupled to a core polypeptide by a modified core polypeptide.

Without being bound to any particular theory of operation, it is believed that flu polypeptides comprising a core polypeptide or modified core polypeptide and a CD8 T cell epitope can elicit broadly neutralizing antibodies and prime for a broad spectrum CD8 T cell response. Highly conserved influenza virus regions that contain CD8 T cell epitopes are found, for example, in influenza nuclear protein (NP), matrix 1 (M1), neuraminidase (NA) and polymerase basic-1 (PB1). See Alexander et al., 2010, *Hum Immunol* 71: 468-74, incorporated by reference herein in its entirety. In some embodiments, the CD8 T cell epitope is a nuclear protein (NP) or fragment thereof. In other embodiments, the CD8 T cell epitope polypeptide is a matrix 1 (M1) protein or fragment the or fragment thereof In a specific embodiment, a flu polypeptide comprises a core polypeptide or a modified core polypeptide linked to a T cell epitope. The T cell epitope (e.g., CD8 T cell epitope) can be attached to the core polypeptide or modified core polypeptide described herein using any technique known to one of skill in the art, including, but not limited to, single point attachment to a primary amino group or sulfhydryl group using amine to amine crosslinker BS (Bis[sulfosuccinimidyl] suberate), an amine-to-sulfhydryl NHS-PEG-Maleimide crosslinker, or a sulfhydryl-to-sulfhydryl $BM(PEG)_n$ PEG crosslinker. In other embodiments, the T cell epitope (e.g., CD8 T cell epitope) is covalently linked to the N- or C-terminus of a flu polypeptide. In other embodiments, the T cell epitope (e.g., CD8 T cell epitope) is linked to a core polypeptide or modified core polypeptide via a linker as described herein in Section 5.1.3 supra.

In certain embodiments, a flu polypeptide in addition to comprising one or more core polypeptides or modified core polypeptides and a T cell epitope, comprises one, two, three or more or all of the following: a protein tag, an immunogenic polypeptide, a carrier and/or a polypeptide that facilitates the multimerization of the flu polypeptide (e.g., a T4 foldon domain).

In some embodiments, a flu polypeptide comprises one, two, three, four or more core polypeptides or modified core polypeptides and a T cell epitope(s). In specific embodiments, a flu polypeptide comprises the formula H-X-L-X-L-X-F-T, wherein H (which is optional) is a His tag or another protein tag that facilitates purification and/or solubility, X is a core polypeptide or a modified core polypeptide, L is a linker (such as described in Section 5.1.3), F (which is optional) is a FLAG-tag or another protein tag different that H which facilitates purification and/or solubility, and T is a T cell epitope. In certain embodiments, the polypeptide comprises the formula H-X-L-X-L-X-T, wherein H (which is optional) is a His tag or another protein tag that facilitates purification and/or solubility, X is a core polypeptide or a modified core polypeptide, L is a linker (such as described in Section 5.1.3), and T is a T cell epitope.

In certain embodiments, L is three glycine residues. In some embodiments, L is the same each time it occurs in the formula and in other embodiments, L is different or varies each time it occurs in the formula. In certain embodiments, there is linker between F and T. In other embodiments, F is directly linked to T. In certain embodiments, the core polypeptide or modified core polypeptide is the same each time it occurs in the formula. In other embodiments, the core polypeptide or modified core polypeptide is different or varies each time it occurs in the formula.

In some embodiments, there is a linker between X and T. In other embodiments, X is directly linked to T.

5.1.6 Flu Polypeptide Comprising an Immunogenic Polypeptide

In certain embodiments provided herein, a flu polypeptide comprises one or more core polypeptides or modified core polypeptides and an immunogenic polypeptide. In a specific embodiment, a flu polypeptide comprises a core polypeptide or a modified core polypeptide directly or indirectly linked/coupled to an immunogenic polypeptide. The immunogenic polypeptide can be linked/coupled to the N- and/or C-terminus of the core polypeptide or modified core polypeptide. In certain embodiments, the immunogenic polypeptide is linked to the core polypeptide or modified core polypeptide via a linker such as described in Section 5.1.3 supra.

Examples of immunogenic polypeptides include, but are not limited to, Toll Like Receptor (TLR) ligands, such as the *Salmonella* flagellin (a Toll like receptor 5 ligand). See, e.g., Huleatt et al., 2008, *Vaccine* 26: 201-14; Song et al., 2009, *Vaccine* 27: 5875-84; and Wang et al., 2010, *PLos One* 5: e13972. In a specific embodiment, a flu polypeptide comprises a core polypeptide linked to FljB flagellin from *Salmonella enterica.*

In certain embodiments, a flu polypeptide comprises one or more core polypeptides or modified core polypeptides and an immunogenic polypeptide. In certain embodiments, a flu polypeptide, in addition to comprising one or more core polypeptides or modified polypeptides and an immunogenic polypeptide, comprises one, two three, or more or all of the following: a protein tag that facilitates purification and/or increases solubility of the flu polypeptide, a T cell epitope and/or a polypeptide (e.g., a T4 foldon domain) that facilitates multimerization of the flu polypeptide.

In certain embodiments, a flu polypeptide comprises two, three, four or more core polypeptides or modified core polypeptides and an immunogenic polypeptide(s). In specific embodiments, a flu polypeptide comprises H-X-L-X-L-X-F-I, wherein H is an optional His tag or another protein tag that facilitates purification and/or solubility, X is a core polypeptide or modified core polypeptide, L is an optional linker, such as described in Section 5.1.3, F is an optional FLAG-tag or another protein tag different than H that facilitates purification and/or solubility of the flu polypeptide, and I is an immunogenic polypeptide. In certain embodiments, L is three glycine residues. In some embodiments, L is the same throughout the flu polypeptide and in other embodiments, L is different throughout the polypeptide. In certain embodiments there is a linker between F and I. In other embodiments, F is directly linked to I.

In specific embodiments, a flu polypeptide comprises H-X-L-X-L-X-I, wherein H is an optional His tag or another protein tag that facilitates purification and/or solubility, X is a core polypeptide or modified core polypeptide, L is an optional linker, such as described in Section 5.1.3, and I is an immunogenic polypeptide. In certain embodiments, L is three glycine residues. In some embodiments, L is the same throughout the flu polypeptide and in other embodiments, L is different throughout the polypeptide. In certain embodiments there is a linker between X and I. In other embodiments, X is directly linked to I.

5.1.7 Flu Polypeptides Comprising a Carrier

In some embodiments, a flu polypeptides comprise a core polypeptide or modified core polypeptide described herein and a carrier. In a specific embodiment, a flu polypeptide comprises a core polypeptide or a modified core polypeptide coupled/linked to a carrier. The core polypeptide or modified core polypeptide can be directly or indirectly linked/coupled to a carrier. A core polypeptide or modified core polypeptide described herein can be coupled/linked (e.g., directly linked by a linker) to a carrier, including but not limited to, tetanus toxoid (e.g., chemically-inactivated tetanus toxin), diphtheria toxin (e.g., chemically-inactivated diphtheria toxoid or CRM197—a non-toxic diphtheria toxin point mutant), keyhole limpet hemocyanin (KLH), bovine serum albumin, ovalbumin, thyroglobulin or meningococcal outer membrane protein, using methods known to those of skill in the art. In specific embodiments, a core polypeptide(s) or modified core polypeptide(s) described herein are linked to KLH.

In certain embodiments, a core polypeptide(s) or modified core polypeptide(s) described herein are directly linked to a carrier protein, i.e., the core polypeptide or modified core polypeptide and carrier protein are linked to one another without an intervening linker molecule. In certain embodiments, the core polypeptide(s) or modified core polypeptide(s) described herein are linked to a carrier protein by a linker. In specific embodiments, a core polypeptide(s) or modified core polypeptide(s) described herein is linked to a carrier protein by a linker described in section 5.1.3, supra.

In certain embodiments, a flu polypeptide comprises a core polypeptide or modified core polypeptide coupled/linked to more than one carrier. In specific embodiments, a flu polypeptide comprises a core polypeptide or modified core polypeptide coupled/linked to 2, 3, 4, 5 or more carriers.

In certain embodiments, 2, 3, 4, 5, 6 or more of the same core polypeptide or modified core polypeptide described herein are linked to a carrier. In some embodiments, 2, 3, 4, 5, 6 or more different core polypeptides or modified core polypeptides described herein are linked to a carrier.

In certain embodiments, the core polypeptides or modified core polypeptides described herein are couple/linked to a carrier by chemical cross-linking. For example, the cross-linker 1-ethyl-3-(3-dimethylaminopropyl) carbodiimide ("EDC") or the cross-linker Sulfosuccinimidyl 4[N-maleimidomethyl]cyclohexane-1-carboxylate ("Sulfo-SMCC") can be used to cross-link a core polypeptide to a carrier. Other cross-linkers include Glutaraldehyde and Bis-Diazotized Benzidine. Methods of cross-linking are well known to those of skill in the art and common cross-linking chemistries can be found at the website: piercenet.com.

In a particular embodiment, a flu polypeptide comprises (i) the long alpha-helix of the HA2 hemagglutinin subunit of the influenza virus strain A/Hong Kong/1/1968 (H3) (i.e., amino acids 76-130, numbered according to the classic H3 subtype numbering system); (ii) a FLAG-tag; and (iii) a C-terminal cysteine residue which can be used, e.g., to couple/link the core polypeptide to a carrier (e.g., KLH). In a specific embodiment, such a flu polypeptide comprises the following amino acid sequence:

(SEQ ID NO: 1)
RIQDLEKYVEDTKIDLWSYNAELLVALENQHTIDLTDSEMNKLFEKT

RRQLRENADYKDDDDKC, wherein the FLAG-tag is represented by the amino acid sequence DYKDDDDK (SEQ ID NO: 61). In some embodiments, the N-terminus of the modified core polypeptide is acetylated.

5.1.8 Multimerization Polypeptides

In certain embodiments, a flu polypeptide comprises a core polypeptide or a modified core polypeptide described herein and a polypeptide that facilitates the formation of multimers (e.g., trimers). In some embodiments, the core polypeptide or modified polypeptide is coupled/linked to a polypeptide, such as a T4 foldon domain, to allow/facilitate the formation of a trimer.

In specific embodiments the core polypeptide or modified core polypeptide is indirectly or directly linked/coupled to a polypeptide that facilitates multimerization (e.g., trimerization, such as by a T4 foldon domain) at its C-terminus. Meier et al., 2004, *J Mol Biol* 344: 1051-69, incorporated by reference herein in its entirety. Without being bound by any particular theory of operation, a T4 foldon domain may allow for the formation of the trimeric configuration of the influenza A long alpha helix seen in the native hemagglutinin molecule.

In certain embodiments, a flu polypeptide comprises two or more core polypeptides or modified polypeptides and a polypeptide that facilitates the formation of a trimer. In a specific embodiment, the polypeptide that facilitates formation of a trimer is a T4 foldon domain.

In certain embodiments, the polypeptide that facilitates the formation of a multimer is linked/coupled to a core polypeptide or a modified pore polypeptide by a linker, such as described in section 5.1.3 supra. In other words, in certain embodiments, the flu polypeptide comprises a core polypeptide or a modified core polypeptide, a linker and a polypeptide, such as a T4 foldon domain, that facilitates the formation of multimers.

In certain embodiments a flu polypeptide in addition to comprising 2, 3, 4 or more core polypeptides or modified core polypeptides and a polypeptide that facilitates multimerization, such as a T4 foldon domain, comprises one, two, three or more, or all of the following: a protein tag facilitates purification and/or solubility of the flu polypeptide, an immunogenic polypeptide, and/or carrier such as described herein. In specific embodiments, a flu polypeptide comprises a protein tag (e.g., a His tag) that facilitates purification and/or solubility, a core polypeptide or a modified core polypeptide and a polypeptide that facilitates trimerization, such as a T4 foldon domain.

5.2 Nucleic Acids Encoding Flu Polypeptides

Provided herein are nucleic acids that encode flu polypeptides described herein. Due to the degeneracy of the genetic code, any nucleic acid that encodes a flu polypeptide described herein is encompassed herein. In certain embodiments, nucleic acids corresponding to naturally occurring influenza virus nucleic acids encoding a region of the HA2 domain (e.g., the long alpha helix region) of the hemagglutinin protein are used to produce a flu polypeptide.

Also provided herein are nucleic acids capable of hybridizing to a nucleic acid encoding a flu polypeptide. In certain embodiments, provided herein are nucleic acids capable of hybridizing to a fragment of a nucleic acid encoding a flu polypeptide. In other embodiments, provided herein are nucleic acids capable of hybridizing to the full length of a nucleic acid encoding a flu polypeptide. General parameters for hybridization conditions for nucleic acids are described in Sambrook et al., Molecular Cloning—A Laboratory Manual (2nd Ed.), Vols. 1-3, Cold Spring Harbor Laboratory, Cold Spring Harbor, N.Y. (1989), and in Ausubel et al., Current Protocols in Molecular Biology, vol. 2, Current Protocols Publishing, New York (1994). Hybridization may be performed under high stringency conditions, medium stringency conditions, or low stringency conditions. Those of skill in the art will understand that low, medium and high stringency conditions are contingent upon multiple factors, all of which interact and are also dependent upon the nucleic acids in question. For example, high stringency conditions may include temperatures within 5° C. melting temperature of the nucleic acid(s), a low salt concentration (e.g., less than 250 mM), and a high co-solvent concentration (e.g., 1-20% of co-solvent, e.g., DMSO). Low stringency conditions, on the other hand, may include temperatures greater than 10° C. below the melting temperature of the nucleic acid(s), a high salt concentration (e.g., greater than 1000 mM) and the absence of co-solvents.

In some embodiments, a nucleic acid encoding an influenza virus flu polypeptide is isolated, i.e., a flu polypeptide described herein is isolated. In some embodiments, a nucleic acid encoding an influenza virus core polypeptide or modified core polypeptide as described herein is isolated. In certain embodiments, an "isolated" nucleic acid refers to a nucleic acid molecule which is separated from other nucleic acid molecules which are present in the natural source of the nucleic acid. In other words, the isolated nucleic acid can comprise heterologous nucleic acids that are not associated with it in nature. In other embodiments, an "isolated" nucleic acid, such as a cDNA molecule, can be substantially free of other cellular material, or culture medium when produced by recombinant techniques, or substantially free of chemical precursors or other chemicals when chemically synthesized. The term "substantially free of cellular material" includes preparations of nucleic acid in which the nucleic acid is separated from cellular components of the cells from which it is isolated or recombinantly produced. Thus, nucleic acid that is substantially free of cellular material includes preparations of nucleic acid having less than about 30%, 20%, 10%, or 5% (by dry weight) of other nucleic acids. The term "substantially free of culture medium" includes preparations of nucleic acid in which the culture medium represents less than about 50%, 20%, 10%, or 5% of the volume of the preparation. The term "substantially free of chemical precursors or other chemicals" includes preparations in which the nucleic acid is separated from chemical precursors or other chemicals which are involved in the synthesis of the nucleic acid. In specific embodiments, such preparations of the nucleic acid have less than about 50%, 30%, 20%, 10%, 5% (by dry weight) of chemical precursors or compounds other than the nucleic acid of interest.

In certain embodiments, provided herein are nucleic acids that encode a flu polypeptide comprising a core polypeptide and one or more additional components, e.g., a linker, a carrier, a protein tag, and/or a protein that is/are associated with a core polypeptide.

5.3 Production and Purification of Flu Polypeptides

The flu polypeptides described herein can be produced by any method known in the art for the synthesis of polypeptides, in particular, by chemical synthesis or by recombinant expression techniques. The methods provided herein encompass, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) *Molecular Cloning: A Laboratory Manual*, Cold Spring Harbor Laboratory Press; Sambrook et al. (1989), *Molecular Cloning: A Laboratory Manual*, Second Edition, Cold Spring Harbor Laboratory Press; Sambrook et al. (2001) *Molecular Cloning: A Laboratory Manual*, Cold Spring Harbor Laboratory Press, Cold Spring Harbor, N.Y.; Ausubel et al., *Current Protocols in Molecular Biology*, John Wiley & Sons (1987 and annual updates); *Current Protocols in Immunology*, John Wiley & Sons (1987 and annual updates) Gait (ed.) (1984) *Oligonucleotide Synthesis: A Practical Approach*, IRL Press; Eckstein (ed.) (1991) *Oligonucleotides and Analogues: A Practical Approach*, IRL Press; Birren et al. (eds.) (1999) *Genome Analysis: A Laboratory Manual*, Cold Spring Harbor Laboratory Press.

5.3.1 Synthetic Production of Flu Polypeptides

The flu polypeptides described herein may be prepared using conventional step-wise solution or solid phase synthesis (see, e.g., Chemical Approaches to the Synthesis of Peptides and Proteins, Williams et al., Eds., 1997, CRC Press, Boca Raton Fla., and references cited therein; Solid Phase Peptide Synthesis: A Practical Approach, Atherton & Sheppard, Eds., 1989, IRL Press, Oxford, England, and references cited therein).

Alternatively, the flu polypeptides described herein may be prepared by way of segment condensation, as described, for example, in Liu et al., 1996, Tetrahedron Lett. 37(7): 933-936; Baca, et al., 1995, J. Am. Chem. Soc. 117:1881-1887; Tam et al., 1995, Int. J. Peptide Protein Res. 45:209-216; Schnolzer and Kent, 1992, Science 256:221-225; Liu and Tam, 1994, J. Am. Chem. Soc. 116(10):4149-4153; Liu and Tam, 1994, Proc. Natl. Acad. Sci. USA 91:6584-6588; Yamashiro and Li, 1988, Int. J. Peptide Protein Res. 31:322-334. Other methods useful for synthesizing the flu polypeptides described herein are described in Nakagawa et al., 1985, J. Am. Chem. Soc. 107:7087-7092.

Flu polypeptides comprising core polypeptides and linkers can be synthesized by adding the linker(s) to the core polypeptide chain at the appropriate step in the synthesis. Suitable protecting schemes and chemistries are well known, and will be apparent to those of skill in the art.

Formation of disulfide linkages, if desired, is generally conducted in the presence of mild oxidizing agents. Chemical oxidizing agents may be used, or the compounds may simply be exposed to atmospheric oxygen to effect these linkages. Various methods are known in the art, including those described, for example, by Tam et al., 1979, Synthesis 955-957; Stewart et al., 1984, Solid Phase Peptide Synthesis, 2d Ed., Pierce Chemical Company Rockford, Ill.; Ahmed et al., 1975, J. Biol. Chem. 250:8477-8482; and Pennington et al., 1991 Peptides 1990 164-166, Giralt and Andreu, Eds., ESCOM Leiden, The Netherlands. An additional alternative is described by Kamber et al., 1980, Helv. Chim. Acta 63:899-915. A method conducted on solid supports is described by Albericio, 1985, Int. J. Peptide Protein Res. 26:92-97, each of which is incorporated by reference herein in its entirety.

5.3.2 Recombinant Expression of Flu Polypeptides

Recombinant expression of a flu polypeptide requires construction of an expression vector containing a polynucleotide that encodes the flu polypeptide. Once a polynucleotide encoding a flu polypeptide has been obtained, the vector for the production of the flu polypeptide may be produced by recombinant DNA technology using techniques well-known in the art. Thus, methods for preparing a flu polypeptide by expressing a polynucleotide containing a flu polypeptide-encoding nucleotide sequence are described herein. Methods which are well known to those skilled in the art can be used to construct expression vectors containing flu polypeptide coding sequences and appropriate transcriptional and translational control signals. These methods include, for example, in vitro recombinant DNA techniques, synthetic techniques, and in vivo genetic recombination. Thus, provided herein are replicable expression vectors comprising a nucleotide sequence encoding a flu polypeptide operably linked to a promoter.

An expression vector comprises a nucleic acid encoding a flu polypeptide in a form suitable for expression of the nucleic acid in a host cell. In specific embodiments, the host cell is an isolated host cell. In a specific embodiment, an expression vector includes one or more regulatory sequences, selected on the basis of the host cells to be used for expression, which is operably linked to the nucleic acid to be expressed. Within an expression vector, "operably linked" is intended to mean that a nucleic acid of interest is linked to the regulatory sequence(s) in a manner which allows for expression of the nucleic acid (e.g., in an in vitro transcription/translation system or in a host cell when the vector is introduced into the host cell). Regulatory sequences include promoters, enhancers and other expression control elements (e.g., polyadenylation signals). Regulatory sequences include those which direct constitutive expression of a nucleic acid in many types of host cells, those which direct expression of the nucleic acid only in certain host cells (e.g., tissue-specific regulatory sequences), and those which direct the expression of the nucleic acid upon stimulation with a particular agent (e.g., inducible regulatory sequences). It will be appreciated by those skilled in the art that the design of the expression vector can depend on such factors as the choice of the host cell to be transformed, the level of expression of protein desired, etc. The term "host cell" is intended to include a particular subject cell transformed or transfected with a nucleic acid and the progeny or potential progeny of such a cell. Progeny of such a cell may not be identical to the parent cell transformed or transfected with the nucleic acid due to mutations or environmental influences that may occur in succeeding generations or integration of the nucleic acid into the host cell genome. In specific embodiments, the host cell is isolated.

An expression vector can be introduced into host cells via conventional transformation or transfection techniques. Such techniques include, but are not limited to, calcium phosphate or calcium chloride co-precipitation, DEAE-dextran-mediated transfection, lipofection, and electroporation. Suitable methods for transforming or transfecting host cells can be found in Sambrook et al., 1989, Molecular Cloning—A Laboratory Manual, 2nd Edition, Cold Spring Harbor Press, New York, and other laboratory manuals. In certain embodiments, a host cell is transiently transfected with an expression vector containing a nucleic acid encoding a flu polypeptide. In other embodiments, a host cell is stably transfected with an expression vector containing a nucleic acid encoding a flu polypeptide. Thus, provided herein are host cells containing a polynucleotide encoding a flu polypeptide described herein or generated in accordance with the methods provided herein.

A variety of host-expression vector systems may be utilized to express a flu polypeptide. Such host-expression systems represent vehicles by which the coding sequences of interest may be produced and subsequently purified, but also represent cells which may, when transformed or transfected with the appropriate nucleotide coding sequences, express a flu polypeptide in situ. These include but are not limited to microorganisms such as bacteria (e.g., *E. coli* and *B. subtilis*) transformed with recombinant bacteriophage DNA, plasmid DNA or cosmid DNA expression vectors containing flu polypeptide coding sequences; yeast (e.g., *Saccharomyces Pichia*) transformed with recombinant yeast expression vectors containing flu polypeptide coding sequences; insect cell systems infected with recombinant virus expression vectors (e.g., baculovirus) containing flu polypeptide coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing flu polypeptide coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells are used for the expression of a flu polypeptide. For example, mammalian cells such as Chinese hamster ovary cells (CHO), in conjunction with a vector such as the major intermediate early gene promoter element from human cytomegalovirus is an effective expression system for flu polypeptides (Foecking et al., 1986, Gene 45:101; and Cockett et al., 1990, Bio/Technology 8:2). In a specific embodiment, the expression of nucleotide sequences encoding the flu polypeptides described herein or generated in accordance with the methods provided herein is regulated by a constitutive promoter, inducible promoter or tissue specific promoter.

In bacterial systems, a number of expression vectors may be advantageously selected depending upon the use intended for the flu polypeptide being expressed. For example, when a large quantity of flu polypeptide is to be produced, for the generation of pharmaceutical compositions of a flu polypeptide, vectors which direct the expression of high levels of fusion protein products that are readily purified may be desirable. Such vectors include, but are not limited to, the *E. coli* expression vector pUR278 (Ruther et al., 1983, EMBO 12:1791), in which the flu polypeptide coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The flu polypeptide coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the flu polypeptide coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the flu polypeptide in infected hosts (e.g., see Logan & Shenk, 1984, Proc. Natl. Acad. Sci. USA 8 1:355-359). Specific initiation signals may also be required for efficient translation of inserted flu polypeptide coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the flu polypeptide. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, Vero, MDCK, 293, 3T3, W138, BT483, Hs578T, HTB2, BT2O and T47D, NS0 (a murine myeloma cell line that does not endogenously produce any immunoglobulin chains), CRL7O3O and HsS78Bst cells.

For long-term, high-yield production of recombinant flu polypeptide, stable expression is preferred. For example, cell lines which stably express the flu polypeptide molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the flu polypeptide. Such engineered cell lines may be particularly useful in screening and evaluation of compositions that interact directly or indirectly with the flu polypeptide. Methods commonly known in the art of recombinant DNA technology may be routinely applied to select the desired recombinant clone, and such methods are described, for example, in Ausubel et al. (eds.), *Current Protocols in Molecular Biology*, John Wiley & Sons, N Y (1993); Kriegler, *Gene Transfer and Expression*, A Laboratory Manual, Stockton Press, N Y (1990); and in Chapters 12 and 13, Dracopoli et al. (eds.), *Current Protocols in Human Genetics*, John Wiley & Sons, N Y (1994); Colberre-Garapin et al., 1981, *J. Mol. Biol.* 150:1, which are incorporated by reference herein in their entireties.

The expression levels of a flu polypeptide can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing the flu polypeptide is amplifiable, increase in the level of inhibitor present in culture of host cell will increase the number of copies of the marker gene. Since the amplified region is associated with the flu polypeptide, production of the flu polypeptide will also increase (Crouse et al., 1983, Mol. Cell. Biol. 3:257).

As an alternative to recombinant expression of a flu polypeptide using a host cell, an expression vector containing a nucleic acid encoding a flu polypeptide can be transcribed and translated in vitro using, e.g., T7 promoter regulatory sequences and T7 polymerase. In a specific embodiment, a coupled transcription/translation system, such as Promega TNT®, or a cell lysate or cell extract comprising the components necessary for transcription and translation may be used to produce a flu polypeptide.

Accordingly, provided herein are methods for producing a flu polypeptide. In one embodiment, the method comprises culturing a host cell containing a nucleic acid encoding the polypeptide in a suitable medium such that the polypeptide is produced. In some embodiments, the method further comprises isolating the polypeptide from the medium or the host cell.

In certain embodiments, plants (e.g., plants of the genus *Nicotiana*) may be engineered to express a flu polypeptide described herein. In specific embodiments, plants are engineered to express a flu polypeptide described herein via an agroinfiltration procedure using methods known in the art. For example, nucleic acids encoding a gene of interest, e.g., a gene encoding a flu polypeptide described herein, are introduced into a strain of *Agrobacterium*. Subsequently the strain is grown in a liquid culture and the resulting bacteria are washed and suspended into a buffer solution. The plants are then exposed (e.g., via injection or submersion) to the *Agrobacterium* that comprises the nucleic acids encoding a flu polypeptide described herein such that the *Agrobacterium* transforms the gene of interest to a portion of the plant cells. The flu polypeptide is then transiently expressed by the plant and can be isolated using methods known in the art and described herein. (For specific examples see Shoji et al., 2008, Vaccine, 26(23):2930-2934; and D'Aoust et al., 2008, J. Plant Biotechnology, 6(9):930-940). In a specific embodiment, the plant is a tobacco plant (i.e., *Nicotiana tabacum*). In another specific embodiment, the plant is a relative of the tobacco plant (e.g., *Nicotiana benthamiana*).

In some embodiments, a plant cell culture system is used for expression of a flu polypeptide. See, e.g., U.S. Pat. Nos. 5,929,304; 7,504,560; 6,770,799; 6,551,820; 6,136,320; 6,034,298; 5,914,935; 5,612,487; and 5,484,719, U.S. patent application publication Nos. 2009/0208477, 2009/0082548, 2009/0053762, 2008/0038232, 2007/0275014 and 2006/0204487, and Shoji et al., 2008, Vaccine, 26(23):2930-2934, and D'Aoust et al., 2008, J. Plant Biotechnology, 6(9):930-940 (which are incorporated herein by reference in their entirety) for plant cells and methods for the production of proteins utilizing plant cell culture systems. In a specific embodiment, carrot cells are engineered to express a flu polypeptide. In certain embodiments, algae (e.g., *Chlamydomonas reinhardtii*) may be engineered to express a flu polypeptide (see, e.g., Rasala et al., 2010, Plant Biotechnology Journal (Published online Mar. 7, 2010, which is incorporated herein by reference in its entirety).

5.3.3 Purification of Flu Polypeptides

The flu polypeptides described herein and generated using the approaches described in Sections 5.3.1 and 5.3.1, supra, may be purified by any method known in the art for purification of a polypeptide, for example, by chromatography (e.g., ion exchange, affinity, particularly by affinity for the specific antigen after Protein A, and sizing column chromatography), centrifugation, differential solubility, or by any other standard technique for the purification of proteins. Further, the flu polypeptides may be fused to heterologous polypeptide sequences described herein or otherwise known in the art to facilitate purification. The actual conditions used to purify a particular flu polypeptide will depend, in part, on the synthesis strategy (e.g., synthetic production vs. recombinant production) and on factors such as net charge, hydrophobicity, and/or hydrophilicity of the flu polypeptide, and will be apparent to those having skill in the art.

5.4 Influenza Virus Vectors

In one aspect, provided herein are influenza viruses containing a flu polypeptide. In a specific embodiment, the flu polypeptide is incorporated into the virions of the influenza virus. The influenza viruses may be conjugated to moieties that target the viruses to particular cell types, such as immune cells. In some embodiments, the virions of the influenza virus have incorporated into them or express a heterologous polypeptide in addition to a flu polypeptide. The heterologous polypeptide may be a polypeptide that has immunopotentiating activity, or that targets the influenza virus to a particular cell type, such as an antibody that binds to an antigen on a specific cell type or a ligand that binds a specific receptor on a specific cell type.

Influenza viruses containing a flu polypeptide may be produced by supplying in trans the flu polypeptide during production of virions using techniques known to one skilled in the art, such as reverse genetics and helper-free plasmid rescue. Alternatively, a parental influenza virus comprises a genome engineered to express a flu polypeptide in cells susceptible to infection with the virus wherein hemagglutinin function is provided in trans to produce progeny influenza viruses containing the influenza flu polypeptide.

In another aspect, provided herein are influenza viruses comprising a genome engineered to express a flu polypeptide. In a specific embodiment, the genome of a parental influenza virus is engineered to encode a flu polypeptide, which is expressed by progeny influenza virus. In another specific embodiment, the genome of a parental influenza virus is engineered to encode a flu polypeptide, which is expressed and incorporated into the virions of progeny influenza virus. Thus, the progeny influenza virus resulting from the replication of the parental influenza virus contain a flu polypeptide.

In some embodiments, the virions of the parental influenza virus have incorporated into them a heterologous polypeptide. In certain embodiments, the genome of a parental influenza virus is engineered to encode a heterologous polypeptide and an influenza virus flu polypeptide, which are expressed by progeny influenza virus. In specific embodiments, the influenza flu polypeptide, the heterologous polypeptide or both are incorporated into virions of the progeny influenza virus.

The heterologous polypeptide may be a polypeptide that targets the influenza virus to a particular cell type, such as an antibody that recognizes an antigen on a specific cell type or a ligand that binds a specific receptor on a specific cell type. In some embodiments, the targeting polypeptide replaces the target cell recognition function of the virus. In a specific embodiment, the heterologous polypeptide targets the influenza virus to the same cell types that influenza virus infects in nature. In other specific embodiments, the heterologous polypeptide targets the progeny influenza virus to immune cells, such as B cells, T cells, macrophages or dendritic cells. In some embodiments, the heterologous polypeptide recognizes and binds to cell-specific markers of antigen presenting cells, such as dendritic cells (e.g., such as CD44). In one embodiment, the heterologous polypeptide is DC-SIGN which targets the virus to dendritic cells. In another embodiment, the heterologous polypeptide is an antibody (e.g., a single-chain antibody) that targets the virus to an immune cell, which may be fused with a transmembrane domain from another polypeptide so that it is incorporated into the influenza virus virion. In some embodiments, the antibody is a CD20 antibody, a CD34 antibody, or an antibody against DEC-205. Techniques for engineering viruses to express polypeptides with targeting functions are known in the art. See, e.g., Yang et al., 2006, PNAS 103: 11479-11484 and United States patent application Publication No. 20080019998, published Jan. 24, 2008, and No. 20070020238, published Jan. 25, 2007, the contents of each of which are incorporated herein in their entirety.

In another embodiment, the heterologous polypeptide is a viral attachment protein. Non-limiting examples of viruses whose attachment protein(s) can be used in this aspect are viruses selected from the group of: Lassa fever virus, Hepatitis B virus, Rabies virus, Newcastle disease virus (NDV), a retrovirus such as human immunodeficiency virus, tick-borne encephalitis virus, vaccinia virus, herpesvirus, poliovirus, alphaviruses such as Semliki Forest virus, Ross River virus, and Aura virus (which comprise surface glycoproteins such as E1, E2, and E3), Borna disease virus, Hantaan virus, foamyvirus, and SARS-CoV virus.

In a specific embodiment, an influenza A virus is engineered to encode a flu polypeptide and an influenza C HEF protein, wherein the influenza C HEF protein is substituted for the influenza A neuraminidase (NA) protein.

In one embodiment, a flavivirus surface glycoprotein may be used, such as Dengue virus (DV) E protein. In some embodiments, a Sindbis virus glycoprotein from the alphavirus family is used (K. S. Wang, R. J. Kuhn, E. G. Strauss, S. Ou, J. H. Strauss, J. Virol. 66, 4992 (1992)). In certain embodiments, the heterologous polypeptide is derived from an NDV HN or F protein; a human immunodeficiency virus (HIV) gp160 (or a product thereof, such as gp41 or gp120); a hepatitis B virus surface antigen (HBsAg); a glycoprotein of herpesvirus (e.g., gD, gE); or VP1 of poliovirus.

In another embodiment, the heterologous polypeptide is derived from any non-viral targeting system known in the art. In certain embodiments, a protein of a nonviral pathogen such as an intracellular bacteria or protozoa is used. In some embodiments, the bacterial polypeptide is provided by, e.g., *Chlamydia, Rikettsia, Coxelia, Listeria, Brucella,* or *Legionella*. In some embodiments, protozoan polypeptide is provided by, e.g., Plasmodia species, *Leishmania* spp., *Toxoplasma gondii*, or *Trypanosoma cruzi*. Other exemplary targeting systems are described in Waehler et al., 2007, "Engineering targeted viral vectors for gene therapy," Nature Reviews Genetics 8: 573-587, which is incorporated herein in its entirety.

In certain embodiments, the heterologous polypeptide expressed by an influenza virus has immunopotentiating (immune stimulating) activity. Non-limiting examples of immunopotentiating polypeptides include, but are not limited to, stimulation molecules, cytokines, chemokines, antibodies and other agents such as Flt-3 ligands. Specific examples of polypeptides with immunopotentiating activity include: interferon type 1, alpha, beta, or gamma interferon, colony stimulating factors such as granulocyte-macrophage colony-stimulating factor (GM-CSF), interleukin (IL)-1, IL-2, IL-4, IL-5, IL-6, IL-7, IL-12, IL-15, IL-18, IL-21, IL-23, tumor necrosis factor (TNF)-β, TNFα, B7.1, B7.2, 4-1BB, CD40 ligand (CD40L), and drug-inducible CD40 (iCD40) (see, e.g., Hanks, B. A., et al. 2005. Nat Med 11:130-137, which is incorporated herein by reference in its entirety.)

Since the genome of influenza A and B viruses consist of eight (8) single-stranded, negative sense segments (influenza C viruses consist of seven (7) single-stranded, negative sense segments), the genome of a parental influenza virus may be engineered to express a flu polypeptide (and any other polypeptide, such as a heterologous polypeptide) using a recombinant segment and techniques known to one skilled in the art, such a reverse genetics and helper-free plasmid rescue. In one embodiment, the recombinant segment comprises a nucleic acid encoding the flu polypeptide as well as the 3' and 5' incorporation signals which are required for proper replication, transcription and packaging of the vRNAs (Gao et al., 2010, J. of Virology 84:8062-8074, Fujii et al., 2003, Proc. Natl. Acad. Sci. USA 100:2002-2007; Zheng, et al., 1996, Virology 217:242-251, and PCT/US2010/043697, all of which are incorporated by reference herein in their entireties). In certain embodiments, the recombinant segment encoding the flu polypeptide may replace the HA segment of a parental influenza virus. In some embodiments, the recombinant segment encoding the flu polypeptide may replace the NS1 gene of the parental influenza virus. In some embodiments, the recombinant segment encoding the flu polypeptide may replace the NA gene of the parental influenza virus. Exemplary influenza virus strains that can be used to express the flu polypeptides include Ann Arbor/1/50, A/Puerto Rico/8/34, A/South Dakota/6/2007, A/Uruguay/716/2007, and B/Brisbane/60/2008.

In some embodiments, the genome of a parental influenza virus may be engineered to express a flu polypeptide using a recombinant segment that is bicistronic. Bicistronic techniques allow the engineering of coding sequences of multiple proteins into a single mRNA through the use of internal ribosome entry site (IRES) sequences. IRES sequences direct the internal recruitment of ribosomes to the RNA molecule and allow downstream translation in a cap independent manner. Briefly, a coding region of one protein is inserted into the open reading frame (ORF) of a second protein. The insertion is flanked by an IRES and any untranslated signal sequences necessary for proper expression and/or function. The insertion must not disrupt the ORF, polyadenylation or transcriptional promoters of the second protein (see, e.g., Garcia-Sastre et al., 1994, J. Virol. 68:6254-6261 and Garcia-Sastre et al., 1994 Dev. Biol. Stand. 82:237-246, each of which is hereby incorporated by reference in its entirety). See also, e.g., U.S. Pat. No. 6,887,699, U.S. Pat. No. 6,001,634, U.S. Pat. No. 5,854,037 and U.S. Pat. No. 5,820,871, each of which is incorporated herein by reference in its entirety. Any IRES known in the art or described herein may be used in accordance with the invention (e.g., the IRES of BiP gene, nucleotides 372 to 592 of GenBank database entry HUMGRP78; or the IRES of encephalomyocarditis virus (EMCV), nucleotides 1430-2115 of GenBank database entry CQ867238.). Thus, in certain embodiments, a parental influenza virus is engineered to contain a bicistronic RNA segment that expresses a flu polypeptide and another polypeptide, such as gene expressed by the parental influenza virus.

Techniques known to one skilled in the art may be used to produce an influenza virus containing a flu polypeptide and an influenza virus comprising a genome engineered to express a flu polypeptide. For example, reverse genetics techniques may be used to generate such an influenza virus. Briefly, reverse genetics techniques generally involve the preparation of synthetic recombinant viral RNAs that contain the non-coding regions of the negative-strand, viral RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO 97/12032 published Apr. 3, 1997; WO 96/34625 published Nov. 7, 1996; in European Patent Publication EP A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 475A1 published Jun. 25, 1997, each of which is incorporated by reference herein in its entirety.

Alternatively, helper-free plasmid technology may be used to produce an influenza virus containing a flu polypeptide and/or an influenza virus comprising a genome engineered to express a flu polypeptide. Briefly, full length cDNAs of viral segments are amplified using PCR with primers that include unique restriction sites, which allow the insertion of the PCR product into the plasmid vector (Flandorfer et al., 2003, J. Virol. 77:9116-9123; Nakaya et al., 2001, J. Virol. 75:11868-11873; both of which are incorporated herein by reference in their entireties). The plasmid vector is designed so that an exact negative (vRNA sense) transcript is expressed. For example, the plasmid vector may be designed to position the PCR product between a truncated human RNA polymerase I promoter and a hepatitis delta virus ribozyme sequence such that an exact negative (vRNA sense) transcript is produced from the polymerase I promoter. Separate plasmid vectors comprising each viral segment as well as expression vectors comprising necessary viral proteins may be transfected into cells leading to production of recombinant viral particles. In another example, plasmid vectors from which both the viral genomic RNA and mRNA encoding the necessary viral proteins are expressed may be used. For a detailed description of helper-free plasmid technology see, e.g., International Publication No. WO 01/04333; U.S. Pat. Nos. 6,951,754, 7,384,774, 6,649,372, and 7,312,064; Fodor et al., 1999, J. Virol. 73:9679-9682; Quinlivan et al., 2005, J. Virol. 79:8431-8439; Hoffmann et al., 2000, Proc. Natl. Acad. Sci. USA 97:6108-6113; and Neumann et al., 1999, Proc. Natl. Acad. Sci. USA 96:9345-9350, which are incorporated herein by reference in their entireties.

The influenza viruses described herein may be propagated in any substrate that allows the virus to grow to titers that permit their use in accordance with the methods described herein. In one embodiment, the substrate allows the viruses to grow to titers comparable to those determined for the corresponding wild-type viruses. In certain embodiments, the substrate is one which is biologically relevant to the influenza virus. In a specific embodiment, an attenuated influenza virus by virtue of, e.g., a mutation in the NS1 gene, may be propagated in an IFN-deficient substrate. For example, a suitable IFN-deficient substrate may be one that is defective in its ability to produce or respond to interferon, or is one which an IFN-deficient substrate may be used for the growth of any number of viruses which may require interferon-deficient growth environment. See, for example, U.S. Pat. No. 6,573,079, issued Jun. 3, 2003, U.S. Pat. No. 6,852,522, issued Feb. 8, 2005, and U.S. Pat. No. 7,494,808, issued Feb. 24, 2009, the entire contents of each of which is incorporated herein by reference in its entirety.

The influenza viruses described herein may be isolated and purified by any method known to those of skill in the art. In one embodiment, the virus is removed from cell culture and separated from cellular components, typically by well known clarification procedures, e.g., such as gradient centrifugation and column chromatography, and may be further purified as desired using procedures well known to those skilled in the art, e.g., plaque assays.

In certain embodiments, the influenza viruses, or influenza virus polypeptides, genes or genome segments for use as described herein are obtained or derived from an influenza A virus. In certain embodiments, the influenza viruses, or influenza virus polypeptides, genes or genome segments for use as described herein are obtained or derived from a single influenza A virus subtype or strain. In other embodiments, the influenza viruses, or influenza virus polypeptides, genes or genome segments for use as described herein are obtained or derived from two or more influenza A virus subtypes or strains.

In some embodiments, the influenza viruses, or influenza virus polypeptides, genes or genome segments for use as described herein are obtained or derived from an influenza B virus. In certain embodiments, the influenza viruses, or influenza virus polypeptides, genes or genome segments for use as described herein are obtained or derived from a single influenza B virus subtype or strain. In other embodiments, the influenza viruses, or influenza virus polypeptides, genes or genome segments for use as described herein are obtained or derived from two or more influenza B virus subtypes or strains. In other embodiments, the influenza viruses, or influenza virus polypeptides, genes or genome segments for use as described herein are obtained or derived from a combination of influenza A and influenza B virus subtypes or strains.

In some embodiments, the influenza viruses, or influenza virus polypeptides, genes or genome segments for use as described herein are obtained or derived from an influenza C virus. In certain embodiments, the influenza viruses, or influenza virus polypeptides, genes or genome segments for use as described herein are obtained or derived from a single influenza C virus subtype or strain. In other embodiments, the influenza viruses, or influenza virus polypeptides, genes or genome segments for use as described herein are obtained or derived from two or more influenza C virus subtypes or strains. In other embodiments, the influenza viruses, or influenza virus polypeptides, genes or genome segments for use as described herein are obtained or derived from a combination of influenza C virus and influenza A virus and/or influenza B virus subtypes or strains.

Non-limiting examples of influenza A viruses include subtype H10N4, subtype H10N5, subtype H10N7, subtype H10N8, subtype H10N9, subtype H11N1, subtype H11N13, subtype H11N2, subtype H11N4, subtype H11N6, subtype H11N8, subtype H11N9, subtype H12N1, subtype H12N4, subtype H12N5, subtype H12N8, subtype H13N2, subtype H13N3, subtype H13N6, subtype H13N7, subtype H14N5, subtype H14N6, subtype H15N8, subtype H15N9, subtype H16N3, subtype H1N1, subtype H1N2, subtype H1N3, subtype H1N6, subtype H1N9, subtype H2N1, subtype H2N2, subtype H2N3, subtype H2N5, subtype H2N7, subtype H2N8, subtype H2N9, subtype H3N1, subtype H3N2, subtype H3N3, subtype H3N4, subtype H3N5, subtype H3N6, subtype H3N8, subtype H3N9, subtype H4N1, subtype H4N2, subtype H4N3, subtype H4N4, subtype H4N5, subtype H4N6, subtype H4N8, subtype H4N9, subtype H5N1, subtype H5N2, subtype H5N3, subtype H5N4, subtype H5N6, subtype H5N7, subtype H5N8, subtype H5N9, subtype H6N1, subtype H6N2, subtype H6N3, subtype H6N4, subtype H6N5, subtype H6N6, subtype H6N7, subtype H6N8, subtype H6N9, subtype H7N1, subtype H7N2, subtype H7N3, subtype H7N4, subtype H7N5, subtype H7N7, subtype H7N8, subtype H7N9, subtype H8N4, subtype H8N5, subtype H9N1, subtype H9N2, subtype H9N3, subtype H9N5, subtype H9N6, subtype H9N7, subtype H9N8, and subtype H9N9.

Specific examples of strains of influenza A virus include, but are not limited to: A/sw/Iowa/15/30 (H1N1); A/WSN/33 (H1N1); A/eq/Prague/1/56 (H7N7); A/PR/8/34; A/mallard/Potsdam/178-4/83 (H2N2); A/herring gull/DE/712/88 (H16N3); A/sw/Hong Kong/168/1993 (H1N1); A/mallard/Alberta/211/98 (H1N1); A/shorebird/Delaware/168/06 (H16N3); A/sw/Netherlands/25/80 (H1N1); A/sw/Germany/2/81 (H1N1); A/sw/Hannover/1/81 (H1N1); A/sw/Potsdam/1/81 (H1N1); A/sw/Potsdam/15/81 (H1N1); A/sw/Potsdam/268/81 (H1N1); A/sw/Finistere/2899/82 (H1N1); A/sw/Potsdam/35/82 (H3N2); A/sw/Cote d'Armor/3633/84 (H3N2); A/sw/Gent/1/84 (H3N2); A/sw/Netherlands/12/85 (H1N1); A/sw/Karrenzien/2/87 (H3N2); A/sw/Schwerin/103/89 (H1N1); A/turkey/Germany/3/91 (H1N1); A/sw/Germany/8533/91 (H1N1); A/sw/Belgium/220/92 (H3N2); A/sw/GentN230/92 (H1N1); A/sw/Leipzig/145/92 (H3N2); A/sw/Re220/92 hp (H3N2); A/sw/Bakum/909/93 (H3N2); A/sw/Schleswig-Holstein/1/93 (H1N1); A/sw/Scotland/419440/94 (H1N2); A/sw/Bakum/5/95 (H1N1); A/sw/Best/5C/96 (H1N1); A/sw/England/17394/96 (H1N2); A/sw/Jena/5/96 (H3N2); A/sw/Oedenrode/7C/96 (H3N2); A/sw/Lohne/1/97 (H3N2); A/sw/Cote d'Armor/790/97 (H1N2); A/sw/Bakum/1362/98 (H3N2); A/sw/Italy/1521/98 (H1N2); A/sw/Italy/1553-2/98 (H3N2); A/sw/Italy/1566/98 (H1N1); A/sw/Italy/1589/98 (H1N1); A/sw/Bakum/8602/99 (H3N2); A/sw/Cotes d'Armor/604/99 (H1N2); A/sw/Cote d'Armor/1482/99 (H1N1); A/sw/Gent/7625/99 (H1N2); A/Hong Kong/1774/99 (H3N2); A/sw/Hong Kong/5190/99 (H3N2); A/sw/Hong Kong/5200/99 (H3N2); A/sw/Hong Kong/5212/99 (H3N2); A/sw/Ille et Villaine/1455/99 (H1N1); A/sw/Italy/1654-1/99 (H1N2); A/sw/Italy/2034/99 (H1N1); A/sw/Italy/2064/99 (H1N2); A/sw/Berlin/1578/00 (H3N2); A/sw/Bakum/1832/00 (H1N2); A/sw/Bakum/1833/00 (H1N2); A/sw/Cote d'Armor/800/00 (H1N2); A/sw/Hong Kong/7982/00 (H3N2); A/sw/Italy/1081/00 (H1N2); A/sw/Belzig/2/01 (H1N1); A/sw/Belzig/54/01 (H3N2); A/sw/Hong Kong/9296/01 (H3N2); A/sw/Hong Kong/9745/01 (H3N2); A/sw/Spain/33601/01 (H3N2); A/sw/Hong Kong/1144/02 (H3N2); A/sw/Hong Kong/1197/02 (H3N2); A/sw/Spain/39139/02 (H3N2); A/sw/Spain/42386/02 (H3N2); A/Switzerland/8808/2002 (H1N1); A/sw/Bakum/1769/03 (H3N2); A/sw/Bissendorf/IDT1864/03 (H3N2); A/sw/Ehren/IDT2570/03 (H1N2); A/sw/Gescher/IDT2702/03 (H1N2); A/sw/Haselünne/2617/03 hp (H1N1); A/sw/Loningen/IDT2530/03 (H1N2); A/sw/IVD/IDT2674/03 (H1N2); A/sw/Nordkirchen/IDT1993/03 (H3N2); A/sw/Nordwalde/IDT2197/03 (H1N2); A/sw/Norden/IDT2308/03 (H1N2);

A/sw/Spain/50047/03 (H1N1); A/sw/Spain/51915/03 (H1N1); A/sw/Vechta/2623/03 (H1N1); A/sw/Visbek/IDT2869/03 (H1N2); A/sw/Waltersdorf/IDT2527/03 (H1N2); A/sw/Damme/IDT2890/04 (H3N2); A/sw/Geldern/IDT2888/04 (H1N1); A/sw/Granstedt/IDT3475/04 (H1N2); A/sw/Greven/IDT2889/04 (H1N1); A/sw/Gudensberg/IDT2930/04 (H1N2); A/sw/Gudensberg/IDT2931/04 (H1N2); A/sw/Lohne/IDT3357/04 (H3N2); A/sw/Nortrup/IDT3685/04 (H1N2); A/sw/Seesen/IDT3055/04 (H3N2); A/sw/Spain/53207/04 (H1N1); A/sw/Spain/54008/04 (H3N2); A/sw/Stolzenau/IDT3296/04 (H1N2); A/sw/Wedel/IDT2965/04 (H1N1); A/sw/Bad Griesbach/IDT4191/05 (H3N2); A/sw/Cloppenburg/IDT4777/05 (H1N2); A/sw/Dotlingen/IDT3780/05 (H1N2); A/sw/Dotlingen/IDT4735/05 (H1N2); A/sw/Egglham/IDT5250/05 (H3N2); A/sw/Harkenblek/IDT4097/05 (H3N2); A/sw/Hertzen/IDT4317/05 (H3N2); A/sw/Krogel/IDT4192/05 (H1N1); A/sw/Laer/IDT3893/05 (H1N1); A/sw/Laer/IDT4126/05 (H3N2); A/sw/Merzen/IDT4114/05 (H3N2); A/sw/Muesleringen-S./IDT4263/05 (H3N2); A/sw/Osterhofen/IDT4004/05 (H3N2); A/sw/Sprenge/IDT3805/05 (H1N2); A/sw/Stadtlohn/IDT3853/05 (H1N2); A/swNoglarn/IDT4096/05 (H1N1); A/sw/Wohlerst/IDT4093/05 (H1N1); A/sw/Bad Griesbach/IDT5604/06 (H1N1); A/sw/Herzlake/IDT5335/06 (H3N2); A/sw/Herzlake/IDT5336/06 (H3N2); A/sw/Herzlake/IDT5337/06 (H3N2); and A/wild boar/Germany/R169/2006 (H3N2).

Other specific examples of strains of influenza A virus include, but are not limited to: A/Toronto/3141/2009 (H1N1); A/Regensburg/D6/2009 (H1N1); A/Bayern/62/2009 (H1N1); A/Bayern/62/2009 (H1N1); A/Bradenburg/19/2009 (H1N1); A/Bradenburg/20/2009 (H1N1); A/Distrito Federal/2611/2009 (H1N1); A/Mato Grosso/2329/2009 (H1N1); A/Sao Paulo/1454/2009 (H1N1); A/Sao Paulo/2233/2009 (H1N1); A/Stockholm/37/2009 (H1N1); A/Stockholm/41/2009 (H1N1); A/Stockholm/45/2009 (H1N1); A/swine/Alberta/OTH-33-1/2009 (H1N1); A/swine/Alberta/OTH-33-14/2009 (H1N1); A/swine/Alberta/OTH-33-2/2009 (H1N1); A/swine/Alberta/OTH-33-21/2009 (H1N1); A/swine/Alberta/OTH-33-22/2009 (H1N1); A/swine/Alberta/OTH-33-23/2009 (H1N1); A/swine/Alberta/OTH-33-24/2009 (H1N1); A/swine/Alberta/OTH-33-25/2009 (H1N1); A/swine/Alberta/OTH-33-3/2009 (H1N1); A/swine/Alberta/OTH-33-7/2009 (H1N1); A/Beijing/502/2009 (H1N1); A/Firenze/10/2009 (H1N1); A/Hong Kong/2369/2009 (H1N1); A/Italy/85/2009 (H1N1); A/Santo Domingo/572N/2009 (H1N1); A/Catalonia/385/2009 (H1N1); A/Catalonia/386/2009 (H1N1); A/Catalonia/387/2009 (H1N1); A/Catalonia/390/2009 (H1N1); A/Catalonia/394/2009 (H1N1); A/Catalonia/397/2009 (H1N1); A/Catalonia/398/2009 (H1N1); A/Catalonia/399/2009 (H1N1); A/Sao Paulo/2303/2009 (H1N1); A/Akita/1/2009 (H1N1); A/Castro/JXP/2009 (H1N1); A/Fukushima/1/2009 (H1N1); A/Israel/276/2009 (H1N1); A/Israel/277/2009 (H1N1); A/Israel/70/2009 (H1N1); A/Iwate/1/2009 (H1N1); A/Iwate/2/2009 (H1N1); A/Kagoshima/1/2009 (H1N1); A/Osaka/180/2009 (H1N1); A/Puerto Montt/Bio87/2009 (H1N1); A/Sao Paulo/2303/2009 (H1N1); A/Sapporo/1/2009 (H1N1); A/Stockholm/30/2009 (H1N1); A/Stockholm/31/2009 (H1N1); A/Stockholm/32/2009 (H1N1); A/Stockholm/33/2009 (H1N1); A/Stockholm/34/2009 (H1N1); A/Stockholm/35/2009 (H1N1); A/Stockholm/36/2009 (H1N1); A/Stockholm/38/2009 (H1N1); A/Stockholm/39/2009 (H1N1); A/Stockholm/40/2009 (H1N1;) A/Stockholm/42/2009 (H1N1); A/Stockholm/43/2009 (H1N1); A/Stockholm/44/2009 (H1N1); A/Utsunomiya/2/2009 (H1N1); A/WRAIR/0573N/2009 (H1N1); and A/Zhejiang/DTID-ZJU01/2009 (H1N1).

Non-limiting examples of influenza B viruses include strain Aichi/5/88, strain Akita/27/2001, strain Akita/5/2001, strain Alaska/16/2000, strain Alaska/1777/2005, strain Argentina/69/2001, strain Arizona/146/2005, strain Arizona/148/2005, strain Bangkok/163/90, strain Bangkok/34/99, strain Bangkok/460/03, strain Bangkok/54/99, strain Barcelona/215/03, strain Beijing/15/84, strain Beijing/184/93, strain Beijing/243/97, strain Beijing/43/75, strain Beijing/5/76, strain Beijing/76/98, strain Belgium/WV106/2002, strain Belgium/WV107/2002, strain Belgium/WV109/2002, strain Belgium/WV114/2002, strain Belgium/WV122/2002, strain Bonn/43, strain Brazil/952/2001, strain Bucharest/795/03, strain Buenos Aires/161/00), strain Buenos Aires/9/95, strain Buenos Aires/SW16/97, strain Buenos AiresNL518/99, strain Canada/464/2001, strain Canada/464/2002, strain Chaco/366/00, strain Chaco/R113/00, strain Cheju/303/03, strain Chiba/447/98, strain Chongqing/3/2000, strain clinical isolate SA1 Thailand/2002, strain clinical isolate SA10 Thailand/2002, strain clinical isolate SA100 Philippines/2002, strain clinical isolate SA101 Philippines/2002, strain clinical isolate SA1 10 Philippines/2002), strain clinical isolate SA112 Philippines/2002, strain clinical isolate SA113 Philippines/2002, strain clinical isolate SA114 Philippines/2002, strain clinical isolate SA2 Thailand/2002, strain clinical isolate SA20 Thailand/2002, strain clinical isolate SA38 Philippines/2002, strain clinical isolate SA39 Thailand/2002, strain clinical isolate SA99 Philippines/2002, strain CNIC/27/2001, strain Colorado/2597/2004, strain CordobaNA418/99, strain Czechoslovakia/16/89, strain Czechoslovakia/69/90, strain Daeku/10/97, strain Daeku/45/97, strain Daeku/47/97, strain Daeku/9/97, strain B/Du/4/78, strain B/Durban/39/98, strain Durban/43/98, strain Durban/44/98, strain B/Durban/52/98, strain Durban/55/98, strain Durban/56/98, strain England/1716/2005, strain England/2054/2005), strain England/23/04, strain Finland/154/2002, strain Finland/159/2002, strain Finland/160/2002, strain Finland/161/2002, strain Finland/162/03, strain Finland/162/2002, strain Finland/162/91, strain Finland/164/2003, strain Finland/172/91, strain Finland/173/2003, strain Finland/176/2003, strain Finland/184/91, strain Finland/188/2003, strain Finland/190/2003, strain Finland/220/2003, strain Finland/WV5/2002, strain Fujian/36/82, strain Geneva/5079/03, strain Genoa/11/02, strain Genoa/2/02, strain Genoa/21/02, strain Genova/54/02, strain Genova/55/02, strain Guangdong/05/94, strain Guangdong/08/93, strain Guangdong/5/94, strain Guangdong/55/89, strain Guangdong/8/93, strain Guangzhou/7/97, strain Guangzhou/86/92, strain Guangzhou/87/92, strain Gyeonggi/592/2005, strain Hannover/2/90, strain Harbin/07/94, strain Hawaii/10/2001, strain Hawaii/1990/2004, strain Hawaii/38/2001, strain Hawaii/9/2001, strain Hebei/19/94, strain Hebei/3/94), strain Henan/22/97, strain Hiroshima/23/2001, strain Hong Kong/110/99, strain Hong Kong/1115/2002, strain Hong Kong/112/2001, strain Hong Kong/123/2001, strain Hong Kong/1351/2002, strain Hong Kong/1434/2002, strain Hong Kong/147/99, strain Hong Kong/156/99, strain Hong Kong/157/99, strain Hong Kong/22/2001, strain Hong Kong/22/89, strain Hong Kong/336/2001, strain Hong Kong/666/2001, strain Hong Kong/9/89, strain Houston/1/91, strain Houston/1/96, strain Houston/2/96, strain Hunan/4/72, strain Ibaraki/2/85, strain ncheon/297/2005, strain India/3/89, strain India/77276/2001, strain Israel/95/03, strain Israel/WV187/2002, strain Japan/1224/2005, strain Jiangsu/10/03, strain Johannesburg/1/99, strain Johannesburg/96/01, strain Kadoma/1076/99, strain Kadoma/122/99, strain Kagoshima/15/94, strain Kansas/22992/99, strain Khazkov/224/91, strain Kobe/1/2002, strain, strain Kouchi/193/99, strain Lazio/1/02, strain Lee/40, strain Leningrad/129/91, strain Lissabon/2/90), strain Los Angeles/1/02, strain Lusaka/270/99, strain Lyon/1271/96, strain Malaysia/83077/2001, strain Maputo/1/99, strain Mar del Plata/595/99, strain Maryland/1/01, strain Memphis/1/01, strain Memphis/12/97-MA, strain Michigan/22572/99, strain Mie/1/93, strain Milano/1/01, strain Minsk/318/90, strain Moscow/3/03, strain Nagoya/20/99, strain Nanchang/1/00, strain Nashville/107/93, strain Nashville/45/91, strain Nebraska/2/01, strain Netherland/801/90, strain Netherlands/429/98, strain New York/1/2002, strain NIB/48/90, strain Ningxia/45/83, strain Norway/1/84, strain Oman/16299/2001, strain Osaka/1059/97, strain Osaka/983/97-V2, strain Oslo/1329/2002, strain Oslo/1846/2002, strain Panama/45/90, strain Paris/329/90, strain Parma/23/02, strain Perth/211/2001, strain Peru/1364/2004, strain Philippines/5072/2001, strain Pusan/270/99, strain Quebec/173/98, strain Quebec/465/98, strain Quebec/7/01, strain Roma/1/03, strain Saga/S172/99, strain Seoul/13/95, strain Seoul/37/91, strain Shangdong/7/97, strain Shanghai/361/2002), strain Shiga/T30/98, strain Sichuan/379/99, strain Singapore/222/79, strain Spain/WV27/2002, strain Stockholm/10/90, strain Switzerland/5441/90, strain Taiwan/0409/00, strain Taiwan/0722/02, strain Taiwan/97271/2001, strain Tehran/80/02, strain Tokyo/6/98, strain Trieste/28/02, strain Ulan Ude/4/02, strain United Kingdom/34304/99, strain USSR/100/83, strain Victoria/103/89, strain Vienna/1/99, strain Wuhan/356/2000, strain WV194/2002, strain Xuanwu/23/82, strain Yamagata/1311/2003, strain Yamagata/K500/2001, strain Alaska/12/96, strain GA/86, strain NAGASAKI/1/87, strain Tokyo/942/96, and strain Rochester/02/2001.

Non-limiting examples of influenza C viruses include strain Aichi/1/81, strain Ann Arbor/1/50, strain Aomori/74, strain California/78, strain England/83, strain Greece/79, strain Hiroshima/246/2000, strain Hiroshima/252/2000, strain Hyogo/1/83, strain Johannesburg/66, strain Kanagawa/1/76, strain Kyoto/1/79, strain Mississippi/80, strain Miyagi/1/97, strain Miyagi/5/2000, strain Miyagi/9/96, strain Nara/2/85, strain NewJersey/76, strain pig/Beijing/115/81, strain Saitama/3/2000), strain Shizuoka/79, strain Yamagata/2/98, strain Yamagata/6/2000, strain Yamagata/9/96, strain BERLIN/1/85, strain ENGLAND/892/8, strain GREAT LAKES/1167/54, strain JJ/50, strain PIG/BEIJING/10/81, strain PIG/BEIJING/439/82), strain TAYLOR/1233/47, and strain C/YAMAGATA/10/81.

In certain embodiments, the influenza viruses provided herein have an attenuated phenotype. In specific embodiments, the attenuated influenza virus is based on influenza A virus. In other embodiments, the attenuated influenza virus is based on influenza B virus. In yet other embodiments, the attenuated influenza virus is based on influenza C virus. In other embodiments, the attenuated influenza virus may comprise genes or genome segments from one or more strains or subtypes of influenza A, influenza B, and/or influenza C virus. In some embodiments, the attenuated backbone virus comprises genes from an influenza A virus and an influenza B virus.

In specific embodiments, attenuation of influenza virus is desired such that the virus remains, at least partially, infectious and can replicate in vivo, but only generate low titers resulting in subclinical levels of infection that are non-pathogenic. Such attenuated viruses are especially suited for embodiments described herein wherein the virus or an immunogenic composition thereof is administered to a subject to induce an immune response. Attenuation of the influenza virus can be accomplished according to any method known in the art, such as, e.g., selecting viral mutants generated by chemical mutagenesis, mutation of the genome by genetic engineering, selecting reassortant viruses that contain segments with attenuated function, or selecting for conditional virus mutants (e.g., cold-adapted viruses). Alternatively, naturally occurring attenuated influenza viruses may be used as influenza virus backbones for the influenza virus vectors.

In some embodiments, an influenza virus may be attenuated, at least in part, by engineering the influenza virus to express a mutated NS1 gene that impairs the ability of the virus to antagonize the cellular interferon (IFN) response. Examples of the types of mutations that can be introduced into the influenza virus NS1 gene include deletions, substitutions, insertions and combinations thereof. One or more mutations can be introduced anywhere throughout the NS1 gene (e.g., the N-terminus, the C-terminus or somewhere in between) and/or the regulatory element of the NS1 gene. In one embodiment, an attenuated influenza virus comprises a genome having a mutation in an influenza virus NS1 gene resulting in a deletion consisting of 5, preferably 10, 15, 20, 25, 30, 35, 40, 45, 50, 55, 60, 65, 75, 80, 85, 90, 95, 99, 100, 105, 110, 115, 120, 125, 126, 130, 135, 140, 145, 150, 155, 160, 165, 170 or 175 amino acid residues from the C-terminus of NS1, or a deletion of between 5-170, 25-170, 50-170, 100-170, 100-160, or 105-160 amino acid residues from the C-terminus. In another embodiment, an attenuated influenza virus comprises a genome having a mutation in an influenza virus NS1 gene such that it encodes an NS1 protein of amino acid residues 1-130, amino acid residues 1-126, amino acid residues 1-120, amino acid residues 1-115, amino acid residues 1-110, amino acid residues 1-100, amino acid residues 1-99, amino acid residues 1-95, amino acid residues 1-85, amino acid residues 1-83, amino acid residues 1-80, amino acid residues 1-75, amino acid residues 1-73, amino acid residues 1-70, amino acid residues 1-65, or amino acid residues 1-60, wherein the N-terminus amino acid is number 1. In another embodiment, the amino acid residues of NS1 are counted based on the PR8 virus. For examples of NS1 mutations and influenza viruses comprising a mutated NS1, see, e.g., U.S. Pat. Nos. 6,468,544 and 6,669,943; and Li et al., 1999, J. Infect. Dis. 179:1132-1138, each of which is incorporated by reference herein in its entirety.

5.5 Non-Influenza Virus Vectors

In one aspect, provided herein are non-influenza viruses containing a flu polypeptide. In a specific embodiment, the flu polypeptide is incorporated into the virions of the non-influenza virus. The non-influenza viruses may be conjugated to moieties that target the viruses to particular cell types, such as immune cells. In some embodiments, the virions of the non-influenza virus have incorporated into them or express a heterologous polypeptide in addition to a flu polypeptide. The heterologous polypeptide may be a polypeptide that has immunopotentiating activity, or that targets the non-influenza virus to a particular cell type, such as an antibody that recognizes an antigen on a specific cell type or a ligand that binds a specific receptor on a specific cell type. See Section 5.4, supra, for examples of such heterologous polypeptides.

Non-influenza viruses containing a flu polypeptide may be produced by supplying in trans the flu polypeptide during production of virions using techniques known to one skilled in the art. Alternatively, a parental non-influenza virus comprises a genome engineered to express a flu polypeptide in cells susceptible to infection with the virus wherein hemagglutinin function is provided in trans to produce progeny viruses containing the influenza flu polypeptide.

Any virus type, subtype or strain including, but not limited to, naturally occurring strains, variants or mutants, mutagenized viruses, reassortants and/or genetically modified viruses may be used as a non-influenza virus vector. In a specific embodiment, the parental non-influenza virus is not a naturally occurring virus. In another specific embodiment, the parental non-influenza virus is a genetically engineered virus. In certain embodiments, an enveloped virus is preferred for the expression of a membrane bound flu polypeptide described herein.

In an exemplary embodiment, the non-influenza virus vector is a Newcastle disease virus (NDV). In another embodiment, the non-influenza virus vector is a vaccinia virus. In other exemplary, non-limiting, embodiments, the non-influenza virus vector is adenovirus, adeno-associated virus (AAV), hepatitis B virus, retrovirus (such as, e.g., a gammaretrovirus such as Mouse Stem Cell Virus (MSCV) genome or Murine Leukemia Virus (MLV), e.g., Moloney murine leukemia virus, oncoretrovirus, or lentivirus), an alphavirus (e.g., Venezuelan equine encephalitis virus), a rhabdovirus, such as vesicular stomatitis virus or papillomaviruses, poxvirus (such as, e.g., vaccinia virus, a MVA-T7 vector, or fowlpox), metapneumovirus, measles virus, herpesvirus, such as herpes simplex virus, or foamyvirus. See, e.g., Lawrie and Tumin, 1993, Cur. Opin. Genet. Develop. 3, 102-109 (retroviral vectors); Bett et al., 1993, J. Virol. 67, 5911 (adenoviral vectors); Zhou et al., 1994, J. Exp. Med. 179, 1867 (adeno-associated virus vectors); Dubensky et al., 1996, J. Virol. 70, 508-519 (viral vectors from the pox family including vaccinia virus and the avian pox viruses and viral vectors from the alpha virus genus such as those derived from Sindbis and Semliki Forest Viruses); U.S. Pat. No. 5,643,576 (Venezuelan equine encephalitis virus); WO 96/34625 (VSV); Ohe et al., 1995, Human Gene Therapy 6, 325-333; Woo et al., WO 94/12629; Xiao & Brandsma, 1996, Nucleic Acids. Res. 24, 2630-2622 (papillomaviruses); and Bukreyev and Collins, 2008, Curr Opin Mol Ther. 10:46-55 (NDV), each of which is incorporated by reference herein in its entirety.

In a specific embodiment, the non-influenza virus vector is NDV. Any NDV type, subtype or strain may serve as the backbone that is engineered to express a flu polypeptide, including, but not limited to, naturally-occurring strains, variants or mutants, mutagenized viruses, reassortants and/or genetically engineered viruses. In a specific embodiment, the NDV that serves as the backbone for genetic engineering is a naturally-occurring strain. In certain embodiments, the NDV that serves as the backbone for genetic engineering is a lytic strain. In other embodiments, the NDV that serves as the backbone for genetic engineering is a non-lytic strain. In certain embodiments, the NDV that serves as the backbone for genetic engineering is lentogenic strain. In some embodiments, the NDV that serves as the backbone for genetic engineering is a mesogenic strain. In other embodiments, the NDV that serves as the backbone for genetic engineering is a velogenic strain. Specific examples of NDV strains include, but are not limited to, the 73-T strain, Ulster strain, MTH-68 strain, Italien strain, Hickman strain, PV701 strain, Hitchner B1 strain, La Sota strain, YG97 strain, MET95 strain, and F48E9 strain. In a specific embodiment, the NDV that serves as the backbone for genetic engineering is the Hitchner B1 strain. In another specific embodiment, the NDV that serves as the backbone for genetic engineering is the La Sota strain.

In one embodiment, the NDV used as the backbone for a non-influenza virus vector is engineered to express a modified F protein in which the cleavage site of the F protein is replaced with one containing one or two extra arginine residues, allowing the mutant cleavage site to be activated by ubiquitously expressed proteases of the furin family. Specific examples of NDVs that express such a modified F protein include, but are not limited to, rNDV/F2aa and rNDV/F3aa. For a description of mutations introduced into a NDV F protein to produce a modified F protein with a mutated cleavage site, see, e.g., Park et al. (2006) "Engineered viral vaccine constructs with dual specificity: Avian influenza and Newcastle disease." PNAS USA 103: 8203-2808, which is incorporated herein by reference in its entirety.

In one embodiment, the non-influenza virus vector is a poxvirus. A poxvirus vector may be based on any member of the poxviridae, in particular, a vaccinia virus or an avipox virus (e.g., such as canarypox, fowlpox, etc.) that provides suitable sequences for vaccine vectors. In a specific embodiment, the poxviral vector is a vaccinia virus vector. Suitable vaccinia viruses include, but are not limited to, the Copenhagen (VC-2) strain (Goebel, et al., Virol 179: 247-266, 1990; Johnson, et al., Virol. 196: 381-401, 1993), modified Copenhagen strain (NYVAC) (U.S. Pat. No. 6,265,189), the WYETH strain and the modified Ankara (MVA) strain (Antoine, et al., Virol. 244: 365-396, 1998). Other suitable poxviruses include fowlpox strains such as ALVAC and TROVAC vectors that provide desirable properties and are highly attenuated (see, e.g., U.S. Pat. No. 6,265,189; Tartaglia et al., In AIDS Research Reviews, Koff, et al., eds., Vol. 3, Marcel Dekker, N.Y., 1993; and Tartaglia et al., 1990, Reviews in Immunology 10: 13-30, 1990).

Methods of engineering non-influenza viruses to express a flu polypeptide are well known in the art, as are methods for attenuating, propagating, and isolating and purifying such viruses. For such techniques with respect to NDV vectors, see, e.g., International Publication No. WO 01/04333; U.S. Pat. Nos. 7,442,379, 6,146,642, 6,649,372, 6,544,785 and 7,384,774; Swayne et al. (2003). Avian Dis. 47:1047-1050; and Swayne et al. (2001). J. Virol. 11868-11873, each of which is incorporated by reference in its entirety. For such techniques with respect to poxviruses, see, e.g., Piccini, et al., Methods of Enzymology 153: 545-563, 1987; International Publication No. WO 96/11279; U.S. Pat. No. 4,769,330; U.S. Pat. No. 4,722,848; U.S. Pat. No. 4,769,330; U.S. Pat. No. 4,603,112; U.S. Pat. No. 5,110,587; U.S. Pat. No. 5,174,993; EP 83 286; EP 206 920; Mayr et al., Infection 3: 6-14, 1975; and Sutter and Moss, Proc. Natl. Acad. Sci. USA 89: 10847-10851, 1992. In certain embodiments, the non-influenza virus is attenuated.

Exemplary considerations for the selection of a non-influenza virus vector, particularly for use in compositions for administration to a subject, are safety, low toxicity, stability, cell type specificity, and immunogenicity, particularly, antigenicity of the flu polypeptide expressed by the non-influenza virus vector.

5.6 Viral-Like Particles and Virosomes

Flu polypeptides can be incorporated into viral-like particle (VLP) vectors. VLPs generally comprise a viral polypeptide(s) typically derived from a structural protein(s) of a virus. In some embodiments, the VLPs are not capable of replicating. In certain embodiments, the VLPs may lack the complete genome of a virus or comprise a portion of the genome of a virus. In some embodiments, the VLPs are not capable of infecting a cell. In some embodiments, the VLPs express on their surface one or more of viral (e.g., virus surface glycoprotein) or non-viral (e.g., antibody or protein) targeting moieties known to one skilled in the art or described herein. In some embodiments, the VLP comprises a flu polypeptide and a viral structural protein such as HIV gag.

Methods for producing and characterizing recombinantly produced VLPs have been described based on several viruses, including influenza virus (Bright et al. (2007) Vaccine. 25:3871), human papilloma virus type 1 (Hagnesee et al. (1991) J. Virol. 67:315), human papilloma virus type 16 (Kirnbauer et al. Proc. Natl. Acad. Sci. (1992)89:12180), HIV-1 (Haffer et al., (1990) J. Virol. 64:2653), and hepatitis A (Winokur (1991) 65:5029), each of which is incorporated herein in its entirety. Methods for expressing VLPs that contain NDV proteins are provided by Pantua et al. (2006) J. Virol. 80:11062-11073, and in United States patent application Publication No. 20090068221, published Mar. 12, 2009, each of which is incorporated in its entirety herein.

In a specific embodiment, a flu polypeptide may be incorporated into a virosome. A virosome containing a flu polypeptide may be produced using techniques known to those skilled in the art. For example, a virosome may be produced by disrupting a purified virus, extracting the genome, and reassembling particles with the viral proteins (e.g., a flu polypeptide) and lipids to form lipid particles containing viral proteins.

5.7 Bacterial Vectors

In a specific embodiment, bacteria may be engineered to express a flu polypeptide described herein. Suitable bacteria for expression of a flu polypeptide include, but are not limited to, *Listeria, Salmonella, Shigella* sp., *Mycobacterium tuberculosis, E. coli, Neisseria meningitides, Brucella abortus, Brucella melitensis, Borrelia burgdorferi*, and *Francisella tularensis*. In a specific embodiment, the bacteria engineered to express a flu polypeptide are attenuated. Techniques for the production of bacteria engineered to express a heterologous polypeptide are known in the art and can be applied to the expression of a flu polypeptide. See, e.g., United States Patent Application Publication No. 20080248066, published Oct. 9, 2008, and United States Patent Application Publication No. 20070207171, published Sep. 6, 2007, each of which are incorporated by reference herein in their entirety.

5.8 Generation of Antibodies Against Flu Polypeptides

The flu polypeptides, nucleic acids encoding such polypeptides, or vectors comprising such nucleic acids or polypeptides described herein may be used to elicit neutralizing antibodies against influenza, for example, against the long alpha-helix region of the HA2 domain of the flu polypeptide. In a specific embodiment, the flu polypeptides, nucleic acids encoding such polypeptides, or vectors comprising such nucleic acids or polypeptides described herein may be administered to a non-human subject (e.g., a mouse, rabbit, rat, guinea pig, etc.) to induce an immune response that includes the production of antibodies which may be isolated using techniques known to one of skill in the art (e.g., immunoaffinity chromatography, centrifugation, precipitation, etc.).

Alternatively, the flu polypeptides described herein may be used to screen for antibodies from antibody libraries. For example, an isolated flu polypeptide comprising a flu polypeptide may be immobilized to a solid support (e.g., a silica gel, a resin, a derivatized plastic film, a glass bead, cotton, a plastic bead, a polystyrene bead, an alumina gel, or a polysaccharide, a magnetic bead), and screened for binding to antibodies. As an alternative, the antibodies may be immobilized to a solid support and screened for binding to the isolated flu polypeptide. Any screening assay, such as a panning assay, ELISA, surface plasmon resonance, or other antibody screening assay known in the art may be used to screen for antibodies that bind to the flu polypeptide. The antibody library screened may be a commercially available antibody library, an in vitro generated library, or a library obtained by identifying and cloning or isolating antibodies from an individual infected with influenza. In particular embodiments, the antibody library is generated from a survivor of an influenza virus outbreak. Antibody libraries may be generated in accordance with methods known in the art. In a particular embodiment, the antibody library is generated by cloning the antibodies and using them in phage display libraries or a phagemid display library.

Antibodies identified in the methods described herein may be tested for neutralizing activity and lack of autoreactivity using the biological assays known in the art or described herein. In one embodiment, an antibody isolated from a non-human animal or an antibody library neutralizes a hemagglutinin polypeptide from more than one influenza subtype. In some embodiments, an antibody elicited or identified using a flu polypeptide, a nucleic acid encoding such a polypeptide, or a vector encoding such a nucleic acid or polypeptide neutralizes an influenza H3 virus. In some embodiments, an antibody elicited or identified using a flu polypeptide, a nucleic acid encoding such a polypeptide, or a vector comprising such a nucleic acid or polypeptide neutralizes 1, 2, 3, 4, 5, 6, 7, 8, 9, 10, 11, 12, 13, 14, 15, or 16 or more subtypes or strains of influenza virus. In one embodiment, the neutralizing antibody neutralizes one or more influenza A viruses and one or more influenza B viruses. In particular embodiments, the neutralizing antibody is not an antibody described in Wang et al. (2010) "Broadly Protective Monoclonal Antibodies against H3 Influenza Viruses following Sequential Immunization with Different Hemagglutinins," PLOS Pathogens 6(2):1-9.

Antibodies identified or elicited using a flu polypeptide, a nucleic acid encoding such a polypeptide, or a vector comprising such a nucleic acid or polypeptide include immunoglobulin molecules and immunologically active portions of immunoglobulin molecules, i.e., molecules that contain an antigen binding site that specifically binds to a flu polypeptide. The immunoglobulin molecules may be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass of immunoglobulin molecule. Antibodies include, but are not limited to, monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), and antiidiotypic (anti-Id) antibodies (including, e.g., anti-Id antibodies to antibodies elicited or identified using a method described herein), and epitope-binding fragments of any of the above. In a specific embodiment, an antibody elicited or identified using a flu polypeptide, a nucleic acid encoding such a polypeptide, or a vector comprising such a nucleic acid or polypeptide is a human or humanized monoclonal antibody.

Antibodies elicited or identified using a flu polypeptide, a nucleic acid encoding such a polypeptide, or a vector comprising such a nucleic acid or polypeptide may be used to monitor the efficacy of a therapy and/or disease progression. Any immunoassay system known in the art may be used for this purpose including, but not limited to, competitive and noncompetitive assay systems using techniques such as radioimmunoassays, ELISA (enzyme linked immunosorbent assays), "sandwich" immunoassays, precipitin reactions, gel diffusion precipitin reactions, immunodiffusion assays, agglutination assays, complement fixation assays, immunoradiometric assays, fluorescent immunoassays, protein A immunoassays and immunoelectrophoresis assays, to name but a few.

Antibodies elicited or identified using a flu polypeptide, a nucleic acid encoding such a polypeptide, or a vector comprising such a nucleic acid or polypeptide may be used to detect influenza virus, for example, from a plurality of influenza virus strains from a single subtype or 2, 3, 4 or more different subtypes and/or to diagnosis an influenza virus infection by, for example, a plurality of influenza virus strains from a single subtype or 2, 3, 4 or more different subtypes.

Antibodies elicited or identified using a flu polypeptide, a nucleic acid encoding such a polypeptide, or a vector comprising such a nucleic acid or polypeptide may be used in the production of antiidiotypic antibody. The antiidiotypic antibody can then in turn be used for immunization, in order to produce a subpopulation of antibodies that bind a particular antigen of influenza, e.g., a flu polypeptide (Jerne, 1974, Ann. Immunol. (Paris) 125c:373; Jerne et al., 1982, EMBO J. 1:234, incorporated herein by reference in its entirety).

In certain embodiments, the non-human subjects administered flu polypeptides, nucleic acids encoding such polypeptides, or vectors comprising such nucleic acids or polypeptides to generate antibodies in accordance with the methods described herein are transgenic animals (e.g., transgenic mice) that are capable of producing human antibodies. Human antibodies can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. Companies such as Abgenix, Inc. (Freemont, Calif.), Genpharm (San Jose, Calif.), and Medarex, Inc. (Princeton, N.J.) can be engaged to provide human antibodies directed against a selected antigen.

5.9 Stimulation of Cells with Flu Polypeptides

In another aspect, provided herein are methods for stimulating cells ex vivo with a flu polypeptide described herein. Such cells, e.g., dendritic cells, may be used in vitro to generate antibodies against the flu polypeptide or may themselves be administered to a subject by, e.g., an adoptive transfer technique known in the art. See, e.g., United States patent application Publication No. 20080019998, published Jan. 24, 2008, which is incorporated herein by reference in its entirety, for a description of adoptive transfer techniques. In certain embodiments, when cells that have been stimulated ex vivo with a flu polypeptide described herein are administered to a subject, the cells are not mammalian cells (e.g., CB-1 cells). In certain embodiments, when cells that have been stimulated ex vivo with a flu polypeptide described herein are administered to a subject, the cells are mammalian cells (e.g., CB-1 cells).

In one non-limiting example, a vector, e.g., an influenza virus vector, engineered to express a flu polypeptide described herein can be used to generate dendritic cells (DCs) that express the flu polypeptide and display immunostimulatory properties directed against a flu polypeptide. Such DCs may be used to expand memory T cells and are potent stimulators of T cells, including influenza flu polypeptide-specific cytotoxic T lymphocyte clones. See Strobel et al., 2000, Human Gene Therapy 11:2207-2218, which is incorporated herein by reference in its entirety.

A flu polypeptide described herein may be delivered to a target cell in any way that allows the polypeptide to contact the target cell, e.g., a DC, and deliver the polypeptide to the target cell. In certain embodiments, the flu polypeptide is delivered to a subject, as described herein. In some such embodiments, cells contacted with the polypeptide may be isolated and propagated.

In certain embodiments, a flu polypeptide is delivered to a target cell in vitro. Techniques known to one of skill in the art may be used to deliver the polypeptide to target cells. For example, target cells may be contacted with the polypeptide in a tissue culture plate, tube or other container. The polypeptide may be suspended in media and added to the wells of a culture plate, tube or other container. The media containing the polypeptide may be added prior to plating of the cells or after the cells have been plated. The target cells are preferably incubated with the polypeptide for a sufficient amount of time to allow the polypeptide to contact the cells. In certain embodiments, the cells are incubated with the polypeptide for about 1 hour or more, about 5 hours or more, about 10 hours or more, about 12 hours or more, about 16 hours or more, about 24, hours or more, about 48 hours or more, about 1 hour to about 12 hours, about 3 hours to about 6 hours, about 6 hours to about 12 hours, about 12 hours to about 24 hours, or about 24 hours to about 48 hours. In certain embodiments, wherein the flu polypeptide is in a virus, the contacting of the target cells comprises infecting the cells with the virus.

The target cells may be from any species, including, e.g., humans, mice, rats, rabbits and guinea pigs. In some embodiments, target cells are DCs obtained from a healthy subject or a subject in need of treatment. In certain embodiments, target cells are DCs obtained from a subject in whom it is desired to stimulate an immune response to the polypeptide. Methods of obtaining cells from a subject are well known in the art.

5.10 Compositions

The flu polypeptides, nucleic acids, vectors, bacteria, antibodies, or cells described herein (sometimes referred to herein as "active compounds") may be incorporated into compositions. In a specific embodiment, the compositions are pharmaceutical compositions, such as immunogenic compositions (e.g., vaccine formulations). The pharmaceutical compositions provided herein can be in any form that allows for the composition to be administered to a subject. In a specific embodiment, the pharmaceutical compositions are suitable for veterinary and/or human administration. The compositions may be used in methods of preventing or treating an influenza virus disease.

In one embodiment, a pharmaceutical composition comprises a flu polypeptide, in an admixture with a pharmaceutically acceptable carrier. In another embodiment, a pharmaceutical composition comprises a nucleic acid encoding a flu polypeptide described herein, in an admixture with a pharmaceutically acceptable carrier. In another embodiment, a pharmaceutical composition comprises an expression vector comprising a nucleic acid encoding a flu polypeptide, in an admixture with a pharmaceutically acceptable carrier. In another embodiment, a pharmaceutical composition comprises an influenza virus or non-influenza virus containing a flu polypeptide, in an admixture with a pharmaceutically acceptable carrier. In another embodiment, a pharmaceutical composition comprises an influenza virus or non-influenza virus having a genome engineered to express a flu polypeptide, in admixture with a pharmaceutically acceptable carrier. In another embodiment, a pharmaceutical composition comprises a viral-like particle or virosome containing a flu polypeptide, in an admixture with a pharmaceutically acceptable carrier. In another embodiment, a pharmaceutical composition comprises a bacteria expressing or engineered to express a flu polypeptide, in an admixture with a pharmaceutically acceptable carrier. In another embodiment, a pharmaceutical composition comprises cells stimulated with a flu polypeptide, in an admixture with a pharmaceutically acceptable carrier.

In some embodiments, a pharmaceutical composition may comprise one or more other therapies in addition to an active compound.

As used herein, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should suit the mode of administration.

In a specific embodiment, pharmaceutical compositions are formulated to be suitable for the intended route of administration to a subject. For example, the pharmaceutical composition may be formulated to be suitable for subcutaneous, parenteral, oral, intradermal, transdermal, colorectal, intraperitoneal, and rectal administration. In a specific embodiment, the pharmaceutical composition may be formulated for intravenous, oral, intraperitoneal, intranasal, intratracheal, subcutaneous, intramuscular, topical, intradermal, transdermal or pulmonary administration.

In certain embodiments, biodegradable polymers, such as ethylene vinyl acetate, polyanhydrides, polyethylene glycol (PEGylation), polymethyl methacrylate polymers, polylactides, poly(lactide-co-glycolides), polyglycolic acid, collagen, polyorthoesters, and polylactic acid, may be used as carriers. In some embodiments, the active compounds are prepared with carriers that increase the protection of the compound against rapid elimination from the body, such as a controlled release formulation, including implants and microencapsulated delivery systems. Methods for preparation of such formulations will be apparent to those skilled in the art. Liposomes or micelles can also be used as pharmaceutically acceptable carriers. These can be prepared according to methods known to those skilled in the art, for example, as described in U.S. Pat. No. 4,522,811. In certain embodiments, the pharmaceutical compositions comprise one or more adjuvants.

In specific embodiments, immunogenic compositions described herein are monovalent formulations. In other embodiments, immunogenic compositions described herein are multivalent formulations. In one example, a multivalent formulation comprises one or more vectors expressing a flu polypeptide derived from an influenza A virus and one or more vectors expressing a flu polypeptide derived from an influenza B virus. In another example, a multivalent formulation comprises a vector expressing a flu polypeptide derived from an H3 influenza A virus and a vector expressing a flu polypeptide derived from an H1 influenza A virus. In another example, a multivalent formulation comprises a vector expressing a flu polypeptide derived from an H3 influenza A virus, a vector expressing a flu polypeptide derived from an H1 influenza A virus, and a vector expressing a flu polypeptide derived from an influenza B virus. In certain embodiments, a multivalent formulation may comprise one or more different flu polypeptides expressed using a single vector.

In certain embodiments, the pharmaceutical compositions described herein additionally comprise a preservative, e.g., the mercury derivative thimerosal. In a specific embodiment, the pharmaceutical compositions described herein comprises 0.001% to 0.01% thimerosal. In other embodiments, the pharmaceutical compositions described herein do not comprise a preservative. In a specific embodiment, thimerosal is used during the manufacture of a pharmaceutical composition described herein and the thimerosal is removed via purification steps following production of the pharmaceutical composition, i.e., the pharmaceutical composition contains trace amounts of thimerosal (<0.3 μg of mercury per dose after purification; such pharmaceutical compositions are considered thimerosal-free products).

In certain embodiments, the pharmaceutical compositions described herein additionally comprise egg protein (e.g., ovalbumin or other egg proteins). The amount of egg protein in the pharmaceutical compositions described herein may range from about 0.0005 to about 1.2. μg of egg protein to 1 ml of pharmaceutical composition. In other embodiments, the pharmaceutical compositions described herein do not comprise egg protein.

In certain embodiments, the pharmaceutical compositions described herein additionally comprise one or more antimicrobial agents (e.g., antibiotics) including, but not limited to gentamicin, neomycin, polymyxin (e.g., polymyxin B), and kanamycin, streptomycin. In other embodiments, the pharmaceutical compositions described herein do not comprise any antibiotics.

In certain embodiments, the pharmaceutical compositions described herein additionally comprise one or more components used to inactivate a virus, e.g., formalin or formaldehyde or a detergent such as sodium deoxycholate, octoxynol 9 (Triton X-100), and octoxynol 10. In other embodiments, the pharmaceutical compositions described herein do not comprise any components used to inactivate a virus.

In certain embodiments, the pharmaceutical compositions described herein additionally comprise gelatin. In other embodiments, the pharmaceutical compositions described herein do not comprise gelatin.

In certain embodiments, the pharmaceutical compositions described herein additionally comprise one or more buffers, e.g., phosphate buffer and sucrose phosphate glutamate buffer. In other embodiments, the pharmaceutical compositions described herein do not comprise buffers.

In certain embodiments, the pharmaceutical compositions described herein additionally comprise one or more salts, e.g., sodium chloride, calcium chloride, sodium phosphate, monosodium glutamate, and aluminum salts (e.g., aluminum hydroxide, aluminum phosphate, alum (potassium aluminum sulfate), or a mixture of such aluminum salts). In other embodiments, the pharmaceutical compositions described herein do not comprise salts.

In specific embodiments, the pharmaceutical compositions described herein are low-additive influenza virus vaccines, i.e., the pharmaceutical compositions do not comprise one or more additives commonly found in influenza virus vaccines. Low-additive influenza vaccines have been described (see, e.g., International Application No. PCT/IB2008/002238 published as International Publication No. WO 09/001217 which is herein incorporated by reference in its entirety).

The pharmaceutical compositions described herein can be included in a container, pack, or dispenser together with instructions for administration.

The pharmaceutical compositions described herein can be stored before use, e.g., the pharmaceutical compositions can be stored frozen (e.g., at about −20° C. or at about −70° C.); stored in refrigerated conditions (e.g., at about 4° C.); or stored at room temperature (see International Application No. PCT/IB2007/001149 published as International Publication No. WO 07/110776, which is herein incorporated by reference in its entirety, for methods of storing compositions comprising influenza vaccines without refrigeration).

In certain embodiments, when the active compound in a pharmaceutical composition described herein is a cell engineered to express a flu polypeptide, the cells in the pharmaceutical composition are not mammalian cells (e.g., CB-1 cells). In certain embodiments, when the active compound in a pharmaceutical composition described herein is a cell engineered to express a flu polypeptide, the cells in the pharmaceutical composition are mammalian cells.

5.10.1 Subunit Vaccines

In a specific embodiment, provided herein are subunit vaccines comprising a core polypeptide described herein. In some embodiments, a subunit vaccine comprises a flu polypeptide and one or more surface glycoproteins (e.g., influenza virus neuraminidase), other targeting moieties or adjuvants. In specific embodiments, a subunit vaccine comprises a single influenza flu polypeptide. In other embodiments, a subunit vaccine comprises two, three, four or more influenza flu polypeptides. In specific embodiments, the influenza flu polypeptide(s) used in a subunit vaccine is not membrane-bound, i.e., it is soluble.

In certain embodiments, provided herein are subunit vaccines comprising about 10 µg to about 60 µg of one or more flu polypeptides described herein, about 0.001% to 0.01% thimerosal, about 0.1 µg to about 1.0 µg chicken egg protein, about 1.0 µg to about 5.0 µg polymyxin, about 1.0 µg to about 5.0 µg neomycin, about 0.1 µg to about 0.5 µg betapropiolactone, and about 0.001 to about 0.05% w/v of nonylphenol ethoxylate per dose.

In a specific embodiment, a subunit vaccine provided herein comprises or consists of a 0.5 ml dose that comprises 45 µg of a flu polypeptide(s) provided herein, ≤1.0 µg of mercury (from thimerosal), ≤1.0 µg chicken egg protein (i.e., ovalbumin), ≤3.75 µg polymyxin, and ≤2.5 µg neomycin. In some embodiments, a subunit vaccine provided herein additionally comprises or consists of not more than 0.5 µg betapropiolactone, and not more than 0.015% w/v of nonylphenol ethoxylate per dose. In some embodiments, the 0.5 ml dose subunit vaccine is packaged in a pre-filled syringe.

In a specific embodiment, a subunit vaccine provided herein consists of a 5.0 ml multidose vial (0.5 ml per dose) that comprises 45 µg of a flu polypeptide(s) provided herein, 25.0 µg of mercury (from thimerosal), ≤1.0 µg chicken egg protein (i.e., ovalbumin), ≤3.75 µg polymyxin, and ≤2.5 µg neomycin. In some embodiments, a subunit vaccine provided herein additionally comprises or consists of not more than 0.5 µg betapropiolactone, and not more than 0.015% w/v of nonylphenol ethoxylate per dose.

In a specific embodiment, the subunit vaccine is prepared using influenza virus that was propagated in embryonated chicken eggs (i.e., the components of the subunit vaccine (e.g., a flu polypeptide) are isolated from virus that was propagated in embryonated chicken eggs). In another specific embodiment, the subunit vaccine is prepared using influenza virus that was not propagated in embryonated chicken eggs (i.e., the components of the subunit vaccine (e.g., a flu polypeptide) are isolated from virus that was not propagated in embryonated chicken eggs). In another specific embodiment, the subunit vaccine is prepared using influenza virus that was propagated in mammalian cells, e.g., immortalized human cells (see, e.g., International Application No. PCT/EP2006/067566 published as International Publication No. WO 07/045674 which is herein incorporated by reference in its entirety) or canine kidney cells such as MDCK cells (see, e.g., International Application No. PCT/IB2007/003536 published as International Publication No. WO 08/032219 which is herein incorporated by reference in its entirety) (i.e., the components of the subunit vaccine (e.g., a flu polypeptide) are isolated from virus that was propagated in mammalian cells). In another specific embodiment, the flu polypeptide(s) in a subunit vaccine are prepared using an expression vector, e.g., a viral vector, plant vector or a bacterial vector (i.e., the flu polypeptide(s) in the subunit vaccine are obtained/isolated from an expression vector).

5.10.2 Live Virus Vaccines

In one embodiment, provided herein are immunogenic compositions (e.g., vaccines) comprising live virus containing a flu polypeptide. In another embodiment, provided herein are immunogenic compositions (e.g., vaccines) comprising live virus that is engineered to encode a flu polypeptide, which is expressed by progeny virus produced in the subjects administered the compositions. In specific embodiments, the flu polypeptide is membrane-bound. In other specific embodiments, the influenza virus flu polypeptide is not membrane-bound, i.e., soluble. In particular embodiments, the live virus is an influenza virus, such as described in Section 5.4, supra. In other embodiments, the live virus is a non-influenza virus, such as described in Section 5.5, supra. In some embodiments, the live virus is attenuated. In some embodiments, an immunogenic composition comprises two, three, four or more live viruses containing or engineered to express two, three, four or more different flu polypeptides.

In certain embodiments, provided herein are immunogenic compositions (e.g., vaccines) comprising about $10^5$ to about $10^{10}$ fluorescent focus units (FFU) of live attenuated influenza virus containing one or more flu polypeptides described herein, about 0.1 to about 0.5 mg monosodium glutamate, about 1.0 to about 5.0 mg hydrolyzed procine gelatin, about 1.0 to about 5.0 mg arginine, about 10 to about 15 mg sucrose, about 1.0 to about 5.0 mg dibasic potassium phosphate, about 0.5 to about 2.0 mg monobasic potassium phosphate, and about 0.001 to about 0.05 µg/ml gentamicin sulfate per dose. In some embodiments, the immunogenic compositions (e.g., vaccines) are packaged as pre-filled sprayers containing single 0.2 ml doses.

In a specific embodiment, provided herein are immunogenic compositions (e.g., vaccines) comprising $10^{6.5}$ to $10^{7.5}$ FFU of live attenuated influenza virus containing one or more flu polypeptides described herein, 0.188 mg monosodium glutamate, 2.0 mg hydrolyzed procine gelatin, 2.42 mg arginine, 13.68 mg sucrose, 2.26 mg dibasic potassium phosphate, 0.96 mg monobasic potassium phosphate, and <0.015 μg/ml gentamicin sulfate per dose. In some embodiments, the immunogenic compositions (e.g., vaccines) are packaged as pre-filled sprayers containing single 0.2 ml doses.

In a specific embodiment, the live virus that contains a flu polypeptide is propagated in embryonated chicken eggs before its use in an immunogenic composition described herein. In another specific embodiment, the live virus that contains a flu polypeptide is not propagated in embryonated chicken eggs before its use in an immunogenic composition described herein. In another specific embodiment, the live virus that contains a flu polypeptide is propagated in mammalian cells, e.g., immortalized human cells (see, e.g., International Application No. PCT/EP2006/067566 published as International Publication No. WO 07/045674 which is herein incorporated by reference in its entirety) or canine kidney cells such as MDCK cells (see, e.g., International Application No. PCT/IB2007/003536 published as International Publication No. WO 08/032219 which is herein incorporated by reference in its entirety) before its use in an immunogenic composition described herein.

An immunogenic composition comprising a live virus for administration to a subject may be preferred because multiplication of the virus in the subject may lead to a prolonged stimulus of similar kind and magnitude to that occurring in natural infections, and therefore, confer substantial, long lasting immunity.

5.10.3 Inactivated Virus Vaccines

In one embodiment, provided herein are immunogenic compositions (e.g., vaccines) comprising an inactivated virus containing a flu polypeptide. In specific embodiments, the flu polypeptide is membrane-bound. In particular embodiments, the inactivated virus is an influenza virus, such as described in Section 5.4, supra. In other embodiments, the inactivated virus is a non-influenza virus, such as described in Section 5.5, supra. In some embodiments, an immunogenic composition comprises two, three, four or more inactivated viruses containing two, three, four or more different flu polypeptides. In certain embodiments, the inactivated virus immunogenic compositions comprise one or more adjuvants.

Techniques known to one of skill in the art may be used to inactivate viruses containing a flu polypeptide. Common methods use formalin, heat, or detergent for inactivation. See, e.g., U.S. Pat. No. 6,635,246, which is herein incorporated by reference in its entirety. Other methods include those described in U.S. Pat. Nos. 5,891,705; 5,106,619 and 4,693,981, which are incorporated herein by reference in their entireties.

In certain embodiments, provided herein are immunogenic compositions (e.g., vaccines) comprising inactivated influenza virus such that each dose of the immunogenic composition comprises about 15 to about 60 μg of flu polypeptide described herein, about 1.0 to about 5.0 mg sodium chloride, about 20 to about 100 μg monobasic sodium phosphate, about 100 to about 500 μg dibasic sodium phosphate, about 5 to about 30 μg monobasic potassium phosphate, about 5 to about 30 μg potassium chloride, and about 0.5 to about 3.0 μg calcium chloride. In some embodiments, the immunogenic compositions (e.g., vaccines) are packaged as single 0.25 ml or single 0.5 ml doses. In other embodiments, the immunogenic compositions (e.g., vaccines) are packaged as multi-dose formulations.

In certain embodiments, provided herein are immunogenic compositions (e.g., vaccines) comprising inactivated influenza virus such that each dose of the immunogenic composition comprises about 15 to about 60 μg of flu polypeptide described herein, about 0.001% to 0.01% thimerosal, about 1.0 to about 5.0 mg sodium chloride, about 20 to about 100 μg monobasic sodium phosphate, about 100 to about 500 μg dibasic sodium phosphate, about 5 to about 30 μg monobasic potassium phosphate, about 5 to about 30 μg potassium chloride, and about 0.5 to about 3.0 μg calcium chloride per dose. In some embodiments, the immunogenic compositions (e.g., vaccines) are packaged as single 0.25 ml or single 0.5 ml doses. In other embodiments, the immunogenic compositions (e.g., vaccines) are packaged as multi-dose formulations.

In a specific embodiment, immunogenic compositions (e.g., vaccines) provided herein are packaged as single 0.25 ml doses and comprise 22.5 μg of flu polypeptide described herein, 2.05 mg sodium chloride, 40 μg monobasic sodium phosphate, 150 μg dibasic sodium phosphate, 10 μg monobasic potassium phosphate, 10 μg potassium chloride, and 0.75 μg calcium chloride per dose.

In a specific embodiment, immunogenic compositions (e.g., vaccines) provided herein are packaged as single 0.5 ml doses and comprise 45 μg of flu polypeptide described herein, 4.1 mg sodium chloride, 80 μg monobasic sodium phosphate, 300 μg dibasic sodium phosphate, 20 μg monobasic potassium phosphate, 20 μg potassium chloride, and 1.5 μg calcium chloride per dose.

In a specific embodiment, immunogenic compositions (e.g., vaccines) are packaged as multi-dose formulations comprising or consisting of 5.0 ml of vaccine (0.5 ml per dose) and comprise 24.5 μg of mercury (from thimerosal), 45 μg of flu polypeptide described herein, 4.1 mg sodium chloride, 80 μg monobasic sodium phosphate, 300 μg dibasic sodium phosphate, 20 μg monobasic potassium phosphate, 20 μg potassium chloride, and 1.5 μg calcium chloride per dose.

In a specific embodiment, the inactivated virus that contains a flu polypeptide was propagated in embryonated chicken eggs before its inactivation and subsequent use in an immunogenic composition described herein. In another specific embodiment, the inactivated virus that contains a flu polypeptide was not propagated in embryonated chicken eggs before its inactivation and subsequent use in an immunogenic composition described herein. In another specific embodiment, the inactivated virus that contains a flu polypeptide was propagated in mammalian cells, e.g., immortalized human cells (see, e.g., International Application No. PCT/EP2006/067566 published as International Publication No. WO 07/045674 which is herein incorporated by reference in its entirety) or canine kidney cells such as MDCK cells (see, e.g., International Application No. PCT/IB2007/003536 published as International Publication No. WO 08/032219 which is herein incorporated by reference in its entirety) before its inactivation and subsequent use in an immunogenic composition described herein.

5.10.4 Split Virus Vaccines

In one embodiment, an immunogenic composition comprising a flu polypeptide is a split virus vaccine. In some embodiments, split virus vaccine contains two, three, four or more different flu polypeptides. In certain embodiments, the flu polypeptide is/was membrane-bound. In certain embodiments, the split virus vaccines comprise one or more adjuvants.

Techniques for producing split virus vaccines are known to those skilled in the art. By way of non-limiting example, an influenza virus split vaccine may be prepared using inactivated particles disrupted with detergents. One example of a split virus vaccine that can be adapted for use in accordance with the methods described herein is the Fluzone®, Influenza Virus Vaccine (Zonal Purified, Subvirion) for intramuscular use, which is formulated as a sterile suspension prepared from influenza viruses propagated in embryonated chicken eggs. The virus-containing fluids are harvested and inactivated with formaldehyde. Influenza virus is concentrated and purified in a linear sucrose density gradient solution using a continuous flow centrifuge. The virus is then chemically disrupted using a nonionic surfactant, octoxinol-9, (Triton® X-100—A registered trademark of Union Carbide, Co.) producing a "split virus." The split virus is then further purified by chemical means and suspended in sodium phosphate-buffered isotonic sodium chloride solution.

In certain embodiments, provided herein are split virus vaccines comprising about 10 µg to about 60 µg of one or more flu polypeptides described herein, about 0.01 to about 1.0 mg octoxynol-10 (TRITON X-100®, about 0.5 to 0.5 mg α-tocopheryl hydrogen succinate, about 0.1 to 1.0 mg polysorbate 80 (Tween 80), about 0.001 to about 0.003 µg hydrocortisone, about 0.05 to about 0.3 µg gentamcin sulfate, about 0.5 to about 2.0 µg chicken egg protein (ovalbumin), about 25 to 75 µg formaldehyde, and about 25 to 75 µg sodium deoxycholate.

In a specific embodiment, a split virus vaccine provided herein comprises or consists of a 0.5 ml dose that comprises 45 µg of influenza flu polypeptide(s) provided herein, ≤0.085 mg octoxynol-10 (TRITON X-100®, ≤0.1 mg α-tocopheryl hydrogen succinate, ≤0.415 mg polysorbate 80 (Tween 80), ≤0.0016 µg hydrocortisone, ≤0.15 µg gentamcin sulfate, ≤1.0 chicken egg protein (ovalbumin), ≤50 µg formaldehyde, and ≤50 µg sodium deoxycholate. In some embodiments, the 0.5 ml dose subunit vaccine is packaged in a pre-filled syringe.

In a specific embodiment, the split virus vaccine is prepared using influenza virus that was propagated in embryonated chicken eggs. In another specific embodiment, the split virus vaccine is prepared using influenza virus that was not propagated in embryonated chicken eggs. In another specific embodiment, the split virus vaccine is prepared using influenza virus that was propagated in mammalian cells, e.g., immortalized human cells (see, e.g., PCT/EP2006/067566 published as WO 07/045674 which is herein incorporated by reference in its entirety) or canine kidney cells such as MDCK cells (see, e.g., PCT/IB2007/003536 published as WO 08/032219 which is herein incorporated by reference in its entirety).

5.10.5 Adjuvants

In certain embodiments, the compositions described herein comprise, or are administered in combination with, an adjuvant. The adjuvant for administration in combination with a composition described herein may be administered before, concomitantly with, or after administration of said composition. In some embodiments, the term "adjuvant" refers to a compound that when administered in conjunction with or as part of a composition described herein augments, enhances and/or boosts the immune response to a flu polypeptide, but when the compound is administered alone does not generate an immune response to the polypeptide. In some embodiments, the adjuvant generates an immune response to the polypeptide and does not produce an allergy or other adverse reaction. Adjuvants can enhance an immune response by several mechanisms including, e.g., lymphocyte recruitment, stimulation of B and/or T cells, and stimulation of macrophages.

In certain embodiments, an adjuvant augments the intrinsic response to the flu polypeptide without causing conformational changes in the polypeptide that affect the qualitative form of the response. Specific examples of adjuvants include, but are not limited to, aluminum salts (alum) (such as aluminum hydroxide, aluminum phosphate, and aluminum sulfate), 3 De-O-acylated monophosphoryl lipid A (MPL) (see GB 2220211), MF59 (Novartis), AS03 (GlaxoSmithKline), ASO4 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., in Vaccine Design: The Subunit and Adjuvant Approach (eds. Powell & Newman, Plenum Press, N Y, 1995); U.S. Pat. No. 5,057, 540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Such adjuvants can be used with or without other specific immunostimulating agents such as MPL or 3-DMP, QS21, polymeric or monomeric amino acids such as polyglutamic acid or polylysine, or other immunopotentiating agents described in Section 5.4, supra. It should be understood that different formulations of flu polypeptide may comprise different adjuvants or may comprise the same adjuvant.

5.11 Prophylactic and Therapeutic Uses

In one aspect, provided herein are methods for inducing an immune response in a subject utilizing an active compound, i.e., a flu polypeptide described herein, a nucleic acid encoding such a polypeptide, a vector (e.g., a viral vector, or a bacteria) containing or expressing such a polypeptide, or cells stimulated with such a polypeptide. In a specific embodiment, a method for inducing an immune response to an influenza virus in a subject comprises administering to a subject in need thereof an effective amount of a flu polypeptide or an immunogenic composition thereof. In another embodiment, a method for inducing an immune response to an influenza virus in a subject comprises administering to a subject in need thereof an effective amount of a nucleic acid encoding a flu polypeptide or an immunogenic composition thereof. In another embodiment, a method for inducing an immune response to an influenza virus in a subject comprises administering to a subject in need thereof an effective amount of a viral vector containing or expressing a flu polypeptide or an immunogenic composition thereof. In yet another embodiment, a method for inducing an immune response to an influenza virus in a subject comprises administering to a subject in need thereof an effective amount of cells stimulated with a flu polypeptide or a pharmaceutical composition thereof. In certain embodiments, a flu polypeptide used in the method is a purified flu polypeptide derived from a mammalian cell, a plant cell, or an insect cell.

In a specific embodiment, a method for inducing an immune response to an influenza virus in a subject comprises administering to a subject in need thereof a subunit vaccine described herein. In another embodiment, a method for inducing an immune response to an influenza virus in a subject comprises administering to a subject in need thereof a live virus vaccine described herein. In particular embodiments, the live virus vaccine comprises an attenuated virus. In another embodiment, a method for inducing an immune response to an influenza virus in a subject comprises administering to a subject in need thereof an inactivated virus vaccine described herein. In another embodiment, a method for inducing an immune response to an influenza virus in a subject comprises administering to a subject in need thereof a split virus vaccine described herein. In another embodiment, a method for inducing an immune response to an influenza virus in a subject comprises administering to a subject in need thereof a viral-like particle vaccine described herein. In another embodiment, a method for inducing an immune response to an influenza virus in a subject comprises administering to a subject in need thereof a virosome described herein. In another embodiment, a method for inducing an immune response to an influenza virus in a subject comprises administering to a subject in need thereof a bacteria expressing or engineered to express a flu polypeptide or a composition thereof. In certain embodiments, a flu polypeptide used in the method is a purified flu polypeptide derived from a mammalian cell, a plant cell, or an insect cell.

In some embodiments, the immune response induced by an active compound or a composition described herein is effective to prevent and/or treat an influenza virus infection caused by any subtype or strain of influenza virus. In certain embodiments, the immune response induced by an active compound or a composition described herein is effective to prevent and/or treat an influenza virus infection caused by a subtype of influenza virus that belongs to one HA group (e.g., Group 1, which comprises H1, H2, H5, H6, H8, H9, H11, H12, H13, and H16) and not the other HA group (e.g., Group 2, which comprises H3, H4, H7, H10, H14, and H15). For example, the immune response induced may be effective to prevent and/or treat an influenza virus infection caused by an influenza virus that belongs to the HA group consisting of H11, H13, H16, H9, H8, H12, H6, H1, H5 and H2. Alternatively, the immune response induced may be effective to prevent and/or treat an influenza virus infection caused by an influenza virus that belongs to the HA group consisting of H3, H4, H14, H10, H15 and H7. In some embodiments, the immune response induced by an active compound or a composition described herein is effective to prevent and/or treat an influenza virus infection caused by one, two, three, four or five subtypes of influenza virus. In certain embodiments, the immune response induced by an active compound or a composition described herein is effective to prevent and/or treat an influenza virus infection caused by six, seven, eight, nine, ten, eleven, twelve, thirteen, fourteen or fifteen subtypes of influenza virus. In some embodiments, the immune response induced by an active compound or a composition described herein is effective to prevent and/or treat an influenza virus infection caused by one or more variants within the same subtype of influenza virus.

In some embodiments, the immune response induced by an active compound or a composition described herein is effective to prevent and/or treat an influenza virus infection caused by both H1N1 and H2N2 subtypes. In other embodiments, the immune response induced by an active compound or a composition described herein is not effective to prevent and/or treat an influenza virus infection caused by both H1N1 and H2N2 subtypes. In some embodiments, the immune response induced by an active compound or a composition described herein is effective to prevent and/or treat an influenza virus infection caused by H1N1, H2N2, and H3N2 subtypes. In some embodiments, the immune response induced by an active compound or a composition described herein is effective to prevent and/or treat an influenza virus infection caused by H3N2 subtypes. In other embodiments, the immune response induced by an active compound or a composition described herein is not effective to prevent and/or treat an influenza virus infection caused by H3N2 subtypes.

In some embodiments, the immune response induced by an active compound or a composition described herein is effective to prevent and/or treat an influenza virus disease caused by any subtype or strain of influenza virus. In certain embodiments, the immune response induced by an active compound or a composition described herein is effective to prevent and/or treat an influenza virus disease caused by a subtype of influenza virus that belongs to one HA group and not the other HA group. For example, the immune response induced may be effective to prevent and/or treat an influenza virus disease caused by an influenza virus that belongs to the HA group consisting of H11, H13, H16, H9, H8, H12, H6, H1, H5 and H2. Alternatively, the immune response induced may be effective to prevent and/or treat an influenza virus disease caused by an influenza virus that belongs to the HA group consisting of H3, H4, H14, H10, H15 and H7. In some embodiments, the immune response induced by an active compound or a composition described herein is effective to prevent and/or treat an influenza virus disease caused by any of one, two, three, four or five subtypes of influenza virus. In certain embodiments, the immune response induced by an active compound or a composition described herein is effective to prevent and/or treat an influenza virus disease caused by any of six, seven, eight, nine, ten, eleven, twelve, thirteen, fourteen or fifteen subtypes of influenza virus. In some embodiments, the immune response induced by an active compound or a composition described herein is effective to prevent and/or treat an influenza virus disease caused by one or more variants within the same subtype of influenza virus.

In some embodiments, the immune response induced by an active compound or a composition described herein is effective to reduce symptoms resulting from an influenza virus disease/infection. Symptoms of influenza virus disease/infection include, but are not limited to, body aches (especially joints and throat), fever, nausea, headaches, irritated eyes, fatigue, sore throat, reddened eyes or skin, and abdominal pain.

In some embodiments, the immune response induced by an active compound or a composition described herein is effective to reduce the hospitalization of a subject suffering from an influenza virus disease/infection. In some embodiments, the immune response induced by an active compound or a composition described herein is effective to reduce the duration of hospitalization of a subject suffering from an influenza virus disease/infection.

In another aspect, provided herein are methods for preventing and/or treating an influenza virus infection in a subject utilizing an active compound (e.g., a flu polypeptide described herein, a nucleic acid encoding such a polypeptide, a vector containing or expressing such a polypeptide, or cells stimulated with such a polypeptide) or a composition described herein. In one embodiment, a method for preventing or treating an influenza virus infection in a subject comprises administering to a subject in need thereof a flu polypeptide, a nucleic acid encoding such a polypeptide, a vector containing or expressing such a polypeptide, or a composition of any one of the foregoing. In a specific embodiment, a method for preventing or treating an influenza virus infection in a subject comprises administering to a subject in need thereof a subunit vaccine, a live virus vaccine, an inactivated virus vaccine, a split virus vaccine or a viral-like particle vaccine. In specific embodiments, the influenza virus infection is caused by an influenza A virus. In other embodiments, the influenza virus infection is caused by an influenza B or C virus.

In another aspect, provided herein are methods for preventing and/or treating an influenza virus disease in a subject utilizing a flu polypeptide described herein, a nucleic acid encoding such a polypeptide, a vector containing or expressing such a polypeptide, or cells stimulated with such a polypeptide. In a specific embodiment, a method for preventing or treating an influenza virus disease in a subject comprises administering to a subject in need thereof an effective amount of a flu polypeptide or an immunogenic composition thereof. In another embodiment, a method for preventing or treating an influenza virus disease in a subject comprises administering to a subject in need thereof an effective amount of a nucleic acid encoding a flu polypeptide or an immunogenic composition thereof. In another embodiment, a method for preventing or treating an influenza virus disease in a subject comprises administering to a subject in need thereof an effective amount of a viral vector containing or expressing a flu polypeptide or an immunogenic composition thereof. In yet another embodiment, a method for preventing or treating an influenza virus disease in a subject comprises administering to a subject in need thereof an effective amount of cells stimulated with a flu polypeptide or a pharmaceutical composition thereof.

In a specific embodiment, a method for preventing or treating an influenza virus disease in a subject comprises administering to a subject in need thereof a subunit vaccine described herein. In another embodiment, a method for preventing or treating an influenza virus disease in a subject comprises administering to a subject in need thereof a live virus vaccine described herein. In particular embodiments, the live virus vaccine comprises an attenuated virus. In another embodiment, a method for preventing or treating an influenza virus disease in a subject comprises administering to a subject in need thereof an inactivated virus vaccine described herein. In another embodiment, a method for preventing or treating an influenza virus disease in a subject comprises administering to a subject in need thereof a split virus vaccine described herein. In another embodiment, a method for preventing or treating an influenza virus disease comprises administering to a subject in need thereof a viral-like particle vaccine described herein. In another embodiment, a method for preventing or treating an influenza virus disease in a subject, comprising administering to a subject in need thereof a virosome described herein. In another embodiment, a method for preventing or treating an influenza virus disease in a subject comprising administering to a subject in need thereof a bacteria expressing or engineered to express a flu polypeptide or a composition thereof. In specific embodiments, the influenza virus disease is caused by or associated with the presence of an influenza A virus. In other embodiments, the influenza virus disease is caused by or associated with the presence of an influenza B virus.

In another aspect, provided herein are methods of preventing and/or treating an influenza virus disease in a subject by administering neutralizing antibodies described herein. In a specific embodiment, a method for preventing or treating an influenza virus disease in a subject comprises administering to a subject in need thereof an effective amount of a neutralizing antibody described herein, or a pharmaceutical composition thereof. In particular embodiments, the neutralizing antibody is a monoclonal antibody. In certain embodiments, the neutralizing antibody is not an antibody described in Wang et al. (2010) "Broadly Protective Monoclonal Antibodies against H3 Influenza Viruses following Sequential Immunization with Different Hemagglutinins," PLOS Pathogens 6(2):1-9. In certain embodiments, the neutralizing antibody is not an antibody described in PCT/US2010/036170.

In certain embodiments, the methods for preventing or treating an influenza virus disease or infection in a subject (e.g., a human or non-human animal) provided herein result in a reduction in the replication of the influenza virus in the subject as measured by in vivo and in vitro assays known to those of skill in the art and described herein. In some embodiments, the replication of the influenza virus is reduced by approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs.

5.11.1 Combination Therapies

In various embodiments, a flu polypeptide described herein, a nucleic acid encoding such a polypeptide, a vector (e.g., a viral vector or a bacteria) containing or expressing such a polypeptide, cells stimulated with such a polypeptide, or a neutralizing antibody may be administered to a subject in combination with one or more other therapies (e.g., antiviral, antibacterial, or immunomodulatory therapies). In some embodiments, a pharmaceutical composition (e.g., an immunogenic composition) described herein may be administered to a subject in combination with one or more therapies. The one or more other therapies may be beneficial in the treatment or prevention of an influenza virus disease or may ameliorate a symptom or condition associated with an influenza virus disease. In some embodiments, the one or more other therapies are pain relievers, anti-fever medications, or therapies that alleviate or assist with breathing. In certain embodiments, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In specific embodiments, two or more therapies are administered within the same patent visit.

Any anti-viral agents well-known to one of skill in the art may used in combination with an active compound or pharmaceutical composition described herein. Non-limiting examples of anti-viral agents include proteins, polypeptides, peptides, fusion proteins antibodies, nucleic acid molecules, organic molecules, inorganic molecules, and small molecules that inhibit and/or reduce the attachment of a virus to its receptor, the internalization of a virus into a cell, the replication of a virus, or release of virus from a cell. In particular, anti-viral agents include, but are not limited to, nucleoside analogs (e.g., zidovudine, acyclovir, gangcyclovir, vidarabine, idoxuridine, trifluridine, and ribavirin), foscarnet, amantadine, peramivir, rimantadine, saquinavir, indinavir, ritonavir, alpha-interferons and other interferons, AZT, zanamivir (Relenza®), and oseltamivir (Tamiflu®). Other anti-viral agents include influenza virus vaccines, e.g., Fluarix® (GlaxoSmithKline), FluMist® (MedImmune Vaccines), Fluvirin® (Chiron Corporation), Flulaval® (GlaxoSmithKline), Afluria® (CSL Biotherapies Inc.), Agriflu® (Novartis) or Fluzone® (Aventis Pasteur).

In specific embodiments, the anti-viral agent is an immunomodulatory agent that is specific for a viral antigen. In particular embodiments, the viral antigen is an influenza virus polypeptide other than a hemagglutinin polypeptide. In other embodiments, the viral antigen is an flu polypeptide.

Any anti-bacterial agents known to one of skill in the art may used in combination with an active compound or pharmaceutical composition described herein. Non-limiting examples of anti-bacterial agents include Amikacin, Amoxicillin, Amoxicillin-clavulanic acid, Amphothericin-B, Ampicillin, Ampicllin-sulbactam, Apramycin, Azithromycin, Aztreonam, Bacitracin, Benzylpenicillin, Caspofungin, Cefaclor, Cefadroxil, Cefalexin, Cefalothin, Cefazolin, Cefdinir, Cefepime, Cefixime, Cefmenoxime, Cefoperazone, Cefoperazone-sulbactam, Cefotaxime, Cefoxitin, Cefpirome, Cefpodoxime, Cefpodoxime-clavulanic acid, Cefpodoxime-sulbactam, Cefprozil, Cefquinome, Ceftazidime, Ceftibutin, Ceftiofur, Ceftobiprole, Ceftriaxon, Cefuroxime, Chloramphenicole, Florfenicole, Ciprofloxacin, Clarithromycin, Clinafloxacin, Clindamycin, Cloxacillin, Colistin, Cotrimoxazol (Trimthoprim/sulphamethoxazole), Dalbavancin, Dalfopristin/Quinopristin, Daptomycin, Dibekacin, Dicloxacillin, Doripenem, Doxycycline, Enrofloxacin, Ertapenem, Erythromycin, Flucloxacillin, Fluconazol, Flucytosin, Fosfomycin, Fusidic acid, Garenoxacin, Gatifloxacin, Gemifloxacin, Gentamicin, Imipenem, Itraconazole, Kanamycin, Ketoconazole, Levofloxacin, Lincomycin, Linezolid, Loracarbef, Mecillnam (amdinocillin), Meropenem, Metronidazole, Meziocillin, Mezlocillin-sulbactam, Minocycline, Moxifloxacin, Mupirocin, Nalidixic acid, Neomycin, Netilmicin, Nitrofurantoin, Norfloxacin, Ofloxacin, Oxacillin, Pefloxacin, Penicillin V, Piperacillin, Piperacillin-sulbactam, Piperacillin-tazobactam, Rifampicin, Roxythromycin, Sparfloxacin, Spectinomycin, Spiramycin, Strepto-mycin, Sulbactam, Sulfamethoxazole, Teicoplanin, Telavancin, Telithromycin, Temocillin, Tetracyklin, Ticarcillin, Ticarcillin-clavulanic acid, Tigecycline, Tobramycin, Trimethoprim, Trovafloxacin, Tylosin, Vancomycin, Virginiamycin, and Voriconazole.

In some embodiments, a combination therapy comprises administration of two or more different vectors described in Sections 5.4-5.7. In one example, one or more vectors expressing a flu polypeptide derived from an influenza A virus and one or more vectors expressing a flu polypeptide derived from an influenza B virus are administered in combination. In some embodiments, a combination therapy comprises administration of a vector expressing a flu polypeptide derived from an H3 influenza A virus and a vector expressing a flu polypeptide derived from an H1 influenza A virus. In some embodiments, the combination therapy comprises administration of a vector expressing a flu polypeptide derived from an H3 influenza A virus, a vector expressing a flu polypeptide derived from an H1 influenza A virus, and a vector expressing a flu polypeptide derived from an influenza B virus.

In some embodiments, a combination therapy comprises active immunization with an active compound that induces an immune response to one, two, three, or more HA subtypes in one HA group (e.g., Group 1) in combination with an active compound that induces an immune response to one, two, three, or more HA subtypes in the other HA group (e.g., Group 2).

In some embodiments, a combination therapy comprises active immunization with two or more flu polypeptides described in Section 5.1.

In certain embodiments, a combination therapy comprises active immunization with one, two, or more flu polypeptides derived from an influenza A virus and one or more flu polypeptides derived from an influenza B virus.

5.11.2 Patient Populations

In certain embodiments, an active compound or composition described herein may be administered to a naïve subject, i.e., a subject that does not have a disease caused by influenza virus infection or has not been and is not currently infected with an influenza virus infection. In one embodiment, an active compound or composition described herein is administered to a naïve subject that is at risk of acquiring an influenza virus infection. In one embodiment, an active compound or composition described herein is administered to a subject that does not have a disease caused by the specific influenza virus, or has not been and is not infected with the specific influenza virus to which the flu polypeptide induces an immune response. An active compound or composition described herein may also be administered to a subject that is and/or has been infected with the influenza virus or another type, subtype or strain of the influenza virus to which the flu polypeptide induces an immune response.

In certain embodiments, an active compound or composition described herein is administered to a patient who has been diagnosed with an influenza virus infection. In some embodiments, an active compound or composition described herein is administered to a patient infected with an influenza virus before symptoms manifest or symptoms become severe (e.g., before the patient requires hospitalization). In some embodiments, an active compound or composition described herein is administered to a patient that is infected with or has been diagnosed with a different type of influenza virus than that of the influenza virus from which the flu polypeptide of the active compound or composition was derived.

In certain embodiments, an active compound or composition described herein is administered to a patient that may be or is infected with an influenza virus that belongs to the same HA group as that of the influenza flu polypeptide. In certain embodiments, an active compound or composition described herein is administered to a patient that may be or is infected with an influenza virus of the same subtype as that of the influenza flu polypeptide.

In some embodiments, a subject to be administered an active compound or composition described herein is an animal. In certain embodiments, the animal is a bird. In certain embodiments, the animal is a canine. In certain embodiments, the animal is a feline. In certain embodiments, the animal is a horse. In certain embodiments, the animal is a cow. In certain embodiments, the animal is a mammal, e.g., a horse, swine, mouse, or primate, preferably a human.

In certain embodiments, a subject to be administered an active compound or composition described herein is a human adult. In certain embodiments, a subject to be administered an active compound or composition described herein is a human adult more than 50 years old. In certain embodiments, a subject to be administered an active compound or composition described herein is an elderly human subject.

In certain embodiments, a subject to be administered an active compound or composition described herein is a human child. In certain embodiments, a subject to be administered an active compound or composition described herein is a human infant. In certain embodiments, a subject to be administered an active compound or composition described herein is a premature human infant. In some embodiments, a patient treated or prevented in accordance with the methods provided herein is a human toddler. In certain embodiments, a subject to whom an active compound or composition described herein is administered is not an infant of less than 6 months old. In a specific embodiment, a subject to be administered an active compound or composition described herein is 2 years old or younger.

In specific embodiments, a subject to be administered an active compound or composition described herein is any infant or child more than 6 months of age and any adult over 50 years of age. In other embodiments, the subject is an individual who is pregnant. In another embodiment, the subject is an individual who may or will be pregnant during the influenza season (e.g., November to April). In specific embodiments, a subject to be administered an active compound or composition described herein is a woman who has given birth 1, 2, 3, 4, 5, 6, 7, or 8 weeks earlier.

In some embodiments, the human subject to be administered an active compound or composition described herein is any individual at increased risk of influenza virus infection or disease resulting from influenza virus infection (e.g., an immunocompromised or immunodeficient individual). In some embodiments, the human subject to be administered an active compound or composition described herein is any individual in close contact with an individual with increased risk of influenza virus infection or disease resulting from influenza virus infection (e.g., immunocompromised or immunosuppressed individuals).

In some embodiments, the human subject to be administered an active compound or composition described herein is an individual affected by any condition that increases susceptibility to influenza virus infection or complications or disease resulting from influenza virus infection. In other embodiments, an active compound or composition described herein is administered to a subject in which an influenza virus infection has the potential to increase complications of another condition that the individual is affected by, or for which they are at risk. In particular embodiments, such conditions that increase susceptibility to influenza virus complications or for which influenza virus increases complications associated with the condition are, e.g., conditions that affect the lung, such as cystic fibrosis, emphysema, asthma, or bacterial infections (e.g., infections caused by *Haemophilus influenzae, Streptococcus pneumoniae, Legionella pneumophila*, and *Chlamydia trachomatus*); cardiovascular disease (e.g., congenital heart disease, congestive heart failure, and coronary artery disease); endocrine disorders (e.g., diabetes), neurological and neuron-developmental conditions (e.g., disorders of the brain, the spinal cord, the peripheral nerve, and muscle (such as cerebral palsy, epilepsy (seizure disorders), stroke, intellectual disability (e.g., mental retardation), muscular dystrophy, and spinal cord injury)).

In some embodiments, the human subject to be administered an active compound or composition described herein is an individual that resides in a group home, such as a nursing home. In some embodiments, the human subject to be administered an active compound or composition described herein works in, or spends a significant amount of time in, a group home, e.g., a nursing home. In some embodiments, the human subject to be administered an active compound or composition described herein is a health care worker (e.g., a doctor or nurse). In some embodiments, the human subject to be administered an active compound or composition described herein is a smoker. In a specific embodiment, the human subject to be administered an active compound or composition described herein is immunocompromised or immunosuppressed.

In addition, subjects at increased risk of developing complications from influenza who may be administered an active compound or composition described herein include: any individual who can transmit influenza viruses to those at high risk for complications, such as, e.g., members of households with high-risk individuals, including households that will include infants younger than 6 months, individuals coming into contact with infants less than 6 months of age, or individuals who will come into contact with individuals who live in nursing homes or other long-term care facilities; individuals with long-term disorders of the lungs, heart, or circulation; individuals with metabolic diseases (e.g., diabetes); individuals with kidney disorders; individuals with blood disorders (including anemia or sickle cell disease); individuals with weakened immune systems (including immunosuppression caused by medications, malignancies such as cancer, organ transplant, or HIV infection); children who receive long-term aspirin therapy (and therefore have a higher chance of developing Reye syndrome if infected with influenza).

In other embodiments, subjects for administration of an active compound or composition described herein include healthy individuals six months of age or older, who: plan to travel to foreign countries and areas where flu outbreaks may be occurring, such, e.g., as the tropics and the Southern Hemisphere from April through September; travel as a part of large organized tourist groups that may include persons from areas of the world where influenza viruses are circulating; attend school or college and reside in dormitories, or reside in institutional settings; or wish to reduce their risk of becoming ill with influenza.

In some embodiments, a subject for whom administration of an active compound or composition described herein is contraindicated include any individual for whom influenza vaccination is contraindicated, such as: infants younger than six months of age; and individuals who have had an anaphylactic reaction (allergic reactions that cause difficulty breathing, which is often followed by shock) to eggs, egg products, or other components used in the production of the immunogenic formulation. In certain embodiments, when administration of an active compound or composition described herein is contraindicated due to one or more components used in the production of the immunogenic formulation (e.g., due to the presence of egg or egg products), the active compound or composition may be produced in a manner that does not include the component that causes the administration of an active compound or composition to be contraindicated (e.g., the active compound or composition may be produced without the use of eggs or egg products).

In some embodiments, it may be advisable not to administer a live virus vaccine to one or more of the following patient populations: elderly humans; infants younger than 6 months old; pregnant individuals; infants under the age of 1 years old; children under the age of 2 years old; children under the age of 3 years old; children under the age of 4 years old; children under the age of 5 years old; adults under the age of 20 years old; adults under the age of 25 years old; adults under the age of 30 years old; adults under the age of 35 years old; adults under the age of 40 years old; adults under the age of 45 years old; adults under the age of 50 years old; elderly humans over the age of 70 years old; elderly humans over the age of 75 years old; elderly humans over the age of 80 years old; elderly humans over the age of 85 years old; elderly humans over the age of 90 years old; elderly humans over the age of 95 years old; children and adolescents (2-17 years of age) receiving aspirin or aspirin-containing medications, because of the complications associated with aspirin and wild-type influenza virus infections in this age group; individuals with a history of asthma or other reactive airway diseases; individuals with chronic underlying medical conditions that may predispose them to severe influenza infections; individuals with a history of Guillain-Barre syndrome; individuals with acute serious illness with fever; or individuals who are moderately or severely ill. For such individuals, administration of inactivated virus vaccines, split virus vaccines, subunit vaccines, virosomes, viral-like particles or the non-viral vectors described herein may be preferred. In certain embodiments, subjects preferably administered a live virus vaccine may include healthy children and adolescents, ages 2-17 years, and healthy adults, ages 18-49.

In certain embodiments, an immunogenic formulation comprising a live virus vector is not given concurrently with other live-virus vaccines.

5.12 Modes of Administration 5.12.1 Routes of Delivery

An active compound or composition described herein may be delivered to a subject by a variety of routes. These include, but are not limited to, intranasal, intratracheal, oral, intradermal, intramuscular, intraperitoneal, transdermal, intravenous, conjunctival and subcutaneous routes. In a specific embodiment, an active compound or composition described herein is delivered to a subject by the subcutaneous route. In some embodiments, a composition is formulated for topical administration, for example, for application to the skin. In specific embodiments, the route of administration is nasal, e.g., as part of a nasal spray. In certain embodiments, a composition is formulated for intramuscular administration. In some embodiments, a composition is formulated for subcutaneous administration. In certain embodiments, a composition is not formulated for administration by injection. In specific embodiments for live virus vaccines, the vaccine is formulated for administration by a route other than injection.

In cases where the antigen is a viral vector, a virus-like particle vector, or a bacterial vector, for example, it may be preferable to introduce an immunogenic composition via the natural route of infection of the backbone virus or bacteria from which the vector was derived. Alternatively, it may be preferable to introduce a flu polypeptide via the natural route of infection of the influenza virus from which polypeptide is derived. The ability of an antigen, particularly a viral vector, to induce a vigorous secretory and cellular immune response can be used advantageously. For example, infection of the respiratory tract by a viral vector may induce a strong secretory immune response, for example in the urogenital system, with concomitant protection against an influenza virus. In addition, in a preferred embodiment it may be desirable to introduce the pharmaceutical compositions into the lungs by any suitable route. Pulmonary administration can also be employed, e.g., by use of an inhaler or nebulizer, and formulation with an aerosolizing agent for use as a spray.

In a specific embodiment, a subunit vaccine is administered intranasally. In a specific embodiment, a subunit vaccine is administered intramuscularly. In another specific embodiment, a subunit vaccine is administered subcutaneously. In another specific embodiment, a subunit vaccine is administered intradermally.

In a specific embodiment, a live virus vaccine is administered intranasally. In a specific embodiment, a live virus vaccine is administered intramuscularly. In another specific embodiment, a live virus vaccine is administered subcutaneously. In another specific embodiment, a live virus vaccine is administered intradermally.

In a specific embodiment, an inactivated virus vaccine is administered intranasally. In a specific embodiment, an inactivated virus vaccine is administered intramuscularly. In another specific embodiment, an inactivated virus vaccine is administered subcutaneously. In another specific embodiment, an inactivated virus vaccine is administered intradermally.

In a specific embodiment, a split virus vaccine is administered intranasally. In a specific embodiment, a split virus vaccine is administered intramuscularly. In another specific embodiment, a split virus vaccine is administered subcutaneously. In another specific embodiment, a split virus vaccine is administered intradermally.

In a specific embodiment, a viral-like particle or composition thereof is administered intranasally. In a specific embodiment, a viral-like particle or composition thereof is administered intramuscularly. In another specific embodiment, a sp viral-like particle or composition thereof is administered subcutaneously. In another specific embodiment, a viral-like particle or composition thereof is administered intradermally.

In some embodiments, cells stimulated with a flu polypeptide in vitro may be introduced (or re-introduced) into a subject using techniques known to one of skill in the art. In some embodiments, the cells can be introduced into the dermis, under the dermis, or into the peripheral blood stream. In some embodiments, the cells introduced into a subject are preferably cells derived from that subject, to avoid an adverse immune response. In other embodiments, cells also can be used that are derived from a donor host having a similar immune background. Other cells also can be used, including those designed to avoid an adverse immunogenic response.

5.12.2 Dosage and Frequency of Administration

The amount of an active compound or composition which will be effective in the treatment and/or prevention of an influenza virus infection or an influenza virus disease will depend on the nature of the disease, and can be determined by standard clinical techniques.

The precise dose to be employed in the formulation will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight, health), whether the patient is human or an animal, other medications administered, and whether treatment is prophylactic or therapeutic. Usually, the patient is a human but nonhuman mammals including transgenic mammals can also be treated. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

Exemplary doses for nucleic acids encoding flu polypeptides range from about 10 ng to 1 g, 100 ng to 100 mg, 1 μg to 10 mg, or 30-300 μg nucleic acid, e.g., DNA, per patient.

In certain embodiments, exemplary doses for flu polypeptide(s) (e.g., as provided in split virus vaccines and subunit vaccines) range from about 5 μg to 100 mg, 15 μg to 50 mg, 15 μg to 25 mg, 15 μg to 10 mg, 15 μg to 5 mg, 15 μg to 1 mg, 15 μg to 100 μg, 15 μg to 75 μg, 5 μg to 50 μg, 10 μg to 50 μg, 15 μg to 45 μg, 20 μg to 40 μg, or 25 to 35 μg per kilogram of the patient. In other embodiments, exemplary doses for flu polypeptide(s) range from about 1 μg to 50 mg, 5 μg to 50 mg, 1 μg to 100 mg, 5 μg to 100 mg, 15 μg to 50 mg, 15 μg to 25 mg, 15 μg to 10 mg, 15 μg to 5 mg, 15 μg to 1 mg, 15 μg to 100 μg, 15 μg to 75 μg, 5 μg to 50 μg, 10 μg to 50 μg, 15 μg to 45 μg, 20 μg to 40 μg, or 25 to 35 μg of flu polypeptide(s) per dose. In certain embodiments, an exemplary dose for a flu polypeptide(s) comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 μg of flu polypeptide(s) per dose. In certain embodiments, an exemplary dose for a flu polypeptide(s) comprises 50, 55, 60, 65, 70, 75, 80, 85, 90, 95, or 100 μg of flu polypeptide(s) per dose.

Doses for infectious viral vectors may vary from 10-100, or more, virions per dose. In some embodiments, suitable dosages of a virus vector are $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu, and can be administered to a subject once, twice, three or more times with intervals as often as needed.

In certain embodiments, exemplary doses for VLPs range from about 0.01 μg to about 100 mg, about 0.1 μg to about 100 mg, about 5 μg to about 100 mg, about 15 μg to about 50 mg, about 15 μg to about 25 mg, about 15 μg to about 10 mg, about 15 μg to about 5 mg, about 15 μg to about 1 mg, about 15 μg to about 100 μg, about 15 μg to about 75 μg, about 5 μg to about 50 μg, about 10 μg to about 50 μg, about 15 μg to about 45 μg, about 20 μg to about 40 μg, or about 25 to about 35 μg per kilogram of the patient. In other embodiments, exemplary doses for flu polypeptides range from about 1 μg to about 50 mg, about 5 μg to about 50 mg, about 1 μg to about 100 mg, about 5 μg to about 100 mg, about 15 μg to about 50 mg, about 15 μg to about 25 mg, about 15 μg to about 10 mg, about 15 μg to about 5 mg, about 15 μg to about 1 mg, about 15 μg to about 100 μg, about 15 μg to about 75 μg, about 5 μg to about 50 μg, about 10 μg to about 50 μg, about 15 μg to about 45 μg, about 20 μg to about 40 μg, or about 25 to about 35 μg of flu polypeptide(s) per dose, and can be administered to a subject once, twice, three or more times with intervals as often as needed.

In one embodiment, an inactivated vaccine is formulated such that it contains about 5 μg to about 50 μg, about 10 μg to about 50 μg, about 15 μg to about 100 μg, about 15 μg to about 75 μg, about 15 μg to about 50 μg, about 15 μg to about 30 μg, about 20 μg to about 50 μg, about 25 μg to about 40 μg, about 25 μg to about 35 μg of a flu polypeptide(s). Such a vaccine may contain a combination of one or more different flu polypeptides, for example, one or more flu polypeptides from an influenza A virus and one or more flu polypeptides from an influenza B virus. In one embodiment, a live attenuated influenza vaccine (LAIV) is formulated such that a 0.2-mL dose contains $10^{6.5-7.5}$ fluorescent focal units of live attenuated influenza viruses from three strains expressing at least one influenza flu polypeptide.

In certain embodiments, an active compound or composition is administered to a subject once as a single dose. In certain embodiments, an active compound or composition is administered to a subject as a single dose followed by a second dose 3 to 6 weeks later. In accordance with these embodiments, booster inoculations may be administered to the subject at 6 to 12 month intervals following the second inoculation. In certain embodiments, the booster inoculations may utilize a different active compound or composition. In some embodiments, the administration of the same active compound or composition may be repeated and the administrations may be separated by at least 1 day, 2 days, 3 days, 5 days, 10 days, 15 days, 30 days, 45 days, 2 months, 75 days, 3 months, or at least 6 months. In certain embodiments, an active compound or composition is administered to a subject as a single dose once per year.

In specific embodiments for administration to children, two doses of an active compound or composition, given at least one month apart, are administered to a child. In specific embodiments for administration to adults, a single dose is given. In another embodiment, two doses of an active compound or composition, given at least one month apart, are administered to an adult. In another embodiment, a young child (six months to nine years old) may be administered an active compound or composition for the first time in two doses given one month apart. In a particular embodiment, a child who received only one dose in their first year of vaccination should receive two doses in the following year. In some embodiments, two doses administered 4 weeks apart are preferred for children 2-8 years of age who are administered an influenza vaccine, e.g., an immunogenic formulation described herein, for the first time. In certain embodiments, for children 6-35 months of age, a half dose (0.25 ml) may be preferred, in contrast to 0.5 ml which may be preferred for subjects over three years of age.

In particular embodiments, an active compound or composition is administered to a subject in the fall or winter, i.e., prior to or during the influenza season in each hemisphere. In one embodiment, children are administered their first dose early in the season, e.g., late September or early October, so that the second dose can be given prior to the peak of the influenza season.

In certain embodiments, an active compound or composition thereof is administered to a subject as 2, 3, 4, 5 or more doses 2 weeks, 3 weeks, 4 weeks, 5 weeks or 6 weeks apart. In some embodiments, 2, 3, 4, 5 or more doses of an active compound or compositions thereof are administered to a subject 2, 3, 4, 5 or 6 weeks apart at a dosage of 1 μg to 20 mg, 10 μg to 20 mg, 500 μg to 20 mg, 1 mg to 20 mg or 5 mg to 20 mg. In certain embodiments, the active compounds or compositions thereof administered is the same each time. In certain embodiments, the flu polypeptides or compositions thereof administered are different each time.

For passive immunization with an antibody that binds to a flu polypeptide, the dosage ranges from about 0.0001 to 100 mg/kg, and more usually 0.01 to 5 mg/kg, of the patient body weight. For example, dosages can be 1 mg/kg body weight or 10 mg/kg body weight or within the range of 1-10 mg/kg or in other words, 70 mg or 700 mg or within the range of 70-700 mg, respectively, for a 70 kg patient. An exemplary treatment regime entails administration once per every two weeks or once a month or once every 3 to 6 months for a period of one year or over several years, or over several year-intervals. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to the flu polypeptide in the patient.

5.13 Biological Assays 5.13.1 Assays for Testing Activity of Influenza Flu Polypeptide Assays for testing the expression of a flu polypeptide in a vector disclosed herein may be conducted using any assay known in the art. For example, an assay for incorporation into a viral vector comprises growing the virus as described in this section or Sections 5.4 or 5.5, purifying the viral particles by centrifugation through a sucrose cushion, and subsequent analysis for flu polypeptide expression by an immunoassay, such as Western blotting, using methods well known in the art.

In one embodiment, a flu polypeptide disclosed herein is assayed for proper folding and functionality by testing its ability to bind specifically to an antibody directed to a flu polypeptide using any assay for antibody-antigen interaction known in the art. Antibodies for use in such assays include, for example the neutralizing antibodies described in Wang et al. (2010) "Broadly Protective Monoclonal Antibodies against H3 Influenza Viruses following Sequential Immunization with Different Hemagglutinins," PLOS Pathogens 6(2):1-9, International Publication No. PCT/US2010/036170 and U.S. Ser. No. 12/778,103.

In another embodiment, a flu polypeptide disclosed herein is assayed for proper folding by determination of the structure or conformation of the flu polypeptide using any method known in the art such as, e.g., NMR, X-ray crystallographic methods, or secondary structure prediction methods, e.g., circular dichroism.

5.13.2 Assays for Testing Activity of Antibodies Generated Using Influenza Flu Polypeptides Antibodies described herein may be characterized in a variety of ways known to one of skill in the art (e.g. ELISA, Surface Plasmon resonance display (BIAcore), Western blot, immunofluorescence, immunostaining and/or microneutralization assays). In some embodiments, antibodies are assayed for the ability to specifically bind to a flu polypeptide, or a vector comprising said polypeptide. Such an assay may be performed in solution (e.g., Houghten, 1992, Bio/Techniques 13:412 421), on beads (Lam, 1991, Nature 354:82 84), on chips (Fodor, 1993, Nature 364:555 556), on bacteria (U.S. Pat. No. 5,223,409), on spores (U.S. Pat. Nos. 5,571,698; 5,403,484; and 5,223,409), on plasmids (Cull et al., 1992, Proc. Natl. Acad. Sci. USA 89:1865 1869) or on phage (Scott and Smith, 1990, Science 249:386 390; Cwirla et al., 1990, Proc. Natl. Acad. Sci. USA 87:6378 6382; and Felici, 1991, J. Mol. Biol. 222:301 310) (each of these references is incorporated herein in its entirety by reference).

Specific binding of an antibody to the flu polypeptide and cross-reactivity with other antigens can be assessed by any method known in the art. Immunoassays which can be used to analyze specific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds., 1994, Current Protocols in Molecular Biology, Vol. 1, John Wiley & Sons, Inc., New York, which is incorporated by reference herein in its entirety).

The binding affinity of an antibody to a flu polypeptide and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody for a flu polypeptide and the binding off-rates can be determined from the data by Scatchard plot analysis. Competition with a second antibody can also be determined using radioimmunoassays. In this case, a flu polypeptide is incubated with the test antibody conjugated to a labeled compound (e.g., $^3$H or $^{125}$I) in the presence of increasing amounts of an unlabeled second antibody.

In certain embodiments, antibody binding affinity and rate constants are measured using the KinExA 3000 System (Sapidyne Instruments, Boise, Id.). In some embodiments, surface plasmon resonance (e.g., BIAcore kinetic) analysis is used to determine the binding on and off rates of the antibodies to a flu polypeptide. BIAcore kinetic analysis comprises analyzing the binding and dissociation of flu polypeptide from chips with immobilized antibodies to a flu polypeptide on their surface. A typical BIAcore kinetic study involves the injection of 250 μL of an antibody reagent (mAb, Fab) at varying concentration in HBS buffer containing 0.005% Tween-20 over a sensor chip surface, onto which has been immobilized the flu polypeptide. The flow rate is maintained constant at 75 μL/min. Dissociation data is collected for 15 min or longer as necessary. Following each injection/dissociation cycle, the bound antibody is removed from the flu polypeptide surface using brief, 1 min pulses of dilute acid, typically 10-100 mM HCl, though other regenerants are employed as the circumstances warrant. More specifically, for measurement of the rates of association, $k_{on}$, and dissociation, $k_{off}$, the polypeptide is directly immobilized onto the sensor chip surface through the use of standard amine coupling chemistries, namely the EDC/NHS method (EDC=N— diethylaminopropyl)-carbodiimide). Briefly, a 5-100 nM solution of the polypeptide in 10 mM NaOAc, pH 4 or pH 5 is prepared and passed over the EDC/NHS-activated surface until approximately 30-50 RU's worth of polypeptide are immobilized. Following this, the unreacted active esters are "capped" off with an injection of 1M Et-NH$_2$. A blank surface, containing no polypeptide, is prepared under identical immobilization conditions for reference purposes. Once an appropriate surface has been prepared, a suitable dilution series of each one of the antibody reagents is prepared in HBS/Tween-20, and passed over both the polypeptide and reference cell surfaces, which are connected in series. The range of antibody concentrations that are prepared varies, depending on what the equilibrium binding constant, K$_D$, is estimated to be. As described above, the bound antibody is removed after each injection/dissociation cycle using an appropriate regenerant.

The neutralizing activity of an antibody can be determined utilizing any assay known to one skilled in the art. Antibodies described herein can be assayed for their ability to inhibit the binding of an influenza virus to its host cell receptor (i.e., sialic acid) using techniques known to those of skill in the art. For example, cells expressing influenza virus receptors can be contacted with a composition comprising an influenza virus in the presence or absence of the antibody and the ability of the antibody to inhibit the influenza virus' binding can be measured. Alternatively, the ability of antibodies to inhibit an influenza virus from binding to its receptor can be determined in cell-free assays.

In other embodiments, an antibody suitable for use in the methods described herein does not inhibit influenza virus receptor binding, yet is still found to be neutralizing in an assay described herein. In some embodiments, an antibody suitable for use in accordance with the methods described herein reduces or inhibits virus-host membrane fusion in an assay known in the art or described herein.

In one embodiment, virus-host membrane fusion is assayed in an in vitro assay using an influenza virus containing a reporter and a host cell capable of being infected with the virus. An antibody inhibits fusion if reporter activity is inhibited or reduced compared to a negative control (e.g., reporter activity in the presence of a control antibody or in the absence of antibody).

5.13.3 Assays for Testing Activity of Stimulated Cells

Cells stimulated in accordance with the methods described herein may be analyzed, for example, for integration, transcription and/or expression of the polynucleotide or gene(s) of interest, the number of copies of the gene integrated, and the location of the integration. Such analysis may be carried out at any time and may be carried out by any methods known in the art. In other embodiments, successful stimulation of the target cell with a flu polypeptide described herein is determined by detecting production of neutralizing antibodies against the flu polypeptide using methods known in the art or described herein.

In certain embodiments, subjects in which the stimulated cells, e.g., DCs, are administered can be analyzed for location of the cells, expression of a vector-delivered polynucleotide or gene encoding the flu polypeptide, stimulation of an immune response (e.g., production of neutralizing antibodies against the flu polypeptide), and/or monitored for symptoms associated with influenza virus infection or a disease associated therewith by any methods known in the art or described herein.

Reporter assays can be used to determine the specificity of the targeting of the flu polypeptide. For example, a mixed population of bone marrow cells can be obtained from a subject and cultured in vitro. The flu polypeptide can be administered to the mixed population of bone marrow cells, and expression of a reporter gene associated with the flu polypeptide can be assayed in the cultured cells. In some embodiments, at least about 50%, more preferably at least about 60%, 70%, 80% or 90%, still more preferably at least about 95% of stimulated cells in the mixed cell population are dendritic cells.

5.13.4 Viral Activity Assays

Antibodies described herein or compositions thereof can be assessed in vitro for antiviral activity. In one embodiment, the antibodies or compositions thereof are tested in vitro for their effect on growth of an influenza virus. Growth of influenza virus can be assessed by any method known in the art or described herein (e.g. in cell culture). In a specific embodiment, cells are infected at a MOI of 0.0005 and 0.001, 0.001 and 0.01, 0.01 and 0.1, 0.1 and 1, or 1 and 10, or a MOI of 0.0005, 0.001, 0.005, 0.01, 0.05, 0.1, 0.5, 1, 5 or 10 and incubated with serum free media supplemented. Viral titers are determined in the supernatant by hemagglutinin plaques or any other viral assay described herein. Cells in which viral titers can be assessed include, but are not limited to, EFK-2 cells, Vero cells, MDCK cells, primary human umbilical vein endothelial cells (HUVEC), H292 human epithelial cell line and HeLa cells. In vitro assays include those that measure altered viral replication (as determined, e.g., by plaque formation) or the production of viral proteins (as determined, e.g., by Western blot analysis) or viral RNAs (as determined, e.g., by RT-PCR or northern blot analysis) in cultured cells in vitro using methods which are well known in the art or described herein.

In one non-limiting example, a monolayer of the target mammalian cell line is infected with different amounts (e.g., multiplicity of 3 plaque forming units (pfu) or 5 pfu) of virus (e.g., influenza) and subsequently cultured in the presence or absence of various dilutions of antibodies (e.g., 0.1 µg/ml, 1 µg/ml, 5 µg/ml, or 10 µg/ml). Infected cultures are harvested 48 hours or 72 hours post infection and titered by standard plaque assays known in the art on the appropriate target cell line (e.g., Vero cells).

In a non-limiting example of a hemagglutination assay, cells are contacted with an antibody and are concurrently or subsequently infected with the virus (e.g., at an MOI of 1) and the virus is incubated under conditions to permit virus replication (e.g., 20-24 hours). The antibodies are preferably present throughout the course of infection. Viral replication and release of viral particles is then determined by hemagglutination assays using 0.5% chicken red blood cells. See, e.g., Kashyap et al., PNAS USA 105: 5986-5991. In some embodiments, a compound is considered an inhibitor of viral replication if it reduces viral replication by at least 2 wells of HA, which equals approximately a 75% reduction in viral titer. In specific embodiments, an inhibitor reduces viral titer in this assay by 50% or more, by 55% or more, by 60% or more, by 65% or more, by 70% or more, by 75% or more, by 80% or more, by 85% or more, by 90% or more, or by 95% or more. In other specific embodiments an inhibitor results in a reduction of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs in influenza virus titer in the subject. The log-reduction in influenza virus titer may be as compared to a negative control, as compared to another treatment, or as compared to the titer in the patient prior to antibody administration.

5.13.5 Cytotoxicity Assays

Many assays well-known in the art can be used to assess viability of cells (infected or uninfected) or cell lines following exposure to an active compound or a composition thereof and, thus, determine the cytotoxicity of the compound or composition. For example, cell proliferation can be assayed by measuring Bromodeoxyuridine (BrdU) incorporation (See, e.g., Hoshino et al., 1986, Int. J. Cancer 38, 369; Campana et al., 1988, J. Immunol. Meth. 107:79), (3H) thymidine incorporation (See, e.g., Chen, J., 1996, Oncogene 13:1395-403; Jeoung, J., 1995, J. Biol. Chem. 270: 18367 73), by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes. These changes are given a designation of T (100% toxic), PVH (partially toxic—very heavy—80%), PH (partially toxic—heavy—60%), P (partially toxic—40%), Ps (partially toxic—slight—20%), or 0 (no toxicity—0%), conforming to the degree of cytotoxicity seen. A 50% cell inhibitory (cytotoxic) concentration ($IC_{50}$) is determined by regression analysis of these data.

In a specific embodiment, the cells used in the cytotoxicity assay are animal cells, including primary cells and cell lines. In some embodiments, the cells are human cells. In certain embodiments, cytotoxicity is assessed in one or more of the following cell lines: U937, a human monocyte cell line; primary peripheral blood mononuclear cells (PBMC); Huh7, a human hepatoblastoma cell line; 293T, a human embryonic kidney cell line; and THP-1, monocytic cells. In certain embodiments, cytotoxicity is assessed in one or more of the following cell lines: MDCK, MEF, Huh 7.5, Detroit, or human tracheobronchial epithelial (HTBE) cells.

Active compounds or compositions thereof can be tested for in vivo toxicity in animal models. For example, animal models, described herein and/or others known in the art, used to test the activities of active compounds can also be used to determine the in vivo toxicity of these compounds. For example, animals are administered a range of concentrations of active compounds. Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of an active compound can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. An active compound that exhibits large therapeutic indices is preferred. While an active compound that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of an active compound for use in humans. The dosage of such agents lies preferably within a range of circulating concentrations that include the $ED_{50}$ with little or no toxicity. The dosage may vary within this range depending upon the dosage form employed and the route of administration utilized. For any active compound used in a method described herein, the effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high-performance liquid chromatography. Additional information concerning dosage determination is provided herein.

Further, any assays known to those skilled in the art can be used to evaluate the prophylactic and/or therapeutic utility of the active compounds and compositions described herein, for example, by measuring viral infection or a condition or symptoms associated therewith.

5.13.6 Assay for Assessing Ability of Flu Polypeptides to Induce an Immune Response The ability of a flu polypeptide to generate an immune response in a subject that is capable of cross-reacting with, and preferably protecting against, a plurality of influenza virus strains can be assessed using any approach known to those of skill in the art or described herein. In some embodiments, the ability of a flu polypeptide to generate an immune response in a subject that is capable of cross-reacting with, and preferably protecting against, a plurality of influenza virus strains can be assessed by immunizing a subject (e.g., a mouse) or set of subjects with a flu polypeptide described herein and immunizing an additional subject (e.g., a mouse) or set of subjects with a control (PBS). The subjects or set of subjects can subsequently be challenged with a plurality of virulent influenza virus strains and the ability of the virulent influenza virus strains to cause influenza virus disease in the subjects or set of subjects can be determined. Those skilled in the art will recognize that if the subject or set of subjects immunized with the control suffer from an influenza virus disease subsequent to challenge with the virulent influenza virus strains but the subject or set of subjects immunized with a flu polypeptide described herein do not suffer from influenza virus disease, then the flu polypeptide is able to generate an immune response in a subject that is capable of cross-reacting with a plurality of influenza virus strains. Further, in certain embodiments, a flu polypeptide described herein is able to generate an immune response that is capable of cross-reacting with a plurality of influenza virus strains if the subject or set of subjects immunized with the flu polypeptide suffer from influenza virus disease for shorter periods of time, receive less hospitalization time, exhibit a reduction in/absence of one or more symptoms associated with influenza virus disease or have symptoms that manifest themselves for shorter periods of time compared to subjects immunized with control. Methods for determining whether a subject suffers from influenza virus disease are known in the art and described herein. See, e.g., Sections 5.13.7 and 6.3, infra. The ability of a flu polypeptide to induce antiserum that simply cross-reacts with a plurality of influenza virus strains, or with multiple hemagglutinin subtypes can be tested by an immunoassay, such as an ELISA.

5.13.7 Methods of Assaying Influenza Activity in Animals

Active compounds and compositions thereof are preferably assayed in vivo for the desired therapeutic or prophylactic activity prior to use in humans. For example, in vivo assays can be used to determine whether it is preferable to administer an active compound or composition thereof and/or another therapy. For example, to assess the use of an active compound or composition thereof to prevent an influenza virus disease, the composition can be administered before the animal is infected with influenza virus. Alternatively, or in addition, an active compound or composition thereof can be administered to the animal at the same time that the animal is infected with influenza virus. To assess the use of an active compound or composition thereof to treat an influenza virus infection or disease associated therewith, the compound or composition may be administered after infecting the animal with influenza virus. In a specific embodiment, an active compound or composition thereof is administered to the animal more than one time.

Active compounds and compositions thereof can be tested for antiviral activity in animal model systems including, but are not limited to, rats, mice, chicken, cows, monkeys, pigs, goats, sheep, dogs, rabbits, guinea pigs, etc. In a specific embodiment, active compounds and compositions thereof are tested in a mouse model system. Such model systems are widely used and well-known to the skilled artisan. In a specific embodiment, active compounds and compositions thereof are tested in a mouse model system. Non-limiting examples of animal models for influenza virus are provided in this section.

In general, animals are infected with influenza virus and concurrently or subsequently treated with an active compound or composition thereof, or placebo. Alternatively, animals are treated with an active compound or composition thereof or placebo and subsequently infected with influenza virus. Samples obtained from these animals (e.g., serum, urine, sputum, semen, saliva, plasma, or tissue sample) can be tested for viral replication via well known methods in the art, e.g., those that measure altered viral titers (as determined, e.g., by plaque formation), the production of viral proteins (as determined, e.g., by Western blot, ELISA, or flow cytometry analysis) or the production of viral nucleic acids (as determined, e.g., by RT-PCR or northern blot analysis). For quantitation of virus in tissue samples, tissue samples are homogenized in phosphate-buffered saline (PBS), and dilutions of clarified homogenates are adsorbed for 1 hour at 37° C. onto monolayers of cells (e.g., Vero, CEF or MDCK cells). In other assays, histopathologic evaluations are performed after infection, preferably evaluations of the organ(s) the virus is known to target for infection. Virus immunohistochemistry can be performed using a viral-specific monoclonal antibody.

The effect of an active compound or composition thereof on the virulence of a virus can also be determined using in vivo assays in which the titer of the virus in an infected subject administered an active compound or composition thereof, the length of survival of an infected subject administered an active compound or composition thereof, the immune response in an infected subject administered an active compound or composition thereof, the number, duration and/or severity of the symptoms in an infected subject administered an active compound or composition thereof, and/or the time period before onset of one or more symptoms in an infected subject administered an active compound or composition thereof, is assessed. Techniques known to one of skill in the art can be used to measure such effects. In certain embodiments, an active compound or composition thereof results in a 0.5 fold, 1 fold, 2 fold, 4 fold, 6 fold, 8 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of influenza virus relative to an untreated subject. In some embodiments, an active compound or composition thereof results in a reduction in titer of influenza virus relative to an untreated subject of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs.

Influenza virus animal models, such as ferret, mouse, guinea pig, squirrel monkey, macaque, and chicken, developed for use to test antiviral agents against influenza virus have been described. See, e.g., Sidwell et al., Antiviral Res., 2000, 48:1-16; Lowen A. C. et al. PNAS., 2006, 103: 9988-92; and McCauley et al., Antiviral Res., 1995, 27:179-186 and Rimmelzwann et al., Avian Diseases, 2003, 47:931-933. For mouse models of influenza, non-limiting examples of parameters that can be used to assay antiviral activity of active compounds administered to the influenza-infected mice include pneumonia-associated death, serum al-acid glycoprotein increase, animal weight, lung virus assayed by hemagglutinin, lung virus assayed by plaque assays, and histopathological change in the lung. Statistical analysis is carried out to calculate significance (e.g., a P value of 0.05 or less).

In other assays, histopathologic evaluations are performed after infection of an animal model subject. Nasal turbinates and trachea may be examined for epithelial changes and subepithelial inflammation. The lungs may be examined for bronchiolar epithelial changes and peribronchiolar inflammation in large, medium, and small or terminal bronchioles. The alveoli are also evaluated for inflammatory changes. The medium bronchioles are graded on a scale of 0 to 3+ as follows: 0 (normal: lined by medium to tall columnar epithelial cells with ciliated apical borders and basal pseudostratified nuclei; minimal inflammation); 1+ (epithelial layer columnar and even in outline with only slightly increased proliferation; cilia still visible on many cells); 2+ (prominent changes in the epithelial layer ranging from attenuation to marked proliferation; cells disorganized and layer outline irregular at the luminal border); 3+ (epithelial layer markedly disrupted and disorganized with necrotic cells visible in the lumen; some bronchioles attenuated and others in marked reactive proliferation).

The trachea is graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+ (focal squamous metaplasia of the epithelial layer); 2+ (diffuse squamous metaplasia of much of the epithelial layer, cilia may be evident focally); 2.5+ (diffuse squamous metaplasia with very few cilia evident).

Virus immunohistochemistry is performed using a viral-specific monoclonal antibody (e.g. NP-, N- or HN-specific monoclonal antibodies). Staining is graded 0 to 3+ as follows: 0 (no infected cells); 0.5+ (few infected cells); 1+ (few infected cells, as widely separated individual cells); 1.5+ (few infected cells, as widely separated singles and in small clusters); 2+ (moderate numbers of infected cells, usually affecting clusters of adjacent cells in portions of the epithelial layer lining bronchioles, or in small sublobular foci in alveoli); 3+ (numerous infected cells, affecting most of the epithelial layer in bronchioles, or widespread in large sublobular foci in alveoli).

In one example, the ability to induce lung lesions and cause infection in an animal model of virus infection is compared using wild-type virus and mock virus. Lung lesions can be assessed as a percentage of lung lobes that are healthy by visual inspection. Animals are euthanized 5 days p.i. by intravenous administration of pentobarbital, and their lungs are removed in toto. The percentage of the surface of each pulmonary lobe that is affected by macroscopic lesions is estimated visually. The percentages are averaged to obtain a mean value for the 7 pulmonary lobes of each animal. In other assays, nasal swabs can be tested to determine virus burden or titer. Nasal swabs can be taken during necropsy to determine viral burden post-infection.

In one embodiment, virus is quantified in tissue samples. For example, tissue samples are homogenized in phosphate-buffered saline (PBS), and dilutions of clarified homogenates adsorbed for 1 h at 37° C. onto monolayers of cells (e.g., MDCK cells). Infected monolayers are then overlaid with a solution of minimal essential medium containing 0.1% bovine serum albumin (BSA), 0.01% DEAE-dextran, 0.1% NaHCO$_3$, and 1% agar. Plates are incubated 2 to 3 days until plaques could be visualized. Tissue culture infectious dose (TCID) assays to titrate virus from PR8-infected samples are carried out as follows. Confluent monolayers of cells (e.g., MDCK cells) in 96-well plates are incubated with log dilutions of clarified tissue homogenates in media. Two to three days after inoculation, 0.05-ml aliquots from each well are assessed for viral growth by hemagglutination assay (HA assay).

5.13.8 Methods of Assaying Influenza Activity in Humans

In one embodiment, an active compound or composition thereof is assessed in infected human subjects. In accordance with this embodiment, an active compound or composition thereof is administered to the human subject, and the effect of the active compound or composition on viral replication and/or survival is determined by, e.g., analyzing the level of the virus or viral nucleic acids in a biological sample (e.g., serum or plasma). An active compound or composition thereof that alters virus replication and/or survival can be identified by comparing the level of virus replication and/or survival in a subject or group of subjects treated with a control to that in a subject or group of subjects treated with an active compound or composition thereof. Alternatively, alterations in viral replication and/or survival can be identified by comparing the level of the virus replication and/or survival in a subject or group of subjects before and after the administration of an active compound or composition thereof. Techniques known to those of skill in the art can be used to obtain the biological sample and analyze the mRNA or protein expression.

In another embodiment, the effect of an active compound or composition thereof on the severity of one or more symptoms associated with an influenza virus infection/disease are assessed in an infected subject. In accordance with this embodiment, an active compound or composition thereof or a control is administered to a human subject suffering from influenza virus infection and the effect of the active compound or composition on one or more symptoms of the virus infection is determined. An active compound or composition thereof that reduces one or more symptoms can be identified by comparing the subjects treated with a control to the subjects treated with the active compound or composition. In another embodiment, an active compound or composition thereof is administered to a healthy human subject and monitored for efficacy as a vaccine (e.g., the subject is monitored for the onset of symptoms of influenza virus infection; reduction in hospitalization, the ability of influenza virus to infect the subject; and/or a reduction in/absence of one or more symptoms and/or duration of symptoms associated with influenza virus infection). Techniques known to physicians familiar with infectious diseases can be used to determine whether an active compound or composition thereof reduces one or more symptoms associated with the influenza virus disease.

5.14 Kits

Provided herein is a pharmaceutical pack or kit comprising one or more containers filled with one or more of the ingredients of the pharmaceutical compositions described herein, such as one or more active compounds provided herein. Optionally associated with such container(s) can be a notice in the form prescribed by a governmental agency regulating the manufacture, use or sale of pharmaceuticals or biological products, which notice reflects approval by the agency of manufacture, use or sale for human administration.

The kits encompassed herein can be used in the above methods. In one embodiment, a kit comprises an active compound described herein, preferably one or more influenza flu polypeptides, in one or more containers. In certain embodiments, a kit comprises a vaccine described herein, e.g., a split virus vaccine, a subunit vaccine, an inactivated influenza virus vaccine, or a live influenza virus vaccine.

6. EXAMPLES 6.1 Monoclonal Antibody 12D1

This example demonstrates that an anti-influenza virus antibody, monoclonal antibody 12D1, reacts with the long alpha-helix of HA2.

6.1.1 Materials and Methods 6.1.1.1 Truncated Hemagglutinin Subunit 2 (HA2)

The whole coding region of A/HK/1/68 HA was reversed-transcribed and amplified from viral RNA and subsequently sub-clone into a pCAGGs expression vector. Truncated versions of the HA2 portion were generated by PCR amplification from pCAGGs-HK68 HA and sub-cloned further into a pCAGGs-green fluorescent protein (GFP) expression plasmid. The resulting plasmid thus consists of a expression vector encoding a GFP fused to a portion of a truncated HA2. All constructs were sequenced and confirmed.

6.1.1.2 Western Blot

Blots were produced by methods previously described (Towbin et al., Proc Natl Acad Sci USA, 1979. 76(9):4350-4). Samples were boiled for 5 minutes at 100° C. in loading buffer containing SDS and 0.6M DTT. Immuno-precipitated complexes, cell lysates or purified virus were resolved in a 4-20% Tris-HCl SDS-PAGE gel (Bio-Rad, Inc.) and samples were blotted onto a Protran nitrocellulose membrane (Whatman). GFP and fusion GFP-HA truncated peptides were detected using rabbit anti-GFP (Santa Cruz Biotechnology, Inc) and/or mAb 12D1. Secondary antibodies were anti-rabbit IgG HRP (Dako) and anti-mouse Ig (GE Healthcare, Inc.).

6.1.1.3 Immunoprecipitation 293T cells were transfected with various pCAGGs encoding the GFP-truncated HA2 fusion proteins using Lipofectamine 2000 (Invitrogen, Inc). At 24 hours post transfection cells were lysed with radioimmuno-precipitation assay (RIPA) buffer and the truncated fusion peptides were immuno-precipitated with 1 to 5 μg of mAB 12D1 bound to protein G-Agarose (Roche, Inc) overnight at 4° C. Immunoprecipitation was analyzed by Western blotting under reducing and denaturing conditions

Figure 2B:
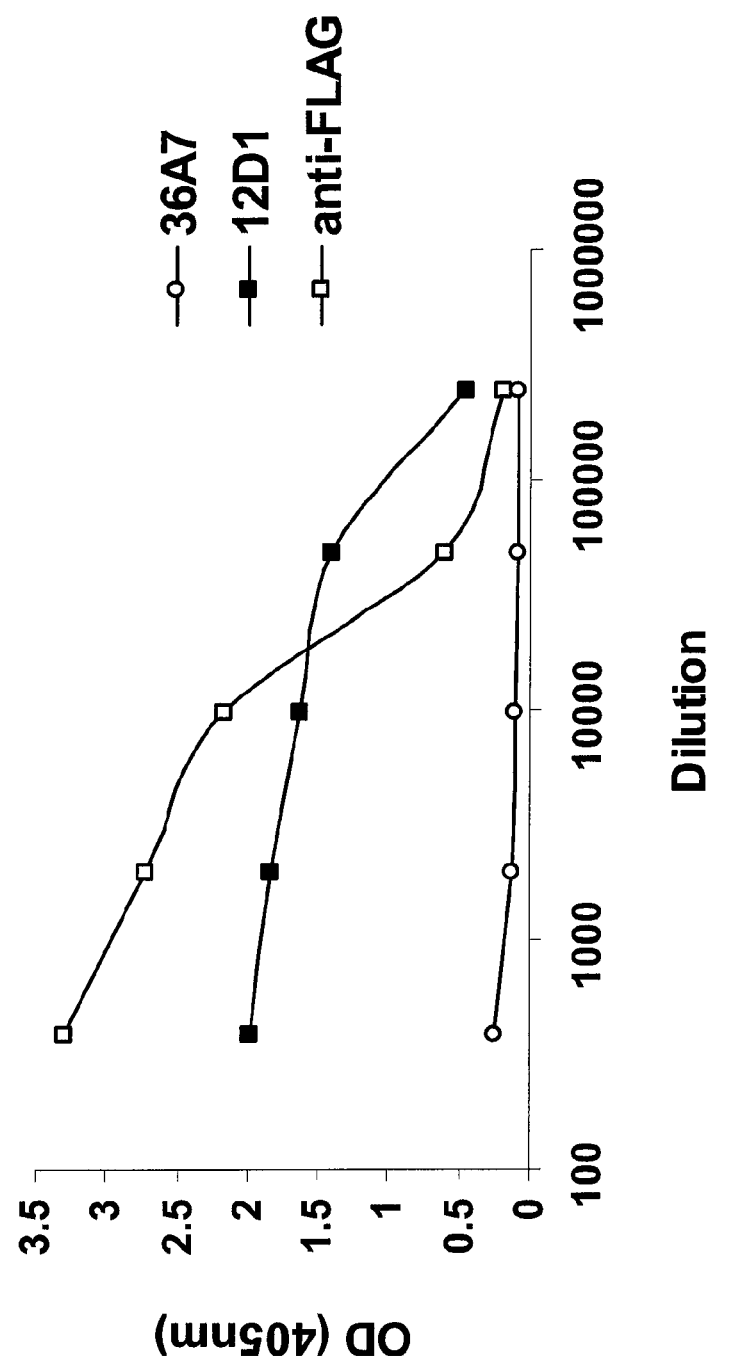

6.1.1.4 ELISA 96 well plates (Nunc Immulon 2) were coated with 2 ug/ml HApep-KLH conjugate (FIG. 2B) or purified HA (FIG. 2A,C) in PBS overnight, 4° C. Plates were blocked for 30 minutes at room temperature with 1% BSA/PBS and washed twice with PBS/0.025% Tween. Antibodies or antiserum were serially diluted in 1% BSA/PBS, added to the plate followed by 3 hour incubation at 37° C. Plates were washed three times, anti-mouse-AP (Southern Biotech) diluted 1:2000 was added to wells followed by 3 hour incubation, 37° C. P-nitrophenyl phosphate (PNPP) substrate was then added to wells and allowed to develop for 20-30 minutes at room temperature. Optical density measurements were taken at 405 nm.

6.1.2 Results

As demonstrated in FIG. 1, mAb 12D1 reacts within the region of amino acids 76-130 of the HA2 molecule; this region comprises the "long alpha-helix" of HA2. As mAb 12D1 is known to have protective activity in vivo against H3 virus infection (demonstrated by passive transfer of mAb 12D1 prior to virus challenge),

6.2 Design and Production of Flu Polypeptide

It was hypothesized that immunization with the 76-130 region of HA2 might elicit a similarly protective immune response against influenza viruses of the H3 subtype or of multiple subtypes.

In order to increase the immunogenicity of the 76-130 peptide of HA2 a construct with a C-terminal spacer domain was designed consisting of eight amino acids followed by a cysteine residue which facilitated primary amine-mediated coupling to the carrier protein Keyhole limpet hemacyanin (KLH). In order to increase serum half-life the peptide was acetylated at the N-terminus.

To verify the structural integrity of the long alpha-helix within the KLH conjugate, binding of mAb 12D1 to the conjugate was tested by direct-binding ELISA and found that the 12D1 binding region was intact (FIG. 1B).

6.2.1 the HA2 Binding Region of mAb 12D1

The identity of the region of the H3 hemagglutinin that might elicit antibodies similar to the 12D1 monoclonal antibody (mAb) was examined. Sixteen passages of A/HK/1968 virus in the presence of the anti-H3 mAb did not yield escape variants which might have assisted in identification of the binding epitopes. The hemagglutinin of six plaques present after incubation of A/HK/1968 virus with 50 ug/ml mAb 12D1 in a plaque assay was sequenced and no changes from the wild-type hemagglutinin were found. Because mAb 12D1 mediates protection against influenza disease in vivo and reacts with a continuous epitope of the viral hemagglutinin (no trimeric structure required), as evidenced by reactivity with the denatured hemagglutinin monomer by Western blot, the 12D1 binding epitope was focused on. Truncated hemagglutinin constructs consisting of hemagglutinin segments of varying length fused to GFP were generated. GFP expression was utilized to assess expression of the constructs in transfected 293T cells. By analysis of the truncated hemagglutinin constructs, it was determined that the 12D1 paratope makes dominant interactions with the HA2 subunit in the region of amino acids 30-106. Diminished 12D1 binding without diminished GFP expression in the 76-184 and 91-184 truncations along with loss of binding with the 106-184 truncation suggested that 12D1 binding is dependent on contacts with amino acids in the HA2 76-106 region (FIG. 1). Additional truncated HAs were designed and constructed to further narrow down the minimal binding site of 12D1. Amongst those, the region spanning from aa 76 to aa 130—representing the long alpha-helix of HA2 not only was detected by 12D1 in a Western blot, but also positive by immuno-precipitation.

These 30 amino acids fall within the membrane distal half of the long alpha-helix of HA2. The 12D1 paratope may have additional contacts with amino acids outside of this region (in HA1 or HA2) that are not required for binding by Western blot.

6.3. Serum Antibodies Induced by Flu Polypeptide React with Multiple Ha Subtypes

6.3.1 Materials and Methods

Western blots and ELISA were performed as described in Section 6.1.1, supra.

6.3.2 Results

Figures 3A, 3B:
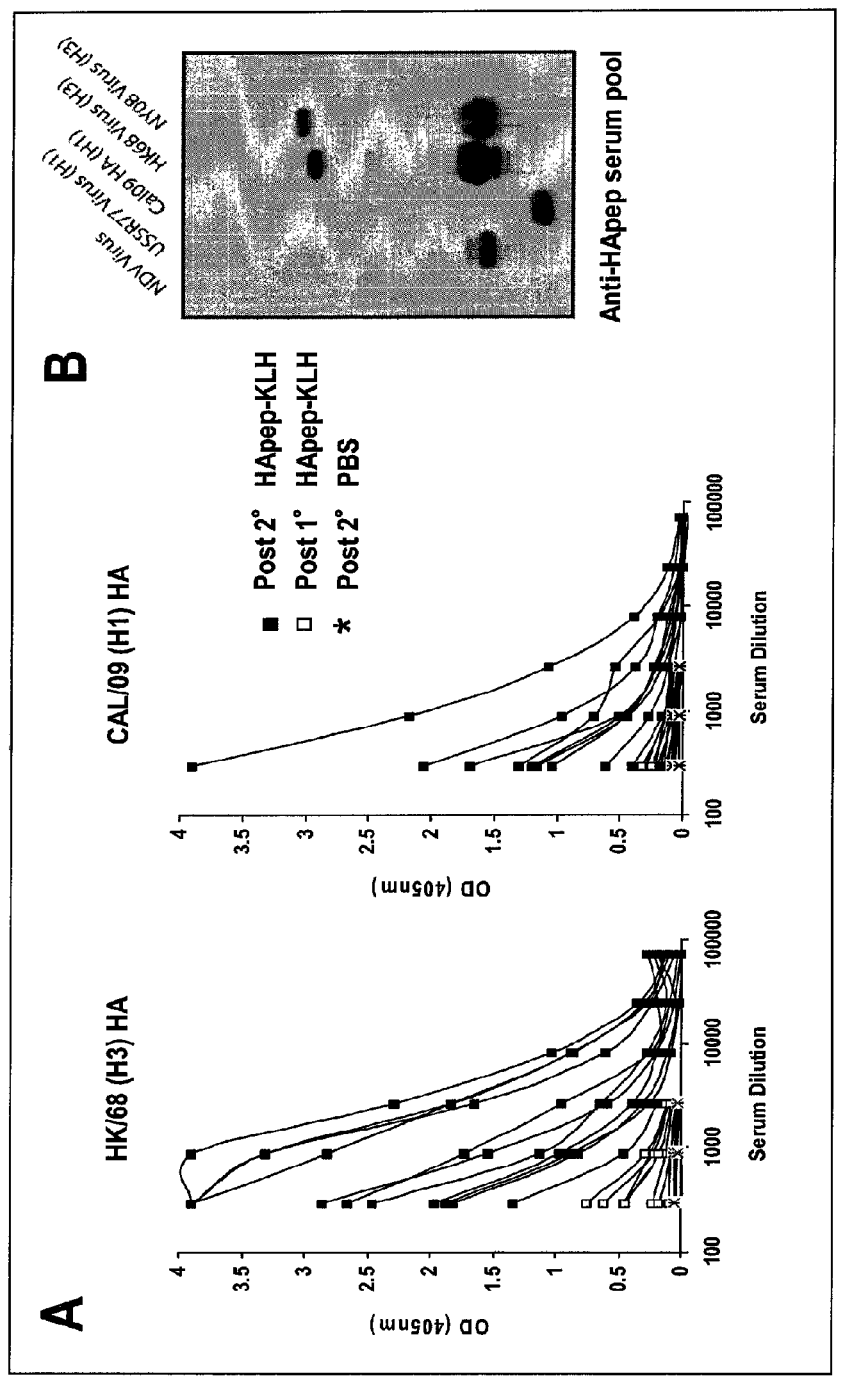
Figure 3C:
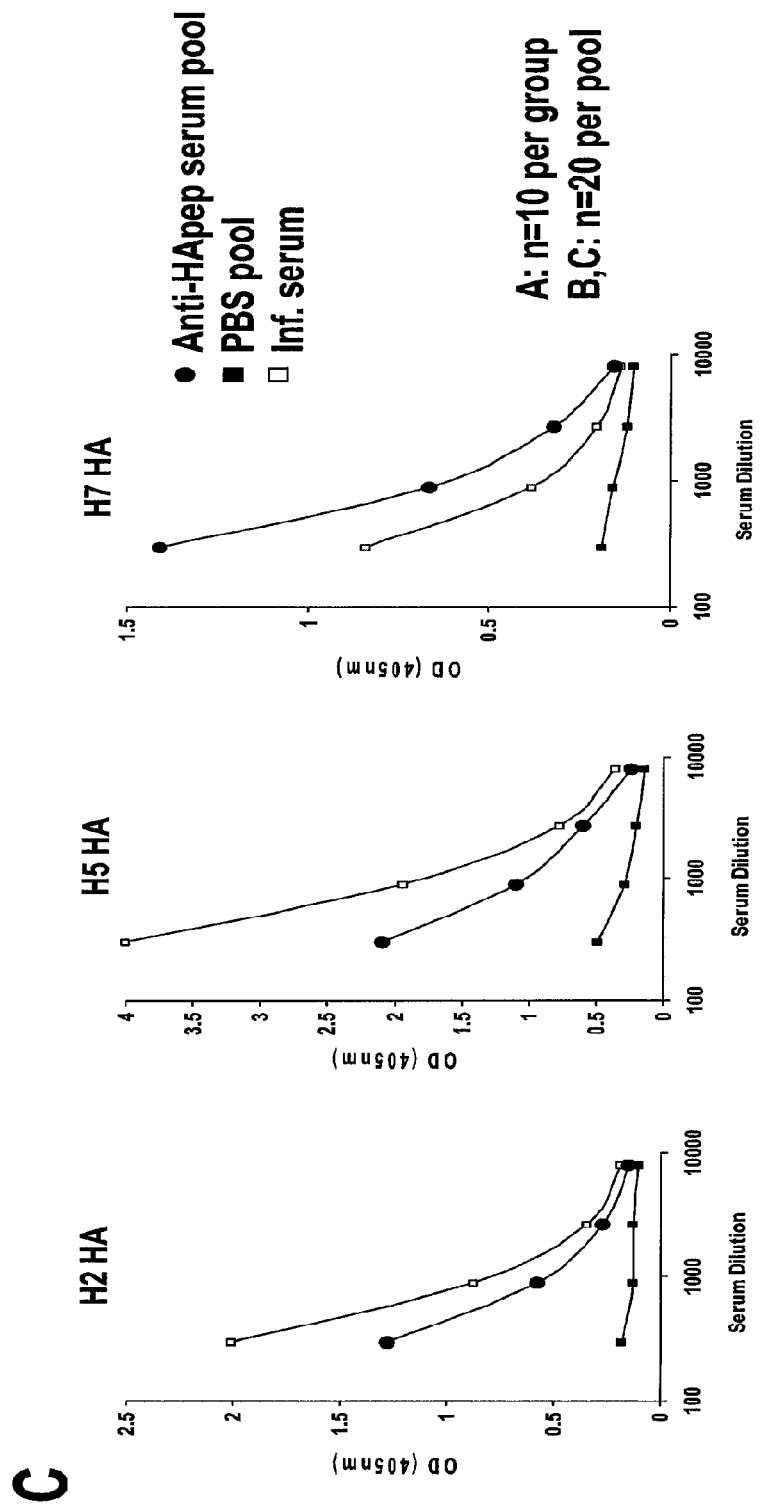
Figure 4A:
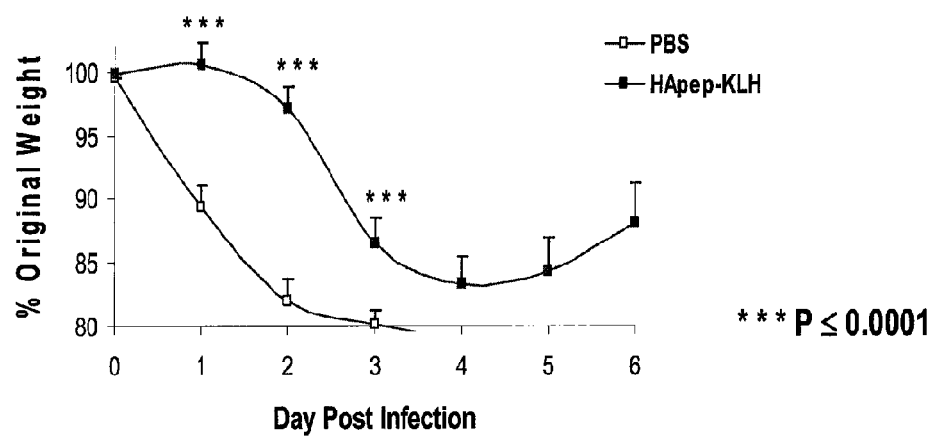
Figure 4B:
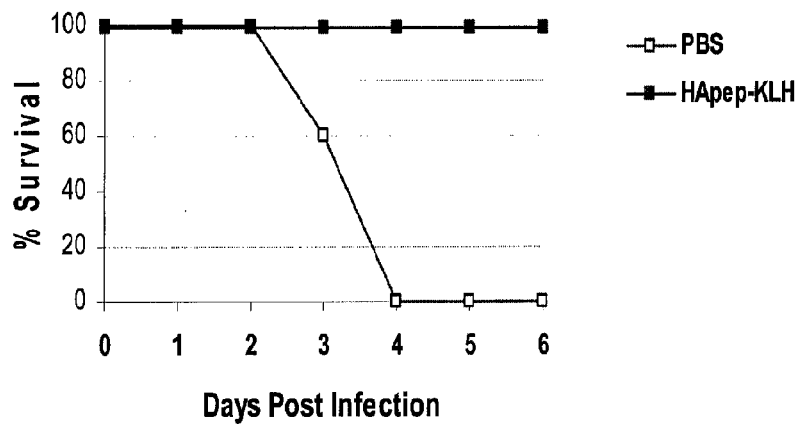
Figure 4C:
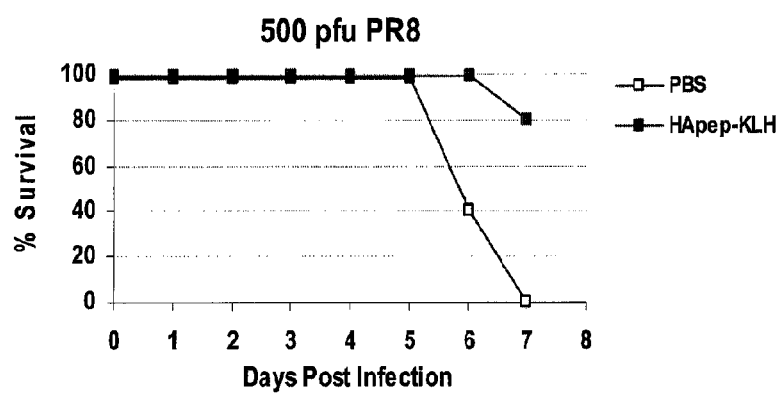
Figure 4D:
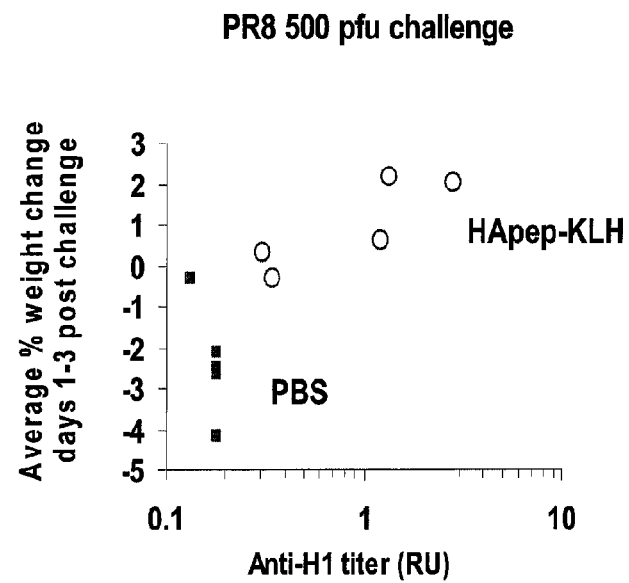

As demonstrated in FIG. 3, flu polypeptide (76-130)-KLH ("HApep-KLH") acts as a robust immunogen and serum antibody elicited by HApep-KLH reacts with multiple hemagglutinin subtypes.

To evaluate the efficacy of the HApep-KLH construct as an immunogen, sera were taken from mice 10 days post primary and secondary immunizations. These sera were tested for reactivity with recombinantly expressed, purified hemagglutinins of different subtypes. First, it was noted that the HApep-KLH vaccine construct did elicit serum antibody reactive with purified hemagglutinin protein. Second, a marked increase in anti-HA titer following secondary immunization was evident, indicating that the construct did act to elicit a robust humoral immune response in mice. Finally, the heterosubtypic reactivity of the HApep-KLH anti-sera was intriguing. Sera from immunized mice demonstrated binding activity with hemagglutinins of H3, H1, H2, H9 and H7 subtypes.

6.4 Immunization with Flu Polypeptides Protects Mice from Lethal Virus Challenge

6.4.1. Materials and Methods 6-8 week old BALB/C mice (Jackson Laboratories) were immunized with 25 ug HApep-KLH or KLH alone in Complete Freund's adjuvant (Sigma) by subcutaneous administration. Three weeks following primary immunization, mice were boosted with 25 ug HApep-KLH or KLH alone in Incomplete Freund's adjuvant. Two to three weeks following boost, mice were challenged with virus. Before virus infection, mice were anesthetized by intraperitoneal administration of a ketamine (75 mg/kg of body weight)/xylazine (15 mg/kg of body weight) mixture. Virus was administered intranasally in 50 ug total PBS; challenge doses consisted of 40,000 pfu X31 or 500 pfu PR8. Body weights were monitored daily.

6.4.2. Results

As demonstrated in FIG. 4, immunization with flu polypeptide (76-130)-KLH ("HApep-KLH") protects mice against lethal challenge.

Mice were immunized with 25 ug HApep-KLH by subcutaneous administration in a prime-boost immunization schedule. Immunizations were spaced 3 weeks apart and mice were challenged with virus 2-3 weeks following secondary immunization. Following virus challenge, mice weights were taken daily as a read-out of disease severity. Immunization with HApep-KLH was found to protect 100% of mice from lethal challenge with X31, a mouse-adapted virus expressing the HA and NA from Hong Kong/1/1968 (H3) (FIG. 4B). Average weights from mice immunized with the HApep-KLH construct or mice receiving PBS were significantly different on all days (FIG. 4A).

In a similar challenge experiment, mice received a lethal dose of mouse adapted PR/8 virus (H1). By seven days post challenge, all mice receiving PBS had succumbed to disease while 80% of mice receiving the HApep-KLH vaccine were protected (FIG. 4C). Serum antibody titer against H1 subtype hemagglutinin was found to correlate with weight change in the days following virus challenge (4D).

6.5 Vaccination with Flu Polypeptides Provides Protection Against Distinct Viral Subtypes This example demonstrates that a flu polypeptide can provide protection in mice against influenza viruses of the structurally divergent subtypes H3N2, H1N1 and H5N1.

6.5.1 Materials and Methods 6.5.1.1 Viruses and Purified Hemagglutinins

Viruses used were: X31 virus (A/Hong Kong/1/1968 hemagglutinin and neuraminidase with remaining 6 segments from PR8), A/Puerto Rico/8/34 (PR8) virus, A/USSR/90/1977 virus, A/Georgia/81 virus, HAlo virus (A/Viet Nam/4/2005 virus with hemagglutinin modified to remove the poly-basic cleavage site). Purified hemagglutinin used were from: A/Hong Kong/1/1968; A/Brisbane/10/2007; A/Viet Nam/1203/2004 (H5); A/Singapore/1/57 (H2); A/Teal/HK/312/97 (H6); A/Netherlands/219/2003 (H7); A/HK/1073/99 (H9); and A/California/04/2009 (H1).

6.5.1.2 Western Blot

Blots were produced by methods previously described (see Towbin et al., (1979) Proc Natl Acad Sci USA 76(9): 4350-4354). Samples were boiled for 5 minutes at 100° C. in loading buffer containing SDS and 0.6M DTT. Immunoprecipitated complexes, cell lysates or purified virus were resolved in a 4-20% Tris-HCl SDS-PAGE gel (Bio-Rad, Inc.) and samples were blotted onto a Protran nitrocellulose membrane (Whatman). GFP and fusion GFP-HA truncated peptides were detected using rabbit anti-GFP (Santa Cruz Biotechnology, Inc) and/or mAb 12D1. Secondary antibodies were anti-rabbit IgG HRP (Dako) and anti-mouse Ig-HRP (GE Healtchare, Inc.).

6.5.1.3 Immunoprecipitation

The 76-130 (LAH) region of the A/HK/1/68 HA2 was generated by PCR amplification of viral RNA and subcloned into a pCAGG-green fluorescent protein (GFP) plasmid (see Basler et al., (2001) Proc Natl Acad Sci USA 98(5):2746-2751). GFP was present at the N-terminus of the HA2 truncation. 293T cells were transfected with the GFP-LAH construct using Lipofectamine 2000 (Invitrogen, Inc). At 24 hours post transfection cells were lysed with radioimmuno-precipitation assay (RIPA) buffer and the GFP-LAH fusion protein was immuno-precipitated with 1 to 5 μg of mAb 12D1 bound to protein G-Agarose (Roche, Inc) overnight at 4° C.

6.5.1.4 Long-Alpha Helix-KLH Vaccine

The A/HK/1/68 HA2 LAH polypeptide (amino acids 76-130) sequence used was:

```
Ac-RIQDLEKYVEDTKIDLWSYNAELLVALENQHTIDLTDSEMNKLFEK

TRRQLRENADYKDDDDKC.
```

The construct was acetylated at the N-terminus and consisted of amino acids 76-130 of the H3 A/Hong Kong/1/1968 HA2 molecule followed by a FLAG-tag (DYKDDDDK, SEQ ID NO: 61), followed by a cysteine. The polypeptide was coupled to the carrier protein keyhole limpet hemocyanin (KLH) by thiol to primary amine coupling. This conjugate was produced by CHI Scientific, Inc., Maynard, Mass. USA.

6.5.1.6 ELISA 96-well plates (Nunc Immulon 2) were coated with 2 μg/ml LAH-KLH conjugate (FIG. 7B), purified hemagglutinin (FIG. 7A, C), or influenza virus vaccine (FLUVIRON®, obtained from BEI Resources) purified surface antigen (Novartis Vaccines) in PBS overnight, 4° C. Plates were blocked for 30 minutes at room temperature with 1% BSA/PBS and washed twice with PBS/0.025% Tween. Antibodies, anti-serum or serum from individuals vaccinated with the 2008-2009 trivalent inactivated influenza virus vaccine (TIV) were serially diluted in 1% BSA/PBS and added to the plate followed by a 3 hour incubation at 37° C. An anti-flag antibody (Sigma) was used as a positive control in wells coated with the LAH-KLH conjugate. Plates were washed three times, and anti-mouse-alkaline phosphatase (AP) (Southern Biotech) diluted 1:2000 was added to wells followed by a 3 hour incubation at 37° C. For human sera, anti-human IgG (Fc specific)-AP (Sigma) antibody was used at 1:500 dilution. Anti-rabbit Ig-AP (Southern Biotech) at 1:500 dilution was used as the secondary for the anti-flag antibody. P-nitrophenyl phosphate (PNPP) substrate was then added to wells and allowed to develop for 20-30 minutes at room temperature. Optical density measurements were taken at 405 nm.

6.5.1.6 Mouse Immunizations and Challenge Experiments 6-8 week old BALB/C mice (Jackson Laboratories) were immunized with 25 μg LAH-KLH, HA2, KLH alone or PBS in Complete Freund's adjuvant (Sigma) by subcutaneous administration. Three weeks following primary immunization, mice were boosted with 25 μg of the same immunogen or PBS in Incomplete Freund's adjuvant. Two to three weeks following boost, mice were challenged with virus. Before virus infection, mice were anesthetized by intraperitoneal administration of a ketamine (75 mg/kg of body weight)/ xylazine (15 mg/kg of body weight) mixture. Virus was administered intranasally in 50 μl total PBS; challenge doses consisted of $4\times10^5$ pfu X31 or 500 pfu PR8 or HAlo virus. Body weights were monitored daily. For passive transfer experiments, mice were bled two weeks following the last immunization with KLH or LAH-KLH or three weeks following infection with PR8 virus or A/Hong Kong/1/1968 virus. Sera from mice were pooled according to vaccination antigen or virus infection and 200 μl serum was transferred to each recipient mouse by intraperitoneal administration 2 hours prior to infection with either 50 pfu PR8 virus or 3700 pfu Georgia/81 virus. Lung titers were assessed by plaque assay 2 days post infection.

6.5.2 Results

Figure 7A:
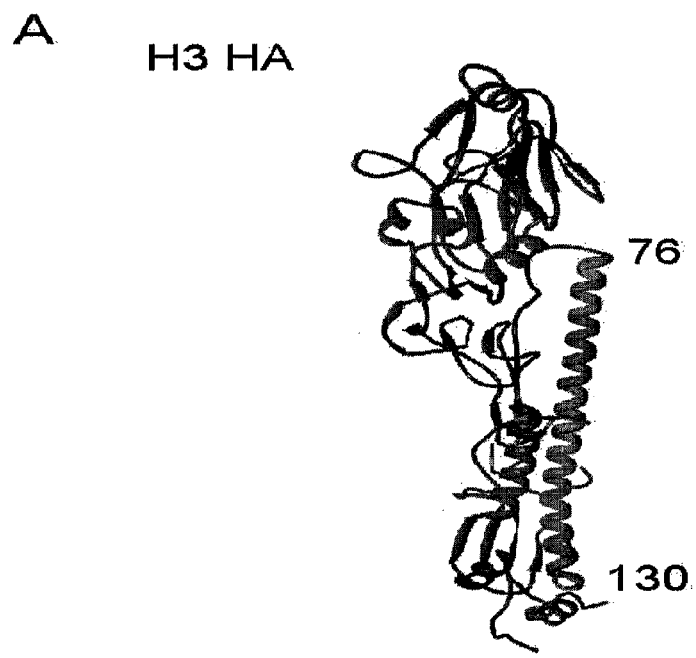
Figure 7B:
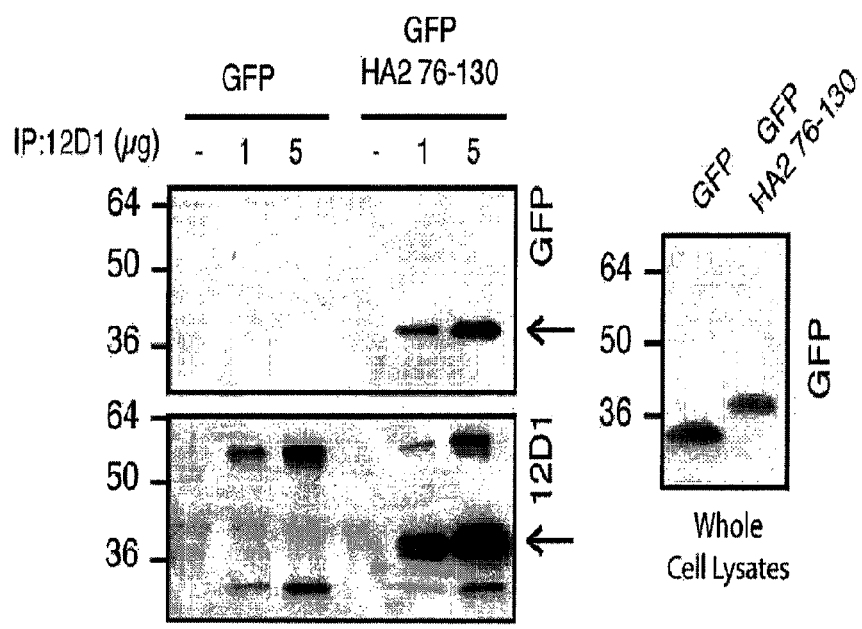

Mouse monoclonal antibody 12D1 binds a continuous portion of the HA2 molecule and has broad-neutralizing activity against influenza viruses of the H3 subtype. By generating constructs designed to express short regions of the HA2 molecule, it was determined that mAb 12D1 binds amino acids within the highly conserved 'long alpha-helix' (LAH) region of the protein. The portion of the hemagglutinin that interacts with mAb 12D1 was originally identified by interpretation of binding data using multiple HA2 truncations of varying lengths. Based on the cumulative truncation data, it was determined that mAb 12D1 binds within the 76-106 region of HA2 (see Wang et al., (2010) PLoS Pathog 6(2):e1000796). Subsequent work, however, revealed that a peptide representing the entire LAH (amino acids 76-130) of the H3 virus A/Hong Kong/1/1968 provided the necessary structural elements for maximal binding by mAb 12D1 (FIG. 7A). This region, amino acids 76-130 of HA2, was expressed in 293T cells and was pulled-down by mAb 12D1 (FIG. 7B). Whether immunization with the 76-130 region of HA2 might elicit an antibody repertoire with functional similarity to that of mAb 12D1 and provide protection against influenza viruses of the H3 subtype or of multiple subtypes was thus determined.

Figure 7C:
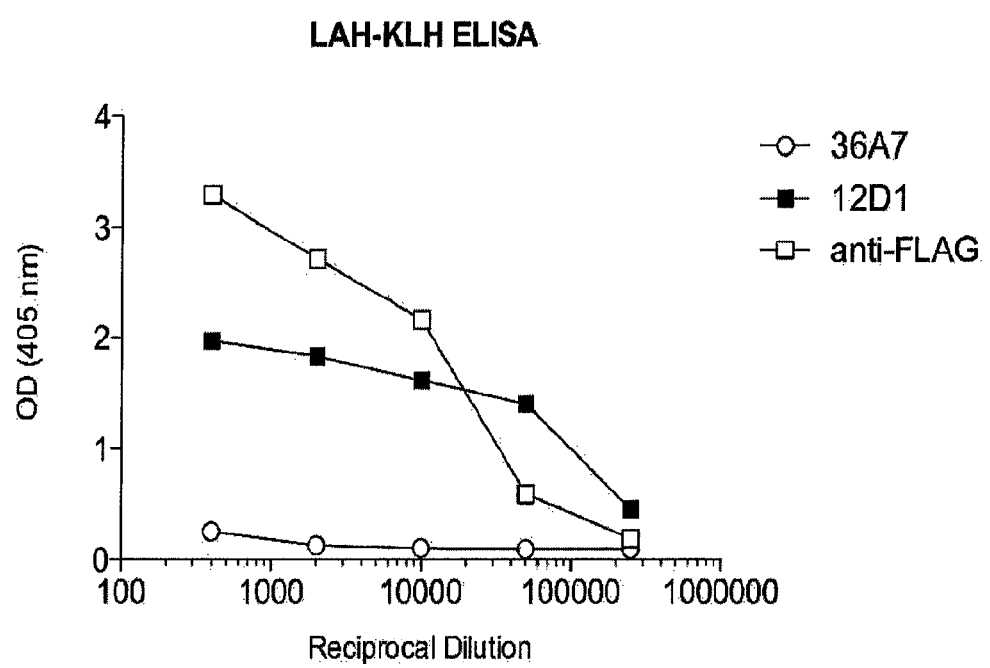

The antigenicity of the 76-130 polypeptide (LAH) was enhanced by designing a conjugate vaccine consisting of the LAH plus a C-terminal spacer domain of eight amino acids (FLAG-tag) followed by a cysteine residue which facilitated thiol to primary amine-mediated coupling to the carrier protein keyhole limpet hemocyanin (KLH). To extend serum half-life, the LAH peptide was acetylated at the N-terminus (see Werle and Bernkop-Schnurch, (2006) Amino Acids 30(4):351-367). The structural integrity of the mAb 12D1 binding region within the conjugate was confirmed by direct-binding ELISA (FIG. 7C).

Figures 8A, 8B, 8C, 8D:
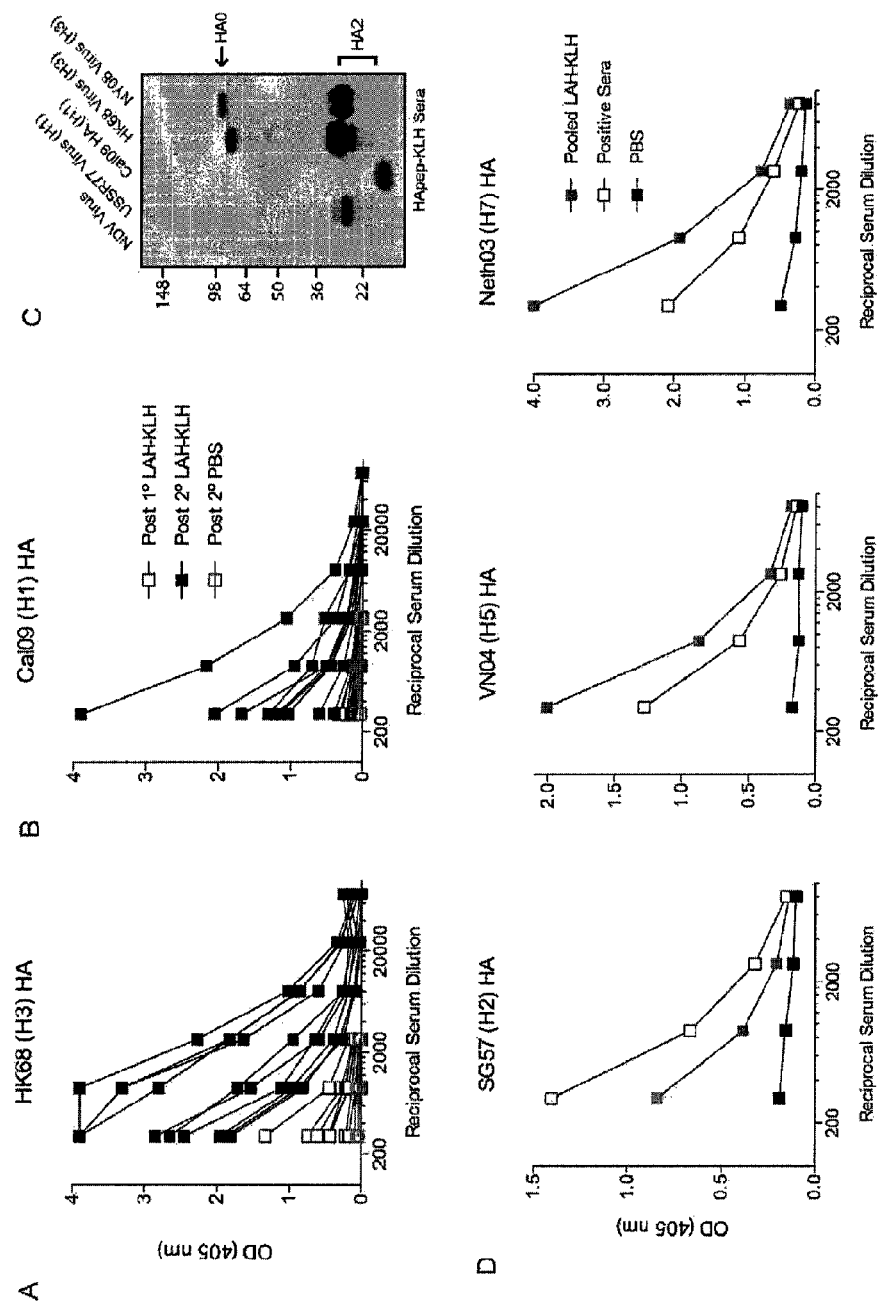
Figures 8E, 8F:
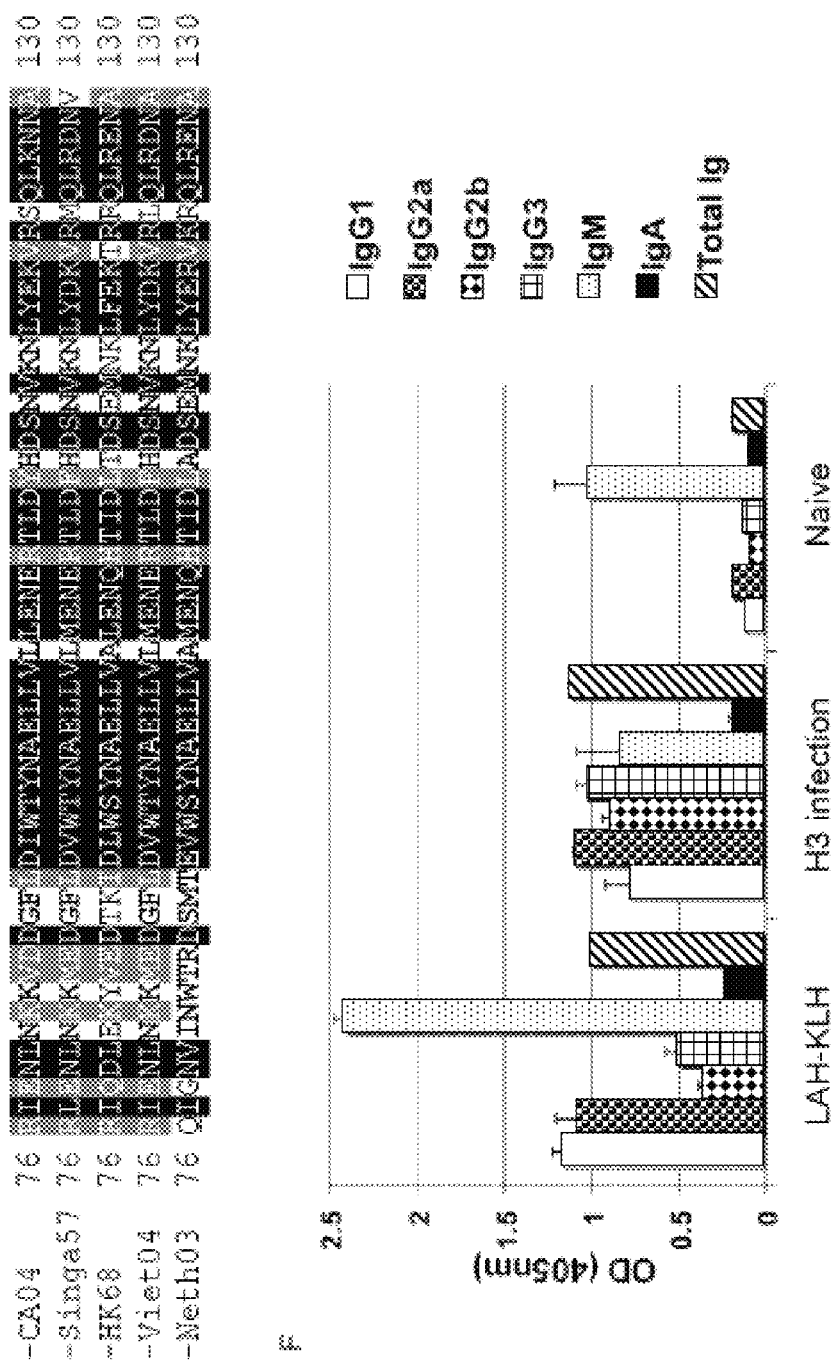

To test the construct in vivo, mice were immunized with the LAH-KLH conjugate in a prime-boost schedule with three weeks lapsing between immunizations. Sera were taken from mice 10 days post primary and secondary immunizations. To evaluate the conjugate for its ability to elicit the production of antibodies of relevant specificity, anti-sera were tested for reactivity with purified hemagglutinin protein of different subtypes. It was first noted that the LAH anti-serum reacted with hemagglutinin protein by both ELISA and by Western blot (FIG. 8A-C). Second, a marked increase in anti-HA titer following secondary immunization demonstrated that the construct acted as a productive immunogen in mice (FIGS. 8A and 8B). Finally, sera from immunized mice had substantial heterosubtypic binding activity. Anti-LAH sera demonstrated activity by ELISA with hemagglutinins from the 1968 pandemic H3 virus A/Hong Kong/1/1968, the 2009 pandemic H1 virus A/California/04/09, as well as hemagglutinins of H2, H5 and H7 subtypes (FIG. 8D). Alignment of the 76-130 region of hemagglutinins from these subtypes demonstrates a high degree of conservation in amino-acid sequence and amino-acid type (FIG. 8E). Further serologic analysis demonstrated that antibody generated in LAH-KLH vaccination boosts serum IgM and IgG subtypes specific for the viral hemagglutinin. The significant boost in IgG subtypes indicates T-cell dependent antibody production and suggests an affinity matured anti-hemagglutinin response (FIG. 8F) (see Jumper et al., (1994) J Immunol 152(2):438-445).

Figures 9A, 9B, 9C, 9D:
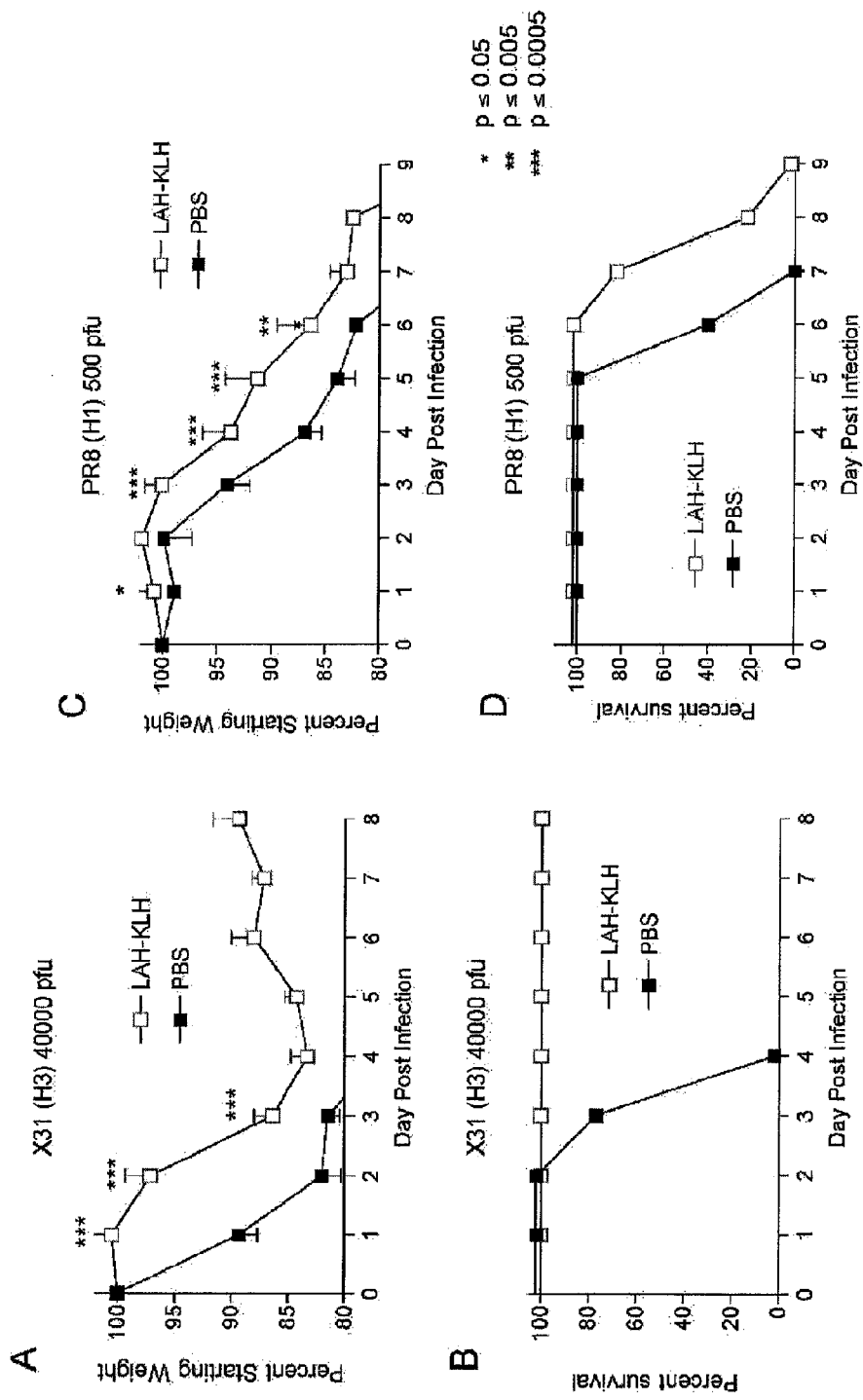
Figure 9E:
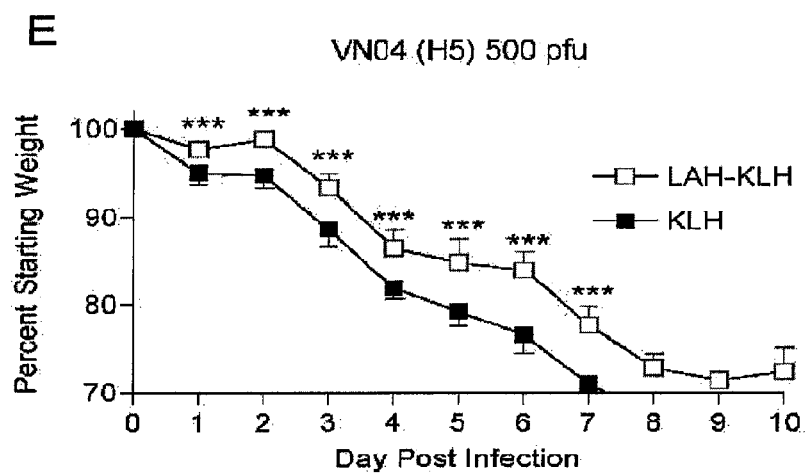
Figure 9F:
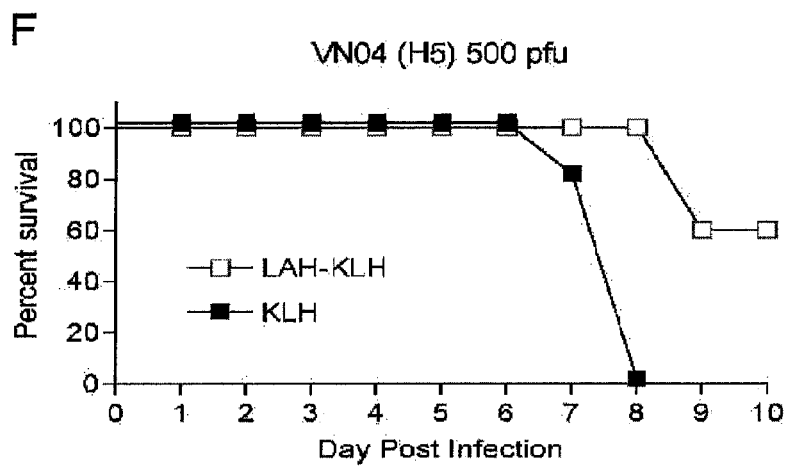

Two to three weeks following secondary immunization, mice were challenged by intranasal administration with $4 \times 10^5$ pfu of X31, a mouse adapted virus expressing the hemagglutinin and neuraminidase of the 1968 pandemic H3 influenza virus. Mice immunized with the LAH-KLH construct lost significantly less weight at all time points than did mice that received PBS with adjuvant. In addition, all immunized mice survived challenge, while control mice succumbed to infection by day 4 (FIGS. 9A and 9B).

Next, immunized mice were challenged with other virus subtypes that cause human influenza disease, but that belong to a distinct phylogenetic class from H3 subtype viruses (see Fields B N, Knipe D M, & Howley P M (2007) *Fields' virology* (Lippincott Williams & Wilkins, Philadelphia) 5th Ed pp 2 v. (xix, 3091, 1-3086 p.)). Mice were infected with 500 pfu (10-15 mLD50) of PR8, a mouse-adapted H1 virus or with 500 pfu of an H5 highly-pathogenic avian influenza virus modified to remove the poly-basic cleavage site in the viral hemagglutinin (see Steel et al., (2009) J Virol 83(4): 1742-1753). Vaccination with the LAH-KLH conjugate was protective against weight loss caused by H1 and H5 influenza disease to a highly significant degree on virtually every day during infection. Vaccinated mice infected with PR8 showed a significant delay in kinetics of weight loss, while 60% of vaccinated mice infected with the H5 avian virus survived lethal challenge to ten days post infection (FIG. 9C-F).

Figures 10A, 10B, 10C:
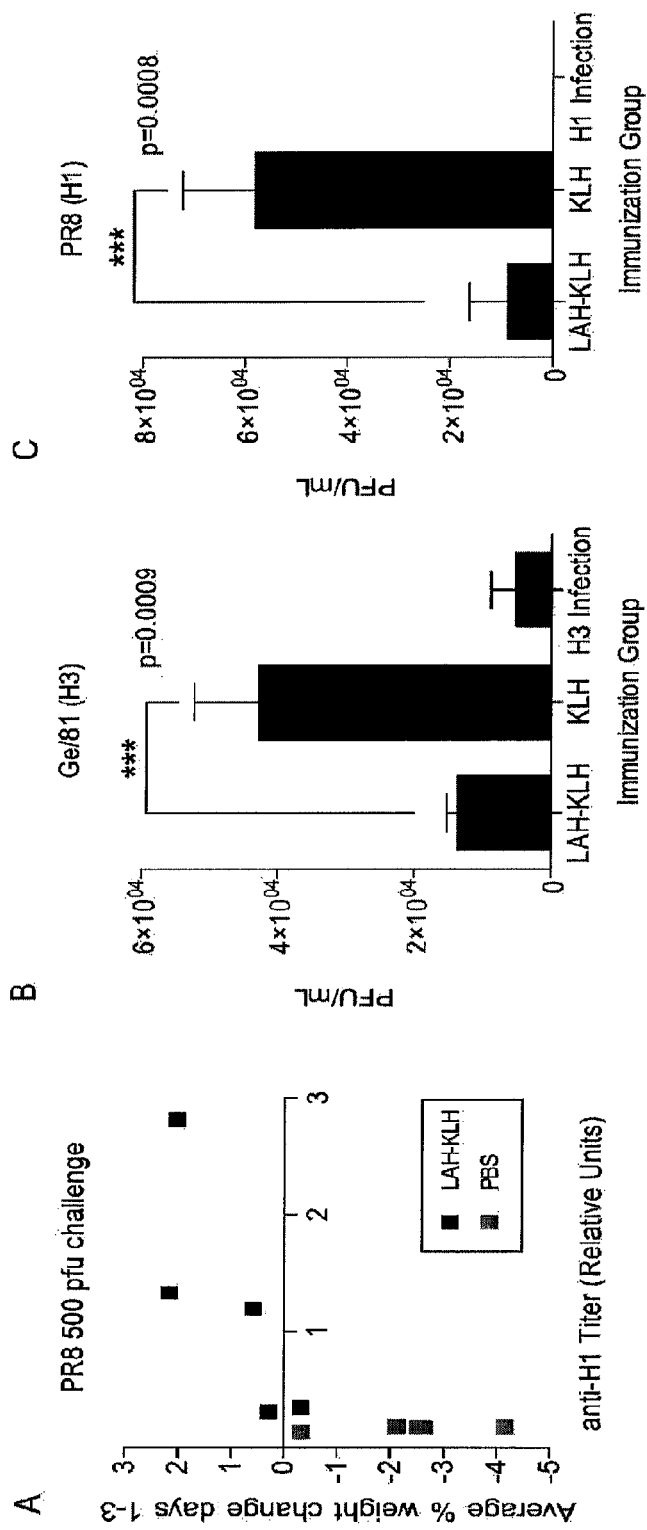

Analysis of pre-challenge sera from mice that were subsequently infected with PR8 revealed a positive correlation between hemagglutinin-specific antibody titer and increase in body weight in days following infection (FIG. 10A). Animals productively immunized (with anti-H1 serum antibody) gained weight during days 1-3 post infection, whereas animals without H1-specific antibody lost weight during this critical period. These data suggested that antibody induced by LAH-KLH vaccination was a requisite component in protection of mice against disease.

To further investigate the role of anti-LAH antibody in protection, in vivo passive transfer experiments were performed. Two hours prior to infection, recipient mice were given 200 µl of serum by intraperitoneal administration from donor mice that had been infected with H1 or H3 virus, vaccinated with KLH alone or vaccinated with the LAH-KLH vaccine. Recipient mice were then infected with a human seasonal H3 virus, A/Georgia/81, or with the H1 virus PR8. Two days following infection, lung titers were evaluated. The transfer of LAH-KLH antiserum was found to significantly reduce lung titers in animals infected with either the human seasonal H3 virus (p=0.0009) or the H1 (p=0.0008) virus (FIGS. 10B and 10C). This transfer experiment suggests that the LAH construct induces neutralizing antibodies in the vaccinated mouse.

Figures 10D, 10E:
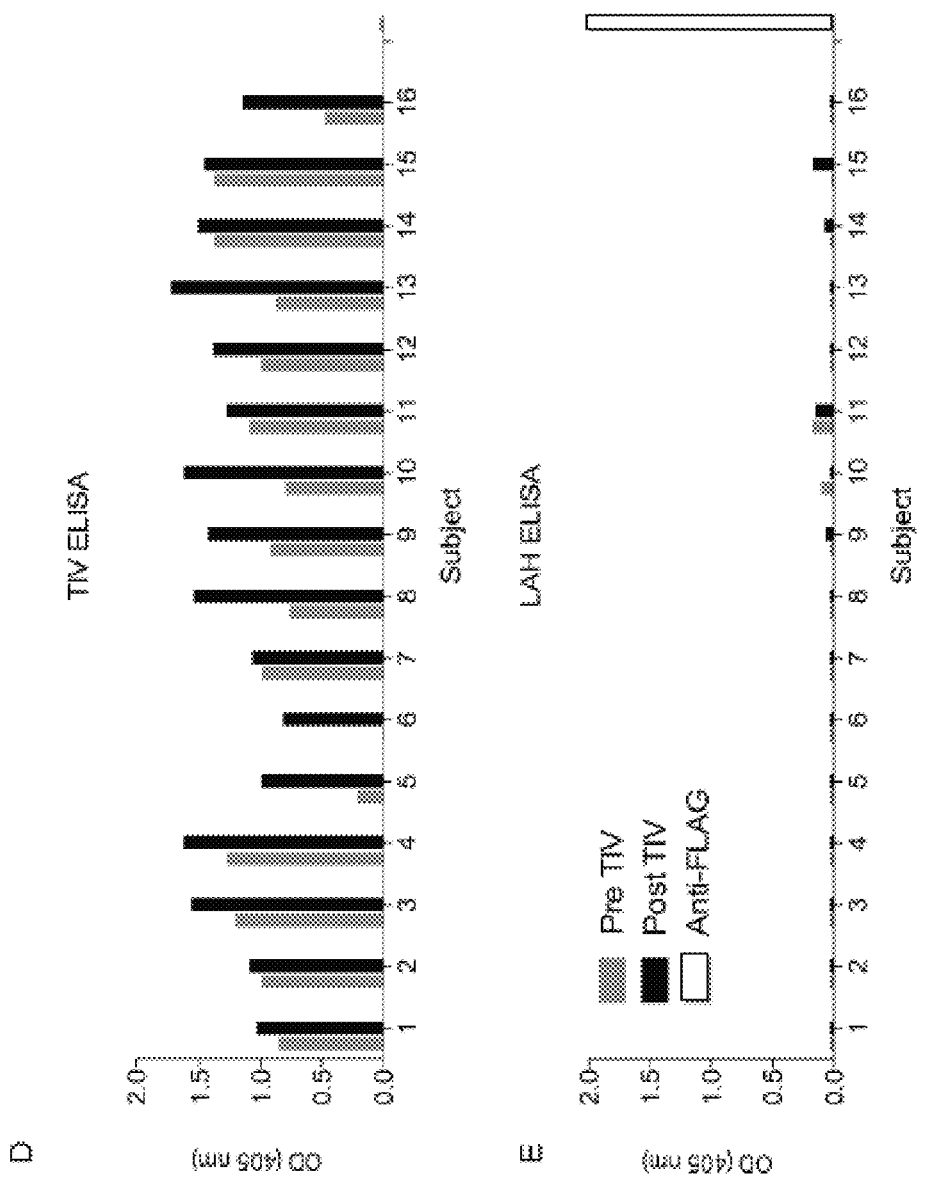

Next, whether seasonal influenza vaccination in humans induces antibody specific for the LAH region of the hemagglutinin was investigated. To explore this possibility, binding activity in human sera taken pre and post-immunization with the 2008-2009 trivalent inactivated influenza virus vaccine (TIV) was evaluated. This seasonal vaccine composition contained an A/Brisbane/59/2007 (H1N1)-like virus, an A/Brisbane/10/2007 (H3N2)-like virus and a B/Florida/4/2006-like virus (see Administration UFaD (2010) Influenza Virus Vaccine for the 2008-2009 Season). Serum samples from human patients were evaluated for a post-vaccination boost in IgG antibody titer against the seasonal TIV composition as a measure of vaccine response. Minimal serum antibody specific for the LAH peptide was detected even in subjects demonstrating the highest response to seasonal vaccination (FIGS. 10D and 10E).

As demonstrated in FIG. 8D, the breadth of reactivity seen in the LAH-KLH antiserum is greater than what has been previously described in studies of hemagglutinin stalk vaccine constructs (see Bommakanti et al., (2010) Proc Natl Acad Sci USA; and Steel, (2010) mBio 1(1):1-9). In order to probe the importance of the design of the conjugate complex in eliciting this broad response, the serum activity elicited by vaccination with the LAH-KLH construct was compared with that elicited by vaccination with the intact HA2 molecule. The ectodomain of the A/Hong Kong/1/1968 HA2 protein was recombinantly expressed as previously described (see Chen et al., (1999) Proc Natl Acad Sci USA 96(16):8967-8972). Mice were vaccinated with pure, uncoupled, HA2 protein by the same methods used to vaccinate mice with LAH-KLH. Pooled antisera from 20 mice taken ten days post secondary vaccination with either LAH-KLH or HA2 protein was evaluated for binding activity against a panel of recombinantly expressed hemagglutinins. While the LAH-KLH antiserum reacted with all hemagglutinin subtypes tested, the HA2 antiserum contained antibody reactive with Group 2 hemagglutinin proteins only (FIG. 11A-H and Table 1). Since the LAH structure is present in the HA2 protein, the broad reactivity seen in the LAH-KLH antiserum must be a consequence of the manner in which the LAH is presented as an antigen within the conjugate complex. Elimination of immunodominant regions of the HA2 may cause the LAH-KLH vaccine to induce a more focused anti-LAH immune response that mediates broad reactivity between hemagglutinin subtypes. Alternately, the induction of broadly-reactive antibody may be a consequence of anchoring the LAH at the C-terminus to a carrier protein, thus rendering regions of the LAH immunogenic that are otherwise antigenically silent in the context of the intact HA2 protein.

6.5.3 Conclusion

This LAH core polypeptide linked to KLH has protective activity against antigenically divergent influenza virus subtypes that currently cause seasonal and pandemic disease in humans. Additionally, the LAH core polypeptide linked to KLH has protective activity against an avian H5N1 virus, a subtype with potential to cause pandemic influenza disease in humans. Thus, the LAH core polypeptide linked to KLH represents a peptide-based influenza virus vaccine that would be inexpensive and uncomplicated to manufacture.

TABLE 1

Summary of ELISA data

|  |  | Anti-LAH-KLH | Anti-HA2 |
|---|---|---|---|
| Group II | HK/68 H3 | + | + |
|  | Bris/07 H3 | + | + |
|  | Neth/03 H7 | + | + |
| Group I | Cal/09 H1 | + | − |
|  | HK/99 H9 | + | − |
|  | Sing/57 H2 | + | − |
|  | Viet/04 H5 | + | − |
|  | HK/97 H6 | + | − |

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An immunogenic composition capable of inducing antibodies that are cross-reactive among influenza hemagglutinin (HA) subtypes, the immunogenic composition comprising a flu polypeptide comprising an immunogenic core polypeptide, wherein the immunogenic core polypeptide is (a) directly or indirectly linked at its N- and/or C-terminus to one or more tags; (b) directly or indirectly linked at its N- and/or C-terminus to a T cell epitope; (c) directly or indirectly linked at its N- and/or C-terminus to a Toll Like Receptor ligand; or (d) directly or indirectly linked at its N- and/or C-terminus to a T4 foldon domain or a fragment thereof, wherein the immunogenic core polypeptide is less than 75 amino acids in length, and wherein the immunogenic core polypeptide comprises:

R-I-Q-D-L-E-K-Y-V-E-D-T-K-I-D-L-W-S-Y-N-A-E-L-L-V-A-L-E-N-Q-H-T-I-D-L-T-D-S-E-M-N-K-L-F-E-$X_1$T-$X_2$-$X_3$-Q-L-R-E-N-A (SEQ ID NO: 15), wherein $X_1$, $X_2$, and $X_3$ are hydrophilic, basic amino acids.

2. The immunogenic composition of claim 1, wherein the immunogenic core polypeptide comprises SEQ ID NO: 16, SEQ ID NO: 17, or SEQ ID NO: 18.

3. The immunogenic composition of claim 1, wherein the immunogenic core polypeptide selectively binds neutralizing antiserum capable of binding an influenza hemagglutinin.

4. The immunogenic composition of claim 1, wherein the immunogenic core polypeptide is further (a) acetylated at its N-terminus; or (b) linked to polyethylene glycol at its N- and/or C-terminus.

5. The immunogenic composition of claim 1, wherein the immunogenic core polypeptide is further linked to a carrier protein.

6. The immunogenic composition of claim 1, wherein the immunogenic core polypeptide has the amino acid sequence RIQDLEKYVEDTKIDLWSYNAELLVALEN-QHTIDLTDSEMNKLFEKTRRQLRENA (SEQ ID NO: 2), and wherein the immunogenic core polypeptide is linked at its C-terminus to a polypeptide having the amino acid sequence DYKDDDDKC (SEQ ID NO: 63).

7. The immunogenic composition of claim 1, wherein $X_1$ is K or R, $X_2$ is K or R, and $X_3$ is K or R.

8. The immunogenic composition of claim 1, wherein the immunogenic core polypeptide is directly or indirectly linked at its N- and/or C-terminus to one or more tags.

9. The immunogenic composition of claim 7, wherein the immunogenic core polypeptide is directly or indirectly linked at its N- and/or C-terminus to one or more tags.

10. The immunogenic composition of claim 1, wherein the immunogenic core polypeptide is directly or indirectly linked at its N- and/or C-terminus to a T cell epitope.

11. The immunogenic composition of claim 7, wherein the immunogenic core polypeptide is directly or indirectly linked at its N- and/or C-terminus to a T cell epitope.

12. The immunogenic composition of claim 1, wherein the immunogenic core polypeptide is directly or indirectly linked at its N- and/or C-terminus to a Toll Like Receptor ligand.

13. The immunogenic composition of claim 7, wherein the immunogenic core polypeptide is directly or indirectly linked at its N- and/or C-terminus to a Toll Like Receptor ligand.

14. The immunogenic composition of claim 1, wherein the immunogenic core polypeptide is directly or indirectly linked at its N- and/or C-terminus to a T4 foldon domain or a fragment thereof.

15. The immunogenic composition of claim 7, wherein the immunogenic core polypeptide is directly or indirectly linked at its N- and/or C-terminus to a T4 foldon domain or a fragment thereof.

16. A method of inducing an immune response to an influenza virus in a subject, comprising administering to the subject an effective amount of the immunogenic composition of claim 1.

17. A method of inducing an immune response to an influenza virus in a subject, comprising administering to the subject an effective amount of the immunogenic composition of claim 7.

18. A method of preventing an influenza virus disease in a subject, comprising administering to the subject an effective amount of the immunogenic composition of claim 1.

19. A method of preventing an influenza virus disease in a subject, comprising administering to the subject an effective amount of the immunogenic composition of claim 7.

20. The method of claim 16, wherein the subject is a human.

21. The method of claim 17, wherein the subject is a human.

22. The method of claim 18, wherein the subject is a human.

23. The method of claim 19, wherein the subject is a human.

* * * * *

SEQUENCE LISTING

<160> NUMBER OF SEQ ID NOS: 64

<210> SEQ ID NO 1
<211> LENGTH: 64
<212> TYPE: PRT
<213> ORGANISM: Artificial Sequence
<220> FEATURE:
<223> OTHER INFORMATION: The long alpha helix domain of the
      hemagglutinin polypeptide of Influenza strain A/Hong Kong/1/1968
      (H3) + flag tag

<400> SEQUENCE: 1

Arg Ile Gln Asp Leu Glu Lys Tyr Val Glu Asp Thr Lys Ile Asp Leu
 1               5                  10                  15

Trp Ser Tyr Asn Ala Glu Leu Leu Val Ala Leu Glu Asn Gln His Thr
                20                  25                  30

Ile Asp Leu Thr Asp Ser Glu Met Asn Lys Leu Phe Glu Lys Thr Arg
            35                  40                  45

Arg Gln Leu Arg Glu Asn Ala Asp Tyr Lys Asp Asp Asp Asp Lys Cys
        50                  55                  60

<210> SEQ ID NO 2
<211> LENGTH: 55
<212> TYPE: PRT
<213> ORGANISM: Artificial Sequence
<220> FEATURE:
<223> OTHER INFORMATION: The long alpha helix domain of the -continued hemagglutinin polypeptide of Influenza strain A/Hong Kong/1/1968
(H3) generic core peptide

<400>

```
<223> OTHER INFORMATION: Xaa is K, L, M, S or R

<400> SEQUENCE: 3

Xaa Xaa Xaa Xaa Xaa Xaa Xaa Xaa Xaa Asp Xaa Xaa Xaa Xaa
  1               5                  10                  15

Trp Xaa Tyr Xaa Ala Glu Leu Leu Val Xaa Xaa Glu Asn Xaa Xaa Thr
         20                  25                  30

Xaa Asp Xaa Xaa Asp Ser Xaa Xaa Xaa Xaa Leu Xaa Xaa Xaa Xaa Xaa
         35                  40                  45

Xaa Gln Leu Xaa Xaa Asn Xaa
     50                  55

<210> SEQ ID NO 4
<211> LENGTH: 55
<212> TYPE: PRT
<213> ORGANISM: Artificial Sequence
<220> FEATURE:
<223> OTHER INFORMATION: Consensus core polypeptide
<220> FEATURE:
<221> NAME/KEY: VARIANT
<222> LOCATION: 9
<223> OTHER INFORMATION: Xaa is M, V, T
<220> FEATURE:
<221> NAME/KEY: VARIANT
<222> LOCATION: 35
<223> OTHER INFORMATION: Xaa is a hydrophobic amino acid
<220> FEATURE:
<221> NAME/KEY: VARIANT
<222> LOCATION: 49
<223> OTHER INFORMATION: Xaa is L, M, S, K, R
<220> FEATURE:
<221> NAME/KEY: VARIANT
<222> LOCATION: 53
<223> OTHER INFORMATION: Xaa is a hydrophilic amino acid

<400> SEQUENCE: 4

Arg Ile Glu Asn Leu Asn Lys Lys Xaa Glu Asp Gly Phe Leu Asp Val
  1               5                  10                  15

Trp Thr Tyr Asn Ala Glu Leu Leu Val Leu Met Glu Asn Glu Arg Thr
         20                  25                  30

Leu Asp Xaa His Asp Ser Asn Val Lys Asn Leu Tyr Glu Lys Val Arg
         35                  40                  45

Xaa Gln Leu Arg Xaa Asn Ala
     50                  55

<210> SEQ ID NO 5
<211> LENGTH: 55
<212> TYPE: PRT
<213> ORGANISM: Artificial Sequence
<220> FEATURE:
<223> OTHER INFORMATION: Group 1 core polypeptide
<220> FEATURE:
<221> NAME/KEY: VARIANT
<222> LOCATION: 2,9,16,27,55
<223> OTHER INFORMATION: Xaa is a hydrophobic amino acid
<220> FEATURE:
<221> NAME/KEY: VARIANT
<222> LOCATION: 10,53
<223> OTHER INFORMATION: Xaa is a hydrophilic amino acid
<220> FEATURE:
<221> NAME/KEY: VARIANT
<222> LOCATION: (35
<223> OTHER INFORMATION: Xaa is a hydrophobic acidic amino acid
<220> FEATURE:
<221> NAME/KEY: VARIANT
<222> LOCATION: 45
<223> OTHER INFORMATION: Xaa is a hydrophilic, acidic amino acid
<220> FEATURE:
<221> NAME/KEY: VARIANT
```

```
<222> LOCATION: 49
<223> OTHER INFORMATION: Xaa is L, M, or S
<220> FEATURE:
<221> NAME/KEY: VARIANT
<222> LOCATION: 52
<223> OTHER INFORMATION: Xaa is a hydrophilic, basic amino acid

<400> SEQUENCE: 5

Arg Xaa Glu Asn Leu Asn Lys Lys Xaa Xaa Asp Gly Phe Leu Asp Xaa
 1               5                  10                  15

Trp Thr Tyr Asn Ala Glu Leu Leu Val Leu Xaa Glu Asn Glu Arg Thr
            20                  25                  30

Leu Asp Xaa His Asp Ser Asn Val Lys Asn Leu Tyr Xaa Lys Val Arg
        35                  40                  45

Xaa Gln Leu Xaa Xaa Asn Xaa
    50                  55

<210> SEQ ID NO 6
<211> LENGTH: 55
<212> TYPE: PRT
<213> ORGANISM: Artificial Sequence
<220> FEATURE:
<223> OTHER INFORMATION: Group 2 core polypeptide
<220> FEATURE:
<221> NAME/KEY: VARIANT
<222> LOCATION: 1,3,4,7,10,12
<223> OTHER INFORMATION: Xaa is a hydrophilic amino acid
<220> FEATURE:
<221> NAME/KEY: VARIANT
<222> LOCATION: 5,8,16,27,44
<223> OTHER INFORMATION: Xaa is a hydrophobic amino acid
<220> FEATURE:
<221> NAME/KEY: VARIANT
<222> LOCATION: 46,48
<223> OTHER INFORMATION: Xaa is a hydrophilic, basic amino acid
<220> FEATURE:
<221> NAME/KEY: VARIANT
<222> LOCATION: 6
<223> OTHER INFORMATION: Xaa is E or I
<220> FEATURE:
<221> NAME/KEY: VARIANT
<222> LOCATION: 9
<223> OTHER INFORMATION: Xaa is V or T
<220> FEATURE:
<221> NAME/KEY: VARIANT
<222> LOCATION: 13
<223> OTHER INFORMATION: Xaa is K or M
<220> FEATURE:
<221> NAME/KEY: VARIANT
<222> LOCATION: 14
<223> OTHER INFORMATION: Xaa is I or T
<220> FEATURE:
<221> NAME/KEY: VARIANT
<222> LOCATION: 15
<223> OTHER INFORMATION: Xaa is a hydrophilic, acidic amino acid
<220> FEATURE:
<221> NAME/KEY: VARIANT
<222> LOCATION: 36
<223> OTHER INFORMATION: Xaa is T or A
<220> FEATURE:
<221> NAME/KEY: VARIANT
<222> LOCATION: 47
<223> OTHER INFORMATION: Xaa is T or V

<400> SEQUENCE: 6

Xaa Ile Xaa Xaa Xaa Xaa Xaa Xaa Xaa Xaa Asp Xaa Xaa Xaa Xaa Xaa
 1               5                  10                  15

Trp Ser Tyr Asn Ala Glu Leu Leu Val Ala Xaa Glu Asn Gln His Thr
            20                  25                  30

Ile Asp Leu Xaa Asp Ser Glu Met Asn Lys Leu Xaa Glu Xaa Xaa Xaa
        35                  40                  45
```

```
Arg Gln Leu Arg Glu Asn Ala
    50                  55

<210> SEQ ID NO 7
<211> LENGTH: 55
<212> TYPE: PRT
<213> ORGANISM: Artificial Sequence
<220> FEATURE:
<223> OTHER INFORMATION: H1 core polypeptides
<220> FEATURE:
<221> NAME/KEY: VARIANT
<222> LOCATION: 2,14,35
<223> OTHER INFORMATION: Xaa is a hydrophobic amino acid
<220> FEATURE:
<221> NAME/KEY: VARIANT
<222> LOCATION: 41,48
<223> OTHER INFORMATION: Xaa is a hydrophilic, basic amino acid

<400> SEQUENCE

```
Ser Gln Leu Lys Asn Asn Ala
    50                  55
```

<210> SEQ ID NO 10
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain A/South
      Carolina/1/1918

<400> SEQUENCE: 10

```
Arg Ile Glu Asn Leu Asn Lys Lys Val Asp Asp Gly Phe Leu Asp Ile
1               5                   10                  15

Trp Thr Tyr Asn Ala Glu Leu Leu Val Leu Leu Glu Asn Glu Arg Thr
            20                  25                  30

Leu Asp Phe His Asp Ser Asn Val Arg Asn Leu Tyr Glu Lys Val Lys
                35                  40                  45

Ser Gln Leu Lys Asn Asn Ala
    50                  55
```

<210> SEQ ID NO 11
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain
      A/California/07/2009

<400> SEQUENCE: 11

```
Arg Ile Glu Asn Leu Asn Lys Lys Val Asp Asp Gly Phe Leu Asp Ile
1               5                   10                  15

Trp Thr Tyr Asn Ala Glu Leu Leu Val Leu Leu Glu Asn Glu Arg Thr
            20                  25                  30

Leu Asp Tyr His Asp Ser Asn Val Lys Asn Leu Tyr Glu Lys Val Arg
                35                  40                  45

Ser Gln Leu Lys Asn Asn Ala
    50                  55
```

<210> SEQ ID NO 12
<211> LENGTH: 55
<212> TYPE: PRT
<213> ORGANISM: Artificial Sequence
<220> FEATURE:
<223> OTHER INFORMATION: H2 core polypeptide
<220> FEATURE:
<221> NAME/KEY: VARIANT
<222> LOCATION: 45
<223> OTHER INFORMATION: Xaa is a hydrophilic, acidic amino acid

<400> SEQUENCE: 12

```
Arg Leu Glu Asn Leu Asn Lys Lys Met Glu Asp Gly Phe Leu Asp Val
1               5                   10                  15

Trp Thr Tyr Asn Ala Glu Leu Leu Val Leu Met Glu Asn Glu Arg Thr
            20                  25                  30

Leu Asp Phe His Asp Ser Asn Val Lys Asn Leu Tyr Xaa Lys Val Arg
                35                  40                  45

Met Gln Leu Arg Asp Asn Val
    50                  55
```

<210> SEQ ID NO 13

<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain A/Singapore/1/1957

<400> SEQUENCE: 13

```
Arg Leu Glu Asn Leu Asn Lys Lys Met Glu Asp Gly Phe Leu Asp Val
 1               5                  10                  15

Trp Thr Tyr Asn Ala Glu Leu Leu Val Leu Met Glu Asn Glu Arg Thr
            20                  25                  30

Leu Asp Phe His Asp Ser Asn Val Lys Asn Leu Tyr Asp Lys Val Arg
        35                  40                  45

Met Gln Leu Arg Asp Asn Val
    50                  55
```

<210> SEQ ID NO 14
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain A/Czech
      Republic/1/1966

<400> SEQUENCE: 14

```
Arg Leu Glu Asn Leu Asn Lys Lys Met Glu Asp Gly Phe Leu Asp Val
 1               5                  10                  15

Trp Thr Tyr Asn Ala Glu Leu Leu Val Leu Met Glu Asn Glu Arg Thr
            20                  25                  30

Leu Asp Phe His Asp Ser Asn Val Lys Asn Leu Tyr Glu Lys Val Arg
        35                  40                  45

Met Gln Leu Arg Asp Asn Val
    50                  55
```

<210> SEQ ID NO 15
<211> LENGTH: 55
<212> TYPE: PRT
<213> ORGANISM: Artificial Sequence
<220> FEATURE:
<223> OTHER INFORMATION: H3 core polypeptide
<220> FEATURE:
<221> NAME/KEY: VARIANT
<222> LOCATION: 46,48,49
<223> OTHER INFORMATION: Xaa is a hydrophilic, basic amino acid

<400> SEQUENCE: 15

```
Arg Ile Gln Asp Leu Glu Lys Tyr Val Glu Asp Thr Lys Ile Asp Leu
 1               5                  10                  15

Trp Ser Tyr Asn Ala Glu Leu Leu Val Ala Leu Glu Asn Gln His Thr
            20                  25                  30

Ile Asp Leu Thr Asp Ser Glu Met Asn Lys Leu Phe Glu Xaa Thr Xaa
        35                  40                  45

Xaa Gln Leu Arg Glu Asn Ala
    50                  55
```

<210> SEQ ID NO 16
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Infuenza strain A/Denmark/191/2005

<400> SEQUENCE: 16

Arg Ile Gln Asp Leu Glu Lys Tyr Val Glu Asp Thr Lys Ile Asp Leu
1               5                   10                  15

Trp Ser Tyr Asn Ala Glu Leu Leu Val Ala Leu Glu Asn Gln His Thr
            20                  25                  30

Ile Asp Leu Thr Asp Ser Glu Met Asn Lys Leu Phe Glu Arg Thr Lys
        35                  40                  45

Lys Gln Leu Arg Glu Asn Ala
    50                  55

<210> SEQ ID NO 17
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain A/Arkansas/05/2008

<400> SEQUENCE: 17

Arg Ile Gln Asp Leu Glu Lys Tyr Val Glu Asp Thr Lys Ile Asp Leu
1               5                   10                  15

Trp Ser Tyr Asn Ala Glu Leu Leu Val Ala Leu Glu Asn Gln His Thr
            20                  25                  30

Ile Asp Leu Thr Asp Ser Glu Met Asn Lys Leu Phe Glu Lys Thr Lys
        35                  40                  45

Lys Gln Leu Arg Glu Asn Ala
    50                  55

<210> SEQ ID NO 18
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain A/Hong Kong/1/68

<400> SEQUENCE: 18

Arg Ile Gln Asp Leu Glu Lys Tyr Val Glu Asp Thr Lys Ile Asp Leu
1               5                   10                  15

Trp Ser Tyr Asn Ala Glu Leu Leu Val Ala Leu Glu Asn Gln His Thr
            20                  25                  30

Ile Asp Leu Thr Asp Ser Glu Met Asn Lys Leu Phe Glu Lys Thr Arg
        35                  40                  45

Arg Gln Leu Arg Glu Asn Ala
    50                  55

<210> SEQ ID NO 19
<211> LENGTH: 55
<212> TYPE: PRT
<213> ORGANISM: Artificial Sequence
<220> FEATURE:
<223> OTHER INFORMATION: H4 core polypeptide
<220> FEATURE:
<221> NAME/KEY: VARIANT
<222> LOCATION: 49
<223> OTHER INFORMATION: Xaa is a hydrophilic, basic amino acid

<400> SEQUENCE: 19

Arg Ile Gln Asp Leu Glu Lys Tyr Val Glu Asp Thr Lys Ile Asp Leu
1               5                   10                  15

Trp Ser Tyr Asn Ala Glu Leu Leu Val Ala Leu Glu Asn Gln His Thr

```
                20                  25                  30

Ile Asp Val Thr Asp Ser Glu Met Asn Lys Leu Phe Glu Arg Val Arg
        35                  40                  45

Xaa Gln Leu Arg Glu Asn Ala
    50                  55

<210> SEQ ID NO 20
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain
      A/mallard/Ohia/324/1988

<400> SEQUENCE: 20

Arg Ile Gln Asp Leu Glu Lys Tyr Val Glu Asp Thr Lys Ile Asp Leu
1               5                   10                  15

Trp Ser Tyr Asn Ala Glu Leu Leu Val Ala Leu Glu Asn Gln His Thr
            20                  25                  30

Ile Asp Val Thr Asp Ser Glu Met Asn Lys Leu Phe Glu Arg Val Arg
        35                  40                  45

Arg Gln Leu Arg Glu Asn Ala
    50                  55

<210> SEQ ID NO 21
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain
      A/mallard/Minnesota/271/1999

<400> SEQUENCE: 21

Arg Ile Gln Asp Leu Glu Lys Tyr Val Glu Asp Thr Lys Ile Asp Leu
1               5                   10                  15

Trp Ser Tyr Asn Ala Glu Leu Leu Val Ala Leu Glu Asn Gln His Thr
            20                  25                  30

Ile Asp Val Thr Asp Ser Glu Met Asn Lys Leu Phe Glu Arg Val Arg
        35                  40                  45

His Gln Leu Arg Glu Asn Ala
    50                  55

<210> SEQ ID NO 22
<211> LENGTH: 55
<212> TYPE: PRT
<213> ORGANISM: Artificial Sequence
<220> FEATURE:
<223> OTHER INFORMATION: H5 core polypeptide

<400> SEQUENCE: 22

Arg Ile Glu Asn Leu Asn Lys Lys Met Glu Asp Gly Phe Leu Asp Val
1               5                   10                  15

Trp Thr Tyr Asn Ala Glu Leu Leu Val Leu Met Glu Asn Glu Arg Thr
            20                  25                  30

Leu Asp Phe His Asp Ser Asn Val Lys Asn Leu Tyr Asp Lys Val Arg
        35                  40                  45

Leu Gln Leu Arg Asp Asn Ala
    50                  55
```

```
<210> SEQ ID NO 23
<211> LENGTH: 55
<212> TYPE: PRT
<213> ORGANISM: Artificial Sequence
<220> FEATURE:
<223> OTHER INFORMATION: H6 core polypeptide
<220> FEATURE:
<221> NAME/KEY: VARIANT
<222> LOCATION: 3
<223> OTHER INFORMATION: Xaa is G or D
<220> FEATURE:
<221> NAME/KEY: VARIANT
<222> LOCATION: 5,35
<223> OTHER INFORMATION: Xaa is a hydrophobic amino acid
<220> FEATURE:
<221> NAME/KEY: VARIANT
<222> LOCATION: 30,42
<223> OTHER INFORMATION: Xaa is a hydrophilic amino acid
<220> FEATURE:
<221> NAME/KEY: VARIANT
<222> LOCATION: 44
<223> OTHER INFORMATION: Xaa is H or Y
<220> FEATURE:
<221> NAME/KEY: VARIANT
<222> LOCATION: 50
<223> OTHER INFORMATION: Xaa is Q or L
<220> FEATURE:
<221> NAME/KEY: VARIANT
<222> LOCATION: 52
<223> OTHER INFORMATION: Xaa is a hydrophilic, basic amino acid

<400> SEQUENCE: 23

Arg Ile Xaa Asn Xaa Asn Lys Arg Met Glu Asp Gly Phe Leu Asp Val
 1               5                  10                  15

Trp Thr Tyr Asn Ala Glu Leu Leu Val Leu Leu Glu Asn Xaa Arg Thr
            20                  25                  30

Leu Asp Xaa His Asp Ala Asn Val Lys Xaa Leu Xaa Glu Lys Val Lys
        35                  40                  45

Ser Xaa Leu Xaa Asp Asn Ala
    50                  55

<210> SEQ ID NO 24
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain A/blue winged
      teal/ALB/69/1985

<400> SEQUENCE: 24

Arg Ile Gly Asn Leu Asn Lys Arg Met Glu Asp Gly Phe Leu Asp Val
 1               5                  10                  15

Trp Thr Tyr Asn Ala Glu Leu Leu Val Leu Leu Glu Asn Glu Arg Thr
            20                  25                  30

Leu Asp Met His Asp Ala Asn Val Lys Asn Leu His Glu Lys Val Lys
        35                  40                  45

Ser Gln Leu Arg Asp Asn Ala
    50                  55

<210> SEQ ID NO 25
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain A/Canada
      goose/Ohio/127/1989
```

```
<400> SEQUENCE: 25

Arg Ile Asp Asn Leu Asn Lys Arg Met Glu Asp Gly Phe Leu Asp Val
1               5                   10                  15

Trp Thr Tyr Asn Ala Glu Leu Leu Val Leu Leu Glu Asn Glu Arg Thr
            20                  25                  30

Leu Asp Met His Asp Ala Asn Val Lys Asn Leu His Glu Lys Val Lys
        35                  40                  45

Ser Gln Leu Lys Asp Asn Ala
    50                  55

<210> SEQ ID NO 26
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain A/blu-winged
      teal/ALB/368/1978

<400> SEQUENCE: 26

Arg Ile Asp Asn Leu Asn Lys Arg Met Glu Asp Gly Phe Leu Asp Val
1               5                   10                  15

Trp Thr Tyr Asn Ala Glu Leu Leu Val Leu Leu Glu Asn Gly Arg Thr
            20                  25                  30

Leu Asp Met His Asp Ala Asn Val Lys Asn Leu His Glu Lys Val Lys
        35                  40                  45

Ser Leu Leu Arg Asp Asn Ala
    50                  55

<210> SEQ ID NO 27
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain A/northern
      pintail/California/HKWF151/2007

<400> SEQUENCE: 27

Arg Ile Asp Asn Leu Asn Lys Arg Met Glu Asp Gly Phe Leu Asp Val
1               5                   10                  15

Trp Thr Tyr Asn Ala Glu Leu Leu Val Leu Leu Glu Asn Glu Arg Thr
            20                  25                  30

Leu Asp Leu His Asp Ala Asn Val Lys Asn Leu Tyr Glu Lys Val Lys
        35                  40                  45

Ser Gln Leu Arg Asp Asn Ala
    50                  55

<210> SEQ ID NO 28
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain
      A/chicken/CA/S0403106/2004

<400> SEQUENCE: 28

Arg Ile Asp Asn Met Asn Lys Arg Met Glu Asp Gly Phe Leu Asp Val
1               5                   10                  15

Trp Thr Tyr Asn Ala Glu Leu Leu Val Leu Leu Glu Asn Glu Arg Thr
            20                  25                  30
```

Leu Asp Leu His Asp Ala Asn Val Lys Ser Leu His Glu Lys Val Lys
        35                  40                  45

Ser Gln Leu Arg Asp Asn Ala
        50                  55

<210> SEQ ID NO 29
<211> LENGTH: 55
<212> TYPE: PRT
<213> ORGANISM: Artificial Sequence
<220> FEATURE:
<223> OTHER INFORMATION: H6 Consensus

<400> SEQUENCE: 29

Arg Ile Asp Asn Leu Asn Lys Arg Met Glu Asp Gly Phe Leu Asp Val
1               5                   10                  15

Trp Thr Tyr Asn Ala Glu Leu Leu Val Leu Leu Glu Asn Glu Arg Thr
            20                  25                  30

Leu Asp Met His Asp Ala Asn Val Lys Asn Leu His Glu Lys Val Lys
        35                  40                  45

Ser Gln Leu Arg Asp Asn Ala
        50                  55

<210> SEQ ID NO 30
<211> LENGTH: 55
<212> TYPE: PRT
<213> ORGANISM: Artificial Sequence
<220> FEATURE:
<223> OTHER INFORMATION: H7 core polypeptide
<220> FEATURE:
<221> NAME/KEY: VARIANT
<222> LOCATION: 12
<223> OTHER INFORMATION: Xaa is a hydrophobic amino acid or a
      hydrophilic amino acid
<220> FEATURE:
<221> NAME/KEY: VARIANT
<222> LOCATION: 16
<223> OTHER INFORMATION: Xaa is a hydrophobic amino acid
<220> FEATURE:
<221> NAME/KEY: VARIANT
<222> LOCATION: 41
<223> OTHER INFORMATION: Xaa is a hydrophilic amino acid
<220> FEATURE:
<221> NAME/KEY: VARIANT
<222> LOCATION: 48
<223> OTHER INFORMATION: Xaa is a hydrophilic, basic amino acid

<400> SEQUENCE: 30

Gln Ile Gly Asn Val Ile Asn Trp Thr Arg Asp Xaa Met Thr Glu Xaa
1               5                   10                  15

Trp Ser Tyr Asn Ala Glu Leu Leu Val Ala Met Glu Asn Gln His Thr
            20                  25                  30

Ile Asp Leu Ala Asp Ser Glu Met Xaa Lys Leu Tyr Glu Arg Val Xaa
        35                  40                  45

Lys Gln Leu Arg Glu Asn Ala
        50                  55

<210> SEQ ID NO 31
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain A/green winged
      teal/California/AKS1370/2008

<400> SEQUENCE: 31

Gln Ile Gly Asn Val Ile Asn Trp Thr Arg Asp Ser Met Thr Glu Val
1               5                   10                  15

Trp Ser Tyr Asn Ala Glu Leu Leu Val Ala Met Glu Asn Gln His Thr
                20                  25                  30

Ile Asp Leu Ala Asp Ser Glu Met Asn Lys Leu Tyr Glu Arg Val Arg
            35                  40                  45

Lys Gln Leu Arg Glu Asn Ala
    50                  55

<210> SEQ ID NO 32
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain A/duck/New
      Jersey/Sg-00286/1996

<400> SEQUENCE: 32

Gln Ile Gly Asn Val Ile Asn Trp Thr Arg Asp Ala Met Thr Glu Val
1               5                   10                  15

Trp Ser Tyr Asn Ala Glu Leu Leu Val Ala Met Glu Asn Gln His Thr
                20                  25                  30

Ile Asp Leu Ala Asp Ser Glu Met Asn Lys Leu Tyr Glu Arg Val Arg
            35                  40                  45

Lys Gln Leu Arg Glu Asn Ala
    50                  55

<210> SEQ ID NO 33
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain A/avian/New
      York/Sg-00338/1999

<400> SEQUENCE: 33

Gln Ile Gly Asn Val Ile Asn Trp Thr Arg Asp Ala Met Thr Glu Ile
1               5                   10                  15

Trp Ser Tyr Asn Ala Glu Leu Leu Val Ala Met Glu Asn Gln His Thr
                20                  25                  30

Ile Asp Leu Ala Asp Ser Glu Met Ser Lys Leu Tyr Glu Arg Val Arg
            35                  40                  45

Lys Gln Leu Arg Glu Asn Ala
    50                  55

<210> SEQ ID NO 34
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain A/chicken/New
      Jersey/Sg-00431/2004

<400> SEQUENCE: 34

Gln Ile Gly Asn Val Ile Asn Trp Thr Arg Asp Ala Met Thr Glu Ile
1               5                   10                  15

Trp Ser Tyr Asn Ala Glu Leu Leu Val Ala Met Glu Asn Gln His Thr
                20                  25                  30

```
Ile Asp Leu Ala Asp Ser Glu Met Ser Lys Leu Tyr Glu Arg Val Lys
        35                  40                  45

Lys Gln Leu Arg Glu Asn Ala
        50                  55
```

<210> SEQ ID NO 35
<211> LENGTH: 55
<212> TYPE: PRT
<213> ORGANISM: Artificial Sequence
<220> FEATURE:
<223> OTHER INFORMATION: H7 Consensus

<400> SEQUENCE: 35

```
Gln Ile Gly Asn Val Ile Asn Trp Thr Arg Asp Ala Met Thr Glu Val
 1               5                  10                  15

Trp Ser Tyr Asn Ala Glu Leu Leu Val Ala Met Glu Asn Gln His Thr
                20                  25                  30

Ile Asp Leu Ala Asp Ser Glu Met Asn Lys Leu Tyr Glu Arg Val Arg
        35                  40                  45

Lys Gln Leu Arg Glu Asn Ala
        50                  55
```

<210> SEQ ID NO 36
<211> LENGTH: 55
<212> TYPE: PRT
<213> ORGANISM: Artificial Sequence
<220> FEATURE:
<223> OTHER INFORMATION: H8 core polypeptide
<220> FEATURE:
<221> NAME/KEY: VARIANT
<222> LOCATION: 15
<223> OTHER INFORMATION: Xaa is a hydrophilic amino acid

<400> SEQUENCE: 36

```
Arg Ile Asn Met Ile Asn Asp Lys Ile Asp Asp Gln Ile Glu Xaa Leu
 1               5                  10                  15

Trp Ala Tyr Asn Ala Glu Leu Leu Val Leu Leu Glu Asn Gln Lys Thr
                20                  25                  30

Leu Asp Glu His Asp Ser Asn Val Lys Asn Leu Phe Asp Glu Val Lys
        35                  40                  45

Arg Arg Leu Ser Ala Asn Ala
        50                  55
```

<210> SEQ ID NO 37
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain A/pintail
      duck/Alberta/114/1979

<400> SEQUENCE: 37

```
Arg Ile Asn Met Ile Asn Asp Lys Ile Asp Asp Gln Ile Glu Asp Leu
 1               5                  10                  15

Trp Ala Tyr Asn Ala Glu Leu Leu Val Leu Leu Glu Asn Gln Lys Thr
                20                  25                  30

Leu Asp Glu His Asp Ser Asn Val Lys Asn Leu Phe Asp Glu Val Lys
        35                  40                  45

Arg Arg Leu Ser Ala Asn Ala
        50                  55
```

-continued

```
<210> SEQ ID NO 38
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain
      A/pintail/Barrow/38/2005

<400> SEQUENCE: 38

Arg Ile Asn Met Ile Asn Asp Lys Ile Asp Asp Gln Ile Glu Asn Leu
 1               5                  10                  15

Trp Ala Tyr Asn Ala Glu Leu Leu Val Leu Leu Glu Asn Gln Lys Thr
             20                  25                  30

Leu Asp Glu His Asp Ser Asn Val Lys Asn Leu Phe Asp Glu Val Lys
         35                  40                  45

Arg Arg Leu Ser Ala Asn Ala
     50                  55

<210> SEQ ID NO 39
<211> LENGTH: 55
<212> TYPE: PRT
<213> ORGANISM: Artificial Sequence
<220> FEATURE:
<223> OTHER INFORMATION: H9 core polypeptide
<220> FEATURE:
<221> NAME/KEY: VARIANT
<222> LOCATION: 16
<223> OTHER INFORMATION: Xaa is a hydrophobic amino acid

<400> SEQUENCE: 39

Arg Leu Asn Met Ile Asn Asn Lys Ile Asp Asp Gln Ile Gln Asp Xaa
 1               5                  10                  15

Trp Ala Tyr Asn Ala Glu Leu Leu Val Leu Leu Glu Asn Gln Lys Thr
             20                  25                  30

Leu Asp Glu His Asp Ala Asn Val Asn Asn Leu Tyr Asn Lys Val Lys
         35                  40                  45

Arg Ala Leu Gly Ser Asn Ala
     50                  55

<210> SEQ ID NO 40
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain A/chicken/Middle
      East/ED-1/1999

<400> SEQUENCE: 40

Arg Leu Asn Met Ile Asn Asn Lys Ile Asp Asp Gln Ile Gln Asp Val
 1               5                  10                  15

Trp Ala Tyr Asn Ala Glu Leu Leu Val Leu Leu Glu Asn Gln Lys Thr
             20                  25                  30

Leu Asp Glu His Asp Ala Asn Val Asn Asn Leu Tyr Asn Lys Val Lys
         35                  40                  45

Arg Ala Leu Gly Ser Asn Ala
     50                  55

<210> SEQ ID NO 41
<211> LENGTH: 55
<212> TYPE: PRT
<213> ORGANISM: Artificial Sequence
<220> FEATURE:
```

<223> OTHER INFORMATION: The long alpha helix domain of the
hemagglutinin polypeptide of Influenza strain A/duck/Hong
Kong/702/1979

<400> SEQUENCE: 41

Arg Leu Asn Met Ile Asn Asn Lys Ile Asp Asp Gln Ile Gln Asp Ile
1               5                   10                  15

Trp Ala Tyr Asn Ala Glu Leu Leu Val Leu Leu Glu Asn Gln Lys Thr
            20                  25                  30

Leu Asp Glu His Asp Ala Asn Val Asn Asn Leu Tyr Asn Lys Val Lys
        35                  40                  45

Arg Ala Leu Gly Ser Asn Ala
    50                  55

<210> SEQ ID NO 42
<211> LENGTH: 55
<212> TYPE: PRT
<213> ORGANISM: Artificial Sequence
<220> FEATURE:
<223> OTHER INFORMATION: H10 core polypeptide
<220> FEATURE:
<221> NAME/KEY: VARIANT
<222> LOCATION: 20
<223> OTHER INFORMATION: Xaa is a hydrophilic amino acid

<400> SEQUENCE: 42

Gln Ile Gly Asn Val Ile Asn Trp Thr Lys Asp Ser Ile Thr Asp Ile
1               5                   10                  15

Trp Thr Tyr Xaa Ala Glu Leu Leu Val Ala Met Glu Asn Gln His Thr
            20                  25                  30

Ile Asp Met Ala Asp Ser Glu Met Leu Asn Leu Tyr Glu Arg Val Arg
        35                  40                  45

Lys Gln Leu Arg Gln Asn Ala
    50                  55

<210> SEQ ID NO 43
<211> LENGTH: 55
<212> TYPE: PRT
<213> ORGANISM: Artificial Sequence
<220> FEATURE:
<223> OTHER INFORMATION: The long alpha helix domain of the
hemagglutinin polypeptide of Influenza strain
A/mallard/Maryland/161/2001

<400> SEQUENCE: 43

Gln Ile Gly Asn Val Ile Asn Trp Thr Lys Asp Ser Ile Thr Asp Ile
1               5                   10                  15

Trp Thr Tyr Gln Ala Glu Leu Leu Val Ala Met Glu Asn Gln His Thr
            20                  25                  30

Ile Asp Met Ala Asp Ser Glu Met Leu Asn Leu Tyr Glu Arg Val Arg
        35                  40                  45

Lys Gln Leu Arg Gln Asn Ala
    50                  55

<210> SEQ ID NO 44
<211> LENGTH: 55
<212> TYPE: PRT
<213> ORGANISM: Artificial Sequence
<220> FEATURE:
<223> OTHER INFORMATION: The long alpha helix domain of the
hemagglutinin polypeptide of Influenza strain
A/chicken/Germany/n/1949

<400> SEQUENCE: 44

```
Gln Ile Gly Asn Val Ile Asn Trp Thr Lys Asp Ser Ile Thr Asp Ile
  1               5                  10                  15

Trp Thr Tyr Asn Ala Glu Leu Leu Val Ala Met Glu Asn Gln His Thr
             20                  25                  30

Ile Asp Met Ala Asp Ser Glu Met Leu Asn Leu Tyr Glu Arg Val Arg
         35                  40                  45

Lys Gln Leu Arg Gln Asn Ala
         50                  55

<210> SEQ ID NO 45
<211> LENGTH: 55
<212> TYPE: PRT
<213> ORGANISM: Artificial Sequence
<220> FEATURE:
<223> OTHER INFORMATION: H11 core polypeptide
<220> FEATURE:
<221> NAME/KEY: VARIANT
<222> LOCATION: 14
<223> OTHER INFORMATION: Xaa is a hydrophobic amino acid

<400> SEQUENCE: 45

Arg Ile Asn Gln Leu Ser Lys His Val Asp Asp Ser Val Xaa Asp Ile
  1               5                  10                  15

Trp Ser Tyr Asn Ala Gln Leu Leu Val Leu Leu Glu Asn Glu Lys Thr
             20                  25                  30

Leu Asp Leu His Asp Ser Asn Val Arg Asn Leu His Glu Lys Val Arg
         35                  40                  45

Arg Met Leu Lys Asp Asn Ala
         50                  55

<210> SEQ ID NO 46
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain
      A/GF/NY/26410-17/1995

<400> SEQUENCE: 46

Arg Ile Asn Gln Leu Ser Lys His Val Asp Asp Ser Val Ile Asp Ile
  1               5                  10                  15

Trp Ser Tyr Asn Ala Gln Leu Leu Val Leu Leu Glu Asn Glu Lys Thr
             20                  25                  30

Leu Asp Leu His Asp Ser Asn Val Arg Asn Leu His Glu Lys Val Arg
         35                  40                  45

Arg Met Leu Lys Asp Asn Ala
         50                  55

<210> SEQ ID NO 47
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain
      A/duck/England/1/1956

<400> SEQUENCE: 47

Arg Ile Asn Gln Leu Ser Lys His Val Asp Asp Ser Val Val Asp Ile
  1               5                  10                  15

Trp Ser Tyr Asn Ala Gln Leu Leu Val Leu Leu Glu Asn Glu Lys Thr
```

```
                20                  25                  30

Leu Asp Leu His Asp Ser Asn Val Arg Asn Leu His Glu Lys Val Arg
        35                  40                  45

Arg Met Leu Lys Asp Asn Ala
        50                  55

<210> SEQ ID NO 48
<211> LENGTH: 55
<212> TYPE: PRT
<213> ORGANISM: Artificial Sequence
<220> FEATURE:
<223> OTHER INFORMATION: H12 core polypeptide
<220> FEATURE:
<221> NAME/KEY: VARIANT
<222> LOCATION: 50
<223> OTHER INFORMATION: Xaa is a hydrophobic amino acid
<220> FEATURE:
<221> NAME/KEY: VARIANT
<222> LOCATION: 52
<223> OTHER INFORMATION: Xaa is a hydrophilic, basic amino acid

<400> SEQUENCE: 48

Arg Ile Asn Met Ile Asn Ser Lys Ile Asp Asp Gln Ile Thr Asp Ile
 1               5                  10                  15

Trp Ala Tyr Asn Ala Glu Leu Leu Val Leu Leu Glu Asn Gln Lys Thr
                20                  25                  30

Leu Asp Glu His Asp Ala Asn Val Arg Asn Leu His Asp Arg Val Arg
        35                  40                  45

Arg Xaa Leu Xaa Glu Asn Ala
        50                  55

<210> SEQ ID NO 49
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain
      A/duck/Alberta/60/1976

<400> SEQUENCE: 49

Arg Ile Asn Met Ile Asn Ser Lys Ile Asp Asp Gln Ile Thr Asp Ile
 1               5                  10                  15

Trp Ala Tyr Asn Ala Glu Leu Leu Val Leu Leu Glu Asn Gln Lys Thr
                20                  25                  30

Leu Asp Glu His Asp Ala Asn Val Arg Asn Leu His Asp Arg Val Arg
        35                  40                  45

Arg Val Leu Arg Glu Asn Ala
        50                  55

<210> SEQ ID NO 50
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain
      A/duck/Hokkaido/66/01

<400> SEQUENCE: 50

Arg Ile Asn Met Ile Asn Ser Lys Ile Asp Asp Gln Ile Thr Asp Ile
 1               5                  10                  15

Trp Ala Tyr Asn Ala Glu Leu Leu Val Leu Leu Glu Asn Gln Lys Thr
                20                  25                  30
```

```
Leu Asp Glu His Asp Ala Asn Val Arg Asn Leu His Asp Arg Val Arg
        35                  40                  45

Arg Ile Leu Lys Glu Asn Ala
    50                  55

<210> SEQ ID NO 51
<211> LENGTH: 55
<212> TYPE: PRT
<213> ORGANISM: Artificial Sequence
<220> FEATURE:
<223> OTHER INFORMATION: H13 core polypeptide
<220> FEATURE:
<221> NAME/KEY: VARIANT
<222> LOCATION: 16
<223> OTHER INFORMATION: Xaa is a hydrophobic amino acid
<220> FEATURE:
<221> NAME/KEY: VARIANT
<222> LOCATION: 45
<223> OTHER INFORMATION: Xaa is a hydrophilic, acidic amino acid
<220> FEATURE:
<221> NAME/KEY: VARIANT
<222> LOCATION: 50
<223> OTHER INFORMATION: Xaa is A, S or E
<220> FEATURE:
<221> NAME/KEY: VARIANT
<222> LOCATION: 53
<223> OTHER INFORMATION: Xaa is a hydrophilic amino acid

<400> SEQUENCE: 51

Arg Ile Asn Met Leu Ala Asp Arg Ile Asp Asp Ala Val Thr Asp Xaa
 1               5                  10                  15

Trp Ser Tyr Asn Ala Lys Leu Leu Val Leu Leu Glu Asn Asp Lys Thr
            20                  25                  30

Leu Asp Met His Asp Ala Asn Val Arg Asn Leu His Xaa Gln Val Arg
        35                  40                  45

Arg Xaa Leu Lys Xaa Asn Ala
    50                  55

<210> SEQ ID NO 52
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain A/black-headed
      gull/Asktrakhan/227/1984

<400> SEQUENCE: 52

Arg Ile Asn Met Leu Ala Asp Arg Ile Asp Asp Ala Val Thr Asp Val
 1               5                  10                  15

Trp Ser Tyr Asn Ala Lys Leu Leu Val Leu Leu Glu Asn Asp Lys Thr
            20                  25                  30

Leu Asp Met His Asp Ala Asn Val Arg Asn Leu His Asp Gln Val Arg
        35                  40                  45

Arg Ala Leu Lys Thr Asn Ala
    50                  55

<210> SEQ ID NO 53
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain A/American while
      pelican/Minnesota/Sg-0611/2008
```

<400> SEQUENCE: 53

Arg Ile Asn Met Leu Ala Asp Arg Ile Asp Asp Ala Val Thr Asp Val
1               5                   10                  15

Trp Ser Tyr Asn Ala Lys Leu Leu Val Leu Leu Glu Asn Asp Lys Thr
                20                  25                  30

Leu Asp Met His Asp Ala Asn Val Arg Asn Leu His Asp Gln Val Arg
            35                  40                  45

Arg Ser Leu Lys Thr Asn Ala
        50                  55

<210> SEQ ID NO 54
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain
      A/duck/Siberia/272PF/1998

<400> SEQUENCE: 54

Arg Ile Asn Met Leu Ala Asp Arg Ile Asp Asp Ala Val Thr Asp Ile
1 5 10 15

Trp Ser Tyr Asn Ala Lys Leu Leu Val Leu Leu Glu Asn Asp Lys Thr
20 25 30

Leu Asp Met His Asp Ala Asn Val Arg Asn Leu His Glu Gln Val Arg
35 40 45

Arg Glu Leu Lys Asp Asn Ala
50 55

<210> SEQ ID NO 55
<211> LENGTH: 55
<212> TYPE: PRT
<213> ORGANISM: Artificial Sequence
<220> FEATURE:
<223> OTHER INFORMATION: H14 core polypeptide

<400> SEQUENCE: 55

Arg Ile Gln Asp Leu Glu Lys Tyr Val Glu Asp Thr Lys Ile Asp Leu
1 5 10 15

Trp Ser Tyr Asn Ala Glu Leu Leu Val Ala Leu Glu Asn Gln His Thr
20 25 30

Ile Asp Val Thr Asp Ser Glu Met Asn Lys Leu Phe Glu Arg Val Arg
35 40 45

Arg Gln Leu Arg Glu Asn Ala
50 55

<210> SEQ ID NO 56
<211> LENGTH: 55
<212> TYPE: PRT
<213> ORGANISM: Artificial Sequence
<220> FEATURE:
<223> OTHER INFORMATION: H15 core polypeptide

<400> SEQUENCE: 56

Gln Ile Gly Asn Val Ile Asn Trp Thr Arg Asp Ser Leu Thr Glu Ile
1 5 10 15

Trp Ser Tyr Asn Ala Glu Leu Leu Val Ala Met Glu Asn Gln His Thr
20 25 30

Ile Asp Leu Ala Asp Ser Glu Met Asn Lys Leu Tyr Glu Arg Val Arg
35 40 45

Arg Gln Leu Arg Glu Asn Ala
    50                  55

<210> SEQ ID NO 57
<211> LENGTH: 55
<212> TYPE: PRT
<213> ORGANISM: Artificial Sequence
<220> FEATURE:
<223> OTHER INFORMATION: H16 core polypeptide
<220> FEATURE:
<221> NAME/KEY: VARIANT
<222> LOCATION: 27
<223> OTHER INFORMATION: Xaa is a hydrophobic amino acid
<220> FEATURE:
<221> NAME/KEY: VARIANT
<222> LOCATION: 41
<223> OTHER INFORMATION: Xaa is a hydrophilic, basic amino acid
<220> FEATURE:
<221> NAME/KEY: VARIANT
<222> LOCATION: 45
<223> OTHER INFORMATION: Xaa is a hydrophilic, acidic amino acid
<220> FEATURE:
<221> NAME/KEY: VARIANT
<222> LOCATION: 53
<223> OTHER INFORMATION: Xaa is a hydrophilic amino acid

<400> SEQUENCE: 57

Arg Ile Asn Met Leu Ala Asp Arg Val Asp Asp Ala Val Thr Asp Ile
1               5                   10                  15

Trp Ser Tyr Asn Ala Lys Leu Leu Val Leu Xaa Glu Asn Asp Arg Thr
            20                  25                  30

Leu Asp Leu His Asp Ala Asn Val Xaa Asn Leu His Xaa Gln Val Lys
        35                  40                  45

Arg Ala Leu Lys Xaa Asn Ala
    50                  55

<210> SEQ ID NO 58
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain A/black-headed
      gull/Turkenistan/13/76

<400> SEQUENCE: 58

Arg Ile Asn Met Leu Ala Asp Arg Val Asp Asp Ala Val Thr Asp Ile
1               5                   10                  15

Trp Ser Tyr Asn Ala Lys Leu Leu Val Leu Ile Glu Asn Asp Arg Thr
            20                  25                  30

Leu Asp Leu His Asp Ala Asn Val Arg Asn Leu His Asp Gln Val Lys
        35                  40                  45

Arg Ala Leu Lys Ser Asn Ala
    50                  55

<210> SEQ ID NO 59
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain A/slender-billed
      gull/Astrakhan/28/76

<400> SEQUENCE: 59

Arg Ile Asn Met Leu Ala Asp Arg Val Asp Asp Ala Val Thr Asp Ile
1               5                   10                  15

-continued

Trp Ser Tyr Asn Ala Lys Leu Leu Val Leu Leu Glu Asn Asp Arg Thr
            20                  25                  30

Leu Asp Leu His Asp Ala Asn Val Arg Asn Leu His Asp Gln Val Lys
        35                  40                  45

Arg Ala Leu Lys Ser Asn Ala
    50                  55

<210> SEQ ID NO 60
<211> LENGTH: 55
<212> TYPE: PRT
<213> ORGANISM: Artificial Sequence
<220> FEATURE:
<223> OTHER INFORMATION: The long alpha helix domain of the
      hemagglutinin polypeptide of Influenza strain A/herring
      gull/DE/712/1988

<400> SEQUENCE: 60

Arg Ile Asn Met Leu Ala Asp Arg Val Asp Asp Ala Val Thr Asp Ile
1               5                   10                  15

Trp Ser Tyr Asn Ala Lys Leu Leu Val Leu Ile Glu Asn Asp Arg Thr
            20                  25                  30

Leu Asp Leu His Asp Ala Asn Val Lys Asn Leu His Glu Gln Val Lys
        35                  40                  45

Arg Ala Leu Lys Asn Asn Ala
    50                  55

<210> SEQ ID NO 61
<211> LENGTH: 8
<212> TYPE: PRT
<213> ORGANISM: Artificial Sequence
<220> FEATURE:
<223> OTHER INFORMATION: FLAG-tag

<400> SEQUENCE: 61

Asp Tyr Lys Asp Asp Asp Asp Lys
1               5

<210> SEQ ID NO 62
<211> LENGTH: 55
<212> TYPE: PRT
<213> ORGANISM: Artificial Sequence
<220> FEATURE:
<223> OTHER INFORMATION: a derivative H16 core polypeptide

<400> SEQUENCE: 62

Glu Ile Leu Glu Leu Asp Glu Lys Val Asp Asp Leu Arg Ala Asp Thr
1               5                   10                  15

Ile Ser Ser Gln Ile Glu Leu Ala Val Leu Leu Ser Asn Glu Gly Ile
            20                  25                  30

Ile Asn Ser Glu Asp Glu His Leu Leu Ala Leu Glu Arg Lys Leu Lys
        35                  40                  45

Lys Met Leu Gly Pro Ser Ala
    50                  55

<210> SEQ ID NO 63
<211> LENGTH: 9
<212> TYPE: PRT
<213> ORGANISM: Artificial Sequence
<220> FEATURE:
<223> OTHER INFORMATION: a linker comprises a FLAG-tag covalently linked
      to a cysteine residue

<400> SEQUENCE: 63

```
Asp Tyr Lys Asp Asp Asp Asp Lys Cys
1               5

<210> SEQ ID NO 64
<211> LENGTH: 55
<212> TYPE: PRT
<213> ORGANISM: Artificial Sequence
<220> FEATURE:
<223> OTHER INFORMATION: a core polypeptide comprises a region
      (aa 79-134) of hemagglutinin subunit of inluenza virus
      A/Hong Kong/1/1968 (H3)

<400> SEQUENCE: 64

Leu Glu Lys Tyr Val Glu Asp Thr Lys Ile Asp Leu Trp Ser Tyr Asn
1               5                   10                  15

Ala Glu Leu Leu Val Ala Leu Glu Asn Gln His Thr Ile Asp Leu Thr
            20                  25                  30

Asp Ser Glu Met Asn Lys Leu Phe Glu Lys Thr Arg Arg Gln Leu Arg
        35                  40                  45

Glu Asn Ala Glu Asp Met Gly
    50                  55
```